US012778862B2

(12) United States Patent
Coon et al.

(10) Patent No.: US 12,778,862 B2
(45) Date of Patent: Nov. 3, 2026

(54) STABLE BIOACTIVE GLASS FORMULATIONS

(71) Applicant: CORNING INCORPORATED, Corning, NY (US)

(72) Inventors: Erin Coon, Providence, RI (US); Qiang Fu, Painted Post, NY (US); Aize Li, Painted Post, NY (US); Hugh Michael McMahon, Millport, NY (US); Charisse Marye Spier, Horseheads, NY (US); Nicholas Michael Stone-Weiss, Corning, NY (US); Joanna E. Warzyszynska, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 264 days.

(21) Appl. No.: 18/642,098

(22) Filed: Apr. 22, 2024

(65) Prior Publication Data

US 2024/0366482 A1 Nov. 7, 2024

Related U.S. Application Data

(60) Provisional application No. 63/463,629, filed on May 3, 2023.

(51) Int. Cl.

*A61K 8/24* (2006.01)
*A61K 8/19* (2006.01)

(Continued)

(52) U.S. Cl.

CPC .................. *A61K 8/24* (2013.01); *A61K 8/19* (2013.01); *A61K 8/25* (2013.01); *A61Q 11/00* (2013.01);

(Continued)

(58) Field of Classification Search

CPC ........................................................ A61K 8/24

See application file for complete search history.

(56) References Cited

U.S. PATENT DOCUMENTS 4,234,972 A 11/1980 Hench
4,358,541 A 11/1982 Andrus et al.

(Continued)

FOREIGN PATENT DOCUMENTS

CN 109476532 A 3/2019
CN 109771319 A 5/2019

(Continued)

OTHER PUBLICATIONS

Zaidel et al.. "Anti-hypersensitivity mechanism of action for a dentifrice containing 0.3% triclosan. 2.0% PVM/MA copolymer. 0.243% NaF and specially-designed silica", American Journal of Dentistry. vol. 24. Special Issue A. Jul. 2011, p. 6A-13A.

(Continued)

*Primary Examiner* — Benjamin J Packard
(74) *Attorney, Agent, or Firm* — Travis B. Gasa

(57) ABSTRACT

An aqueous dentifrice formulation, comprising: a bioactive glass exhibiting at least one of: a hydrolytic resistance of glass grains (HGB) of at most 4, when measured by International Organization for Standardization section 719 (ISO 719); a weight loss of 5 wt. % or less after soaking 5 g of the bioactive glass in powder form in 100 mL of deionized water for 7 days at 37° C.; an XRD spectrum substantially free of crystalline phase after soaking 5 g of the bioactive glass in powder form in 100 mL of deionized water for 7 days at 37° C.; or any combination thereof; wherein, when the bioactive glass is contacted with artificial saliva, the bioactive glass forms a bioactive crystalline phase. A method of using the aqueous dentifrice formulation to remineralize enamel of the tooth, treat caries of the tooth, (Continued)

treat dentin hypersensitivity of the tooth, or any combination thereof.

20 Claims, 39 Drawing Sheets

(51) Int. Cl.

*A61K 8/25* (2006.01)
*A61Q 11/00* (2006.01)
*C03C 3/062* (2006.01)
*C03C 3/097* (2006.01)
*C03C 3/112* (2006.01)
*C03C 4/00* (2006.01)

(52) U.S. Cl.

CPC .............. *C03C 3/062* (2013.01); *C03C 3/097* (2013.01); *C03C 3/112* (2013.01); *C03C 4/0021* (2013.01)

(56) References Cited

U.S. PATENT DOCUMENTS

| | | | |
|---|---|---|---|
| 4,643,982 | A | 2/1987 | Kasuga et al. |
| 4,783,429 | A | 11/1988 | Shibuya et al. |
| 4,820,660 | A | 4/1989 | Mohri et al. |
| 4,960,733 | A | 10/1990 | Kasuga et al. |
| 5,074,916 | A | 12/1991 | Hench et al. |
| 6,197,429 | B1 | 3/2001 | Lapp et al. |
| 6,200,137 | B1 | 3/2001 | Hoeland et al. |
| 7,090,720 | B2 | 8/2006 | Kessler et al. |
| 8,515,625 | B2 | 8/2013 | Watanabe |
| 8,715,625 | B1 | 5/2014 | Rokitowski et al. |
| 8,741,269 | B2 | 6/2014 | Mandadi et al. |
| 9,238,044 | B2 | 1/2016 | Da et al. |
| 9,937,365 | B2 | 4/2018 | Chopra et al. |
| 10,285,916 | B2 | 5/2019 | Sagel et al. |
| 10,500,142 | B2 | 12/2019 | Schankel et al. |
| 11,724,957 | B2 | 8/2023 | Fu |
| 2009/0208428 | A1 | 8/2009 | Hill et al. |
| 2011/0244430 | A1 | 10/2011 | Gibson et al. |
| 2012/0020899 | A1 | 1/2012 | Zaidel et al. |
| 2012/0148646 | A1 | 6/2012 | Stark et al. |
| 2013/0171220 | A1 | 7/2013 | Hill et al. |
| 2014/0193499 | A1 | 7/2014 | Da et al. |
| 2015/0297500 | A1 | 10/2015 | Robinson et al. |
| 2017/0174555 | A1 | 6/2017 | Danielson et al. |
| 2021/0047233 | A1 | 2/2021 | Fu et al. |
| 2021/0093534 | A1 | 4/2021 | Strand et al. |
| 2021/0179484 | A1 | 6/2021 | Beall et al. |
| 2021/0220242 | A1 | 7/2021 | Hodgkinson |
| 2022/0009822 | A1 | 1/2022 | Fu |
| 2022/0220022 | A1 | 7/2022 | Coon et al. |
| 2022/0241165 | A1 | 8/2022 | Drake et al. |
| 2022/0274866 | A1 | 9/2022 | Coon et al. |
| 2023/0045516 | A1 | 2/2023 | Chiang et al. |
| 2023/0133219 | A1 | 5/2023 | Fu et al. |
| 2023/0227350 | A1 | 7/2023 | Coon et al. |
| 2024/0140854 | A1 | 5/2024 | Fu et al. |

FOREIGN PATENT DOCUMENTS

| | | | | |
|---|---|---|---|---|
| DE | 3806215 | A1 | 9/1988 | |
| EP | 2695623 | B1 | 5/2020 | |
| FR | 2612918 | A1 | 9/1988 | |
| GB | 2199027 | A | 6/1988 | |
| JP | 61-197446 | A | 9/1986 | |
| JP | 06-039031 | A | 2/1994 | |
| JP | 2009-120998 | A | 6/2009 | |
| WO | 95/21799 | A1 | 8/1995 | |
| WO | 97/49643 | A1 | 12/1997 | |
| WO | WO-9817236 | A1 * | 4/1998 | ............... A61K 6/69 |
| WO | 2012/137158 | A1 | 10/2012 | |
| WO | 2020/236501 | A1 | 11/2020 | |
| WO | 2021/119043 | A2 | 6/2021 | |
| WO | 2022/005781 | A1 | 1/2022 | |
| WO | 2022/136870 | A1 | 6/2022 | |
| WO | 2022/182544 | A1 | 9/2022 | |
| WO | 2022/187214 | A1 | 9/2022 | |

OTHER PUBLICATIONS

Zhang et al.. "Biomimetic regulation of dentine remineralizationby amino acid in vitro", Dental Materials. 2018 [retrieved on May 15, 2024]. Retrieved from the internet: <URL: https://www.sciencedirect.com/science/article/abs/pii/S0109564I I18304524 ?via%3Dihub>. pp. 1-12.

Zhong et al.. "Effect of a novel bioactive glass-ceramic on dentinal tubule occlusion: an in vitro study", Australian Dental Journal. vol. 60. 2015, pp. 96-103.

Aina, V., et al., "On the dissolution/reaction of small-grain Bioglass® 45S5 and F-modified bioactive glasses in artificial saliva (AS)". Applied Surface Science, 2011. 257(9): pp. 4185-4195.

Aspinall et al., "Oral Care Product Formulations, Properties and Challenges", Colloids Surf. B Biointerfaces 2021, 200, 111567.

Balamurugan et al., "Sol gel derived SiO2—CaO—MgO—P2O5 bioglass system-Preparation and in vitro characterization", Wiley Interscience, Apr. 2007, pp. 546-553.

Berg et al., "Comparative Study of Technologies for Tubule Occlusion and Treatment of Dentin Hypersensitivity", J. Funct. Biomater. 2021, 12 (2), 27.

Boccaccini et al., "Bioactive glasses beyond bone and teeth: emerging applications in contact with soft tissues". Acta Biomaterialia, 2015. 13: pp. 1-15.

Cochrane, N., et al., "New approaches to enhanced remineralization of tooth enamel". Journal of dental research, 2010. 89(11): pp. 1187-1197.

Featherstone, J.D., "The science and practice of caries prevention". The Journal of the American dental association, 2000. 131(7): pp. 887-899.

GBD 2017 Disease and Injury Incidence and Prevalence Collaborators; "Global, regional, and national incidence, prevalence, and years lived with disability for 354 diseases and injuries for 195 countries and territories, 1990-2017: a systematic analysis for the Global Burden of Disease Study 2017". Lancet (London, England), 2018. 392(10159): pp. 1789-1858.

Generosi, A., et al., "Crystallization process of carbonate substituted hydroxyapatite nanoparticles in toothpastes upon physiological conditions: An in situ time-resolved X-ray diffraction study". Journal of Materials Science: Materials in Medicine, 2010. 21(2): pp. 445-450.

Gerth, H.U., et al., "A three layer structure model of fluoridated enamel containing CaF2, Ca (OH) 2 and FAp". Dental Materials, 2007. 23(12): pp. 1521-1528.

Grohe, B.; Mittler, S. "Advanced Non-Fluoride Approaches to Dental Enamel Remineralization: The next Level in Enamel Repair Management", Biomater. Biosyst. 2021, 4, 100029.

Hare et al., "Immediate and Durable Effects of an Oxalate Strip on Human Dentin In Vitro", Compend. Contin. Educ. Dent. Jamesburg NJ 1995 2016, 37, pp. e6-e12.

Hench, L.L., "Bioceramics". Journal of the American Ceramic Society, 1998. 81(7): pp. 1705-1728.

Hill et al., "The ability of a nano hydroxyapatite toothpaste and oral rinse containing fluoride to protect enamel during an acid challenge using 19F solid state NMR spectroscopy". Materials Letters, 2015. 156: pp. 69-71.

James et al., Global, regional, and national incidence, prevalence, and years lived with disability for 354 diseases and injuries for 195 countries and territories, 1990-2017: a systematic analysis for the Global Burden of Disease Study 2017. Lancet (London, England), 2018. 392(10159): pp. 1789-1858.

Jia et al., "Glass-Activated Regeneration of Volumetric Muscle Loss", Acta Biomaterialia, vol. 103, Feb. 2020, pp. 306-317.

Larsen et al., "Saturation of human saliva with respect to calcium salts," Archives of oral biology, vol. 48, No. 4, pp. 317-322, 2003.

Li et al., "The Remineralisation of Enamel: A Review of the Literature", J. Dent. 2014, 42 Suppl 1, pp. S12-S20.

(56) References Cited

OTHER PUBLICATIONS

Miguez-Pacheco et al., "Bioactive Glasses Beyond Bone And Teeth: Emerging Applications In Contact With Soft Tissues", Acta Biomaterialia, vol. 13, Feb. 2015, pp. 1-15.
Moreno et al., "Fluoridated hydroxyapatite solubility and caries formation". Nature, 1974. 247(5435): pp. 64-65.
Papas et al., "Caries clinical trial of a remineralising toothpaste in radiation patients," Gerodontology, vol. 25, No. 2, pp. 76-88, 2008.
Petrou et al., "A Breakthrough Therapy for Dentin Hypersensitivity: How Dental Products Containing 8% Arginine and Calcium Carbonate Work to Deliver Effective Relief of Sensitive Teeth", J. Clin. Dent. 2009, 20 (1), pp. 23-31.
Rahaman et al., "Bioactive Glass in Tissue Engineering". Acta Biomaterialia, 2011, vol. 7, No. 6, pp. 2355-2373.
Robinson, C., et al., "The chemistry of enamel caries". Critical Reviews in Oral Biology & Medicine, 2000. 11(4): pp. 481-495.
Selwitz et al., "Dental caries," The Lancet, vol. 369, No. 9555, pp. 51-59, 2007.
Shiau, H.J., "Dentin Hypersensitivity", Journal of Evidence Based Dental Practice, 2012. 12(3): pp. 220-228.
Tao, J., et al., "Roles of amorphous calcium phosphate and biological additives in the assembly of hydroxyapatite nanoparticles", Journal of Physical Chemistry B, 2007. 111(47): pp. 13410-13418.
Vranic et al., "Formulation Ingredients for Toothpastes and Mouthwashes", Bosn. J. Basic Med. Sci. 2004, 4 (4), pp. 51-58.
Walsh, L. "Contemporary Technologies for Remineralisation Therapies", A Review. 2009, 11, 9 pages.
Wheeler et al., "Evaluation of Particulate Bioglass® in a Rabbit Radius Ostectomy Model", Journal of Biomedical Materials Research, 1997, vol. 35, No. 2, pp. 249-254.
Wheeler, D.L., et al., "Effect of bioactive glass particle size on osseous regeneration of cancellous defects". Journal of biomedical materials research, 1998. 41(4): pp. 527-533.
Yanyan, S., et al., "Effects of amino acids on conversion of calcium carbonate to hydroxyapatite", RSC Advances, 2020. 10: pp. 37005-37013.
Yin Ping et al., "Effect of ZrO2on the bioactivity properties of gel-derived CaO—P2O5—SiO2—SrO glasses", Ceramics International, vol. 43, No. 13, Apr. 2017, pp. 9691-9698.

* cited by examiner

STABLE BIOACTIVE GLASS FORMULATIONS

CROSS REFERENCE TO RELATED APPLICATIONS

This application claims the benefit of priority to U.S. Application No. 63/463,629 filed on May 3, 2023, the content of which is relied upon and incorporated herein by reference in its entirety.

FIELD

This disclosure generally relates to bioactive glasses, and more particularly to shelf-stable aqueous formulations of bioactive glasses for consumer, dental, and cosmetic applications.

BACKGROUND

Bioactive glasses are a group of glass and/or glass ceramic materials that have shown biocompatibility or bioactivity, which has allowed them to be incorporated into human or animal physiology. Generally speaking, bioactive glasses may be able to bond with hard and soft tissues, thereby fostering growth of bone and cartilage cells. Moreover, bioactive glasses may also enable release of ions which activate expression of osteogenic genes and stimulate angiogenesis, as well as promote vascularization, wound healing, and cardiac, lung, nerve, gastrointestinal, urinary tract, and laryngeal tissue repair.

Some bioactive glasses, such as 45S5 Bioglass® sold by Haleon under the Sensodyne® brand featuring NovaMin® technology, are being investigated for their potential ability to mineralize teeth; however, the lower chemical durability of these traditional bioactive glasses is problematic for compositions requiring prolonged shelf times in aqueous environments. For example, 45S5 Bioglass® generally requires development of a non-aqueous environment for glass particulates to be used in toothpaste applications. In addition, the speed at which 45S5 Bioglass® may mineralize teeth also is not ideal.

A significant problem in the field is providing shelf-stable aqueous dentifrice formulations, such as toothpaste or mouthwash, since bioactive glasses tend to form crystalline phases in aqueous formulations over time, such as while stored on a shelf in a warehouse or store, which leads to a bioactive glass that may be less effective at remineralizing teeth once eventually applied to teeth.

Thus, there is generally a need for improved bioactive glasses and formulations thereof.

SUMMARY

A dentifrice formulation (e.g., aqueous or non-aqueous), comprising:

- a bioactive glass exhibiting at least one of:
  - a hydrolytic resistance of glass grains (HGB) of at most 4.5 or at most 4 (e.g., or at most 3), when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum substantially free of crystalline phase after soaking 5 g of the bioactive glass in powder form in 100 mL of deionized water for 7 days at 37° C.; or
  - any combination thereof;
- wherein, when the bioactive glass is contacted with artificial saliva, the bioactive glass forms a bioactive crystalline phase.

A bioactive glass, comprising:

- at least one of:
  - a hydrolytic resistance of glass grains (HGB) of at most 4.5 or at most 4 (e.g., or at most 3), when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum substantially free of crystalline phase after soaking 5 g of the bioactive glass in powder form in 100 mL of deionized water for 7 days at 37° C.; or
  - any combination thereof;
- wherein, when the bioactive glass is contacted with artificial saliva, the bioactive glass forms a bioactive crystalline phase.

A method comprising applying to a tooth a dentifrice formulation (e.g., aqueous or non-aqueous) disclosed herein, optionally wherein the method remineralizes enamel of the tooth, treats caries of the tooth, treats dentin hypersensitivity of the tooth, or any combination thereof.

A method for making a dentifrice formulation (e.g., aqueous or non-aqueous), comprising combining the bioactive glass with a carrier.

A method for making a bioactive glass disclosed herein, comprising:

- combining each component of the bioactive glass to form a mixture,
- heating the mixture to a temperature of 1500° C. or less to form a melted mixture, and
- cooling the melted mixture to form a cooled mixture.

Additional features and advantages of the disclosure will be set forth in the detailed description which follows, and in part will be readily apparent to those skilled in the art from that description or recognized by practicing the aspects as described herein, including the detailed description which follows, the claims, as well as the appended drawings.

It is to be understood that both the foregoing general description and the following detailed description are merely exemplary and are intended to provide an overview or framework for understanding the nature and character of the disclosure and claims. The accompanying drawings are included to provide a further understanding of the disclosure and are incorporated into and constitute a part of this specification. The drawings illustrate various aspects of the disclosure and together with the description serve to explain the principles and operations of the various aspects.

BRIEF DESCRIPTION OF THE DRAWINGS

The following detailed description can be further understood when read in conjunction with the following drawings. Whenever possible, the same reference numerals will be used throughout the drawings to refer to the same or like parts. It is to be understood that the figures are not drawn to scale and the size of each depicted component or the relative size of one component to another is not intended to be limiting.

DETAILED DESCRIPTION

Figure 1:
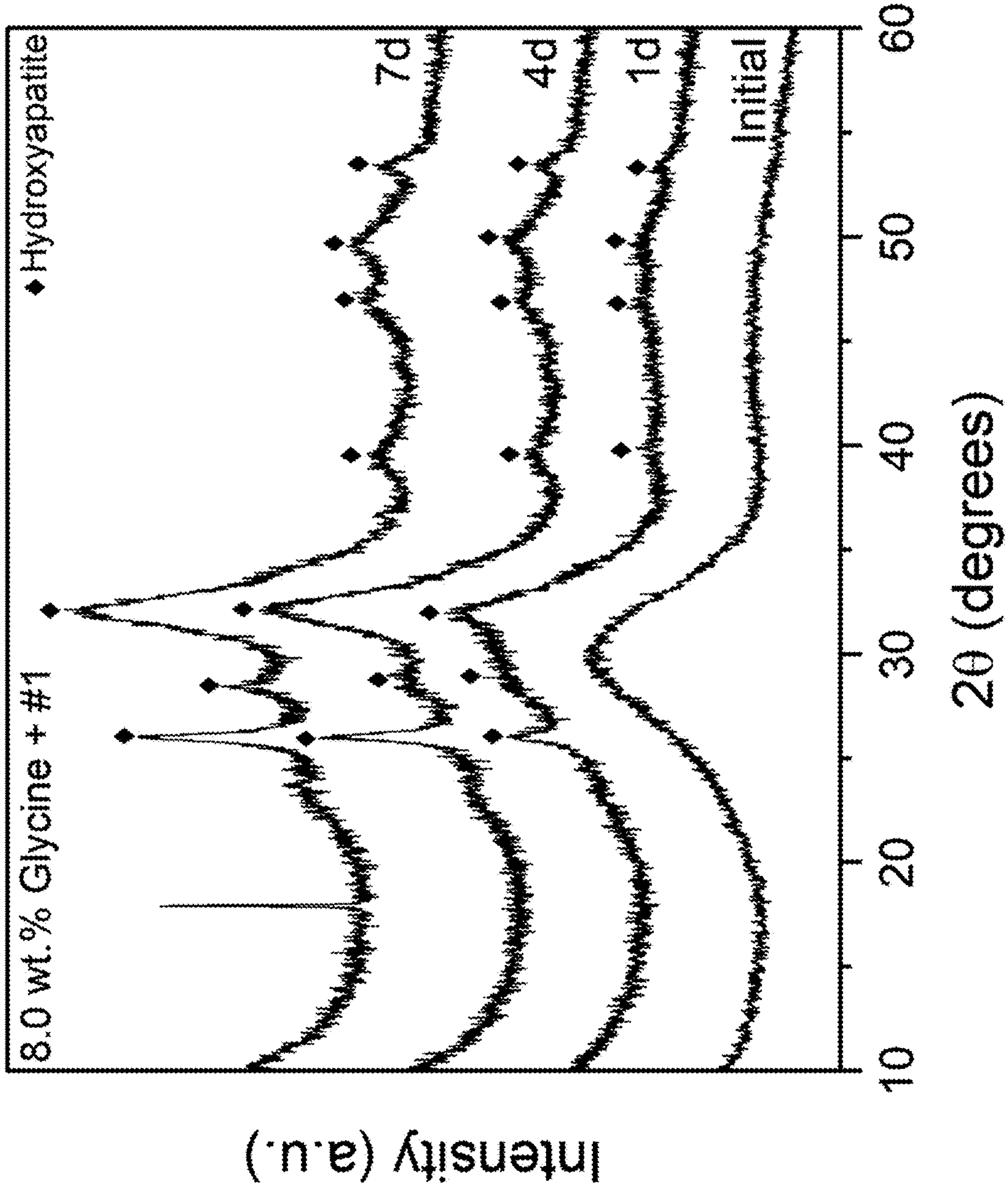
FIG. 1 is a powder X-ray diffraction (XRD) spectrum illustrating hydroxyapatite formation within 1 day for an example bioactive glass upon immersion in an aqueous composition comprising artificial saliva and an amino acid (glycine).

In the following description, whenever a group is described as comprising at least one of a group of elements and combinations thereof, it is understood that the group may comprise, consist essentially of, or consist of any number of those elements recited, either individually or in combination with each other. Similarly, whenever a group is described as consisting of at least one of a group of elements or combinations thereof, it is understood that the group may consist of any number of those elements recited, either individually or in combination with each other.

Where a range of numerical values is recited herein, comprising upper and lower values, unless otherwise stated in specific circumstances, the range is intended to include the endpoints thereof, and all integers and fractions within the range. Further, when an amount, concentration, or other value or parameter is given as a range, one or more ranges, or a list of upper values and lower values, this is to be understood as specifically disclosing all ranges formed from any pair of any upper range limit or value and any lower range limit or value, regardless of whether such pairs are separately disclosed.

If the term "about" is used in describing a value or an end-point of a range, the disclosure should be understood to include the specific value or end-point referred to. As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. It is noted that the terms "substantially" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Thus, for example, a glass or composition that is "free" or "essentially free" or "substantially free" of $Al_2O_3$ (or any other component) is one in which $Al_2O_3$ (or any other component) is not actively added or batched into the glass or composition, but may be present in small amounts, e.g., as a contaminant, such as less than 1 wt. %, less than 0.5 wt. %, less than 0.1 wt. %, less than 0.01 wt. %, and so forth (e.g., 500, 400, 300, 200, or 100 ppm or less). Additionally, for example, a glass that is substantially free of a crystalline phase is one in which an XRD spectrum of the glass does not show any crystal phases and/or one in which total crystallinity of the glass is less than 5 wt. % as measured by XRD analysis.

As used herein, a glass, glass-ceramic, or crystalline phase that is "bioactive" means that the glass, glass-ceramic, or crystalline phase is biologically compatible with bone, teeth, and/or tissue. By way of illustration, in some aspects, "bioactive" in this context refers to (1) the ability to form apatite, brushite, whitlockite, or other bioactive crystalline phases such as hydroxyapatite, fluorapatite, carbonated apatite, or any combination thereof, in a simulated body fluid, such as artificial saliva, according to ASTM F1538-03 (2017), (2) the capability of binding with a desired biological material (e.g., bones, teeth, and/or tissue), and/or (3) the capability of remineralize teeth or bone. Generally, there is also an absence of toxicity or other significant negative effects in a biological environment (e.g., bones, teeth, and/or tissue).

Herein, bioactive glasses are expressed in terms of wt. % amounts of particular components included therein on an oxide bases unless otherwise indicated. Any component having more than one oxidation state may be present in a bioactive glass in any oxidation state. However, concentrations of such component are expressed in terms of the oxide in which such component is at its lowest oxidation state unless otherwise indicated.

The terms "bioactive glass" and "glass composition" generally are used interchangeably herein and should be interpreted as such, unless clearly contradicted by context. In addition, "formulation" and "composition" (e.g., dentifrice formulations or compositions) generally are used interchangeably herein to refer to a matrix or carrier that contains a bioactive glass, unless clearly contradicted by context.

Oral diseases pose a major health burden worldwide, causing pain, discomfort, disfigurement, and even death. The dissolution of apatite crystals and the net loss of calcium, phosphate, and other ions from the tooth (i.e., demineralization) leads to dental caries formation and dentin hypersensitivity. Dentin hypersensitivity in particular can occur through erosion of the enamel, causing exposure of dentin tubules and leading to increased sensitivity to cold or hot temperatures in the mouth. Caries and dentin hypersensitivity can be managed non-invasively through a remineralization process, in which calcium and phosphate ions are supplied from an external source to the tooth to promote crystal deposition into voids in demineralized enamel and at the dentin surface to occlude fluid flow causing hypersensitivity. Calcium phosphate phases in both crystalline form (e.g., brushite, whitlockite, β-tricalcium phosphate, octocalcium phosphate, hydroxyapatite, fluorapatite and enamel apatite) and amorphous form have been used in remineralization processes. Use of amorphous calcium phosphate (e.g., bioactive glass) in remineralization processes has shown promising results. Generally, bioactive glass dissolves at a controlled rate in the mouth and converts to crystalline phases such as hydroxyapatite, fluorapatite, and other calcium phosphate phases that are compatible with tooth mineral. There is a strong desire to develop new bioactive glasses that take advantage of this mechanism promote the remineralization process to prevent or repair tooth caries and/or dentin hypersensitivity.

However, a significant problem in the field is providing shelf-stable aqueous dentifrice formulations, such as toothpaste or mouthwash, since bioactive glasses tend to form crystalline phases in aqueous formulations over time, such as while sitting on a shelf in a warehouse or store, which leads to a bioactive glass that may be less effective at remineralizing teeth once finally applied to teeth. The bioactive glasses disclosed herein generally are more shelf stable than those currently on the market, such as 45S5 Bioglass®, as demonstrated by a lower HGB value when measured by International Organization for Standardization section 719 (ISO 719), less weight loss after soaking in 37° C. deionized water, less leaching of ions after soaking in 37° C. deionized water, an XRD spectrum substantially free of crystal phase after soaking in 37° C. deionized water, or any combination thereof.

Bioactive glasses have widely recognized capabilities to bond strongly with hard and soft tissues, and to foster the growth of bone and cartilage cells. So far, the majority of bioactive glass compositions fall within $Na_2O$—CaO—$SiO_2$ family. A commercially available bioactive glass in this family, 45S5 Bioglass®, was patented in U.S. Pat. No. 4,234,972. The fast degradation and conversion to apatite makes these alkali-containing bioactive glasses attractive for a wide range of applications. However, the low chemical durability of the traditional bioactive glasses can be problematic when a long shelf lifetime is required in an aqueous environment. For example, a non-aqueous formula has to be developed to use 45S5 glass particulates in a dentifrice product as disclosed in U.S. Pat. No. 8,715,625. Alkali-free bioactive glass compositions in CaO—$SiO_2$—$P_2O_5$ system are disclosed in U.S. Pat. No. 5,074,916, but are not as bioactive as alkali-containing compositions. Accordingly, there is a strong demand of new dentifrice formulations, either aqueous or non-aqueous, that contains bioactive glass for regular uses.

Herein, aqueous and non-aqueous dentifrice formulations are provided that contain bioactive glass as an active ingredient. The bioactive glass disclosed and described herein demonstrates significantly improved water durability compared to the conventional 45S5 Bioglass®, making it possible for the creation of aqueous dentifrice formulations.

Fluorapatite shows great promise as an ingredient in consumer compositions, such as dentifrice formulations, since fluorapatite is a naturally occurring mineral of biological and agricultural importance, as well as an inorganic component in human and animal bones and/or teeth.

Fluorides act as caries preventive agents to inhibit demineralization and promote remineralization of dental hard tissues. Interactions of fluoride with dental hard tissues can produce a more stable acid-resistant mineral phase. The reaction products after fluoridation have include calcium fluoride ($CaF_2$), calcium hydroxide ($Ca(OH)_2$), and fluorapatite (FAP, $Ca_5(PO_4)_3F$). Fluoride-containing compounds can provide acid resistance and serve as fluoride reservoirs. In particular, the solubility of fluorapatite ($K_{sp}$=$3.19\times10^{-61}$) is much lower than hydroxyapatite ($K_{sp}$=$7.36\times10^{-61}$) Topical fluoride delivery for caries prevention includes fluoride rinses, fluoridated toothpastes, topical fluoride gels and solutions, and fluoride varnishes. Fluoridated toothpastes generally are cost-effective and widely used products among the topical methods. In some toothpastes, NaF, $SnF_2$, and/or $Na_2PO_3F$ may be formulated as a fluoride source in toothpaste or other oral compositions. However, certain disadvantages exist with such fluoride sources are used in combination with a bioactive glass, and therefore in some aspects such fluoride sources are not contained in certain compositions disclosed herein.

In terms of tooth sensitivity, some previous attempts have also utilized $CaCO_3$. However, bioactive glasses, such as those disclosed herein, in some aspects show a key advantage since they display in some cases at least 10 times faster calcium release in aqueous environments compared to $CaCO_3$, while also providing dissolved phosphate. In some aspects, the disclosed bioactive glasses therefore provide two components, calcium and phosphate, for forming hydroxyapatite. Thus, in some aspects, the present approach uses a unique bioactive glass to mineralize hydroxyapatite, sometimes in combination with one or more amino acids to control the rate of mineralization (e.g., by increasing the rate of mineralization). In some aspects, the compositions disclosed herein are substantially free of, or do not contain, $CaCO_3$.

In some aspects, disclosed are formulations comprising bioactive glasses, optionally in combination with amino acid, to rapidly form apatite in artificial saliva (e.g., and without or minimally forming a crystalline phase such as apatite when present in an aqueous composition, such as a dentifrice formulation, that is not saliva or artificial saliva). In some aspects, when amino acids are employed, they can be employed at various concentrations. In some aspects, the disclosed bioactive glasses display significantly improved mineralization behavior in comparison to 45S5 Bioglass®. In some aspects, the mineralization behavior represents a step-change in the rate of re-mineralization from the current technology in the oral care field, which may benefit multiple oral health applications.

In some aspects, the disclosed bioactive glasses and formulations rapidly mineralize crystalline phases on the surface of bioactive glasses in artificial or real saliva. In some aspects, the disclosed bioactive glasses and formulations, optionally in combination with one or more amino acids (e.g., at various concentrations), remineralizes tooth-compatible phases, such as hydroxyapatite, brushite, and/or whitlockite, on the glass surface. In some aspects, the disclosed bioactive glasses and formulations, optionally in combination with one or more amino acids (e.g., at various concentrations), rapidly mineralize crystalline phases on the surface of teeth in artificial or real saliva. In some aspects, the disclosed bioactive glasses and formulations, optionally in combination with one or more amino acids (e.g., at various concentrations), remineralizes tooth-compatible phases, such as hydroxyapatite, brushite, and/or whitlockite, on the tooth surface. In some aspects, without wishing to be bound by theory, it is believed that the bioactive glass acts as the source of dissolved ions in the artificial or real saliva, while the amino acid, when present, may act to promote the nucleation and/or growth of crystalline phases. It is anticipated that the disclosed compositions will perform similarly in real saliva.

In some aspects, the disclosed formulations are substantially free of amino acid, or contain less than 1 wt. % amino acid, based on total weight of the formulation.

There is a desire to develop new glass compositions, and methods of making, that promote the remineralization process to, for example, prevent or repair/treat tooth caries, to prevent or repair/treat dentin sensitivity.

Bioactive glasses are a group of glass and/or glass ceramic materials that have shown biocompatibility or bioactivity, which has allowed them to be incorporated into human or animal physiology. In some aspects, disclosed is a bioactive glass comprising $SiO_2$, CaO, and $P_2O_5$. In some aspects, the bioactive glass further comprises $ZrO_2$ and/or $F^-$. In some aspects, a dentifrice formulation (aqueous or non-aqueous) containing a bioactive glass (and optionally any other component(s) listed herein, such as one or more amino acids) forms a bioactive crystalline phase when subjected to artificial saliva of Table 1A or 1B. In some aspects, the formation of the bioactive crystalline phase takes place within 10 days, within 9 days, within 8 days, within 7 days, within 6 days, within 5 days, within 4 days, within 3 days, within 2 days, or within 1 day of subjecting to the artificial saliva of Table 1A or 1B or other aqueous compositions. In some aspects, the formation of the bioactive crystalline phase takes place within 7 days. In some aspects, the formation of the bioactive crystalline phase takes place within 1 day. In some aspects, a bioactive crystalline phase forms when subjected to real saliva (e.g., from an organism, such as a mammal, a human, and the like). In some aspects, the bioactive crystalline phase formation takes place in vivo, e.g., in real saliva in an organism, e.g., when brushing teeth of the organism or otherwise subjecting the teeth of the organism to a formulation (e.g., comprising a bioactive glass optionally with an amino acid) or to a bioactive glass.

In some aspects, such as when melting precursor oxides that include a source of $F^-$ at a temperature of 1500° C. or less (e.g., 1400° C. or less), the composition spontaneously forms a crystalline phase upon cooling (e.g., one or more of apatite, brushite, whitlockite, fluorapatite, calcium silicate, calcium phosphate, calcium fluoride, or any combination thereof), without the need to subject the cooled composition to a subsequent heat treatment step. However, in some aspects, it may be desirable to subject the cooled composition to a subsequent heat treatment step, for example, to tune the amounts and types of crystalline phase present.

In some aspects, the aqueous composition and/or artificial saliva comprises phosphate, calcium, fluoride, sodium, potassium, magnesium, a buffer, or any combination thereof. In some aspects, the aqueous composition and/or artificial saliva comprises potassium chloride, ammonium chloride, potassium dihydrogen phosphate, magnesium chloride hexahydrate, calcium chloride, HEPES buffer, sodium azide, sodium hydroxide, a combination thereof, or any combination thereof. In some aspects, the aqueous composition, such as artificial saliva, may include a salt solution comprising NaCl, $NaHCO_3$, KCl, $K_2HPO_4$, $MgCl_2$-$6H_2O$, $CaCl_2$), $NaSO_4$, $(HOCH_2)_3CNH_2$ in nano-pure water, with pH adjusted with acid, such as HCl. In some examples, the simulated body fluid comprises artificial saliva. In some aspects, an artificial saliva composition can comprise one or more of the components set forth below in Table 1A and 1B.

TABLE 1A

| Component | Wt. % Range |
|---|---|
| Potassium Chloride | 0.08-0.17 |
| Ammonium Chloride | 0.01-0.04 |
| Potassium Dihydrogen Phosphate | 0.03-0.08 |
| Magnesium Chloride Hexahydrate | 0.001-0.007 |
| Calcium Chloride | 0.007-0.023 |
| HEPES Buffer | 0.38-0.55 |
| Sodium Azide | 0.01-0.04 |
| Sodium Hydroxide | 0.001-0.025 |

TABLE 1B

| Component | Wt. % Specific Example |
|---|---|
| Potassium Chloride | 0.119 |
| Ammonium Chloride | 0.024 |
| Potassium Dihydrogen Phosphate | 0.054 |
| Magnesium Chloride Hexahydrate | 0.004 |
| Calcium Chloride | 0.011 |
| HEPES Buffer | 0.477 |
| Sodium Azide | 0.02 |
| Sodium Hydroxide | 0.012 |

Without wishing to be bound by theory, it is believed that one or more components of the artificial saliva, which has chemical composition similarities to real saliva, facilitates formation of a bioactive crystalline phase. For example, in some aspects, it is believed that one or more of phosphate, calcium, fluoride, sodium, potassium, magnesium, a buffer, or any combination thereof, but particularly the phosphate, calcium, fluoride, or a combination thereof, facilitates formation of a bioactive crystalline phase. In some aspects, immersion of the bioactive glasses disclosed herein in deionized water (or in some aqueous compositions that do not have one of more of the components described herein) does not result in the formation of a bioactive crystalline phase, such as within 7 days at 37° C.

In some aspects, disclosed herein is a bioactive glass comprising at least one of:

- a hydrolytic resistance of glass grains (HGB) of at most 4.5 or at most 4 (e.g., or at most 3), when measured by International Organization for Standardization section 719 (ISO 719);
- a weight loss of 5 wt. % or less after soaking 5 g of the bioactive glass in powder form in 100 mL of deionized water for 7 days at 37° C.;
- an XRD spectrum substantially free of crystalline phase after soaking 5 g of the bioactive glass in powder form in 100 mL of deionized water for 7 days at 37° C.; or
- any combination thereof;
- wherein, when the bioactive glass is contacted with artificial saliva, the bioactive glass forms a bioactive crystalline phase.

In some aspects, a bioactive glass, when measured by International Organization for Standardization section 719 (ISO 719), exhibits a hydrolytic resistance of glass grains (HGB) of at most 4.5, at most 4, at most 3.5, at most 3, at most 2.5, or at most 2. In some aspects, the HGB is at most 3. In some aspects, the bioactive glass is incorporated into a dentifrice (aqueous or non-aqueous) formulation.

In some aspects, a bioactive glass, after soaking 5 g of the bioactive glass in powder form in 100 mL of deionized water for 7 days at 37° C., exhibits a weight loss of 8 wt. % or less, 7.5 wt. % or less, 7 wt. % or less, 6.5 wt. % or less, 6 wt. % or less, 5.5 wt. % or less, 5 wt. % or less, 4.5 wt. % or less, 4 wt. % or less, 3.5 wt. % or less, 3 wt. % or less, 2.5 wt.

% or less, 2 wt. % or less, 1.5 wt. % or less, 1 wt. % or less, 0.5 wt. % or less, or 0.1 wt. % or less. In some aspects, the bioactive glass is incorporated into a dentifrice (aqueous or non-aqueous) formulation. The weight loss measurements herein are performed as follows. A cullet of bioactive glass is ground into a powder using an air jet mill to a size of less than 10 microns. An example particle size distribution of the powder is shown below:

| Metric | Actual (μm) |
|---|---|
| 10% | 1.365 |
| 20% | 1.851 |
| 30% | 2.207 |
| 40% | 2.521 |
| 50% | 2.83 |
| 60% | 3.16 |
| 70% | 3.55 |
| 80% | 4.06 |
| 90% | 4.93 |
| 95% | 5.86 |

Prior to all weight measurements, each powder sample is dried at 100° C. for 1 hour to remove residual water. A 5 g sample of dried powder is weighed and then added to 100 mL of deionized water to soak for a given time period (e.g., 0-7 days). After soaking, the glass powder is dried at 100° C. for 1 hour to remove residual water, followed by weighing. The mass loss, if any, of the glass powder is then calculated as a percent of the original mass of the dried glass powder sample prior soaking. As used herein, the terms "mass" and "weight" are used interchangeably with no difference in meaning.

In some aspects, a bioactive glass, after soaking 5 g of the bioactive glass in powder form in 100 mL of deionized water for 7 days at 37° C., exhibits an XRD spectrum substantially free of crystalline phase. In some aspects, a bioactive glass, after soaking 5 g of the bioactive glass in powder form in 100 mL of deionized water for 7 days at 37° C., exhibits a total crystallinity of less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.5 wt. %, less than 0.1 wt. %, or about 0 wt. %, or 0 wt. %. In some aspects, the bioactive glass is incorporated into a dentifrice (aqueous or non-aqueous) formulation. The glass powder for XRD analysis is prepared in the same manner as in the weight loss measurements (e.g., grinding to a size of less than 10 microns, etc.).

In some aspects, a bioactive glass releases less than 690 ppm (or less than 600 ppm) of sodium ions and/or less than 168 ppm (or less than 150 ppm) of silicon ions upon soaking 5 g of the bioactive glass in powder form in 100 mL of deionized water for 7 days at 37° C., when measured using inductively coupled plasma—optical emission spectrometer (ICP-OES). In some aspects, a bioactive glass releases less than X amount of (ppm) sodium ions upon such soaking, where X is 690, 680, 670, 660, 650, 640, 630, 620, 610, 600, 575, 550, 475, 450, 425, 400, 350, 300, 250, 200, 150, 100, 50, 25, 10, 5, or 1. Alternatively, or additionally, in some aspects, a bioactive glass releases less than Y amount (ppm) of silicon ions upon such soaking, where Y is 168, 165, 160, 150, 140, 130, 120, 110, 100, 90, 80, 70, 60, 50, 40, 30, 20, 10, 5, or 1. Alternatively, or additionally, in some aspects a bioactive glass releases at least X amount (ppm) of sodium ions upon such soaking, where X is 680, 670, 660, 650, 640, 630, 620, 610, 600, 575, 550, 475, 450, 425, 400, 350, 300, 250, 200, 150, 100, 50, 25, 10, 5, 1, or 0.5, and any of such numbers can be combined with the "less than" amounts listed hereinabove for sodium ions. Alternatively, or additionally, in some aspects, a bioactive glass releases at least Y amount (ppm) of silicon ions upon such soaking, where Y is 165, 160, 150, 140, 130, 120, 110, 100, 90, 80, 70, 60, 50, 40, 30, 20, 10, 5, 1, or 0.5, and any of such numbers can be combined with the "less than" amounts listed hereinabove for silicon ions. In some aspects, the bioactive glass is incorporated into a dentifrice (aqueous or non-aqueous) formulation. The glass powder for ICP-OES analysis is prepared in the same manner as in the weight loss measurements (e.g., grinding to a size of less than 10 microns, etc.).

In some aspects, the bioactive glass comprises a combination of $SiO_2$, CaO, and $P_2O_5$. In some aspects, the bioactive glass further comprises $ZrO_2$. In some aspects, the bioactive glass further comprises F. In some aspects, the bioactive glass further also comprises MgO. In some aspects, the bioactive glass further comprises $Li_2O$, $Na_2O$, $K_2O$, or any combination thereof. In some aspects, the amount of $Li_2O+Na_2O+K_2O$ is less than or equal to 5 wt. %.

In some aspects, the bioactive glass comprises $SiO_2$, CaO, and $P_2O_5$. In some aspects, the bioactive glass comprises $SiO_2$, CaO, $P_2O_5$, $ZrO_2$, and $F^-$. In some aspects, when subjected to an aqueous composition, such as artificial saliva, such a bioactive glass forms a bioactive crystalline phase (e.g., within 7 days).

In some aspects, the bioactive glass comprises $SiO_2$ in an amount of 15-65 wt. %. In some aspects, the bioactive glass comprises CaO in an amount of 15-60 wt. %. In some aspects, the bioactive glass comprises $P_2O_5$ in an amount of 1-30 wt. %. In some aspects, the bioactive glass comprises $ZrO_2$ in an amount of 0-20 wt. % (e.g., 0.1-15 wt. %). In some aspects, the bioactive glass comprises $F^-$ in an amount of 0-10 wt. % (e.g., >0-5 wt. %).

In some aspects, the bioactive glass comprises 15-65 wt. % $SiO_2$; 15-60 wt. % CaO; and 1-30 wt. % $P_2O_5$. In some aspects, the bioactive glass comprises >0-20 wt. % $ZrO_2$. In some aspects, the bioactive glass comprises >0-10 wt. % F. In some aspects, the bioactive glass comprises at least one of: >0-25 wt. % MgO; >0-25 SrO; >0-25 ZnO; >0-5 $B_2O_3$; >0-10 $Al_2O_3$; 0-10 $Li_2O$; 0-10 $Na_2O$; 0-10 $K_2O$; 15-70 wt. % MO, wherein MO is the sum of MgO, CaO, SrO, BeO, and BaO; 0-30 wt. % $R_2O$, wherein $R_2O$ is the sum of $Na_2O$, $K_2O$, $Li_2O$, $Rb_2O$, and $Cs_2O$; 0-10 wt. % $Li_2O+Na_2O+K_2O$; 20-70 wt. % $CaO+P_2O_5$; 5-35 wt. % $F^-+P_2O_5$; or any combination thereof.

In some aspects, the glass composition comprises: 15-45 wt. % $SiO_2$; 10-30 wt. % $P_2O_5$; 30-60 wt. % CaO; 0.5-15 wt. % $ZrO_2$; 0.1-10 wt. % $F^-$; 0-25 wt. % MgO; 0-5 wt. % $B_2O_3$; 0-5 wt. % $Al_2O_3$; 0-10 wt. % $Li_2O$; 0-10 wt. % $Na_2O$; 0-10 wt. % $K_2O$; 0-10 wt. % SrO; 0-10 wt. % ZnO; and $Li_2O+Na_2O+K_2O$ of less than or equal to 10 wt. %; based on total weight of the glass composition. In some aspects, the glass compositions comprise: 25-45 wt. % $SiO_2$; 10-25 wt. % $P_2O_5$; 37-50 wt. % CaO; 0.5-8 wt. % $ZrO_2$; 0.1-5 wt. % $F^-$; >0-10 wt. % MgO; based on total weight of the glass composition. In some aspects, the glass compositions comprise: at least one of: >0-25 wt. % MgO; >0-5 wt. % $B_2O_3$; >0-5 wt. % $Al_2O_3$; >0-10 wt. % $Li_2O$; >0-10 wt. % $Na_2O$; >0-10 wt. % $K_2O$; >0-10 wt. % SrO; or >0-10 wt. % ZnO; provided that $Li_2O+Na_2O+K_2O$ is less than or equal to 10 wt. %; based on total weight of the glass composition.

In some aspects, the glass composition comprises: 15-50 wt. % $SiO_2$, 25-60 wt. % CaO, 3-30 wt. % $P_2O_5$, 0.5-15 wt. % $ZrO_2$, and >0-5 wt. % $F^-$, wherein, when subjected to artificial saliva of Table 1A or Table 1B, the glass composition forms a bioactive crystalline phase. In some aspects, the glass compositions comprise: 25-45 wt. % $SiO_2$, 30-50 wt. % CaO, 5-25 wt. % $P_2O_5$, 2-10 wt. % $ZrO_2$, and 0.01-3 wt. % $F^-$, wherein, when subjected to artificial saliva of Table 1A or Table 1B, the glass composition forms a bioactive crystalline phase. In some aspects, a glass composition comprises at least one of: >0-25 wt. % MgO; >0-5 wt. % $B_2O_3$; >0-5 wt. % $Al_2O_3$; >0-10 wt. % $Li_2O$; >0-10 wt. % $Na_2O$; >0-10 wt. % $K_2O$; >0-10 wt. % SrO; >0-10 wt. % ZnO; $Li_2O+Na_2O+K_2O$ in an amount of 10 wt. % or less; $F^-+P_2O_5$ in an amount of 5-30 wt. %; MgO+CaO in an amount of 30-70 wt. %; $CaO+P_2O_5$ in an amount of 40-70 wt. %; or any combination thereof.

In some aspects, the bioactive glass comprises: 25-55 wt. % $SiO_2$, 0.1-15 wt. % $ZrO_2$; 20-55 wt. % CaO, and 5-30 wt. % $P_2O_5$, based on total weight of bioactive glass, wherein, when the composition (e.g., containing bioactive glass and amino acid) is subjected to artificial saliva, a bioactive crystalline phase is formed (e.g., within 7 days or any of the other timeframes specified herein, such as within 1 day). In some aspects, the bioactive glasses comprise: 25-35 wt. % $SiO_2$, 0.1-15 wt. % $ZrO_2$; 35-50 wt. % CaO, and 15-25 wt. % $P_2O_5$, based on total weight of bioactive glass, wherein, when the composition (e.g., containing bioactive glass and amino acid) is subjected to artificial saliva, a bioactive crystalline phase is formed (e.g., within 7 days or any of the other timeframes specified herein, such as within 1 day). In some aspects, the bioactive glasses comprise at least one of: 3-12 wt. % $ZrO_2$; >0-10 wt. % MgO; >0-5 wt. % $F^-$; 0-5 wt. % $Na_2O+K_2O+Li_2O$; $CaO+P_2O_5$ in an amount of 40-70 wt. %; or any combination thereof.

In some aspects, a silicate-based glass composition comprises 15-65 wt. % $SiO_2$, 15-50 wt. % CaO, 1-30 wt. % $P_2O_5$, and 1-20 wt. % $ZrO_2$, wherein the composition: has a hydrolytic resistance of glass grains (HGB) of at most 4.5 or at most 4 (e.g., or at most 3), when measured by International Organization for Standardization section 719 (ISO 719), and forms a bioactive crystalline phase in simulated body fluid. In some aspects, which are combinable with any of the other aspects or embodiments, the glass composition comprises: 15-45 wt. % $SiO_2$, 30-60 wt. % CaO, 8-30 wt. % $P_205$, and 2-15 wt. % $ZrO_2$. In aspects, which are combinable with any of the other aspects or embodiments, the glass composition further comprises >0-25 wt. % MgO. In aspects, which are combinable with any of the other aspects or embodiments, the glass composition further comprises 3-15 wt. % MgO. In aspects, which are combinable with any of the other aspects or embodiments, the glass composition further comprises >0-25 wt. % SrO. In aspects, which are combinable with any of the other aspects or embodiments, the glass composition further comprises 10-20 wt. % SrO. In aspects, which are combinable with any of the other aspects or embodiments, the glass composition further comprises >0-25 wt. % ZnO. In aspects, which are combinable with any of the other aspects or embodiments, the glass composition further comprises 10-20 wt. % ZnO. In aspects, which are combinable with any of the other aspects or embodiments, the glass comprises: 15-50 wt. % MO, and 0-30 wt. % $R_2O$, wherein MO is the sum of MgO, CaO, SrO, BeO, and BaO, and $R_2O$ is the sum of $Na_2O$, $K_2O$, $Li_2O$, $Rb_2O$, and $Cs_2O$.

In some aspects, a bioactive glass comprises: greater than or equal to 15 wt % and less than or equal to 45 wt % $SiO_2$, greater than or equal to 30 wt % and less than or equal to 60 wt % CaO, greater than or equal to 8 wt % and less than or equal to 30 wt % $P_2O_5$, and greater than or equal to 2 wt % and less than or equal to 15 wt % $ZrO_2$. In some aspects, a bioactive glass comprises: greater than or equal to 20.0 wt % and less than or equal to 39.5 wt % $SiO_2$; greater than or equal to 0.0 wt % and less than or equal to 14.5 wt % MgO; greater than or equal to 32.5 wt % and less than or equal to 47.0 wt % CaO; greater than or equal to 0.0 wt % and less than or equal to 14.5 wt % SrO; greater than or equal to 0.0 wt % and less than or equal to 14.5 wt % ZnO; greater than or equal to 9.5 wt % and less than or equal to 24.5 wt % $P_2O_5$; and greater than or equal to 4.0 wt % and less than or equal to 10.0 wt % $ZrO_2$.

In some embodiments, a silicate-based glass composition comprises: 15-65 wt. % $SiO_2$, 2.5-25 wt. % MgO, 1-30 wt. % $P_2O_5$, and 15-50 wt. % CaO. In one aspect, which is combinable with any of the other aspects or embodiments, the composition further comprises: 0-5 wt. % $F^-$, and 0-10 wt. % $ZrO_2$. In one aspect, which is combinable with any of the other aspects or embodiments, the composition further comprises: 0-10 wt. % $Al_2O_3$, 0-10 wt. % SrO, and 0-10 wt. % ZnO. In one aspect, which is combinable with any of the other aspects or embodiments, the glass comprises: 15-50 wt. % MO, and 0-30 wt. % $R_2O$, wherein MO is the sum of MgO, CaO, SrO, BeO, and BaO, and $R_2O$ is the sum of $Na_2O$, $K_2O$, $Li_2O$, $Rb_2O$, and $Cs_2O$. In some embodiments, a silicate-based glass composition comprises: 15-65 wt. % $SiO_2$, 2.5-25 wt. % MgO, 1-30 wt. % $P_2O_5$, 15-50 wt. % CaO, 0-5 wt. % $F^-$, and 0-10 wt. % $ZrO_2$. In one aspect, which is combinable with any of the other aspects or embodiments, the composition further comprises one of: 0-10 wt. % $Al_2O_3$, 0-10 wt. % SrO, and 0-10 wt. % ZnO. In some embodiments, a silicate-based glass composition comprises: 20-55 wt. % $SiO_2$, 5-20 wt. % MgO, 5-25 wt. % $P_2O_5$, and 25-45 wt. % CaO. In one aspect, which is combinable with any of the other aspects or embodiments, the composition further comprises: 0-3 wt. % $F^-$, and 0-6 wt. % $ZrO_2$. In one aspect, which is combinable with any of the other aspects or embodiments, the composition further comprises: 0-5 wt. % $Al_2O_3$, 0-5 wt. % SrO, and 0-5 wt. % ZnO.

In some aspects, a silicate-based glass composition, comprises 15-65 wt. % $SiO_2$, 2.5-25 wt. % MgO, 1-30 wt. % $P_2O_5$, and 15-50 wt. % CaO, wherein the composition: has a hydrolytic resistance of glass grains (HGB) of at most 4.5 or at most 4 (e.g., or at most 3), when measured by International Organization for Standardization section 719 (ISO 719), and forms a bioactive crystalline phase in a simulated body fluid. In one aspect, which is combinable with any of the other aspects or embodiments, the glass composition further comprises >0-5 wt. % $F^-$. In one aspect, which is combinable with any of the other aspects or embodiments, the glass composition further comprises one of >0-10 wt. % $Li_2O$, >0-10 wt. % $Na_2O$, or >0-10 wt. % $K_2O$. In one aspect, which is combinable with any of the other aspects or embodiments, the glass composition further comprises >0 to 10 wt. % $ZrO_2$. In one aspect, which is combinable with any of the other aspects or embodiments, the glass composition further comprises 0-10 wt. % $Al_2O_3$, 0-10 wt. % SrO, 0-10 wt. % ZnO, and 0-5 wt. % $B_2O_3$. In one aspect, which is combinable with any of the other aspects or embodiments, the glass comprises 15-50 wt. % MO, and 0-30 wt. % $R_2O$, wherein MO is the sum of MgO, CaO, SrO, BeO, and BaO, and $R_2O$ is the sum of $Na_2O$, $K_2O$, $Li_2O$, $Rb_2O$, and $Cs_2O$. In one aspect, which is combinable with any of the other aspects or embodiments, the bioactive crystalline phase comprises apatite. In one aspect, which is combinable with any of the other aspects or embodiments, a sum of $P_2O_5$ and CaO is from 25-65 wt. %. In some aspects, a silicate-based glass composition comprises 30-50 wt. % $SiO_2$, 10-20 wt. % MgO, 5-15 wt. % $P_2O_5$, and 25-40 wt. % CaO, wherein the composition has a hydrolytic resistance of glass grains (HGB) of at most 4.5 or at most 4 (e.g., or at most 3), when measured by International Organization for Standardization section 719 (ISO 719), and forms a bioactive crystalline phase in a simulated body fluid, such as artificial saliva.

The bioactivity is influenced by the composition of the glass.

Silicon dioxide ($SiO_2$) may serve as the primary glass-forming oxide component of the bioactive glasses disclosed herein. $SiO_2$ may be included to provide high temperature stability and chemical durability. However, if too much $SiO_2$ is included, such as a glass containing pure $SiO_2$, the melting temperature is too high to be readily workable (e.g., greater than 200 poise temperature). In addition, bioactive glasses including too much $SiO_2$ may suffer from decreased bioactivity.

In some aspects, the bioactive glasses comprise $SiO_2$ in an amount of at least 15 wt. %. In some aspects, the bioactive glasses comprise $SiO_2$ in an amount of 65 wt. % or less. In some aspects, the bioactive glasses comprise $SiO_2$ in an amount (wt. %) of 15-65, 15-60, 15-55, 15-50, 15-45, 15-40, 15-35, 15-30, 15-25, 15-20, 20-65, 20-60, 20-55, 20-50, 20-45, 20-40, 20-35, 20-30, 20-25, 25-65, 25-60, 25-55, 25-50, 25-45, 25-40, 25-35, 25-30, 30-65, 30-60, 30-55, 30-50, 30-45, 30-40, 30-35, 35-65, 35-60, 35-55, 35-50, 35-45, 35-40, 40-65, 40-060, 40-55,40-50, 40-45, 45-65, 45-60, 45-55, 45-50, 50-65, 50-60, 50-55, 55-65, 55-60, or 60-65. In some aspects, the bioactive glass is substantially free of, or does not contain, $SiO_2$.

Phosphorus pentoxide ($P_2O_5$) may serve as a network former in bioactive glasses. Furthermore, the liberation of phosphate ions to the surface of bioactive glasses contributes to the formation of apatite. Apatite is an inorganic mineral in bone and teeth, and formation of apatite in a simulated body fluid, such as artificial saliva, is one criterion for a material to be bioactive, according to ASTM F1538-03 (2017), hereby incorporated by reference in its entirety for all purposes. The inclusion of phosphate ions in the bioactive glass increases apatite formation rate and the binding capacity of the hard tissues (e.g., bone, tooth, etc.). In addition, $P_2O_5$ can increase the viscosity of the glass, which in turn expands the range of operating temperatures, and is therefore an advantage to the manufacture and formation of the glass.

In some aspects, the bioactive glasses comprise $P_2O_5$ in an amount of at least 1 wt. %. In some aspects, the bioactive glasses comprise $P_2O_5$ in an amount of 30 wt. % or less. In some aspects, the bioactive glasses comprise $P_2O_5$ in an amount (wt. %) of 1-30, 1-25, 1-20, 1-15, 1-10, 1-5, 1-2, 1-3, 1-4, 1-5, 5-30, 5-25, 5-20, 5-15, 5-10, 10-30, 10-25, 10-20, 10-15, 15-30, 15-25, 15-20, 20-30, 20-25, or 25-30.

Zirconium dioxide ($ZrO_2$) may also be present and serves to function as a network former or intermediate in precursor glasses, as well as a key oxide for improving glass thermal stability by significantly reducing glass devitrification during forming and lowering liquidus temperature. In aspects, $ZrO_2$ may play a similar role as alumina ($Al_2O_3$) in the composition.

In some aspects, the bioactive glasses comprise $ZrO_2$ in an amount of 0 wt. % or greater than 0 wt. %. In some aspects, the bioactive glasses comprise $ZrO_2$ in an amount of 20 wt. % or less. In some aspects, the bioactive glasses comprise $ZrO_2$ in an amount (wt. %) of 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, 0-0.8, 0-0.6, 0-0.4, 0-0.2, 0-0.1, >0-20, >0-19, >0-18, >0-17, >0-16, >0-15, >0-14, >0-13, >0-12, >0-11, >0-10, >0-9, >0-8, >0- 7, >0-6, >0-5, >0-4, >0-3, >0-2, >0-1, >0-0.8, >0-0.6, >0-0.4, >0-0.2, >0-0.1, 0.1-20, 0.1-19, 0.1-18, 0.1-17, 0.1-16, 0.1-15, 0.1-14, 0.1-13, 0.1-12, 0.1-11, 0.1-10, 0.1-9, 0.1-8, 0.1-7, 0.1-6, 0.1-5, 0.1-4, 0.1-3, 0.1-2, 0.1-1, 0.1-0.8, 0.1-0.6, 0.1-0.4, 0.1-0.2, 0.2-20, 0.2-19, 0.2-18, 0.2-17, 0.2-16, 0.2-15, 0.2-14, 0.2-13, 0.2-12, 0.2-11, 0.2-10, 0.2-9, 0.2-8, 0.2-7, 0.2-6, 0.2-5, 0.2-4, 0.2-3, 0.2-2, 0.2-1, 0.2-0.8, 0.2-0.6, 0.2-0.4, 0.4-20, 0.4-19, 0.4-18, 0.4-17, 0.4-16, 0.4-15, 0.4-14, 0.4-13, 0.4-12, 0.4-11, 0.4-10, 0.4-9, 0.4-8, 0.4-7, 0.4-6, 0.4-5, 0.4-4, 0.4-3, 0.4-2, 0.4-1, 0.4-0.8, 0.4-0.6, 0.6-20, 0.6-19, 0.6-18, 0.6-17, 0.6-16, 0.6-15, 0.6-14, 0.6-13, 0.6-12, 0.6-11, 0.6-10, 0.6-9, 0.6-8, 0.6-7, 0.6-6, 0.6-5, 0.6-4, 0.6-3, 0.6-2, 0.6-1, 0.6-0.8, 0.8-20, 0.8-19, 0.8-18, 0.8-17, 0.8-16, 0.8-15, 0.8-14, 0.8-13, 0.8-12, 0.8-11, 0.8-10, 0.8-9, 0.8-8, 0.8-7, 0.8-6, 0.8-5, 0.8-4, 0.8-3, 0.8-2, 0.8-1, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20,5-19,5-18, 5-17, 5-16, 5-15, 5-14,5-13, 5-12, 5-11, 5-10, 5-9, 5-8, 5-7, 5-6, 6-20, 6-19, 6-18, 6-17, 6-16, 6-15, 6-4, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-4, 11-13, 11-12, 12-20,12-19, 12-18, 12-17, 12-16, 12-15, 12-4, 12-13, 13-20, 13-19, 13-18, 13-17,13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20. In some aspects, the bioactive glass is substantially free of, or does not contain, $ZrO_2$.

In some aspects, the bioactive glasses comprise fluoride ($F^-$), which facilitates remineralization of enamel. Such remineralization can form bioactive crystalline phases, such as hydroxyapatite, fluorapatite, carbonated apatite, brushite, whitlockite, or any combination thereof. In some aspects, at least some of such bioactive crystalline phases are resistant to acid corrosion, such as fluorapatite. $F^-$ can combine with CaO and $P_2O_5$ to form fluorapatite to improve the bioactivity of the bioactive glasses. Fluorapatite is an inorganic mineral in dental enamel. The ability to form fluorapatite can help regeneration of the enamel that has become demineralized, for example, due to tooth caries (e.g., cavities). In some aspects, formation of apatite ensures the high bioactivity of the compositions disclosed herein.

In some aspects, the $F^-$ in the bioactive glasses is derived from calcium fluoride, magnesium fluoride, sodium fluoride, potassium fluoride, stannous fluoride, sodium monofluorophosphate, sodium difluorophosphate, or any combination thereof.

In some aspects, the bioactive glasses comprise $F^-$ in an amount of 0 wt. % or greater than 0 wt. %. In some aspects, the bioactive glasses comprise $F^-$ in an amount of 10 wt. % or less. In some aspects, the bioactive glasses comprise $F^-$ in an amount (wt. %) of 0-10, 0-9, 0-8, 0-7, 0-6, 0-5, 0-4.5, 0-4, 0-3.5, 0-3, 0-2.5, 0-2, 0-1.5, 0-1, 0-0.5, 0-0.1, >0-10, >0-9, >0-8, >0-7, >0-6, >0-5, >0-4.5, >0-4, >0-3.5, >0-3, >0-2.5, >0-2, >0-1.5, >0-1, >0-0.5, >0-0.4, >0-0.3, >0-0.2, >0-0.1, >0-0.01, 0.01-10, 0.01-9, 0.01-8, 0.01-7, 0.01-6, 0.01-5, 0.01-4.5, 0.01-4, 0.01-3.5, 0.01-3, 0.01-2.5, 0.01-2, 0.01-1.5, 0.01-1, 0.01-0.5, 0.01-0.4, 0.01-0.3, 0.01-0.2, 0.01-0.1, 0.1-10, 0.1-9, 0.1-8, 0.1-7, 0.1-6, 0.1-5, 0.1-4.5, 0.1-4, 0.1-3.5, 0.1-3, 0.1-2.5, 0.1-2, 0.1-1.5, 0.1-1, 0.1-0.5, 0.1-0.4, 0.1-0.3, 0.1-0.2, 0.2-10, 0.2-9, 0.2-8, 0.2-7, 0.2-6, 0.2-5, 0.2-4.5, 0.2-4, 0.2-3.5, 0.2-3, 0.2-2.5, 0.2-2, 0.2-1.5, 0.2-1, 0.2-0.5, 0.2-0.4, 0.2-0.3, 0.3-10, 0.3-9, 0.3-8, 0.3-7, 0.3-6, 0.3-5, 0.3-4.5, 0.3-4, 0.3-3.5, 0.3-3, 0.3-2.5, 0.3-2, 0.3-1.5, 0.3-1, 0.3-1.5, 0.3-0.4, 0.4-10, 0.4-9, 0.4-8, 0.4-7, 0.4-6, 0.4-5, 0.4-4.5, 0.4-4, 0.4-3.5, 0.4-3, 0.4-2.5, 0.4-2, 0.4-1.5, 0.4-1, 0.4-0.5, 0.5-10, 0.5-9, 0.5-8, 0.5-7, 0.5-6, 0.5-5, 0.5-4.5, 0.5-4, 0.5-3.5, 0.5-3, 0.5-2.5, 0.5-2, 0.5-1.5, 0.5-1, 1-10, 1-9, 1-8, 1-7, 1-6, 1-5, 1-4.5, 1-4, 1-3.5, 1-3, 1-2.5, 1-2, 1-1.5, 1.5-10, 1.5-9, 1.5-8, 1.5-7, 1.5-6, 1.5-5, 1.5-4.5, 1.5-4, 1.5-3.5, 1.5-3, 1.5-2.5, 1.5-2, 2-10, 2-9, 2-8, 2-7, 2-6, 2-5, 2-4.5, 2-4, 2-3.5, 2-3, 2-2.5, 2.5-10, 2.5-9, 2.5-8, 2.5-7, 2.5-6, 2.5-5, 2.5-4.5, 2.5-4, 2.5-3.5, 2.5-3, 3-10, 3-9, 3-8, 3-7, 3-6, 3-5, 3-4.5, 3-4, 3-3.5, 3.5-10, 3.5-9, 3.5-8, 3.5-7, 3.5-6, 3.5-5, 3.5-4.5, 3.5-4, 4-10, 4-9, 4-8, 4-7, 4-6, 4-5, 4-4.5, 4.5-10, 4.5-9, 4.5-8, 4.5-7, 4.5-6, 4.5-5, 5-10, 5-9, 5-8, 5-7, 5-6, 6-10, 6-9, 6-8, 6-7, 7-10, 7-9, 7-8, 8-10, 8-9, or 9-10. In some aspects, the bioactive glass is substantially free of, or does not contain, $F^-$.

Divalent cation oxides (such as alkaline earth oxides and ZnO) improve the melting behavior, chemical durability, and bioactivity of the glass. In addition, alkaline earth oxides may improve other desirable properties in the materials, including influencing the Young's modulus and the coefficient of thermal expansion. In some aspects, the bioactive glasses comprise from 15-70 wt. % MO, wherein MO is the sum of MgO, CaO, SrO, BeO, and BaO. In some aspects, the bioactive glasses comprise MO in an amount (wt. %) of 15-70, 15-65, 15-60, 15-55, 15-50, 15-45, 15-40, 15-35, 15-30, 15-25, 15-20, 20-70, 20-65, 20-60, 20-55, 20-50, 20-45, 20-40, 20-35, 20-30, 20-25, 25-70, 25-65, 25-60, 25-55, 25-50, 25-45, 25-40, 25-35, 25-30, 30-70, 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70.

In some aspects, the bioactive glasses comprise CaO in an amount of at least 15 wt. %. In some aspects, the bioactive glasses comprise CaO in an amount of 60 wt. % or less. In some aspects, the bioactive glasses comprise CaO in an amount (wt. %) of 15-60, 15-55, 15-50, 15-45, 15-40, 15-35, 15-30, 15-25, 15-20, 20-60, 20-55, 20-50, 20-45, 20-40, 20-35, 20-30, 20-25, 25-60, 25-55, 25-50, 25-45, 25-40, 25-35, 25-30, 30-60, 30-55, 30-50, 30-45, 30-40, 30-35, 35-60, 35-55, 35-50, 35-45, 35-40, 40-60, 40-55, 40-50, 40-45, 45-60, 45-55, 45-50, 50-60, 50-55, or 55-60. In some aspects, the bioactive glass is substantially free of, or does not contain, CaO.

In some aspects, the bioactive glasses comprise MgO. In some aspects, the inclusion of MgO can improve liquidus of the precursor glass to avoid devitrification during forming. In some aspects, the bioactive glasses comprise MgO in an amount of 0 wt. % or greater than 0 wt. %. In some aspects, the bioactive glasses comprise MgO in an amount of 25 wt. % or less. In some aspects, the bioactive glasses comprise MgO in an amount (wt. %) of 0-25, 0-20, 0-15, 0-10, 0-9, 0-8, 0-7, 0-6, 0-5, 0-4, 0-3, 0-2, 0-1, 0-0.5, 0-0.1, >0-25, >0-20, >0-15, >0-10, >0-9, >0-8, >0-7, >0-6, >0-5, >0-4, >0-3, >0-2, >0-1, >0-0.5, >0-0.1, 0.1-25, 0.1-20, 0.1-15, 0.1-10, 0.1-9, 0.1-8, 0.1-7, 0.1-6, 0.1-5, 0.1-4, 0.1-3, 0.1-2, 0.1-1, 0.1-0.5, 0.5-25, 0.5-20, 0.5-15, 0.5-10, 0.5-9, 0.5-8, 0.5-7, 0.5-6, 0.5-5, 0.5-4, 0.5-3, 0.5-2, 0.5-1, 1-25, 1-20, 1-15, 1-10, 1-9, 1-8, 1-7, 1-6, 1-5, 1-4, 1-3, 1-2, 2-25, 2-20, 2-15, 2-10, 2-9, 2-8, 2-7, 2-6, 2-5, 2-4, 2-3, 2.5-25, 2.5-20, 2.5-15, 2.5-10, 2.5-9, 2.5-8, 2.5-7, 2.5-6, 2.5-5, 2.5-4, 2.5-3, 3-25, 3-20, 3-15, 3-10, 3-9, 3-8, 3-7, 3-6, 3-5, 3-4, 4-25, 4-20, 4-15, 4-10, 4-9, 4-8, 4-7, 4-6, 4-5, 5-25, 5-20, 5-15, 5-10, 5-9, 5-8, 5-7, 5-6, 6-25, 6-20, 6-15, 6-10, 6-9, 6-8, 6-7, 7-25, 7-20, 7-15, 7-10, 7-9, 7-8, 8-25, 8-20, 8-15, 8-10, 8-9, 9-25, 9-20, 9-15, 9-10, 10-25, 10-20, 10-15, 15-25, 15-20, or 20-25. In some aspects, the bioactive glass is substantially free of, or does not contain, MgO.

In some aspects, the bioactive glasses comprise SrO. In some aspects, the inclusion of SrO can improve liquidus of the precursor glass to avoid devitrification during forming. Moreover, in some aspects, SrO may also enter the structure of apatite to improve bioactivity. In some aspects, the bioactive glasses comprise SrO in an amount of 0 wt. % or greater than 0 wt. %. In some aspects, the bioactive glasses comprise SrO in an amount of 25 wt. % or less. In some aspects, the bioactive glasses comprise SrO in an amount (wt. %) of 0-25, 0-20, 0-15, 0-10, 0-9, 0-8, 0-7, 0-6, 0-5, 0-4, 0-3, 0-2, 0-1, 0-0.5, 0-0.1, >0-25, >0-20, >0-15, >0-10, >0-9, >0-8, >0-7, >0-6, >0-5, >0-4, >0-3, >0-2, >0-1, >0-0.5, >0-0.1, 0.1-25, 0.1-20, 0.1-15, 0.1-10, 0.1-9, 0.1-8, 0.1-7, 0.1-6, 0.1-5, 0.1-4, 0.1-3, 0.1-2, 0.1-1, 0.1-0.5, 0.5-25, 0.5-20, 0.5-15, 0.5-10, 0.5-9, 0.5-8, 0.5-7, 0.5-6, 0.5-5, 0.5-4, 0.5-3, 0.5-2, 0.5-1, 1-25, 1-20, 1-15, 1-10, 1-9, 1-8, 1-7, 1-6, 1-5, 1-4, 1-3, 1-2, 2-25, 2-20, 2-15, 2-10, 2-9, 2-8, 2-7, 2-6, 2-5, 2-4, 2-3, 2.5-25, 2.5-20, 2.5-15, 2.5-10, 2.5-9, 2.5-8, 2.5-7, 2.5-6, 2.5-5, 2.5-4, 2.5-3, 3-25, 3-20, 3-15, 3-10, 3-9, 3-8, 3-7, 3-6, 3-5, 3-4, 4-25, 4-20, 4-15, 4-10, 4-9, 4-8, 4-7, 4-6, 4-5, 5-25, 5-20, 5-15, 5-10, 5-9, 5-8, 5-7, 5-6, 6-25, 6-20, 6-15, 6-10, 6-9, 6-8, 6-7, 7-25, 7-20, 7-15, 7-10, 7-9, 7-8, 8-25, 8-20, 8-15, 8-10, 8-9, 9-25, 9-20, 9-15, 9-10, 10-25, 10-20, 10-15, 15-25, 15-20, or 20-25. In some aspects, the bioactive glass is substantially free of, or does not contain, SrO.

In some aspects, the bioactive glasses comprise ZnO. In some aspects, the inclusion of ZnO can improve liquidus of the precursor glass to avoid devitrification during forming. Moreover, in some aspects, ZnO may also enter the structure of apatite to improve bioactivity. In some aspects, the bioactive glasses comprise ZnO in an amount of 0 wt. % or greater than 0 wt. %. In some aspects, the bioactive glasses comprise ZnO in an amount of 25 wt. % or less. In some aspects, the bioactive glasses comprise ZnO in an amount (wt. %) of 0-25, 0-20, 0-15, 0-10, 0-9, 0-8, 0-7, 0-6, 0-5, 0-4, 0-3, 0-2, 0-1, 0-0.5, 0-0.1, >0-25, >0-20, >0-15, >0-10, >0-9, >0-8, >0-7, >0-6, >0-5, >0-4, >0-3, >0-2, >0-1, >0-0.5, >0-0.1, 0.1-25, 0.1-20, 0.1-15, 0.1-10, 0.1-9, 0.1-8, 0.1-7, 0.1-6, 0.1-5, 0.1-4, 0.1-3, 0.1-2, 0.1-1, 0.1-0.5, 0.5-25, 0.5-20, 0.5-15, 0.5-10, 0.5-9, 0.5-8, 0.5-7, 0.5-6, 0.5-5, 0.5-4, 0.5-3, 0.5-2, 0.5-1, 1-25, 1-20, 1-15, 1-10, 1-9, 1-8, 1-7, 1-6, 1-5, 1-4, 1-3, 1-2, 2-25, 2-20, 2-15, 2-10, 2-9, 2-8, 2-7, 2-6, 2-5, 2-4, 2-3, 2.5-25, 2.5-20, 2.5-15, 2.5-10, 2.5-9, 2.5-8, 2.5-7, 2.5-6, 2.5-5, 2.5-4, 2.5-3, 3-25, 3-20, 3-15, 3-10, 3-9, 3-8, 3-7, 3-6, 3-5, 3-4, 4-25, 4-20, 4-15, 4-10, 4-9, 4-8, 4-7, 4-6, 4-5, 5-25, 5-20, 5-15, 5-10, 5-9, 5-8, 5-7, 5-6, 6-25, 6-20, 6-15, 6-10, 6-9, 6-8, 6-7, 7-25, 7-20, 7-15, 7-10, 7-9, 7-8, 8-25, 8-20, 8-15, 8-10, 8-9, 9-25, 9-20, 9-15, 9-10, 10-25, 10-20, 10-15, 15-25, 15-20, or 20-25. In some aspects, the bioactive glass is substantially free of, or does not contain, ZnO.

In some aspects, CaO is found to be able to react with $P_2O_5$ to form apatite when immersed in a simulated body fluid (SBF), such as artificial saliva, or in vivo or in real saliva. The release of $Ca^{2+}$ ions from the surface of the glass contributes to the formation of a layer rich in calcium phosphate. Thus, the combination of $P_2O_5$ and CaO may provide advantageous compositions for bioactive glasses.

In some aspects, the bioactive glasses comprise a sum $P_2O_5$+CaO in an amount of 15 wt. % or more. In some aspects, the bioactive glasses comprise the sum $P_2O_5$+CaO in an amount of 70 wt. % or less. In some aspects, the bioactive glasses comprise the sum $P_2O_5$+CaO in an amount (wt. %) of 15-70, 15-65, 15-60, 15-55, 15-50, 15-45, 15-40, 15-35, 15-30, 15-25, 15-20, 20-70, 20-65, 20-60, 20-55, 20-50, 20-45, 20-40, 20-35, 20-30, 20-25, 25-70, 25-65, 25-60, 25-55, 25-50, 25-45, 25-40, 25-35, 25-30, 30-70, 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70. In some aspects, the bioactive glasses comprise a sum $P_2O_5$+CaO in an amount up to 90 wt. %, such as amounts (wt. %) of 15-90, 20-85, 25-80, 30-75, 35-70, 40-65, 45-60, 25-90, 40-90, or 60-90.

In some aspects, the bioactive glasses comprise the sum MgO+CaO in an amount of at least 20 wt. %. In some aspects, the bioactive glasses comprise the sum MgO+CaO in an amount of 70 wt. % or less. In some aspects, the bioactive glasses comprise the sum MgO+CaO in an amount (wt. %) of 20-70, 20-65, 20-60, 20-55, 20-50, 20-45, 20-40, 20-35, 20-30, 20-25, 25-70, 25-65, 25-60, 25-55, 25-50, 25-45, 25-40, 25-35, 25-30, 30-70, 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70.

In some aspects, the bioactive glasses comprise the sum $F^-$+$P_2O_5$ in an amount of at least 5 wt. %. In some aspects, the bioactive glasses comprise the sum $F^-$+$P_2O_5$ in an amount of 35 wt. % or less. In some aspects, the bioactive glasses comprise the sum $F^-$+$P_2O_5$ in an amount (wt. %) of 5-35, 5-30, 5-25, 5-20, 5-15, 5-10, 10-35, 10-30, 10-25, 10-20, 10-15, 15-35, 15-30, 15-25, 15-20, 20-35, 20-30, 20-25, 25-35, 25-30, or 30-35.

In some aspects, the bioactive glasses comprise $B_2O_3$ in an amount of 0 wt. % or greater than 0 wt. %. In some aspects, the bioactive glasses comprise $B_2O_3$ in an amount of 5 wt. % or less. In some aspects, the bioactive glasses comprise $B_2O_3$ in an amount (wt. %) of 0-5, 0-4.5, 0-4, 0-3.5, 0-3, 0-2.5, 0-2, 0-1.5, 0-1, 0-0.5, 0-0.4, 0-0.3, 0-0.2, 0-0.1, 0-0.05, >0-5, >0-4.5, >0-4, >0-3.5, >0-3, >0-2.5, >0-2, >0-1.5, >0-1, >0-0.5, >0-0.4, >0-0.3, >0-0.2, >0-0.1, >0-0.05, 0.05-5, 0.05-4.5, 0.05-4, 0.05-3.5, 0.05-3, 0.05-2.5, 0.05-2, 0.05-1.5, 0.05-1, 0.05-0.5, 0.05-0.4, 0.05-0.3, 0.05-0.2, 0.05-0.1, 0.1-5, 0.1-4.5, 0.1-4, 0.1-3.5, 0.1-3, 0.1-2.5, 0.1-2, 0.1-1.5, 0.1-1, 0.1-0.5, 0.1-0.4, 0.1-0.3, 0.1-0.2, 0.2-5, 0.2-4.5, 0.2-4, 0.2-3.5, 0.2-3, 0.2-2.5, 0.2-2, 0.2-1.5, 0.2-1, 0.2-0.5, 0.2-0.4, 0.2-0.3, 0.3-5, 0.3-4.5, 0.3-4, 0.3-3.5, 0.3-3, 0.3-2.5, 0.3-2, 0.3-1.5, 0.3-1, 0.3-0.5, 0.3-0.4, 0.4-5, 0.4-4.5, 0.4-4, 0.4-3.5, 0.4-3, 0.4-2.5, 0.4-2, 0.4-1.5, 0.4-1, 0.4-0.5, 0.5-5, 0.5-4.5, 0.5-4, 0.5-3.5, 0.5-3, 0.5-2.5, 0.5-2, 0.5-1.5, 0.5-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, or 4.5-5. In some aspects, the bioactive glass is substantially free of, or does not contain, $B_2O_3$.

In some aspects, the bioactive glasses can comprise $Al_2O_3$. In some aspects, $Al_2O_3$ may influence (e.g., stabilize) the network structure of the glass, improve mechanical properties, improve chemical durability, or any combination thereof. In some aspects, $Al_2O_3$ may lower liquidus temperature, lower coefficient of thermal expansion, enhance the strain point, or any combination thereof. In some aspects, in addition to its role as a network former, $Al_2O_3$(and $ZrO_2$) may help improve the chemical durability and mechanical properties in silicate glass while having no toxicity concerns. In some aspects, too high a content of $Al_2O_3$ or $ZrO_2$ (e.g., >20 wt. %) generally increases the viscosity of the melt and decreases bioactivity.

In some aspects, the bioactive glasses comprise $Al_2O_3$ in an amount of 0 wt. % or greater than 0 wt. %. In some aspects, the bioactive glasses comprise $Al_2O_3$ in an amount of 10 wt. % or less. In some aspects, the bioactive glasses comprise $Al_2O_3$ in an amount (wt. %) of 0-10, 0-9, 0-8, 0-7, 0-6, 0-5, 0-4.5, 0-4, 0-3.5, 0-3, 0-2.5, 0-2, 0-1.5, 0-1, 0-0.5, 0-0.1, >0-10, >0-9, >0-8, >0-7, >0-6, >0-5, >0-4.5, >0-4, >0-3.5, >0-3, >0-2.5, >0-2, >0-1.5, >0-1, >0-0.5, >0-0.4, >0-0.3, >0-0.2, >0-0.1, >0-0.01, 0.01-10, 0.01-9, 0.01-8, 0.01-7, 0.01-6, 0.01-5, 0.01-4.5, 0.01-4, 0.01-3.5, 0.01-3, 0.01-2.5, 0.01-2, 0.01-1.5, 0.01-1, 0.01-0.5, 0.01-0.4, 0.01-0.3, 0.01-0.2, 0.01-0.1, 0.1-10, 0.1-9, 0.1-8, 0.1-7, 0.1-6, 0.1-5, 0.1-4.5, 0.1-4, 0.1-3.5, 0.1-3, 0.1-2.5, 0.1-2, 0.1-1.5, 0.1-1, 0.1-0.5, 0.1-0.4, 0.1-0.3, 0.1-0.2, 0.2-10, 0.2-9, 0.2-8, 0.2-7, 0.2-6, 0.2-5, 0.2-4.5, 0.2-4, 0.2-3.5, 0.2-3, 0.2-2.5, 0.2-2, 0.2-1.5, 0.2-1, 0.2-0.5, 0.2-0.4, 0.2-0.3, 0.3-10, 0.3-9, 0.3-8, 0.3-7, 0.3-6, 0.3-5, 0.3-4.5, 0.3-4, 0.3-3.5, 0.3-3, 0.3-2.5, 0.3-2, 0.3-1.5, 0.3-1, 0.3-1.5, 0.3-0.4, 0.4-10, 0.4-9, 0.4-8, 0.4-7, 0.4-6, 0.4-5, 0.4-4.5, 0.4-4, 0.4-3.5, 0.4-3, 0.4-2.5, 0.4-2, 0.4-1.5, 0.4-1, 0.4-0.5, 0.5-10, 0.5-9, 0.5-8, 0.5-7, 0.5-6, 0.5-5, 0.5-4.5, 0.5-4, 0.5-3.5, 0.5-3, 0.5-2.5, 0.5-2, 0.5-1.5, 0.5-1, 1-10, 1-9, 1-8, 1-7, 1-6, 1-5, 1-4.5, 1-4, 1-3.5, 1-3, 1-2.5, 1-2, 1-1.5, 1.5-10, 1.5-9, 1.5-8, 1.5-7, 1.5-6, 1.5-5, 1.5-4.5, 1.5-4, 1.5-3.5, 1.5-3, 1.5-2.5, 1.5-2, 2-10, 2-9, 2-8, 2-7, 2-6, 2-5, 2-4.5, 2-4, 2-3.5, 2-3, 2-2.5, 2.5-10, 2.5-9, 2.5-8, 2.5-7, 2.5-6, 2.5-5, 2.5-4.5, 2.5-4, 2.5-3.5, 2.5-3, 3-10, 3-9, 3-8, 3-7, 3-6, 3-5, 3-4.5, 3-4, 3-3.5, 3.5-10, 3.5-9, 3.5-8, 3.5-7, 3.5-6, 3.5-5, 3.5-4.5, 3.5-4, 4-10, 4-9, 4-8, 4-7, 4-6, 4-5, 4-4.5, 4.5-10, 4.5-9, 4.5-8, 4.5-7, 4.5-6, 4.5-5, 5-10, 5-9, 5-8, 5-7, 5-6, 6-10, 6-9, 6-8, 6-7, 7-10, 7-9, 7-8, 8-10, 8-9, or 9-10. In some aspects, the bioactive glass is substantially free of, or does not contain, $Al_2O_3$.

In some aspects, alkali oxides ($Na_2O$, $K_2O$, $Li_2O$, $Rb_2O$, or $Cs_2O$) serve as aids in achieving low melting temperature and low liquidus temperatures, which can aid glass melting processes. In addition, in some aspects, the addition of alkali oxides can improve bioactivity. However, in some aspects, if the amount of alkali oxides is too high, the bioactive glasses have reduced chemical durability; in other words, in some aspects, keeping the amount of alkali oxides to a certain lower range achieves high chemical durability of the bioactive glasses. In some aspects, the amount of alkali oxides, such as $Na_2O$+$K_2O$+$Li_2O$, is minimized or at least kept to an amount below 10 wt. % or below 5 wt. %, so as to improve durability of the bioactive glass in aqueous compositions, such as in water. In some aspects, however, even keeping the $Na_2O$+$K_2O$+$Li_2O$ amount below 10 wt. % or 5 wt. % does not achieve a desired stability in aqueous compositions, such that other components of the bioactive glass and/or formulation comprising the bioactive glass may be tuned to achieve a desired stability in aqueous compositions. Such tuned bioactive glasses and formulations are disclosed herein. In some aspects, the bioactive glasses do not contain any alkali oxides (e.g., do not contain any added alkali oxides). In some aspects, the bioactive glasses are substantially free of alkali oxides (e.g., contain less than 0.1 wt. % alkali oxides).

In some aspects, the bioactive glasses comprise $Li_2O$ in an amount of 0 wt. % or greater than 0 wt. %. In some aspects, the bioactive glasses comprise $Li_2O$ in an amount of 10 wt.

% or less. In some aspects, the bioactive glasses comprise $Li_2O$ in an amount (wt. %) of 0-10, 0-9, 0-8, 0-7, 0-6, 0-5, 0-4, 0-3, 0-2, 0-1, 0-0.5, 0-0.1, >0-10, >0-9, >0-8, >0-7, >0-6, >0-5, >0-4, >0-3, >0-2, >0-1, >0-0.5, >0-0.1, 0.1-10, 0.1-9, 0.1-8, 0.1-7, 0.1-6, 0.1-5, 0.1-4, 0.1-3, 0.1-2, 0.1-1, 0.1-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5- 8, 5-7, 5-6, 6-10, 6-9, 6-8, 6-7, 7-10, 7-9, 7-8, 8-10, 8-9, or 9-10.

In some aspects, the bioactive glasses comprise $Na_2O$ in an amount of 0 wt. % or greater than 0 wt. %. In some aspects, the bioactive glasses comprise $Na_2O$ in an amount of 10 wt. % or less. In some aspects, the bioactive glasses comprise $Na_2O$ in an amount (wt. %) of 0-10, 0-9, 0-8, 0-7, 0-6, 0-5, 0-4, 0-3, 0-2, 0-1, 0-0.5, 0-0.1, >0-10, >0-9, >0-8, >0-7, >0-6, >0-5, >0-4, >0-3, >0-2, >0-1, >0-0.5, >0-0.1, 0.1-10, 0.1-9, 0.1-8, 0.1-7, 0.1-6, 0.1-5, 0.1-4, 0.1-3, 0.1-2, 0.1-1, 0.1-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5- 8, 5-7, 5-6, 6-10, 6-9, 6-8, 6-7, 7-10, 7-9, 7-8, 8-10, 8-9, or 9-10.

In some aspects, the bioactive glasses comprise $K_2O$ in an amount of 0 wt. % or greater than 0 wt. %. In some aspects, the bioactive glasses comprise $K_2O$ in an amount of 10 wt. % or less. In some aspects, the bioactive glasses comprise $K_2O$ in an amount (wt. %) of 0-10, 0-9, 0-8, 0-7, 0-6, 0-5, 0-4, 0-3, 0-2, 0-1, 0-0.5, 0-0.1, >0-10, >0-9, >0-8, >0-7, >0-6, >0-5, >0-4, >0-3, >0-2, >0-1, >0-0.5, >0-0.1, 0.1-10, 0.1-9, 0.1-8, 0.1-7, 0.1-6, 0.1-5, 0.1-4, 0.1-3, 0.1-2, 0.1-1, 0.1-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5- 8, 5-7, 5-6, 6-10, 6-9, 6-8, 6-7, 7-10, 7-9, 7-8, 8-10, 8-9, or 9-10.

In some aspects, the bioactive glasses comprise the sum $Li_2O+Na_2O+K_2O$ in an amount of 0 wt. % or greater than 0 wt. %. In some aspects, the bioactive glasses comprise the sum $Li_2O+Na_2O+K_2O$ in an amount of 10 wt. % or less or 5 wt. % or less. In some aspects, the bioactive glasses comprise the sum $Li_2O+Na_2O+K_2O$ in an amount (wt. %) of 0-10, 0-9, 0-8, 0-7, 0-6, 0-5, 0-4, 0-3, 0-2, 0-1, 0-0.5, 0-0.1, >0-10, >0-9, >0-8, >0-7, >0-6, >0-5, >0-4, >0-3, >0-2, >0-1, >0-0.5, >0-0.1, 0.1-10, 0.1-9, 0.1-8, 0.1-7, 0.1-6, 0.1-5, 0.1-4, 0.1-3, 0.1-2, 0.1-1, 0.1-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5- 6, 6-10, 6-9, 6-8, 6-7, 7-10, 7-9, 7-8, 8-10, 8-9, or 9-10. In some aspects, the bioactive glasses comprise a sum of $R_2O$, where $R_2O$ is $Na_2O$, $K_2O$, $Li_2O$, $Rb_2O$, and $Cs_2O$, in any of the amounts set forth in this paragraph, or can be any amount from 0-30 wt. %, such as an amount (wt. %) of 0-30, 0-25, 0-20, 0-15, 0-10, 0-5, 0-1, 1-30, 1-25, 1-20, 1-15, 1-10, 1-5, 5-30,5-25, 5-20,5-15, 5-10,10-30, 10-25, 10-20, 10-15, 15-30, 15-25, 15-20, 20-30, 20-25, or 25-30.

In some aspects, additional components can be incorporated into the bioactive glasses to provide additional benefits or may be incorporated as contaminants typically found in commercially-prepared glass. For example, additional components can be added as coloring or fining agents (e.g., to facilitate removal of gaseous inclusions from melted batch materials used to produce the bioactive glasses) and/or for other purposes. In some aspects, the bioactive glasses may comprise one or more compounds useful as ultraviolet radiation absorbers. In some aspects, the bioactive glasses can comprise 3 wt. % or less ZnO, $TiO_2$, CeO, MnO, $Nb_2O_5$, $MoO_3$, $Ta_2O_5$, $WO_3$, $SnO_2$, $Fe_2O_3$, $As_2O_3$, $Sb_2O_3$, Cl, Br, or any combination thereof. In some aspects, the bioactive glasses can comprise from 0 to about 3 wt. %, 0 to about 2 wt. %, 0 to about 1 wt. %, 0 to 0.5 wt. %, 0 to 0.1 wt. %, 0 to 0.05 wt. %, or 0 to 0.01 wt. % ZnO, $TiO_2$, CeO, MnO, $Nb_2O_5$, $MoO_3$, $Ta_2O_5$, $WO_3$, $SnO_2$, $Fe_2O_3$, $As_2O_3$, $Sb_2O_3$, Cl, Br, or any combination thereof. In some aspects, the bioactive glasses can also include various contaminants associated with batch materials and/or introduced into the glass by the melting, fining, and/or forming equipment used to produce the glass. For example, in some aspects, the bioactive glasses can comprise from 0 to about 3 wt. %, 0 to about 2 wt. %, 0 to about 1 wt. %, 0 to about 0.5 wt. %, 0 to about 0.1 wt. %, 0 to about 0.05 wt. %, or 0 to about 0.01 wt. % $SnO_2$ or $Fe_2O_3$, or a combination thereof.

In some aspects, the bioactive glass is substantially free of, or does not contain, a crystalline phase. For example, in some aspects, the bioactive glass has a glassy phase and is substantially free of a crystalline phase. In some aspects, the bioactive glass is a glass (e.g., a glass article).

In some aspects, the bioactive glass contains a crystalline phase. In some aspects, the crystalline phase is selected from apatite, brushite, whitlockite, calcium silicate, calcium phosphate, calcium fluoride, or any combination thereof. In some aspects, the bioactive glass is a glass-ceramic (e.g., a glass-ceramic article). In some aspects, the apatite is selected from hydroxyapatite, fluorapatite, carbonated apatite, or any combination thereof. In some aspects, the glass composition is a glass-ceramic (e.g., a glass-ceramic article). In some aspects, the bioactive glass contains a crystalline phase. In some aspects, the crystalline phase is or comprises fluorapatite. In some aspects, the crystalline phase is or comprises fluorapatite, calcium silicate, calcium phosphate, calcium fluoride, or any combination thereof. In some aspects, the bioactive glass is a glass-ceramic article comprising a fluorapatite crystal phase. In some aspects, any of the crystal phases disclosed herein, such as the fluorapatite crystal phase, is the major crystalline phase (e.g., more than 50 wt. %). In some aspects, any of such crystalline phases, individually or in any combination, is/are present in the bioactive glass in an amount (wt. %) of >50-95, >50-90, >50-85, >50-80, >50-75, >50-70, >50-65, >50-60, >50-55, 55-95, 55-90, 55-85, 55-80, 55-75, 55-70, 55-65, 55-60, 60-95, 60-90, 60-85, 60-80, 60-75, 60-70, 60-65, 65-95, 65-90, 65-85, 65-80, 65-75, 65-70, 70-95, 70-90, 70-85, 70-80, 70-75, 75-95, 75-90, 75-85, 75-80, 80-95, 80-90, 80-85, 85-95, 85-90, or 90-95. Amount of a given crystal phase can be measured by routine XRD analysis.

In some aspects, the bioactive glass comprises at least one minor crystalline phase of calcium silicate, calcium phosphate, calcium fluoride, or any combination thereof. In some aspects, the amount (wt. %) of each minor crystalline phase separately, or the amount (wt. %) of the sum total of all minor crystal phases, can be described by any of the following amounts: 1-<50, 1-49, 1-45, 1-40, 1-35, 1-30, 1-25, 1-20, 1-15, 1-10, 1-9, 1-8, 1-7, 1-6, 1-5, 1-4, 1-3, 1-2, 2-<50, 2-49, 2-45, 2-40, 2-35, 2-30, 2-25, 2-20, 2-15, 2-10, 2-9, 2-8, 2-7, 2-6, 2-5, 2-4, 2-3, 3-<50, 3-49, 3-45, 3-40, 3-35, 3-30, 3-25, 3-20, 3-15, 3-10, 3-9, 3-8, 3-7, 3-6, 3-5, 3-4, 4-<50, 4-49, 4-45, 4-40, 4-35, 4-30, 4-25, 4-20, 4-15, 4-10, 4-9, 4-8, 4-7, 4-6, 4-5, 5-<50, 5-49, 5-45, 5-40, 5-35, 5-30, 5-25, 5-20, 5-15, 5-10, 5-9, 5-8, 5-7, 5-6, 6-<50, 6-49, 6-45, 6-40, 6-35, 6-30, 6-25, 6-20, 6-15, 6-10, 6-9, 6-8, 6-7, 7-<50, 7-49, 7-45, 7-40, 7-35, 7-30, 7-25, 7-20, 7-15, 7-10, 7-9, 7-8, 8-<50, 8-49, 8-45, 8-40, 8-35, 8-30, 8-25, 8-20, 8-15, 8-10, 8-9, 9-<50, 9-49, 9-45, 9-40, 9-35, 9-30, 9-25, 9-20, 9-15, 9-10, 10-<50, 10-49, 10-45, 10-40, 10-35, 10-30, 10-25, 10-20, 10-15, 15-<50, 15-49, 15-45, 15-40, 15-35, 15-30, 15-25, 15-20, 20-<50, 20-49, 20-45, 20-40, 20-35, 20-30, 20-25, 25-<50, 25-49, 25-45, 25-40, 25-35, 25-30, 30-<50, 30-49, 30-45, 30-40, 30-35, 35-<50, 35-49, 35-45, 35-40, 40-<50, 40-49, 40-45, 45-<50, 45-49, or 49-<50. Amount of a given crystal phase can be measured by routine XRD analysis.

In some aspects, the bioactive glass is a glass-ceramic article comprising a glass phase. In some aspects, the glass-ceramic article comprises a glass phase in an amount of at least 5 wt. %. In some aspects, the glass-ceramic article comprises a glass phase in an amount of 95 wt. % or less. In some aspects, the glass-ceramic article comprises a glass phase in an amount of 5-95, 5-90, 5-85, 5-80, 5-75, 5-70, 5-65, 5-60, 5-55, 5-50, 5-45, 5-40, 5-35, 5-30, 5-25, 5-20, 5-15, 5-10, 10-95, 10-90, 10-85, 10-80, 10-75, 10-70, 10-65, 10-60, 10-55, 10-50, 10-45, 10-40, 10-35, 10-30, 10-25, 10-20, 10-15, 15-95, 15-90, 15-85, 15-80, 15-75, 15-70, 15-65, 15-60, 15-55, 15-50, 15-45, 15-40, 15-35, 15-30, 15-25, 15-20, 20-95, 20-90, 20-85, 20-80, 20-75, 20-70, 20-65, 20-60, 20-55, 20-50, 20-45, 20-40, 20-35, 20-30, 20-25, 25-95, 25-90, 25-85, 25-80, 25-75, 25-70, 25-65, 25-60, 25-55, 25-50, 25-45, 25-40, 25-35, 25-30, 30-95, 30-90, 30-85, 30-80, 30-75, 30-70, 30-65, 30-60, 30-55, 30-50, 30-45, 30-40, 30-35, 35-95, 35-90, 35-85, 35-0, 35-75, 35-70, 35-65, 35-60, 35-55, 35-50, 35-45, 35-40, 40-95, 40-90, 40-85, 40-80, 40-75, 40-70, 40-65, 40-60, 40-55, 40-50, 40-45, 45-95, 45-90, 45-5, 45-0, 45-5, 45-0, 45-65, 45-60, 45-55, 45-50, 50-95, 50-90, 50-5, 50-0, 50-75, 50-0, 50-65, 50-60, 50-55, 55-95, 55-90, 55-85, 55-80, 55-75, 55-70, 55-65, 55-60, 60-95, 60-90, 60-85, 60-80, 60-75, 60-70, 60-65, 65-95, 65-90, 65-85, 65-80, 65-75, 65-70, 70-95, 70-90, 70-85, 70-80, 70-75, 75-95, 75-90, 75-85, 75-80, 80-95, 80-90, 80-85, 85-95, 85-90, or 90-95. Amount of glass phase can be measured by routine XRD analysis.

In some aspects, the bioactive glass is a glass-ceramic and comprises a total crystallinity of at least 5 wt. %. In some aspects, the glass composition is a glass-ceramic and comprises a total crystallinity of 50 wt. % or less. In some aspects, the bioactive glass is a glass-ceramic and comprises a total crystallinity (wt. %) of 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50. Total crystallinity can be measured by routine XRD analysis.

In some aspects, the bioactive glass is a glass-ceramic and comprises a total crystallinity of at least 5 wt. %. In some aspects, the bioactive glass is a glass-ceramic and comprises a total crystallinity of 50 wt. % or less. In some aspects, the bioactive glass is a glass-ceramic and comprises a total crystallinity (wt. %) of 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50. Total crystallinity can be measured by routine XRD analysis.

In some aspects, the bioactive glass is substantially free of, or does not contain, a crystalline phase. For example, in some aspects, the glass composition has a glassy phase and is substantially free of crystalline phase. In some aspects, the glass composition is a glass (e.g., a glass article). Crystallinity can be measured by routine XRD analysis.

In some aspects, the bioactive glass is in a form of particulates, microbeads, fibers, or a combination thereof. In some aspects, the particulates are a fine powder. Methods for preparing particulates, microbeads, and/or fibers from bioactive glasses is known in the art. In some aspects, the particulates, microbeads, and/or fibers have an average particle size of at least 1 micron. In some aspects, the particulates and/or microbeads have an average particle size of 50 microns or less. In some aspects, the particulates and/or microbeads have an average particle size (microns) of 1-50, 1-45, 1-40, 1-35, 1-30, 1-25, 1-20, 1-15, 1-10, 1-5, 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50. Average particle size, as used herein, means the average size as measured by dynamic light scattering using commercially available equipment.

In some aspects, the bioactive glasses can be made via traditional methods; however, in some aspects, such as when the precursors to the bioactive glass include $F^-$, the resulting bioactive glass is not subjected to a subsequent heat treatment after melting and cooling, which subsequent heat treatment is normally necessary for prior compositions to provide a crystalline phase, if desired. In contrast, for some of the bioactive glasses disclosed herein (e.g., when $F^-$ is included in the melt), after melting precursor components of a bioactive glass, upon cooling one or more crystalline phases is spontaneously formed without a need for a subsequent heat treatment. However, as disclosed elsewhere herein, a subsequent heat treatment (e.g., crystallization temperature) may be performed to tune crystallinity, if desired. In some aspects, precursor glasses can be formed by thoroughly mixing the requisite batch materials (for example, using a Turbula® mixer) in order to secure a homogeneous melt, and subsequently placing into silica and/or platinum crucibles. The crucibles can be placed into a furnace and the glass batch melted and maintained at temperatures ranging from 1100° C. to 1400° C. for times ranging from about 6 hours to 24 hours. The melts can thereafter be poured into steel molds to yield glass slabs. Upon cooling, some compositions, for example those that include $F^-$ in some aspects, may spontaneously form a crystalline phase, such as fluorapatite (or any of the others disclosed herein). However, some compositions, such as those that do not contain $F^-$ in some aspects, will not spontaneously crystalline upon cooling. Subsequently, any of such slabs optionally can be transferred immediately to an annealer (if employing a subsequent heat treatment) operating at about 400° C. to 700° C., where the glass is held at temperature for about 0.5 hour to 3 hours and subsequently cooled overnight. In another non-limiting example, precursor glasses are prepared by dry blending the appropriate oxides and mineral sources for a time sufficient to thoroughly mix the ingredients. The glasses are melted in platinum crucibles at temperatures ranging from about 1100° C. to 1400° C. and held at temperature for about 6 hours to 16 hours. The resulting glass melts are then poured onto a steel table to cool. The precursor glasses optionally are then annealed at appropriate temperatures.

In some aspects, the resulting bioactive glasses can be ground into fine particles in the range of 1-10 microns (m) by air jet milling. The particle size can be varied in the range of 1-100 m using attrition milling or ball milling of glass frits. Furthermore, these glasses can be processed into short fibers, beads, sheets or three-dimensional scaffolds using different methods. Short fibers are made by melt spinning or electric spinning; beads can be produced by flowing glass particles through a hot vertical furnace or a flame torch; sheets can be manufactured using thin rolling, float or fusion-draw processes; and scaffolds can be produced using rapid prototyping, polymer foam replication and particle sintering. Glasses of desired forms can be used to support cell growth, soft and hard tissue regeneration, stimulation of gene expression or angiogenesis.

Continuous fibers can be easily drawn from the disclosed composition using processes known in the art. For example, fibers can be formed using a directly heated (electricity passing directly through) platinum bushing. Glass cullet is loaded into the bushing, heated up until the glass can melt. Temperatures are set to achieve a desired glass viscosity (usually <1000 poise) allowing a drip to form on the orifice in the bushing (Bushing size is selected to create a restriction that influences possible fiber diameter ranges). The drip is pulled by hand to begin forming a fiber. Once a fiber is established it is connected to a rotating pulling/collection drum to continue the pulling process at a consistent speed. Using the drum speed (or revolutions per minute RPM) and glass viscosity the fiber diameter can be manipulated—in general the faster the pull speed, the smaller the fiber diameter. Glass fibers with diameters in the range of 1-100 μm can be drawn continuously from a glass melt. Fibers can also be created using an updraw process. In this process, fibers are pulled from a glass melt surface sitting in a box furnace. By controlling the viscosity of the glass, a quartz rod is used to pull glass from the melt surface to form a fiber. The fiber can be continuously pulled upward to increase the fiber length. The velocity that the rod is pulled up determines the fiber thickness along with the viscosity of the glass.

Therefore, in some aspects, a method for making the bioactive glasses disclosed herein is provided, the method comprising:

combining each component of the bioactive glass to form a mixture, heating the mixture to a temperature of 1500° C. or less to form a melted mixture, and cooling the melted mixture to form a cooled mixture.

In some aspects, the method further comprising forming the cooled mixture into particulates, microbeads, fibers, or a combination thereof.

In some aspects, the heating step employs any suitable temperature. In some aspects, the heating step employs a temperature sufficient to melt the components to form a mixture. In some aspects, the temperature (° C.) is 1000-1500, 1000-1450, 1000-1400, 1000-1350, 1000-1300, 1000-1250, 1000-1200, 1000-1150, 1000-1100, 1000-1050, 1050-1500, 1050-1450, 1050-1400, 1050-1350, 1050-1300, 1050-1250, 1050-1200, 1050-1150, 1050-1100, 1100-1500, 1100-1450, 1100-1400, 1100-1350, 1100-1300, 1100-1250, 1100-1200, 1100-1150, 1150-1500, 1150-1450, 1150-1400, 1150-1350, 1150-1300, 1150-1250, 1150-1200, 1200-1500, 1200-1450, 1200-1400, 1200-1350, 1200-1300, 1200-1250, 1250-1500, 1250-1450, 1250-1400, 1250-1350, 1250-1300, 1300-1500, 1300-1450, 1300-1400, 1300-1350, 1350-1500, 1350-1450, 1350-1400, 1400-1500, 1400-1450, or 1450-1500.

In some aspects, the heating step is employed for any suitable time period. In some aspects, the heating step employs a time period sufficient to melt the components to form a mixture. In some aspects, the time period is at least 6 hours. In some aspects, the time period is 30 hours or less. In some aspects, the time period (hours) is 6-30, 6-28, 6-26, 6-24, 6-22, 6-20, 6-18, 6-16, 6-14, 6-12, 6-10, 6-8, 8-30, 8-28, 8-26, 8-24, 8-22, 8-20, 8-18, 8-16, 8-14, 8-12, 8-10, 10-30, 10-28, 10-26, 10-24, 10-22, 10-20, 10-18, 10-16, 10-14, 10-12, 12-30, 12-28, 12-26, 12-24, 12-22, 12-20, 12-18, 12-16, 12-14, 14-30, 14-28, 14-26, 14-24, 14-22, 14-20, 14-18, 14-16, 16-30, 16-28, 16-26, 16-24, 16-22, 16-20, 16-18, 18-30,18-28, 18-26, 18-24, 18-22, 18-20, 20-30, 20-28, 20-26, 20-24, 20-22, 22-30, 22-28, 22-26, 22-24, 24-30, 24-28, 24-26, 26-30, 26-28, or 28-30.

In some aspects, e.g., such as when the bioactive glass comprises F, the cooling step spontaneously results in at least partial crystallization into a fluorapatite crystal phase. In some aspects, In some aspects, the cooling step spontaneously results in at least partial crystallization into one or more crystalline phases, such as fluorapatite, calcium silicate, calcium phosphate, calcium fluoride, or any combination thereof. In some aspects, the fluorapatite crystal phase is the major crystal phase. In some aspects, calcium silicate, calcium phosphate, and/or calcium fluoride are minor crystalline phases, taken alone or in combination.

In some aspects, e.g., such as when the bioactive glass comprises F, after the cooling step, the cooled mixture is not heated to a temperature sufficient to result in crystallization. In some aspects, after the cooling step, the cooled mixture is not heated to a crystallization temperature. In some aspects, the crystallization temperature is 500-1000° C. depending on the composition. In some aspects, the crystallization temperature (° C.) is 500-1000, 500-950, 500-900, 500-850, 500-800, 500-750, 500-700, 500-650, 500-600, 500-550, 550-1000, 550-950, 550-900, 550-850, 550-800, 550-750, 550-700, 550-650, 550-600, 600-1000, 600-950, 600-900, 600-850, 600-800, 600-750, 600-700, 600-650, 650-1000, 650-950, 650-900, 650-850, 650-800, 650-750, 650-700, 700-1000, 700-950, 700-900, 700-850, 700-800, 700-750, 750-1000, 750-950, 750-900, 750-850, 750-800, 800-1000, 800-950, 800-900, 800-850, 850-1000, 850-950, 850-900, 900-1000, 900-950, or 950-1000.

In some aspects, when subjected to an aqueous composition (e.g., artificial saliva or real saliva), as described elsewhere herein, a bioactive crystalline phase is formed, e.g., on a tooth and/or on a surface of the bioactive glass. In some aspects, the formation of the bioactive crystalline phase takes place within a certain timeframe, such as within 1, 2, 3, 4, 5, 6, 7, or 8 days, as described elsewhere herein. In some aspects, the bioactive crystalline phase comprises apatite, brushite, whitlockite, or a combination thereof. In some aspects, the apatite comprises hydroxyapatite, fluorapatite, carbonated apatite, or any combination thereof. In some aspects, the brushite is a precursor to apatite.

In some aspects, disclosed is a dentifrice formulation comprising a bioactive glass, as disclosed elsewhere herein. In some aspects, the dentifrice formulation is an aqueous dentifrice formulation. In some aspects, an aqueous dentifrice formulation comprises water in an amount of at least 20 wt. %, based on total weight of the aqueous dentifrice formulation. In some aspects, an aqueous dentifrice formulation comprises water in an amount of 65 wt. % or less, based on total weight of the aqueous dentifrice formulation. In some aspects, an aqueous dentifrice formulation comprises water in an amount (wt. %) of 20-65, 20-60, 20-55, 20-50, 20-45, 20-40, 20-35, 20-30, 20-25, 25-65, 25-60, 25-55, 25-50, 25-45, 25-40, 25-35, 25-30, 30-65, 30-60, 30-55, 30-50, 30-45, 30-40, 30-35, 35-65, 35-60, 35-55, 35-50, 35-45, 35-40, 40-65, 40-60, 40-55, 40-50, 40-45, 45-65, 45-60, 45-55, 45-50, 50-65, 50-60, 50-55, 55-65, 55-60, or 60-65, based on total weight of the aqueous dentifrice formulation.

In some aspects, disclosed is a dentifrice formulation comprising a bioactive glass, as disclosed elsewhere herein. In some aspects, the dentifrice formulation is a non-aqueous dentifrice formulation. In some aspects, a non-aqueous dentifrice formulation comprises a solvent other than water in an amount of at least 25 wt. %, based on total weight of the non-aqueous dentifrice formulation. In some aspects, a non-aqueous dentifrice formulation comprises a solvent other than water in an amount of 65 wt. % or less, based on total weight of the non-aqueous dentifrice formulation. In some aspects, a non-aqueous dentifrice formulation comprises a solvent other than water in an amount (wt. %) of 25-65, 25-60, 25-55, 25-50, 25-45, 25-40, 25-35, 25-30, 30-65, 30-60, 30-55, 30-50, 30-45, 30-40, 30-35, 35-65, 35-60, 35-55, 35-50, 35-45, 35-40, 40-65, 40-60, 40-55, 40-50, 40-45, 45-65, 45-60, 45-55, 45-50, 50-65, 50-60, 50-55, 55-65, 55-60, or 60-65, based on total weight of the non-aqueous dentifrice formulation. In some aspects, the solvent other than water is glycerin.

A formulation or composition herein can be "aqueous" or "non-aqueous." As used herein, a formulation or composition (e.g., a dentifrice formulation) is "aqueous" when water is present in a weight percent amount greater than or equal to glycerin. Similarly, as used herein, a formulation or composition (e.g., dentifrice formulation) is "non-aqueous" when water is present in a weight percent amount less than glycerin. Such weight percent values can be readily calculated and easily compared by dividing the mass of water by the sum total mass of water and glycerin; in this calculation, if the amount of water is 50 wt. % or greater, than the formulation or composition is "aqueous," and if the amount of water is less than 50 wt. % then the formulation or composition is "non-aqueous." Of course, other values can be employed to describe the amount of water and glycerin in the formulations or compositions based on total mass of water and glycerin, such as an amount (wt. %) of water of 0-100, 0-99, 0-95, 0-90, 0-85, 0-80, 0-75, 0-70, 0-65, 0-60, 0-55, 0-50, 0-45, 0-40, 0-35, 0-30, 0-25, 0-20, 0-15, 0-10, 0-5, 5-100, 5-99, 5-95, 5-90, 5-85, 5-80, 5-75, 5-70, 5-65, 5-60, 5-55, 5-50, 5-45, 5-40, 5-35, 5-30, 5-25, 5-20, 5-15, 5-10, 10-100, 10-99, 10-95, 10-90, 10-85, 10-80, 10-75, 10-70, 10-65, 10-60, 10-55, 10-50, 10-45, 10-40, 10-35, 10-30, 10-25, 10-20, 10-15, 15-100, 15-99, 15-95, 15-90, 15-85, 15-80,15-75, 15-70, 15-65, 15-60, 15-55, 15-50, 15-45, 15-40, 15-35, 15-30, 15-25, 15-20, 20-100, 20-99, 20-95, 20-90, 20-85, 20-80, 20-75, 20-70, 20-65, 20-60, 20-55, 20-50, 20-45, 20-40, 20-35, 20-30, 20-25, 25-100, 25-99, 25-95, 25-90, 25-85, 25-80, 25-75, 25-70, 25-65, 25-60, 25-55, 25-50, 25-45, 25-40, 25-35, 25-30, 30-100, 30-99, 30-95, 30-90, 30-85, 30-80, 30-75, 30-70, 30-65, 30-60, 30-55, 30-50, 30-45, 30-40, 30-35, 35-100, 35-99, 35-95, 35-90, 35-85, 35-80, 35-75, 35-70, 35-65, 35-60, 35-55, 35-50, 35-45, 35-40, 40-100, 40-99, 40-95, 40-90, 40-85, 40-80, 40-75, 40-70, 40-65, 40-60, 40-55, 40-50, 40-45, 45-100, 45-99, 45-95, 45-90, 45-85, 45-80, 45-75, 45-70, 45-65, 45-60, 45-55, 45-50, 50-100, 50-99, 50-95, 50-90, 50-85, 50-80, 50-75, 50-70, 50-65, 50-60, 50-55, 55-100, 55-99, 55-95, 55-90, 55-85, 55-80, 55-75, 55-70, 55-65, 55-60, 60-100, 60-99, 60-95, 60-90, 60-85, 60-80, 60-75, 60-70, 60-65, 65-100, 65-99, 65-95, 65-90, 65-85, 65-80, 65-75, 65-70, 70-100, 70-99, 70-95, 70-90, 70-85, 70-80, 70-75, 75-100, 75-99, 75-95, 75-90, 75-85, 75-80, 80-100, 80-99, 80-95, 80-90, 80-85, 85-100, 85-99, 85-95, 85-90, 90-100, 90-99, 90-95, 95-100, 95-99, or 99-100, based on total mass of water and glycerin. In this calculation, water can be present in any of these amounts such as 50-100 wt. %, 55-95 wt. %, 60-80 wt. %, 0-50 wt. %, 5-40 wt. %, or 25-35 wt. %, based on total mass of water and glycerin. In some aspects, a formulation or composition has less than 5 wt. % water, less than 4 wt. % water, less than 3 wt. % water, less than 2 wt. % water, less than 1 wt. % water, less than 0.5 wt. % water, or less than 0.1 wt. % water, based on total mass of the formulation or composition. In some aspects, the formulation or composition is substantially free of water.

In some aspects, disclosed herein is a dentifrice formulation (aqueous or non-aqueous), comprising a bioactive glass (i.e., any bioactive glass disclosed herein). In some aspects, the dentifrice formulation further comprises at least one amino acid.

In some aspects, disclosed herein is a dentifrice formulation (aqueous or non-aqueous), comprising:

- a bioactive glass (i.e., any bioactive glass disclosed herein) exhibiting at least one of:
  - a hydrolytic resistance of glass grains (HGB) of at most 4.5 or at most 4 (e.g., or at most 3), when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum substantially free of crystalline phase after soaking 5 g of the bioactive glass in powder form in 100 mL of deionized water for 7 days at 37° C.; or
  - any combination thereof;
- wherein, when the bioactive glass is contacted with artificial saliva, the bioactive glass forms a bioactive crystalline phase.

In some aspects, a bioactive glass is present in the dentifrice formulation (aqueous or non-aqueous) in an amount of 0 wt. % or greater than 0 wt. %. In some aspects, a bioactive glass is present in the formulation in an amount of 20 wt. % or less, aspects, the bioactive glass is present in the dentifrice formulation (aqueous or non-aqueous) in an amount (wt. %) of 0-20, 0-18, 0-16, 0-14, 0-12, 0-10, 0-8, 0-6, 0-5, 0-4, 0-3, 0-2, 0-1, 0-0.8, 0-0.6, 0-0.4, 0-0.2, 0-0.1, >0-20, >0-18, >0-16, >0-14, >0-12, >0-10, >0-8, >0-6, >0-5, >0-4, >0-3, >0-2, >0-1, >0-0.8, >0-0.6, >0-0.4, >0-0.2, >0-0.1, 0.1- 20, 0.1-18, 0.1-16, 0.1-14, 0.1-12, 0.1-10, 0.1-8, 0.1-6, 0.1-5, 0.1-4, 0.1-3, 0.1-2, 0.1-1, 0.1-0.8, 0.1-0.6, 0.1-0.4, 0.1-0.2, 0.2-20, 0.2-18, 0.2-16, 0.2-14, 0.2-12, 0.2-10, 0.2-8, 0.2-6, 0.2-5, 0.2-4, 0.2-3, 0.2-2, 0.2-1, 0.2-0.8, 0.2-0.6, 0.2-0.4, 0.4-20, 0.4-18, 0.4-16, 0.4-14, 0.4-12, 0.4-10, 0.4-8, 0.4-6, 0.4-5, 0.4-4, 0.4-3, 0.4-2, 0.4-1, 0.4-0.8, 0.4-0.6, 0.6-20, 0.6-18, 0.6-16, 0.6-14, 0.6-12, 0.6-10, 0.6-8, 0.6-6, 0.6-5, 0.6-4, 0.6-3, 0.6-2, 0.6-1, 0.6-0.8, 0.8-20, 0.8-18, 0.8-16, 0.8-14, 0.8-12, 0.8-10, 0.8-8, 0.8-6, 0.8-5, 0.8-4, 0.8-3, 0.8-2, 0.8-1, 1-20, 1-18, 1-16, 1-14, 1-12, 1-10, 1-8, 1-6, 1-5, 1-4, 1-3, 1-2, 2-20, 2-18, 2-16, 2-14, 2-12, 2-10, 2-8, 2-6, 2-5, 2-4, 2-3, 3-20, 3-18, 3-16, 3-14, 3-12, 3-10, 3-8, 3-6, 3-5, 3-4, 4-20, 4-18, 4-16, 4-14, 4-12, 4-10, 4-8, 4-6, 4-5, 5-20, 5-18, 5-16, 5-14, 5-12, 5-10, 5-8, 5-6, 6-20, 6-18, 6-16, 6-14, 6-12, 6-10, 6-8, 8-20, 8-18, 8-16, 8-14, 8-12, 8-10, 10-20, 10-18, 10-16, 10-14, 10-12, 12-20, 12-18, 12-16, 12-14, 14-20, 14-18, 14-16, 16-20, 16-18, or 18-20.

In some aspects, an amino acid is present in the dentifrice formulation (aqueous or non-aqueous) in an amount of 0 wt. % or greater than 0 wt. %. In some aspects, the amino acid is present in the dentifrice formulation (aqueous or non-aqueous) in an amount of 40 wt. % or less. In some aspects, the amino acid is present in the dentifrice formulation (aqueous or non-aqueous) in an amount (wt. %) of 0-40, 0-38, 0-36, 0-34, 0-32, 0-30, 0-28, 0-26, 0-25, 0-24, 0-22, 0-20, 0-18, 0-16, 0-14, 0-12, 0-10, 0-9, 0-8, 0-7, 0-6, 0-5, 0-4, 0-3, 0-2, 0-1, 0-0.5, 0-0.1, >0-40, >0-38, >0-36, >0-34, >0-32, >0-30, >0-28, >0-26, >0-25, >0-24, >0-22, >0-20, >0-18, >0-16, >0-14, >0-12, >0-10, >0-9, >0-8, >0-7, >0-6, >0-5, >0-4, >0-3, >0-2, >0-1, >0-0.5, >0-0.1, 0.1-40, 0.1-38, 0.1-36, 0.1-34, 0.1-32, 0.1-30, 0.1-28, 0.1-26, 0.1-25, 0.1-24, 0.1-22, 0.1-20, 0.1-18, 0.1-16, 0.1-14, 0.1-12, 0.1-10, 0.1-9, 0.1-8, 0.1-7, 0.1-6, 0.1-5, 0.1-4, 0.1-3, 0.1-2, 0.1-1, 0.1-0.5, 0.5-40, 0.5-38, 0.5-36, 0.5-34, 0.5-32, 0.5-30, 0.5-28, 0.5-26, 0.5-25, 0.5-24, 0.5-22, 0.5-20, 0.5-18, 0.5-16, 0.5-14, 0.5-12, 0.5-10, 0.5-9, 0.5-8, 0.5-7, 0.5-6, 0.5-5, 0.5-4, 0.5-3, 0.5-2, 0.5-1, 1-40, 1-38, 1-36, 1-34, 1-32, 1-30, 1-28, 1-26, 1-25, 1-24, 1-22, 1-20, 1-18, 1-16, 1-14, 1-12, 1-10, 1-9, 1-8, 1-7, 1-6, 1-5, 1-4, 1-3, 1-2, 2-40, 2-38, 2-36, 2-34, 2-32, 2-30, 2-28, 2-26, 2-25, 2-24, 2-22, 2-20, 2-18, 2-16, 2-14, 2-12, 2-10, 2-9, 2-8, 2-7, 2-6, 2-5, 2-4, 2-3, 3-40, 3-38, 3-36, 3-34, 3-32, 3-30, 3-28, 3-26, 3-25, 3-24, 3-22, 3-20, 3-18, 3-16, 3-14, 3-12, 3-10, 3-9, 3-8, 3-7, 3-6, 3-5, 3-4, 4-40, 4-38, 4-36, 4-34, 4-32, 4-30, 4-28, 4-26, 4-25, 4-24, 4-22, 4-20, 4-18, 4-16, 4-14, 4-12, 4-10, 4-9, 4-8, 4-7, 4-6, 4-5, 5-40, 5-38, 5-36, 5-34, 5-32, 5-30, 5-28, 5-26, 5-25, 5-24, 5-22, 5-20, 5-18, 5-16, 5-15, 5-14, 5-12, 5-10, 5-9, 5-8, 5-7, 5-6, 6-40, 6-38, 6-36, 6-34, 6-32, 6-30, 6-28, 6-26, 6-25, 6-24, 6-22, 6-20, 6-18, 6-16, 6-14, 6-12, 6-10, 6-9, 6-8, 6-7, 7-40, 7-38, 7-36, 7-34, 7-32, 7-30, 7-28, 7-26, 7-25, 7-24, 7-22, 7-20, 7-18, 7-16, 7-14, 7-12, 7-10, 7-9, 7-8, 8-40, 8-38, 8-36, 8-34, 8-32, 8-30, 8-28, 8-26, 8-25, 8-24, 8-22, 8-20, 8-18, 8-16, 8-14, 8-12, 8-10, 8-9, 9-40, 9-38, 9-36, 9-34, 9-32, 9-30, 9-28, 9-26, 9-25, 9-24, 9-22, 9-20, 9-18, 9-16, 9-14, 9-12, 9-10, 10-40, 10-38, 10-36, 10-34, 10-32, 10-30, 10-28, 10-26, 10-25, 10-24, 10-22, 10-20, 10-18, 10-16, 10-14, 10-12, 12-40, 12-38, 12-36, 12-34, 12-32, 12-30, 12-28, 12-26, 12-25, 12-24, 12-22, 12-20, 12-18, 12-16, 12-14, 14-40, 14-38, 14-36, 14-34, 14-32, 14-30, 14-28, 14-26, 14-25, 14-24, 14-22, 14-20, 14-18, 14-16, 16-40, 16-38, 16-36, 16-34, 16-32, 16-30, 16-28, 16-26, 16-25, 16-24, 16-22, 16-20, 16-18, 18-40, 18-38, 18-36, 18-34, 18-32, 18-30, 18-28, 18-26, 18-25, 18-24, 18-22, 18-20, 20-40, 20-38, 20-36, 20-34, 20-32, 20-30, 20-28, 20-26, 20-25, 20-24, 20-22, 22-40, 22-38, 22-36, 22-34, 22-32, 22-30, 22-28, 22-26, 22-25, 22-24, 24-40, 24-38, 24-36, 24-34, 24-32, 24-30, 24-28, 24-26, 24-25, 25-40, 25-38, 25-36, 25-34, 25-32, 25-30, 25-28, 25-26, 26-40, 26-38, 26-36, 26-34, 26-32, 26-30, 26-28, 28-40, 28-38, 28-36, 28-34, 28-32, 28-30, 30-40, 30-38, 30-36, 30-34, 30-32, 32-40, 32-38, 32-36, 32-34, 34-40, 34-38, 34-36, 36-40, 36-38, or 38-40. In some aspects, the dentifrice formulation (aqueous or non-aqueous) is substantially free of, or does not contain, amino acid. In some aspects, the amino acid is present in the dentifrice formulation (aqueous or non-aqueous) in an amount of 5-15 wt. % or 4-16 wt. %. When more than one amino acid is present, the amounts herein can refer to the sum total of amino acids or to each amino acid individually.

In some aspects, the amino acid (e.g., that is present in the dentifrice formulation (aqueous or non-aqueous)) is glycine, glutamic acid, arginine, histidine, lysine, pyrrolysine, aspartic acid, serine, threonine, asparagine, glutamine, cysteine, selenocysteine, proline, alanine, valine, isoleucine, leucine, methionine, phenylalanine, tyrosine, tryptophan, or any combination thereof. In some aspects, the amino acid is glycine, glutamic acid, or a combination thereof. In some aspects, the amino acid is histidine, lysine, pyrrolysine, aspartic acid, serine, threonine, asparagine, glutamine, cysteine, selenocysteine, proline, alanine, valine, isoleucine, leucine, methionine, phenylalanine, tyrosine, tryptophan, or any combination thereof. In some aspects, the amino acid is arginine. In some aspects, the amino acid is not arginine (i.e., in some aspects the relevant formulation is substantially free of arginine). In some aspects, the amino acid is not one or more of glycine, glutamic acid, arginine, histidine, lysine, pyrrolysine, aspartic acid, serine, threonine, asparagine, glutamine, cysteine, selenocysteine, proline, alanine, valine, isoleucine, leucine, methionine, phenylalanine, tyrosine, tryptophan, or any combination thereof. In some aspects, the amino acid is glycine, glutamic acid, arginine, or any combination thereof. In some aspects, a formulation is substantially free of, or does not contain, an amino acid (e.g., any one or more of any of the amino acids disclosed herein).

In some aspects, disclosed are formulations (e.g., dentifrice formulation (aqueous or non-aqueous)) comprising one or more bioactive glasses (e.g., and one or more amino acids), and the methods of using the compositions to treat medical conditions (e.g., dentin hypersensitivity, tooth caries, remineralization, etc., or any combination thereof). The formulations can be in a form of a toothpaste, mouthwash, gel, varnish, rinse, spray, ointment, salve, cream, bandage, polymer film, oral formulation, pill, capsule, transdermal formulation, or any combination thereof. In some aspects, the composition is a dentifrice composition. The bioactive glasses and/or amino acid(s) can be physically or chemically attached to the formulations (e.g., carrier) or simply mixed in. As noted above, the bioactive glass can be in any form that works in the application, including particles, beads, particulates, short fibers, long fibers, or woolen meshes. The methods of using the formulations (e.g., containing bioactive glass and optionally amino acid) to treat a medical condition can be simply like the use of composition as normally applied.

In some aspects, the formulation (e.g., aqueous or non-aqueous dentifrice formulation) is substantially free of, or does not include, a fluoride ion source other than that derived from the bioactive glass, if any (e.g., is substantially free of or does not include a fluoride ion source that is added to the composition as a component separate from the bioactive glass and which fluoride ion source is not derived from the bioactive glass). In this regard, in some aspects, the formulation is substantially free of, or does not contain, calcium fluoride, magnesium fluoride, sodium fluoride, potassium fluoride, stannous fluoride, sodium monofluorophosphate, sodium difluorophosphate, or any combination thereof. In some aspects, the formulation does not contain a source of fluoride ions that is added to the formulation separately from the bioactive glass. In some aspects, the formulation includes a fluoride ion source that is added separately to the formulation. In some aspects, the formulation comprises calcium fluoride, magnesium fluoride, sodium fluoride, potassium fluoride, stannous fluoride, sodium monofluorophosphate, sodium difluorophosphate, or any combination thereof. In some aspects, the calcium fluoride, magnesium fluoride, sodium fluoride, potassium fluoride, stannous fluoride, sodium monofluorophosphate, sodium difluorophosphate, or any combination thereof are added to the formulation separately from the bioactive glass.

In some aspects, the formulation is or comprises an aqueous or non-aqueous dentifrice formulation. In some aspects, the dentifrice formulation is a toothpaste, a mouthwash, or a gel, or any other formulation that is intended for oral care. In some aspects, without wishing to be bound by theory, it is believed that high chemical durability and high bioactivity of the bioactive glasses makes them advantageous for use in oral care formulations (e.g., dentifrice compositions) and/or cosmetic formulations. In some aspects, the dentifrice formulation is shelf-stable at ambient conditions (e.g., stable for at least X months at ambient conditions, where X is 1, 2, 3, 4, 5, 6, 7, 8, 9, 10, 11, 12, 13, 14, 15, 16, 17, 18, 19, 20, 21, 22, 23, or 24; alternatively, or additionally, the formulation is stable for Y months or less at ambient conditions, where Y is 2, 3, 4, 5, 6, 7, 8, 9, 10, 11, 12, 13, 14, 15, 16, 17, 18, 19, 20, 21, 22, 23, 24, or 25; any of the X and Y numbers can be combined to form a range, such as 12-24 months).

In some aspects, the formulation is or comprises a skin care or cosmetic formulation (e.g., aqueous or non-aqueous). In some aspects, the skin care or cosmetic composition is a gel, a spray, an ointment, a salve, a cream, a lotion, a bandage, a transdermal formulation, or any other formulation that is intended for skin care. In some aspects, without wishing to be bound by theory, it is believed that high chemical durability and high bioactivity of the bioactive glasses makes them advantageous for use in oral care formulations (e.g., dentifrice compositions), skin care, or cosmetic formulations. In some aspects, the cosmetic formulation is shelf-stable at ambient conditions (e.g., stable for at least X months at ambient conditions, where X is 1, 2, 3, 4, 5, 6, 7, 8, 9, 10, 11, 12, 13, 14, 15, 16, 17, 18, 19, 20, 21, 22, 23, or 24; alternatively, or additionally, the formulation is stable for Y months or less at ambient conditions, where Y is 2, 3, 4, 5, 6, 7, 8, 9, 10, 11, 12, 13, 14, 15, 16, 17, 18, 19, 20, 21, 22, 23, 24, or 25; any of the X and Y numbers can be combined to form a range, such as 12-24 months).

In some aspects, the dentifrice, skin care, or cosmetic formulations can comprise any suitable components and amounts of such components. For example, in some aspects, the dentifrice, skin care, or cosmetic formulations comprise the bioactive glass in combination with one or more of an amino acid, a solvent, a humectant, a fluoride ion source, a flavoring, a surfactant, a sweetener, a whitening agent, an abrasive, or any combination thereof.

In some aspects, a suitable dentifrice, skin care, or cosmetic formulation with ranges of components is shown in Table 2. Notably, as indicated in Table 2, there is overlap between components suitable, for example, for a dentifrice formulation and those suitable for a skin care or cosmetic formulation.

TABLE 2

| Component | Amount (wt. %) |
|---|---|
| Bioactive glass | >0-20 |
| Amino Acid(s) | 0-25 |
| Solvent | 10-80 |
| Humectant | 2-50 |
| Fluoride Ion Source | 0-1 |
| Flavoring | 0-0.5 |
| Surfactant | 0-5 |
| Sweetener | 0-5 |
| Whitening Agent | 0-2 |
| Abrasive | 0-20 |
| Other | 0-10 |

In some aspects, the dentifrice, skin care, or cosmetic formulations comprise the bioactive glass in amount of greater than 0 wt. %. In some aspects, the dentifrice, skin care, or cosmetic formulations comprise the bioactive glass in amount of 20 wt. % or less. In some aspects, the dentifrice, skin care, or cosmetic formulations comprise the bioactive glass in amount (wt. %) of >0-20, >0-18, >0-16, >0-14, >0-12, >0-10, >0-8, >0-6, >0-4, >0-2, >0-1, >0-0.5, >0-0.1, 0.1-20, 0.1-18, 0.1-16, 0.1-14, 0.1-12, 0.1-10, 0.1-8, 0.1-6, 0.1-4, 0.1-2, 0.1-1, 0.1-0.5, 0.5-20, 0.5-18, 0.5-16, 0.5-14, 0.5-12, 0.5-10, 0.5-8, 0.5-6, 0.5-4, 0.5-2, 0.5-1, 1-20, 1-18, 1-16, 1-14, 1-12, 1-10, 1-8, 1-6, 1-4, 1-2, 2-20, 2-18, 2-6, 2-14, 2-12, 2-10, 2-8, 2-6, 2-4, 4-20, 4-18, 4-16, 4-14, 4-12, 4-10, 4-8, 4-6, 6-20, 6-18, 6-16, 6-14, 6-12, 6-10, 6-8, 8-20, 8-18, 8-16, 8-14, 8-12, 8-10, 10-20, 10-18, 10-16, 10-14, 10-12, 12-20, 12-18, 12-16, 12-14, 14-20, 14-18, 14-16, 16-20, 16-18, or 18-20.

In some aspects, the dentifrice, skin care, or cosmetic formulations comprise a solvent in an amount of 10 wt. % or more. In some aspects, the dentifrice, skin care, or cosmetic formulations comprise a solvent in an amount of 80 wt. % or less. In some aspects, the dentifrice, skin care, or cosmetic formulations comprise a solvent in an amount (wt. %) of 10-80, 10-75, 10-70, 10-65, 10-60, 10-55, 10-50, 10-45, 10-40, 10-35, 10-30, 10-25, 10-20, 10-15, 15-80, 15-75, 15-70, 15-65, 15-60, 15-55, 15-50, 15-45, 15-40, 15-35, 15-30, 15-25, 15-20, 20-80, 20-75, 20-70, 20-65, 20-60, 20-55, 20-50, 20-45, 20-40, 20-35, 20-30, 20-25, 25-80, 25-75, 25-70, 25-65, 25-60, 25-55, 25-50, 25-45, 25-40, 25-35, 25-30, 30-80, 30-75, 30-70, 30-65, 30-60, 30-55, 30-50, 30-45, 30-40, 30-35, 35-80, 35-75, 35-70, 35-65, 35-60, 35-55, 35-50, 35-45, 35-40, 40-80, 40-75, 40-70, 40-65, 40-60, 40-55, 40-50, 40-45, 45-80, 45-75, 45-70, 45-65, 45-60, 45-55, 45-50, 50-80, 50-75, 50-70, 50-65, 50-60, 50-55, 55-80, 55-75, 55-70, 55-65, 55-60, 60-80, 60-75, 60-70, 60-65, 65-80, 65-75, 65-70, 70-80, 70-75, or 75-80. As disclosed elsewhere herein, the formulation can be aqueous or non-aqueous. In some aspects, a combination of water and glycerin is employed, and the weight percent of glycerin in such a mixture can be 1-99, 5-95, 10-90, 15-85, 20-80, 25-75, 30-70, 35-65, 40-60, 45-55, 1-50, 5-45, 10-40, 15-35, 50-95, 55-90, 60-85, or 65-80. Generally, the terms "solvent" and "carrier" are used interchangeably herein, unless clearly contradicted by context. Suitable solvents include, for example, water, glycerin, polyethylene glycol, or any combination thereof.

In some aspects, the dentifrice, skin care, or cosmetic formulations comprise one or more humectants. In some aspects, the humectants can include short-chained polyalcohols For example, short-chained polyalcohols can include glycerol, sorbitol, propylene glycol, polyethylene glycol, or any combination thereof. In some aspects, the dentifrice, skin care, or cosmetic formulations comprise one or more humectants in an amount of 2 wt. % or more. In some aspects, the dentifrice, skin care, or cosmetic formulations comprise one or more humectants in an amount of 50 wt. % or less. In some aspects, the dentifrice, skin care, or cosmetic formulations comprise one or more humectants in an amount (wt. %) of 2-50, 2-45, 2-40, 2-35, 2-30, 2-25, 2-20, 2-15, 2-10, 2-5, 5-50, 5-45, 5-40, 5-35, 5-30,5-25, 5-20,5-15, 5-10, 10-50, 10-45, 10-40, 10-35, 10-30, 10-25, 10-20, 10-15, 15-50,15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50.

In some aspects, the dentifrice, skin care, or cosmetic formulations comprise one or more fluoride ion sources. In some aspects, the one or more fluoride ion sources includes calcium fluoride, magnesium fluoride, sodium fluoride, potassium fluoride, stannous fluoride, sodium monofluorophosphate, sodium difluorophosphate, or any combination thereof. In some aspects, the dentifrice, skin care, or cosmetic compositions comprise one or more fluoride ion sources in an amount of 0 wt. % or greater than 0 wt. %. In some aspects, the dentifrice, skin care, or cosmetic formulations comprise one or more fluoride ion sources in an amount of 1 wt. % or less. In some aspects, the dentifrice, skin care, or cosmetic formulations comprise one or more fluoride ion sources in an amount (wt. %) of 0-1, 0-0.9, 0-0.8, 0-0.7, 0-0.6, 0-0.5, 0-0.4, 0-0.3, 0-0.2, 0-0.1, 0.-0.05, >0-1, >0-0.9, >0-0.8, >0-0.7, >0-0.6, >0-0.5, >0-0.4, >0-0.3, >0-0.2, >0-0.1, >0-0.05, 0.05-1, 0.05-0.9, 0.05-0.8, 0.05-0.7, 0.05-0.6, 0.05-0.5, 0.05-0.4, 0.05-0.3, 0.05-0.2, 0.05-0.1, 0.1-1, 0.1-0.9, 0.1-0.8, 0.1-0.7, 0.1-0.6, 0.1-0.5, 0.1-0.4, 0.1-0.3, 0.1-0.2, 0.2-1, 0.2-0.9, 0.2-0.8, 0.2-0.7, 0.2-0.6, 0.2-0.5, 0.2-0.4, 0.2-0.3, 0.3-1, 0.3-0.9, 0.3-0.8, 0.3-0.7, 0.3-0.6, 0.3-0.5, 0.3-0.4, 0.4-1, 0.4-0.9, 0.4-0.8, 0.4-0.7, 0.4-0.6, 0.4-0.5, 0.5-1, 0.5-0.9, 0.5-0.8, 0.5-0.7, 0.5-0.6, 0.6-1, 0.6-0.9, 0.6-0.8, 0.6-0.7, 0.7-1, 0.7-0.9, 0.7-0.8, 0.8-1, 0.8-0.9, or 0.9-1. As noted elsewhere herein, in some aspects, the formulation is substantially free of, or does not contain, a fluoride ion source other than that derived from the bioactive glass itself, if any. In some aspects, the formulation contains less than 0.5 wt. %, less than 0.1 weight percent, or less than 0.5 wt. % fluoride ion source other than that derived from the bioactive glass itself, if any.

In some aspects, the dentifrice formulations comprise one or more flavoring agents in an amount of 0 wt. % or greater than 0 wt. %. In some aspects, the dentifrice formulations comprise one or more flavoring agents in an amount of 0.5 wt. % or less. In some aspects, the dentifrice formulations comprise one or more flavoring agents in an amount (wt. %) of 0-0.5, 0-0.4, 0-0.3, 0-0.2, 0-0.1, 0-0.05, >0-0.5, >0-0.4, >0-0.3, >0-0.2, >0-0.1, >0-0.05, 0.05-0.5, 0.05-0.4, 0.05-0.3, 0.05-0.2, 0.05-0.1, 0.1-0.5, 0.1-0.4, 0.1-0.3, 0.1-0.2, 0.2-0.5, 0.2-0.4, 0.2-0.3, 0.3-0.5, 0.3-0.4, or 0.4-0.5.

In some aspects, the dentifrice, skin care, or cosmetic formulations comprise one or more surfactants. In some aspects, the one or more surfactants include sodium lauryl sulfate, poloxamer (such as an ethylene oxide/propylene oxide copolymers), and any combination thereof. In some aspects, sodium lauryl sulfate exacerbates tooth sensitivity issues and therefore in some aspects sodium lauryl sulfate is not included in the dentifrice formulations. In some aspects, the dentifrice, skin care, or cosmetic formulations comprise one or more surfactants in an amount of 0 wt. % or greater than 0 wt. %. In some aspects, the dentifrice, skin care, or cosmetic formulations comprise one or more surfactants in an amount of 5 wt. % or less. In some aspects, the dentifrice formulations comprise one or more surfactants in an amount (wt. %) of 0-5, 0-4.5, 0-4, 0-3.5, 0-3, 0-2.5, 0-2, 0-1.5, 0-1, 0-0.5, 0-0.1, >0-5, >0-4.5, >0-4, >0-3.5, >0-3, >0-2.5, >0-2, >0-1.5, >0-1, >0-0.5, >0-0.1, 0.1-5, 0.1-4.5, 0.1-4, 0.1-3.5, 0.1-3, 0.1-2.5, 0.1-2, 0.1-1.5, 0.1-1, 0.1-0.5, 0.5-5, 0.5-4.5, 0.5-4, 0.5-3.5, 0.5-3, 0.5-2.5, 0.5-2, 0.5-1.5, 0.5-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, or 4.5-5. In some aspects, the dentifrice formulation is substantially free of, or does not include, a surfactant.

In some aspects, the dentifrice formulations comprise one or more sweeteners in an amount of 0 wt. % or greater than 0 wt. %. In some aspects, the dentifrice formulations comprise one or more sweeteners in an amount of 5 wt. % or less. In some aspects, the dentifrice formulations comprise one or more surfactants in an amount (wt. %) of 0-5, 0-4.5, 0-4, 0-3.5, 0-3, 0-2.5, 0-2, 0-1.5, 0-1, 0-0.5, 0-0.1, >0-5, >0-4.5, >0-4, >0-3.5, >0-3, >0-2.5, >0-2, >0-1.5, >0-1, >0-0.5, >0-0.1, 0.1-5, 0.1-4.5, 0.1-4, 0.1-3.5, 0.1-3, 0.1-2.5, 0.1-2, 0.1-1.5, 0.1-1, 0.1-0.5, 0.5-5, 0.5-4.5, 0.5-4, 0.5-3.5, 0.5-3, 0.5-2.5, 0.5-2, 0.5-1.5, 0.5-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, or 4.5-5. In some aspects, the dentifrice formulation is substantially free of, or does not include, a sweetener.

In some aspects, the dentifrice, skin care, or cosmetic formulations comprise one or more whitening agents. In some aspects, the one or more whitening agents comprise titanium dioxide, hydrogen peroxide, sodium tripolyphosphates, or any combination thereof. In some aspects, the dentifrice, skin care, or cosmetic formulations comprise one or more whitening agents in an amount of 0 wt. % or greater than 0 wt. %. In some aspects, the dentifrice, skin care, or cosmetic formulations comprise one or more whitening agents in an amount of 2 wt. % or less. In some aspects, the dentifrice, skin care, or cosmetic formulations comprise one or more whitening agents in an amount (wt. %) of 0-2, 0-1.5, 0-1, 0-0.5, 0-0.1, >0-2, >0-1.5, >0-1, >0-0.5, >0-0.1, 0.1-2, 0.1-1.5, 0.1-1, 0.1-0.5, 0.5-2, 0.5-1.5, 0.5-1, 1-2, 1-1.5, or 1.5-2. In some aspects, the dentifrice, skin care, or cosmetic formulations do not contain a whitening agent.

In some aspects, the dentifrice, skin care, or cosmetic formulations comprise one or more abrasives. In some aspects, the one or more abrasives, skin care, or cosmetic comprise silica, zinc orthophosphate, sodium bicarbonate, alumina, calcium carbonate, calcium pyrophosphate, or any combination thereof. Although the bioactive glasses disclosed herein may have an abrasive effect in the dentifrice, skin care, or cosmetic formulations, the bioactive glasses are not considered an abrasive herein for purposes of the amounts or inclusion of the one or more abrasives. In some aspects, the dentifrice, skin care, or cosmetic formulations comprise one or more abrasives in an amount of 0 wt. % or greater than 0 wt. %. In some aspects, the dentifrice, skin care, or cosmetic formulations comprise one or more abrasives in an amount of 20 wt. % or less. In some aspects, the dentifrice, skin care, or cosmetic formulations comprise one or more abrasives in an amount (wt. %) of 0-20, 0-15, 0-10, 0-5, 0-1, 1-20, 1-15, 1-10, 1-5, 5-20, 5-15, 5-10, 10-20, 10-15, or 15-20. In some aspects, the dentifrice, skin care, or cosmetic formulations do not contain an abrasive. In some aspects, the dentifrice, skin care, or cosmetic formulations are substantially free of, or do not contain, one or more of silica, zinc orthophosphate, sodium bicarbonate, alumina, calcium carbonate, calcium pyrophosphate, or any combination thereof.

In some aspects, the dentifrice, skin care, or cosmetic formulations may comprise other ingredients that impart a desired property or characteristic to the dentifrice, skin care, or cosmetic formulations herein. For example, in some aspects, the dentifrice, skin care, or cosmetic formulations can comprise one or more of a colorant, a fragrance, a medication, a preservative, a desensitizing agent (e.g., potassium salts such as potassium nitrate), a pH modifiers, a preservative, a tartar control agent, and so forth, or any combination thereof. In some aspects, the dentifrice, skin care, or cosmetic formulations comprise one or more of such ingredients in an amount of 0 wt. % or greater than 0 wt. %. In some aspects, the dentifrice, skin care, or cosmetic compositions comprise one or more of such ingredients in an amount of 10 wt. % or less. In some aspects, the dentifrice, skin care, or cosmetic compositions comprise one or more of such ingredients in an amount (wt. %) of 0-10, 0-9, 0-8, 0-7, 0-6, 0-5, 0-4, 0-3, 0-2, 0-1, 0-0.5, >0-10, >0-9, >0-8, >0-7, >0-6, >0-5, >0-4, >0-3, >0-2, >0-1, >0-0.5, 0.5-10, 0.5-9, 0.5-8, 0.5-7, 0.5-6, 0.5-5, 0.5-4, 0.5-3, 0.5-2, 0.5-1, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. For clarity, the amounts of the one or more such ingredients can be used to describe the amount of any one of the other ingredients, or can be used to describe the sum of any two or more (including sum total amount) of the other ingredients.

In some aspects, the formulations (e.g., dentifrice, skin care, or cosmetic) comprise:

- a bioactive glass,
- optionally, an amino acid,
- water, and
- one or more of a humectant, a fluoride ion source, a flavoring, a surfactant, a sweetener, a whitening agent, an abrasive, or any combination thereof.

In some aspects, the formulations (e.g., dentifrice, skin care, or cosmetic) comprise:

- a bioactive glass,
- optionally, an amino acid,
- glycerin, oil, polymer, or any combination thereof, and
- one or more of a humectant, a fluoride ion source, a flavoring, a surfactant, a sweetener, a whitening agent, an abrasive, or any combination thereof.

In some aspects, disclosed is a method for making the formulations disclosed herein, comprising combining the bioactive glass with one or more components, such as one or more of a humectant, a fluoride ion source, a flavoring, a surfactant, a sweetener, a whitening agent, an abrasive, an amino acid, or any combination thereof. In some aspects, disclosed is a method for making the formulations disclosed herein, comprising combining the bioactive glass with a carrier. In some aspects, the carrier is a toothpaste, mouthwash, gel, varnish, rinse, spray, ointment, salve, cream, bandage, polymer film, oral formulation, pill, capsule, or transdermal formulation. In some aspects, disclosed is a method for making the formulations disclosed herein, the method comprising combining the bioactive glass, and optionally one or more of water, glycerin, a humectant, a fluoride ion source, a flavoring, a surfactant, a sweetener, a whitening agent, an abrasive, or any combination thereof.

In some aspects, disclosed is a method comprising applying the formulation to a bone. In some aspects, disclosed is a method comprising applying the composition to a tooth. In some aspects, this method is performed by an end user, for example, by way of brushing teeth with a toothpaste or swishing a mouth with a mouthwash. In some aspects, this method is performed by a professional, such as a doctor, a dentist, or other oral care professional, by way of applying the formulation to a bone, brushing a patient's teeth, directing a patient to swish their mouth with a mouthwash, applying the composition to patient's teeth, and so forth.

In some aspects, the method of applying the formulation to a bone remineralizes the bone. In some aspects, the method of applying the formulation to a tooth remineralizes the tooth. In some aspects, the method of applying the formulation to a tooth treats caries of the tooth, treats dentin hypersensitivity of the tooth, or any combination thereof. In some aspects, the method of applying the formulation to a tooth remineralizes the tooth (e.g., by forming apatite in or on the tooth, such as in or on the enamel of the tooth). In some aspects, the method of applying the formulation to a tooth treats caries of the tooth, treats dentin hypersensitivity of the tooth, or any combination thereof, remineralizes the tooth (e.g., enamel) by forming apatite, brushite, whitlockite, or a combination thereof in or on the tooth (e.g., enamel). In some aspects, the method is facilitated by contact with saliva in a mouth (e.g., a patient's mouth).

In some aspects, disclosed is a method comprising applying the formulation to skin. In some aspects, this method is performed by an end user, for example, by way of applying the formulation as a lotion, salve, etc. to their own skin, such as hands, arms, legs, and/or face. In some aspects, this method is performed by a professional, such as a doctor, a dermatologist, or other skin care professional or pseudo-professional, by way of applying the formulation to a patient's skin, directing a patient to apply the formulation to their skin, and so forth. In some aspects, the method treats or reduces the appearance of one or more skin defects, optionally wherein the one or more skin defects comprises wrinkles, blemishes, sagging skin, or any combination thereof.

Various aspects are contemplated herein, several of which are set forth in the paragraphs below. It is explicitly contemplated that any aspect or portion thereof can be combined to form a combination. Moreover, the terms "any preceding aspect" and "any one of the preceding aspects" (and similar terminology) means any aspect that appears prior to the aspect that contains such phrase (for example, the sentence "Aspect C15. The glass composition of aspect C14, or any preceding aspect, . . . " means that any aspect prior to Aspect C15 is referenced, such as C3, as well as other letter versions, such as aspect B12 and aspect A9, for example).

Aspect A1: A silicate-based glass composition, comprising:

- 15-65 wt. % $SiO_2$,
- 2.5-25 wt. % MgO,
- 1-30 wt. % $P_2O_5$, and
- 15-50 wt. % CaO.

Aspect A2. The glass composition of aspect A1, or any preceding aspect, further comprising:

- 0-5 wt. % $F^-$, and
- 0-10 wt. % $ZrO_2$.

Aspect A3. The glass composition of aspect A1 or aspect A2, or any preceding aspect, further comprising one of:

- 0-10 wt. % $Al_2O_3$,
- 0-10 wt. % SrO, and
- 0-10 wt. % ZnO.

Aspect A4. The glass composition of any one of aspects A1-A3, or any preceding aspect, wherein the glass comprises:

- 15-50 wt. % MO, and
- 0-30 wt. % $R_2O$,
- wherein MO is the sum of MgO, CaO, SrO, BeO, and BaO, and
- $R_2O$ is the sum of $Na_2O$, $K_2O$, $Li_2O$, $Rb_2O$, and $Cs_2O$.

Aspect A5. A silicate-based glass composition, comprising:

- 15-65 wt. % $SiO_2$,
- 2.5-25 wt. % MgO,
- 1-30 wt. % $P_2O_5$,
- 15-50 wt. % CaO,
- 0-5 wt. % $F^-$, and
- 0-10 wt. % $ZrO_2$.

Aspect A6. The glass composition of aspect A5, or any preceding aspect, further comprising one of:

- 0-10 wt. % $Al_2O_3$,
- 0-10 wt. % SrO, and
- 0-10 wt. % ZnO.

Aspect A7. A silicate-based glass composition, comprising:

20-55 wt. % $SiO_2$, 5-20 wt. % MgO, 5-25 wt. % $P_2O_5$, and 25-45 wt. % CaO.

Aspect A8. The glass composition of aspect A7, or any preceding aspect, further comprising:

0-3 wt. % $F^-$, and 0-6 wt. % $ZrO_2$.

Aspect A9. The glass composition of aspect A7 or aspect A8, or any preceding aspect, further comprising one of:

0-5 wt. % $Al_2O_3$, 0-5 wt. % SrO, and 0-5 wt. % ZnO.

Aspect A10. The glass composition of any one of aspects A1-A9, or any preceding aspect, further comprising:

a bioactive ceramic within fourteen days of immersion in a salt solution.

Aspect A11. The glass composition of aspect A10, or any preceding aspect, wherein the bioactive ceramic is brushite and the salt solution is potassium phosphate.

Aspect A12. The glass composition of any one of aspects A1-A11, or any preceding aspect, having a melting temperature of below 1300° C.

Aspect A13. The glass composition of any one of aspects A1-A12, or any preceding aspect, wherein a sum of $P_2O_5$ and CaO is from 25-65 wt. %.

Aspect A14. The glass composition of any one of aspects A1-A13, or any preceding aspect, further comprising:

an apatite when immersed in a simulated body fluid (SBF).

Aspect A15. The glass composition of any one of aspects A1-A14, or any preceding aspect, essentially free of $Na_2O$ and $K_2O$.

Aspect A16. The glass composition of any one of aspects A1-A15, or any preceding aspect, being a particle, bead, particulate, short fiber, long fiber, woolen mesh, combination thereof.

Aspect A17. The glass composition of aspect 16, or any preceding aspect, having at least one size dimension in a range of 1-100 μm.

Aspect A18. A matrix comprising the glass composition of any one of aspects A1-A17, or any preceding aspect, wherein:

the matrix includes at least one of: a toothpaste, mouthwash, rinse, spray, ointment, salve, cream, bandage, polymer film, oral formulation, pill, capsule, or transdermal formulation.

Aspect A19. The matrix of aspect A18, or any preceding aspect, wherein the glass composition is attached to the matrix or mixed therein.

Aspect A20. An aqueous environment comprising the glass composition of any one of aspects A1-A19, or any preceding aspect.

Aspect B1. A silicate-based glass composition, comprising:

15-65 wt. % $SiO_2$, 2.5-25 wt. % MgO, 1-30 wt. % $P_2O_5$, and 15-50 wt. % CaO, wherein the composition:

has a hydrolytic resistance of glass grains (HGB) of at most 4.5 or at most 4 (e.g., or at most 3), when measured by International Organization for Standardization section 719 (ISO 719), and forms a bioactive crystalline phase in a simulated body fluid.

Aspect B2. The glass composition of aspect 1, further comprising:

>0-5 wt. % F.

Aspect B3. The glass composition of any one of aspect B1 or aspect B2, or any preceding aspect, further comprising one of:

>0-10 wt. % $Li_2O$,

>0-10 wt. % $Na_2O$, or

>0-10 wt. % $K_2O$.

Aspect B4. The glass composition of any one of aspects B1-B3, or any preceding aspect, further comprising:

>0 to 10 wt. % $ZrO_2$.

Aspect B5. The glass composition of any one of aspects B1-B4, or any preceding aspect, further comprising:

0-10 wt. % $Al_2O_3$, 0-10 wt. % SrO, 0-10 wt. % ZnO, and 0-5 wt. % $B_2O_3$.

Aspect B6. The glass composition of any one of aspects B1-B5, or any preceding aspect, wherein the glass comprises:

15-50 wt. % MO, and 0-30 wt. % $R_2O$, wherein MO is the sum of MgO, CaO, SrO, BeO, and BaO, and $R_2O$ is the sum of $Na_2O$, $K_2O$, $Li_2O$, $Rb_2O$, and $Cs_2O$.

Aspect B7. The glass composition of any one of aspects B1-B6, or any preceding aspect, wherein the bioactive crystalline phase comprises apatite.

Aspect B8. The glass composition of any one of aspects B1-B7, or any preceding aspect, wherein a sum of $P_2O_5$ and CaO is from 25-65 wt. %.

Aspect B9. A silicate-based glass composition, comprising:

30-50 wt. % $SiO_2$, 10-20 wt. % MgO, 5-15 wt. % $P_2O_5$, and 25-40 wt. % CaO, wherein the composition:

has a hydrolytic resistance of glass grains (HGB) of at most 4.5 or at most 4 (e.g., or at most 3), when measured by International Organization for Standardization section 719 (ISO 719), and forms a bioactive crystalline phase in a simulated body fluid.

Aspect B10. The glass composition of aspect B9, or any preceding aspect, further comprising:

>0-3 wt. % $F^-$.

Aspect B11. The glass composition of any one of aspect B9 or aspect B10, or any preceding aspect, further comprising one of:

>0-10 wt. % $Li_2O$,

>0-10 wt. % $Na_2O$, or

>0-10 wt. % $K_2O$.

Aspect B12. The glass composition of any one of aspects B9-B11, or any preceding aspect, further comprising:

>0 to 10 wt. % $ZrO_2$.

Aspect B13. The glass composition of any one of aspects B9-B12, or any preceding aspect, wherein the bioactive crystalline phase comprises apatite.

Aspect B14. The glass composition of aspects B9-B13, or any preceding aspect, wherein a sum of $P_2O_5$ and CaO is from 25-65 wt. %.

Aspect B15. A matrix comprising the glass composition of any one of aspects B1-B14, or any preceding aspect, wherein:

the matrix includes at least one of: a toothpaste, mouthwash, rinse, spray, ointment, salve, cream, bandage, polymer film, oral formulation, pill, capsule, or transdermal formulation.

Aspect B16. The matrix of aspect B15, or any preceding aspect, wherein the glass composition is attached to the matrix or mixed therein.

Aspect B17. An aqueous environment comprising the glass composition of any one of aspects B1-B16, or any preceding aspect.

Aspect C1. A silicate-based glass composition, comprising:

15-65 wt. % $SiO_2$, 15-50 wt. % CaO, 1-30 wt. % $P_2O_5$, and 1-20 wt. % $ZrO_2$, wherein the composition has a hydrolytic resistance of glass grains (HGB) of at most 4.5 or at most 4 (e.g., or at most 3), when measured by International Organization for Standardization section 719 (ISO 719), and forms a bioactive crystalline phase in simulated body fluid.

Aspect C2. The glass composition of aspect C1, or any preceding aspect, comprising:

15-45 wt. % $SiO_2$, 30-60 wt. % CaO, 8-30 wt. % $P_2O_5$, and 2-15 wt. % $ZrO_2$.

Aspect C3. The glass composition of any one of aspects C1-C2, or any preceding aspect, further comprising >0-25 wt. % MgO.

Aspect C4. The glass composition of any one of aspects C1-C3, or any preceding aspect, further comprising 3-15 wt. % MgO.

Aspect C5. The glass composition of any one of aspects C1-C4, or any preceding aspect, further comprising >0-25 wt. % SrO.

Aspect C6. The glass composition of any one of aspects C1-C5, or any preceding aspect, further comprising 10-20 wt. % SrO.

Aspect C7. The glass composition of any one of aspects C1-C6, or any preceding aspect, further comprising >0-25 wt. % ZnO.

Aspect C8. The glass composition of any one of aspects C1-C7, or any preceding aspect, further comprising 10-20 wt. % ZnO.

Aspect C9. The glass composition of any one of aspects C1-C8, or any preceding aspect, wherein the glass comprises:

15-50 wt. % MO, and 0-30 wt. % $R_2O$, wherein MO is the sum of MgO, CaO, SrO, BeO, and BaO, and $R_2O$ is the sum of $Na_2O$, $K_2O$, $Li_2O$, $Rb_2O$, and $Cs_2O$.

Aspect C10. The glass composition of any one of aspects C1-C9, or any preceding aspect, wherein the bioactive crystalline phase comprises apatite.

Aspect C11. The glass composition of aspect C10, or any preceding aspect, wherein the apatite is hydroxyapatite.

Aspect C12. The glass composition of any one of aspects C1-C11, or any preceding aspect, wherein a sum of $P_2O_5$ and CaO is from 25-65 wt. %.

Aspect C13. The glass composition of any one of aspects C1-C12, or any preceding aspect, wherein the simulated body fluid is an artificial saliva.

Aspect C14. A silicate-based glass composition, comprising:

15-45 wt. % $SiO_2$, 30-60 wt. % CaO, 8-30 wt. % $P_2O_5$, and 2-15 wt. % $ZrO_2$, wherein the composition has a hydrolytic resistance of glass grains (HGB) of at most 4.5 or at most 4 (e.g., or at most 3), when measured by International Organization for Standardization section 719 (ISO 719), and forms an apatite crystalline phase in an artificial saliva, and wherein a sum of $P_2O_5$ and CaO is from 25-65 wt. %.

Aspect C15. The glass composition of aspect C14, or any preceding aspect, further comprising 3-15 wt. % MgO.

Aspect C16. The glass composition of any one of aspects C14-C15, or any preceding aspect, further comprising 10-20 wt. % SrO.

Aspect C17. The glass composition of any one of aspects C14-C16, or any preceding aspect, further comprising 10-20 wt. % ZnO.

Aspect 18. The glass composition of any one of aspects C14-C17, or any preceding aspect, wherein the apatite is hydroxyapatite.

Aspect C19. A matrix comprising the glass composition of any one of aspects C1-C12, or any preceding aspect, wherein:

the glass composition is attached to the matrix or mixed therein, and the matrix includes at least one of: a toothpaste, mouthwash, rinse, spray, ointment, salve, cream, bandage, polymer film, oral formulation, pill, capsule, or transdermal formulation.

Aspect C20. An aqueous environment comprising the glass composition of any one of aspects C1-C12, or any preceding aspect.

Aspect D1: A dentifrice formulation comprising: a solvent; a humectant; and a bioactive glass, wherein the bioactive glass comprises: greater than or equal to 15 wt % and less than or equal to 45 wt % $SiO_2$, greater than or equal to 30 wt % and less than or equal to 60 wt % CaO, greater than or equal to 8 wt % and less than or equal to 30 wt % $P_2O_5$, and greater than or equal to 2 wt % and less than or equal to 15 wt % $ZrO_2$.

Aspect D2: the dentifrice formulation of aspect D1, or any preceding aspect, wherein the bioactive glass comprises: greater than or equal to 20.0 wt % and less than or equal to 39.5 wt % $SiO_2$; greater than or equal to 0.0 wt % and less than or equal to 14.5 wt % MgO; greater than or equal to 32.5 wt % and less than or equal to 47.0 wt % CaO; greater than or equal to 0.0 wt % and less than or equal to 14.5 wt % SrO; greater than or equal to 0.0 wt % and less than or equal to 14.5 wt % ZnO; greater than or equal to 9.5 wt % and less than or equal to 24.5 wt % $P_2O_5$; and greater than or equal to 4.0 wt % and less than or equal to 10.0 wt % $ZrO_2$.

Aspect D3: the dentifrice formulation of aspects D1 or D2, or any preceding aspect, wherein the bioactive glass has a weight loss that is less than or equal to 5 wt % after 7 days of exposure in deionized water.

Aspect D4: the dentifrice formulation of any of aspects D1-D3, or any preceding aspect, wherein the solvent is an aqueous solvent.

Aspect D5: the dentifrice formulation of any of aspects D1-D3, or any preceding aspect, wherein the solvent is a non-aqueous solvent.

Aspect D6: the dentifrice formulation of aspect D5, or any preceding aspect, wherein the solvent is glycerin.

Aspect D7: the dentifrice formulation of any of aspects D1-D6, or any preceding aspect, wherein the dentifrice formulation comprises: greater than or equal to 1 wt % and less than or equal to 20 wt % solvent; greater than or equal to 2 wt % and less than or equal to 50 wt % humectant; and greater than or equal to 1 wt % and less than or equal to 20 wt % bioactive glass.

Aspect D8: the dentifrice formulation of any of aspects D1-D7, or any preceding aspect, wherein the humectant is a short-chained polyalcohol selected from the group consisting of glycerol, sorbitol, propylene glycol, and polyethylene glycol.

Aspect D9: the dentifrice formulation of any of aspects D1-D8, or any preceding aspect, further comprising one or more of a fluoride ion source, a flavoring, a surfactant, a sweetener, a whitening agent, and an abrasive.

Aspect D10: the dentifrice formulation of aspect D9, or any preceding aspect, wherein the dentifrice formulation comprises a fluoride ion source selected from the group consisting of sodium fluoride, potassium fluoride, ammonium fluoride, monofluorophosphates, and mixtures thereof.

Aspect D11: the dentifrice formulation of aspect D10, or any preceding aspect, wherein the dentifrice formulation comprises greater than or equal to 0.01 wt % and less than or equal to 1.00 wt % of fluoride ions.

Aspect D12: the dentifrice formulation of any of aspects D9-D11, or any preceding aspect, wherein the dentifrice formulation comprises greater than or equal to 0.05 wt % and less than or equal to 5.00 wt % flavoring.

Aspect D13: the dentifrice formulation of any of aspects D9-D12, or any preceding aspect, wherein the dentifrice formulation comprises a surfactant selected from the group consisting of sodium lauryl sulfate, poloxamer, and mixtures thereof.

Aspect D14: the dentifrice formulation of aspect D13, or any preceding aspect, wherein the dentifrice formulation comprises greater than or equal to 0.1 wt % and less than or equal to 5.0 wt % surfactant.

Aspect D15: the dentifrice formulation of any of aspects D9-D14, or any preceding aspect, wherein the dentifrice formulation comprises greater than or equal to 0.1 wt % and less than or equal to 5.0 wt % sweetener.

Aspect D16: the dentifrice formulation of any of aspects D9-D15, or any preceding aspect, wherein the dentifrice formulation comprises a whitening agent selected from the group consisting of titanium dioxide, hydrogen peroxide, sodium tripolyphosphates, and mixtures thereof.

Aspect D17: the dentifrice formulation of aspect D16, or any preceding aspect, wherein the dentifrice formulation comprises greater than or equal to 0.1 wt % and less than or equal to 2.0 wt % whitening agents.

Aspect D18: the dentifrice formulation of any of aspects D9-D17, or any preceding aspect, wherein the dentifrice formulation comprises an abrasive selected from the group consisting of silica, zinc orthophosphate, sodium bicarbonate, alumina, calcium carbonate, calcium pyrophosphate, and mixtures thereof.

Aspect D19: the dentifrice formulation of aspect D18, or any preceding aspect, wherein the dentifrice formulation comprises greater than or equal to 0.1 wt % and less than or equal to 20.0 wt % abrasives.

Aspect D20: the dentifrice formulation of any of aspects D1-D19, or any preceding aspect, wherein the dentifrice formulation comprises: greater than or equal to 2 wt % and less than or equal to 15 wt % bioactive glass; greater than or equal to 30 wt % and less than or equal to 45 wt % solvent; greater than or equal to 40 wt % and less than or equal to 50 wt % humectant; greater than or equal to 0.2 wt % and less than or equal to 1.0 wt % fluoride ions; greater than or equal to 0.5 wt % and less than or equal to 1.5 wt % flavoring; greater than or equal to 0.5 wt % and less than or equal to 1.5 wt % surfactant; greater than or equal to 0.1 wt % and less than or equal to 0.5 wt % sweetener; greater than or equal to 2 wt % and less than or equal to 8 wt % abrasives; and greater than or equal to 0.1 wt % and less than or equal to 0.5 wt % whitening agents.

Aspect E1: A glass composition, comprising:

15-45 wt. % $SiO_2$;

10-30 wt. % $P_2O_5$;

30-60 wt. % CaO;

0.5-15 wt. % $ZrO_2$;

0.1-10 wt. % F;

0-25 wt. % MgO;

0-5 wt. % $B_2O_3$;

0-5 wt. % $Al_2O_3$;

0-10 wt. % $Li_2O$;

0-10 wt. % $Na_2O$;

0-10 wt. % $K_2O$;

0-10 wt. % SrO;

0-10 wt. % ZnO; and $Li_2O+Na_2O+K_2O$ of less than or equal to 10 wt. %;

based on total weight of the glass composition.

Aspect E2: The glass composition of aspect E1, or any preceding aspect, wherein the glass composition is a glass-ceramic comprising a fluorapatite crystal phase.

Aspect E3: The glass composition of aspect E2, or any preceding aspect, wherein the fluorapatite crystal phase is the major crystalline phase.

Aspect E4: The glass composition of aspect E2 or E3, or any preceding aspect, further comprising at least one minor crystalline phase of calcium silicate, calcium phosphate, calcium fluoride, or any combination thereof.

Aspect E5: The glass composition of any one of aspects E1-E4, or any preceding aspect, wherein the glass composition is a glass-ceramic comprising a glass phase in an amount of at least 5 wt. %, based on total weight of the glass-ceramic.

Aspect E6: The glass composition of any one of aspects E1-E5, or any preceding aspect, wherein the glass composition is a glass-ceramic comprising a total crystallinity of 5-50 wt. %.

Aspect E7: The glass composition of any one of aspects E1-E6, or any preceding aspect, wherein the F is derived from calcium fluoride, magnesium fluoride, sodium fluoride, potassium fluoride, stannous fluoride, sodium monofluorophosphate, sodium difluorophosphate, or any combination thereof.

Aspect E8: The glass composition of any one of aspects E1-E7, or any preceding aspect, comprising:

25-45 wt. % $SiO_2$;

10-25 wt. % $P_2O_5$;

37-50 wt. % CaO;

0.5-8 wt. % $ZrO_2$;

0.1-5 wt. % F;

>0-10 wt. % MgO;

based on total weight of the glass composition.

Aspect E9: The glass composition of any one of aspects E1-E8, or any preceding aspect, comprising $Li_2O+Na_2O+$ $K_2O$ in an amount of less than or equal to 0.5 wt. %, based on total weight of the glass composition.

Aspect E10: The glass composition of any one of aspects E1-E9, or any preceding aspect, comprising:

at least one of:

>0-25 wt. % MgO;

>0-5 wt. % $B_2O_3$;

>0-5 wt. % $Al_2O_3$;

>0-10 wt. % $Li_2O$;

>0-10 wt. % $Na_2O$;

>0-10 wt. % $K_2O$;

>0-10 wt. % SrO; or

>0-10 wt. % ZnO;

provided that $Li_2O+Na_2O+K_2O$ is less than or equal to 10 wt. %;

based on total weight of the glass composition.

Aspect E11: The glass composition of any one of aspects E1-E10, or any preceding aspect, wherein the glass composition is in a form of particulates, microbeads, fibers, or a combination thereof.

Aspect E12: A matrix comprising the glass composition of any one of aspects E1-E11, or any preceding aspect, wherein:

the glass composition is attached to the matrix or mixed therein, and the matrix includes at least one of: a toothpaste, mouthwash, gel, varnish, rinse, spray, ointment, salve, cream, bandage, polymer film, oral formulation, pill, capsule, or transdermal formulation.

Aspect E13: The matrix of aspect E12, or any preceding aspect, wherein the matrix is a dentifrice composition.

Aspect E14: The matrix of aspect E13, or any preceding aspect, wherein the dentifrice composition comprises:

>0-20 wt. % of the glass composition, based on total weight of the matrix, solvent, and one or more of a humectant, a fluoride ion source, a flavoring, a surfactant, a sweetener, a whitening agent, an abrasive, or any combination thereof.

Aspect E15: A method for making the matrix of any one of aspects E12-E14, or any preceding aspect, comprising combining a carrier with the glass composition.

Aspect E16: A method comprising applying to a tooth the dentifrice composition of aspect E13 or E14, or any preceding aspect.

Aspect E17: The method of aspect E16, or any preceding aspect, wherein the method remineralizes enamel of a tooth, treats caries of a tooth, treats dentin hypersensitivity of the tooth, or any combination thereof.

Aspect E18: A method for making the glass composition of any one of aspects E1-E11, or any preceding aspect, comprising:

combining each component of the glass composition to form a mixture;

heating the mixture to a temperature of 1500° C. or less to form a melted mixture; and cooling the melted mixture to form a cooled mixture.

Aspect E19: The method of aspect E18, or any preceding aspect, wherein the cooling step spontaneously results in at least partial crystallization into a fluorapatite crystal phase.

Aspect E20: The method of aspect E18 or E19, or any preceding aspect, wherein, after the cooling step, the cooled mixture is not heated to a crystallization temperature.

Aspect E21: The method of any one of aspects E18-E20, or any preceding aspect, further comprising forming the cooled mixture into particulates, microbeads, or a combination thereof.

Aspect E22: A combination of any two or more of aspects 1-21, or any one or more portions thereof.

Aspect F1: A glass composition, comprising:

15-50 wt. % $SiO_2$, 25-60 wt. % CaO, 3-30 wt. % $P_2O_5$, 0.5-15 wt. % $ZrO_2$, and >0-5 wt. % $F^-$, wherein, when subjected to artificial saliva of Table 1A or Table 1B, the glass composition forms a bioactive crystalline phase.

Aspect F2: The glass composition of aspect F1, or any preceding aspect, comprising:

25-45 wt. % $SiO_2$, 30-50 wt. % CaO, 5-25 wt. % $P_2O_5$, 2-10 wt. % $ZrO_2$, and 0.01-3 wt. % F.

Aspect F3: The glass composition of any one of aspects F1-F2, or any preceding aspect, comprising >0-25 wt. % MgO.

Aspect F4: The glass composition of any one of aspects F1-F3, or any preceding aspect, comprising >0-5 wt. % $B_2O_3$.

Aspect F5: The glass composition of any one of aspects F1-F4, or any preceding aspect, comprising >0-5 wt. % $Al_2O_3$.

Aspect F6: The glass composition of any one of aspects F1-F5, or any preceding aspect, comprising >0-10 wt. % $Li_2O$.

Aspect F7: The glass composition of any one of aspects F1-F6, or any preceding aspect, comprising >0-10 wt. % $Na_2O$.

Aspect F8: The glass composition of any one of aspects F1-F7, or any preceding aspect, comprising >0-10 wt. % $K_2O$.

Aspect F9: The glass composition of any one of aspects F1-F8, or any preceding aspect, comprising >0-10 wt. % SrO.

Aspect F10: The glass composition of any one of aspects F1-F9, or any preceding aspect, comprising >0-10 wt. % ZnO.

Aspect F11: The glass composition of any one of aspects F1-F10, or any preceding aspect, comprising $Li_2O+Na_2O+K_2O$ in an amount of 10 wt. % or less.

Aspect F12: The glass composition of any one of aspects F1-F11, or any preceding aspect, comprising $F^-+P_2O_5$ in an amount of 5-30 wt. %.

Aspect F13: The glass composition of any one of aspects F1-F12, or any preceding aspect, comprising MgO+CaO in an amount of 30-70 wt. %.

Aspect F14: The glass composition of any one of aspects F1-F13, or any preceding aspect, comprising $CaO+P_2O_5$ in an amount of 40-70 wt. %.

Aspect F15: The glass composition of any one of aspects F1-F14, or any preceding aspect, wherein the $F^-$ is derived from calcium fluoride, magnesium fluoride, sodium fluoride, potassium fluoride, stannous fluoride, sodium monofluorophosphate, sodium difluorophosphate, or any combination thereof.

Aspect F16: The glass composition of any one of aspects F1-F15, or any preceding aspect, wherein the glass composition is substantially free of, or does not contain, a crystalline phase.

Aspect F17: The glass composition of any one of aspects F1-F16, or any preceding aspect, wherein, when subjected to artificial saliva of Table 1A or Table 1B, the bioactive crystalline phase comprises apatite.

Aspect F18: The glass composition of aspect F17, or any preceding aspect, wherein the apatite comprises hydroxyapatite, fluorapatite, carbonated apatite, or any combination thereof.

Aspect F19: The glass composition of any one of aspects F1-F18, or any preceding aspect, wherein the artificial saliva has the composition of Table 1B.

Aspect F20: The glass composition of any one of aspects F1-F19, or any preceding aspect, wherein the glass composition is in a form of particulates, microbeads, fibers or a combination thereof.

Aspect F21: A matrix comprising the glass composition of any one of aspects F1-F20, or any preceding aspect, wherein:

- the glass composition is attached to the matrix or mixed therein, and
- the matrix includes at least one of: a toothpaste, mouthwash, gel, varnish, rinse, spray, ointment, salve, cream, bandage, polymer film, oral formulation, pill, capsule, or transdermal formulation.

Aspect F22: The matrix of aspect F21, or any preceding aspect, wherein the matrix is substantially free of, or does not include, a fluoride ion source.

Aspect F23: The matrix of aspect F21 or F22, or any preceding aspect, wherein the matrix is a dentifrice composition.

Aspect F24: The matrix of aspect F23, or any preceding aspect, wherein the dentifrice composition comprises:

- >0-20 wt. % of the glass composition, based on total weight of the matrix, water, and
- one or more of a humectant, a fluoride ion source, a flavoring, a surfactant, a sweetener, a whitening agent, an abrasive, or any combination thereof.

Aspect F25: The matrix of aspect F23, or any preceding aspect, wherein the dentifrice composition comprises:

- >0-20 wt. % of the glass composition, based on total weight of the matrix, glycerin, and
- one or more of a humectant, a fluoride ion source, a flavoring, a surfactant, a sweetener, a whitening agent, an abrasive, or any combination thereof.

Aspect F26: A method for making the matrix of any one of aspects F21-F25, or any preceding aspect, comprising combining the glass composition with a carrier.

Aspect F27: A method comprising applying to a tooth the matrix of any one of aspects F21-F26, or any preceding aspect.

Aspect F28: The method of aspect F27, or any preceding aspect, wherein the method remineralizes enamel of the tooth, treats caries of the tooth, treats dentin hypersensitivity of the tooth, or any combination thereof.

Aspect F29: A method for making the glass composition of any one of aspects F1-F20, or any preceding aspect, comprising:

- combining each component of the glass composition to form a mixture,
- heating the mixture to a temperature of 1500° C. or less to form a melted mixture, and
- cooling the melted mixture to form a cooled mixture.

Aspect F30: The method of aspect F29, or any preceding aspect, further comprising forming the cooled mixture into particulates, microbeads, fibers, or a combination thereof.

Aspect F31: A combination of any two or more of aspects F1-F30, or any one or more portions thereof.

Aspect G1: An aqueous dentifrice formulation, comprising:

- a carrier; and
- a bioactive glass exhibiting at least one of:
  - a hydrolytic resistance of glass grains (HGB) of at most 4, when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum substantially free of crystalline phase after soaking 5 g of the bioactive glass in powder form in 100 mL of deionized water for 7 days at 37° C.; or
  - any combination thereof;

wherein, when the bioactive glass is contacted with artificial saliva, the bioactive glass forms a bioactive crystalline phase.

Aspect G2: The aqueous dentifrice formulation of aspect G1, or any preceding aspect, wherein the bioactive glass releases less than 600 ppm of sodium ions and less than 150 ppm of silicon ions upon soaking 5 g of the bioactive glass in powder form in 100 mL of deionized water for 7 days at 37° C., when measured using inductively coupled plasma—optical emission spectrometer (ICP-OES).

Aspect G3: The aqueous dentifrice formulation of aspect G1 or G2, or any preceding aspect, wherein the bioactive crystalline phase forms within 1 day when contacted with the artificial saliva.

Aspect G4: The aqueous dentifrice formulation of any one of aspects G1-G3, or any preceding aspect, wherein the bioactive crystalline phase forms within 7 days when contacted with the artificial saliva.

Aspect G5: The aqueous dentifrice formulation of any one of aspects G1-G4, or any preceding aspect, wherein the bioactive crystalline phase comprises apatite, brushite, whitlockite, or a combination thereof.

Aspect G6: The aqueous dentifrice formulation of aspect G5, or any preceding aspect, wherein the bioactive crystalline phase comprises apatite, and the apatite comprises hydroxyapatite, fluorapatite, carbonated apatite, or any combination thereof.

Aspect G7: The aqueous dentifrice formulation of any one of aspects G1-G6, or any preceding aspect, wherein the artificial saliva has the composition of Table 1A or Table 1B.

Aspect G8: The aqueous dentifrice formulation of any one of aspects G1-G7, or any preceding aspect, wherein the bioactive glass comprises:

- 15-65 wt. % $SiO_2$;
- 15-60 wt. % CaO; and
- 1-30 wt. % $P_2O_5$.

Aspect G9: The aqueous dentifrice formulation of aspect G8, or any preceding aspect, wherein the bioactive glass further comprises:

- >0-20 wt. % $ZrO_2$.

Aspect G10: The aqueous dentifrice formulation of aspect G8 or G9, or any preceding aspect, wherein the bioactive glass further comprises:

- >0-10 wt. % $F^-$.

Aspect G11: The aqueous dentifrice formulation of aspect G10, or any preceding aspect, wherein $F^-$ in the bioactive glass is derived from calcium fluoride, magnesium fluoride, sodium fluoride, potassium fluoride, stannous fluoride, sodium monofluorophosphate, sodium difluorophosphate, or any combination thereof.

Aspect G12: The aqueous dentifrice formulation of any one of aspects G8-G10, or any preceding aspect, wherein the bioactive glass further comprises at least one of:

- >0-25 wt. % MgO;
- >0-25 SrO;
- >0-25 ZnO;

>0-5 $B_2O_3$;

>0-10 $Al_2O_3$;

0-10 $Li_2O$;

0-10 $Na_2O$;

0-10 $K_2O$;

15-70 wt. % MO, wherein MO is the sum of MgO, CaO, SrO, BeO, and BaO;

0-30 wt. % $R_2O$, wherein $R_2O$ is the sum of $Na_2O$, $K_2O$, $Li_2O$, $Rb_2O$, and $Cs_2O$;

0-10 wt. % $Li_2O+Na_2O+K_2O$;

20-70 wt. % $CaO+P_2O_5$;

5-35 wt. % $F^-+P_2O_5$; or any combination thereof.

Aspect G13: The aqueous dentifrice formulation of any one of aspects G1-G12, or any preceding aspect, wherein the bioactive glass comprises a crystalline phase optionally selected from apatite, brushite, calcium silicate, calcium phosphate, calcium fluoride, whitlockite, or any combination thereof.

Aspect G14: The aqueous dentifrice formulation of any one of aspects G1-G12, or any preceding aspect, wherein the bioactive glass is substantially free of a crystalline phase.

Aspect G15: The aqueous dentifrice formulation of any one of aspects G1-G14, or any preceding aspect, wherein the bioactive glass is in a form of particulates, microbeads, fibers, or any combination thereof.

Aspect G16: The aqueous dentifrice formulation of any one of aspects G1-G15, or any preceding aspect, wherein the bioactive glass is present in the aqueous dentifrice formulation in an amount of >0-20 wt. %.

Aspect G17: The aqueous dentifrice formulation of any one of aspects G1-G16, or any preceding aspect, further comprising an amino acid, optionally in an amount of >0-40 wt. %.

Aspect G18: The aqueous dentifrice formulation of aspect G17, or any preceding aspect, wherein the amino acid is glycine, glutamic acid, arginine, or any combination thereof.

Aspect G19: The aqueous dentifrice formulation of any one of aspects G1-G18, or any preceding aspect, further comprising at least one of a humectant, a fluoride ion source, a flavoring, a surfactant, a sweetener, a whitening agent, an abrasive, or any combination thereof.

Aspect G20: The aqueous dentifrice formulation of any one of aspects G1-G19, or any preceding aspect, wherein the aqueous dentifrice formulation is substantially free of a fluoride ion source other than that derived from the bioactive glass, if any.

Aspect G21: The aqueous dentifrice formulation of any one of aspects G1-G20, or any preceding aspect, wherein the aqueous dentifrice formulation is in a form of a toothpaste, mouthwash, gel, varnish, rinse, spray, ointment, salve, cream, or oral formulation.

Aspect G22: A method comprising applying to a tooth the aqueous dentifrice formulation of any one of aspects G1-G21, or any preceding aspect.

Aspect G23: The method of aspect G22, or any preceding aspect, wherein the method remineralizes enamel of the tooth, treats caries of the tooth, treats dentin hypersensitivity of the tooth, or any combination thereof.

Aspect G24: A method for making the aqueous dentifrice formulation of any one of aspects G1-G23, or any preceding aspect, comprising combining the bioactive glass with the carrier.

Aspect G25: A bioactive glass, comprising:

at least one of:

a hydrolytic resistance of glass grains (HGB) of at most 4, when measured by International Organization for Standardization section 719 (ISO 719);

a weight loss of 5 wt. % or less after soaking 5 g of the bioactive glass in powder form in 100 mL of deionized water for 7 days at 37° C.;

an XRD spectrum substantially free of crystalline phase after soaking 5 g of the bioactive glass in powder form in 100 mL of deionized water for 7 days at 37° C.; or any combination thereof;

wherein, when the bioactive glass is contacted with artificial saliva, the bioactive glass forms a bioactive crystalline phase.

Aspect G26: The bioactive glass of aspect G25, or any preceding aspect, wherein the bioactive crystalline phase forms within 1 day or within 7 days when contacted with the artificial saliva.

Aspect G27: The bioactive glass of aspect G25 or G26, or any preceding aspect, wherein the artificial saliva has the composition of Table 1A or Table 1B.

Aspect G28: The bioactive glass of any one of aspects G25-G27, or any preceding aspect, wherein the bioactive crystalline phase comprises apatite, brushite, whitlockite, or a combination thereof.

Aspect G29: The bioactive glass of any one of aspects G25-G28, or any preceding aspect, wherein the bioactive crystalline phase comprises apatite, and the apatite comprises hydroxyapatite, fluorapatite, carbonated apatite, or any combination thereof.

Aspect G30: The bioactive glass of any one of aspects G25-G28, or any preceding aspect, comprising:

15-65 wt. % $SiO_2$;

15-60 wt. % CaO; and 1-30 wt. % $P_2O_5$.

Aspect G31: The bioactive glass of aspect 30, or any preceding aspect, further comprising at least one of:

>0-20 wt. % $ZrO_2$;

>0-10 wt. % F;

>0-25 wt. % MgO;

>0-25 SrO;

>0-25 ZnO;

>0-5 $B_2O_3$;

>0-10 $Al_2O_3$;

0-10 $Li_2O$;

0-10 $Na_2O$;

0-10 $K_2O$;

15-70 wt. % MO, wherein MO is the sum of MgO, CaO, SrO, BeO, and BaO;

0-30 wt. % $R_2O$, wherein $R_2O$ is the sum of $Na_2O$, $K_2O$, $Li_2O$, $Rb_2O$, and $Cs_2O$;

0-10 wt. % $Li_2O+Na_2O+K_2O$;

20-70 wt. % $CaO+P_2O_5$;

5-35 wt. % $F^-+P_2O_5$; or any combination thereof.

Aspect G32: A composition comprising the bioactive glass of any one of aspects G25-G31, or any preceding aspect, wherein the composition is in a form of a toothpaste, mouthwash, gel, varnish, rinse, spray, ointment, salve, cream, bandage, polymer film, oral formulation, pill, capsule, transdermal formulation, cosmetic formulation, or any combination thereof.

Aspect G33: A non-aqueous dentifrice formulation comprising the bioactive glass of any one of aspects G25-G31, or any preceding aspect.

Aspect G34: A method for making the bioactive glass of any one of aspects G25-G31, or any preceding aspect, comprising:

combining each component of the bioactive glass to form a mixture, heating the mixture to a temperature of 1500° C. or less to form a melted mixture, and cooling the melted mixture to form a cooled mixture.

Aspect G35: The method of aspect G34, or any preceding aspect, further comprising forming the cooled mixture into particulates, microbeads, fibers, or a combination thereof.

Aspect G36: A combination of any two or more of aspects G1-G35, or any one or more portions thereof.

Aspect H1: A composition, comprising:

an amino acid; and a bioactive glass, comprising:

25-55 wt. % $SiO_2$;

0.1-15 wt. % $ZrO_2$;

20-55 wt. % CaO; and 5-30 wt. % $P_2O_5$;

wherein, when the composition is subjected to artificial saliva of Table 1A or 1B, a bioactive crystalline phase is formed within 7 days.

Aspect H2: The composition of aspect H1, or any preceding aspect, wherein, when the composition is subjected to the artificial saliva of Table 1A or 1B, the bioactive glass forms a bioactive crystalline phase within 1 day.

Aspect H3: The composition of aspect H1 or H2, or any preceding aspect, wherein the artificial saliva has the composition of Table 1A.

Aspect H4: The composition of any one of aspects H1-H3, or any preceding aspect, wherein the artificial saliva has the composition of Table 1B.

Aspect H5: The composition of any one of aspects H1-H4, or any preceding aspect, wherein the bioactive crystalline phase comprises apatite, brushite, or a combination thereof.

Aspect H6: The composition of aspect H5, or any preceding aspect, wherein the apatite comprises hydroxyapatite, fluorapatite, carbonated apatite, or any combination thereof.

Aspect H7: The composition of any one of aspects H1-H6, or any preceding aspect, wherein the bioactive glass is present in an amount of >0-20 wt. %, based on total weight of the composition.

Aspect H8: The composition of any one of aspects H1-H7, or any preceding aspect, wherein the bioactive glass is in a form of particulates, microbeads, or a combination thereof.

Aspect H9: The composition of any one of aspects H1-H8, or any preceding aspect, wherein the bioactive glass comprises:

25-35 wt. % $SiO_2$;

35-50 wt. % CaO; and 15-25 wt. % $P_2O_5$;

based on total weight of the bioactive glass.

Aspect H10: The composition of any one of aspects H1-H9, or any preceding aspect, wherein the bioactive glass comprises: 3-12 wt. % $ZrO_2$, based on total weight of the bioactive glass.

Aspect H11: The composition of any one of aspects H1-H10, or any preceding aspect, wherein the bioactive glass comprises: >0-10 wt. % MgO, based on total weight of the bioactive glass.

Aspect H12: The composition of any one of aspects H1-H11, or any preceding aspect, wherein the bioactive glass comprises: >0-5 wt. % $F^-$, based on total weight of the bioactive glass.

Aspect H13: The composition of any one of aspects H1-H12, or any preceding aspect, wherein the bioactive glass comprises: 0-5 wt. % $Na_2O+K_2O+Li_2O$, based on total weight of the bioactive glass.

Aspect H14: The composition of any one of aspects H1-H13, or any preceding aspect, wherein the bioactive glass comprises: $CaO+P_2O_5$ in an amount of 40-70 wt. %, based on total weight of the bioactive glass.

Aspect H15: The composition of any one of aspects H1-H14, or any preceding aspect, wherein the F in the bioactive glasses is derived from calcium fluoride, magnesium fluoride, sodium fluoride, potassium fluoride, stannous fluoride, sodium monofluorophosphate, sodium difluorophosphate, or any combination thereof.

Aspect H16: The composition of any one of aspects H1-H15, or any preceding aspect, wherein: the amino acid is present in an amount of >0-25 wt. %, based on total weight of the composition.

Aspect H17: The composition of any one of aspects H1-H16, or any preceding aspect, wherein the amino acid is present in an amount of 5-15 wt. %, based on total weight of the composition.

Aspect H18: The composition of any one of aspects H1-H17, or any preceding aspect, wherein the amino acid is glycine, glutamic acid, or a combination thereof.

Aspect H19: The composition of any one of aspects H1-H18, or any preceding aspect, wherein the amino acid is histidine, lysine, pyrrolysine, aspartic acid, serine, threonine, asparagine, glutamine, cysteine, selenocysteine, proline, alanine, valine, isoleucine, leucine, methionine, phenylalanine, tyrosine, tryptophan, or any combination thereof.

Aspect H20: The composition of any one of aspects H1-H19, or any preceding aspect, wherein the amino acid is arginine.

Aspect H21: The composition of any one of aspects H1-H19, or any preceding aspect, wherein the amino acid is not arginine.

Aspect H22: The composition of any one of aspects H1-H21, or any preceding aspect, wherein the composition is substantially free of, or does not contain calcium carbonate.

Aspect H23: The composition of any one of aspects H1-H22, or any preceding aspect, wherein: the composition is in a form of a toothpaste, mouthwash, gel, varnish, rinse, spray, ointment, salve, cream, bandage, polymer film, oral formulation, pill, capsule, transdermal formulation, or any combination thereof.

Aspect H24: The composition of any one of aspects H1-H23, or any preceding aspect, wherein the composition is a dentifrice composition.

Aspect H25: The composition of any one of aspects H1-H23, or any preceding aspect, wherein the composition is a skin care composition.

Aspect H26: The composition of any one of aspects H1-H25, or any preceding aspect, wherein the composition comprises:

water, and one or more of a humectant, a fluoride ion source, a flavoring, a surfactant, a sweetener, a whitening agent, an abrasive, or any combination thereof.

Aspect H27: The composition of any one of aspects H1-H25, or any preceding aspect, wherein the composition comprises:

glycerin, and one or more of a humectant, a fluoride ion source, a flavoring, a surfactant, a sweetener, a whitening agent, an abrasive, or any combination thereof.

Aspect H28: A method for making the composition of any one of aspects H1-H27, or any preceding aspect, comprising combining the amino acid, the bioactive glass, and optionally one or more of water, glycerin, a humectant, a fluoride ion source, a flavoring, a surfactant, a sweetener, a whitening agent, an abrasive, or any combination thereof.

Aspect H29: A method comprising applying to a tooth the composition of any one of aspects H1-H27, or any preceding aspect.

Aspect H30: The method of aspect H29, or any preceding aspect, wherein the method remineralizes enamel of the tooth, treats caries of the tooth, treats dentin hypersensitivity of the tooth, or any combination thereof.

Aspect H31: A method comprising applying to skin the composition of any one of aspects H1-H27, or any preceding aspect.

Aspect H32: The method of aspect H31, or any preceding aspect, wherein the method treats or reduces the appearance of one or more skin defects, optionally wherein the one or more skin defects comprises wrinkles, blemishes, sagging skin, or any combination thereof.

Aspect H33: A method for making the bioactive glass of the composition of any one of aspects H1-H27, or any preceding aspect, comprising:

combining each component of the bioactive glass to form a mixture, heating the mixture to a temperature of 1500° C. or less to form a melted mixture, and cooling the melted mixture to form a cooled mixture.

Aspect H34: A combination of any two or more of aspects H1-H33, or any one or more portions thereof.

Aspect K1: A combination of any two or more of aspects A1-H34, or any one or more portions thereof.

EXAMPLES

The following examples illustrate non-limiting aspects of the disclosure and are not intended to be limiting on the scope of the disclosure or claims.

Example 1—Bioactive Glasses and Immersion Experiments

Non-limiting examples of amounts of precursor oxides for forming bioactive glasses are listed in Table A.

TABLE A

| Oxide (wt. %) | 45S5 | 1 | 2 | 3 | 4 | 5 |
|---|---|---|---|---|---|---|
| $SiO_2$ | 45.0 | 29.5 | 39.5 | 39.5 | 39.5 | 39.5 |
| $Na_2O$ | 24.5 | 0.0 | 0.0 | 0.0 | 0.0 | 0.0 |
| MgO | 0.0 | 4.5 | 4.5 | 9.5 | 14.5 | 0 |
| CaO | 24.5 | 42.5 | 42.5 | 37.5 | 32.5 | 32.5 |
| SrO | 0.0 | 0.0 | 0 | 0 | 0 | 14.5 |
| ZnO | 0.0 | 0.0 | 0 | 0 | 0 | 0 |
| $P_2O_5$ | 6.0 | 19.5 | 9.5 | 9.5 | 9.5 | 9.5 |
| $ZrO_2$ | 0.0 | 4.0 | 4 | 4 | 4 | 4 |
| Density* | 2.71 | 3.03 | 2.96 | 2.95 | 2.99 | 3.18 |

TABLE A-continued

| Oxide (wt. %) | 6 | 7 | 8 | 9 | 10 | 11 | 12 |
|---|---|---|---|---|---|---|---|
| $SiO_2$ | 39.5 | 37.5 | 34.5 | 29.5 | 24.5 | 24.5 | 20.5 |
| $Na_2O$ | 0.0 | 0.0 | 0.0 | 0.0 | 0.0 | 0.0 | 0.0 |
| MgO | 0 | 4.5 | 4.5 | 4.5 | 4.5 | 4.5 | 4.5 |
| CaO | 32.5 | 42.5 | 42.5 | 42.5 | 42.5 | 42.5 | 42.5 |
| SrO | 0 | 0.0 | 0.0 | 0.0 | 0.0 | 0.0 | 0.0 |
| ZnO | 14.5 | 0.0 | 0.0 | 0.0 | 0.0 | 0.0 | 0.0 |
| $P_2O_5$ | 9.5 | 11.5 | 14.5 | 19.5 | 24.5 | 22.5 | 22.5 |
| $ZrO_2$ | 4 | 4.0 | 4.0 | 4.0 | 4.0 | 6 | 10 |
| Density* | 3.15 | 2.98 | 2.99 | 3.03 | 3.12 | 3.16 | 3.26 |

*$g/cm^3$

The bioactive glasses of Table A were prepared by conventional melting and forming techniques. Generally, the compositions may be melted at temperatures below 1500° C., or at temperatures below 1400° C., or at temperatures below 1200° C., thereby making it possible to melt in relatively small commercial glass tanks. The bioactive glasses disclosed herein (e.g., Table A) exhibit significantly higher chemical durability and excellent bioactivity, as compared to currently available glasses, and can be in any form that is useful for the medical, dental, and/or cosmetic processes disclosed. In some aspects, Sample 1 of Table A demonstrates significantly higher chemical durability and bioactivity over the 45S5 glass, which is employed as a comparative example herein.

Table B below includes example concentrations of amino acids used in the artificial saliva submersion experiments with bioactive glass.

TABLE B

| Amino Acid | wt. % |
|---|---|
| Glycine | 0-25 |
| L-Glutamic Acid | 0-8 |
| L-Arginine | 0-8 |

Table C below includes artificial saliva composition and submersion conditions for the bioactive glass and amino acids.

TABLE C

| Artificial Saliva Composition | wt. % | Experiment Details | |
|---|---|---|---|
| Potassium chloride | 0.119 | Temperature | 37° C. |
| Ammonium chloride | 0.024 | Glass Mass | 5.0 g |
| Potassium dihydrogen phosphate | 0.054 | Amino acid mass | 0-25.0 g |
| Magnesium chloride hexahydrate | 0.004 | Solution Volume | 100 mL |
| Calcium chloride | 0.011 | pH | 6.8 |
| HEPES buffer | 0.477 | Time | 1 hour to 7 days |
| Sodium azide | 0.020 | Powder | <10 μm particles |
| Sodium hydroxide | 0.012 | | |

Immersion experiments were performed on the two glasses set forth in Table A, employing the amino acid and artificial saliva concentrations and immersion conditions set forth in Tables B and C. The results are set forth in FIGS. 1-4 and FIGS. 9-11.

Figure 9A:
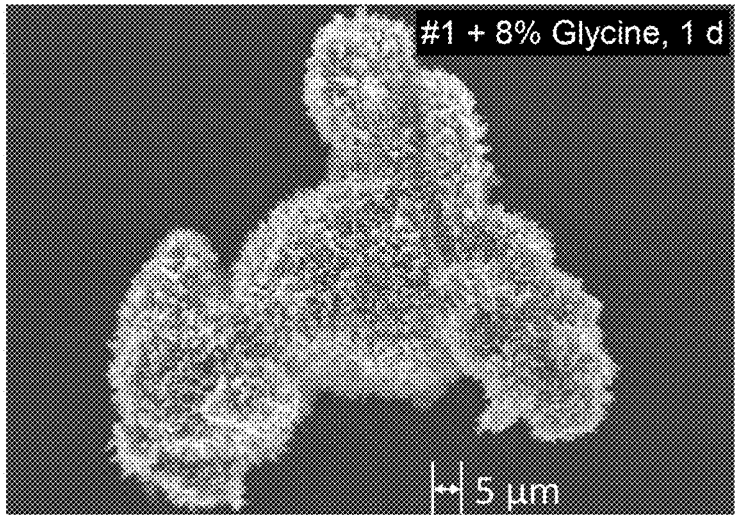
FIGS. 9A, 9B, and 9C are scanning electron microscopy (SEM) images illustrating crystal growth on the surface of a bioactive glass disclosed herein after immersion in artificial saliva comprising glycine.
Figure 9B:
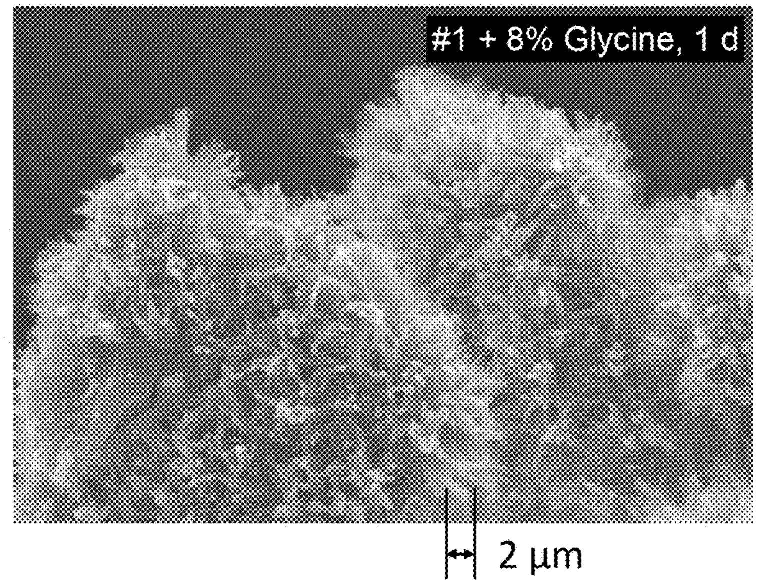
Figure 9C:
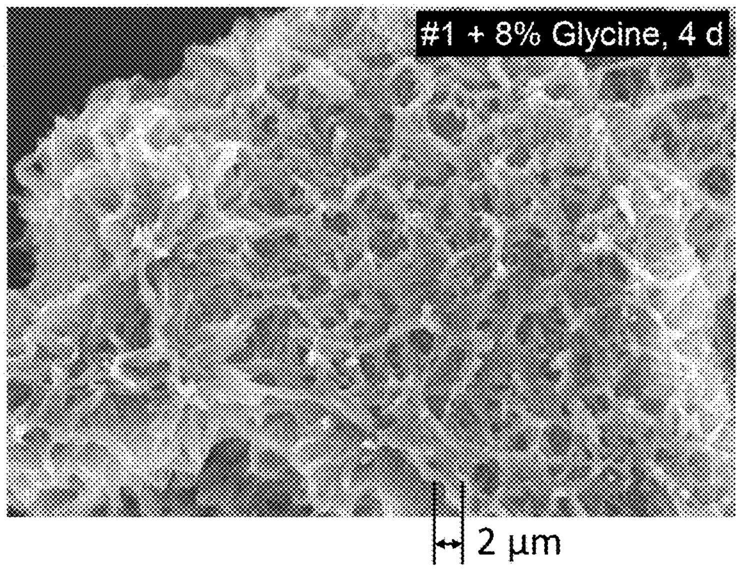

FIG. 1 is a powder XRD spectrum illustrating hydroxyapatite formation within 1 day for bioactive glass 1 of Table A upon immersion in an aqueous composition comprising the artificial saliva of Table C and an amino acid (8 wt. % glycine). The XRD peaks for hydroxyapatite grow as the submersion time increases from 1 day, to 4 days, to 7 days. FIGS. 9A, 9B, and 9C depict scanning electron microscopy (SEM) images of bioactive glass 1 of Table A after immersion in artificial saliva comprising 8 wt. % glycine after 1 day (FIGS. 9A and 9B) and after 4 days (FIG. 9C). The SEM parameters are as follows: FIG. 9A: 5.0 kV 6.2 mm×10.0 k SE(M), scale marks 5.00 microns; FIG. 9B: 5.0 kV 6.2 mm×25.0 k SE(M), scale marks 2.00 microns; FIG. 9C: 5.0 kV 6.4 mm×25.0 k SE(M), scale marks 2.00 microns. Compared with FIGS. 11A, 11B, and 11C (arginine), significantly more crystal growth is observed on the surface of bioactive glass 1 when employing glycine (FIGS. 9A, 9B, and 9C). However, in some aspects, it may be desirable to employ arginine, alone or in combination with other amino acids, so as to tune the amount and type of crystal growth.

Figure 2:
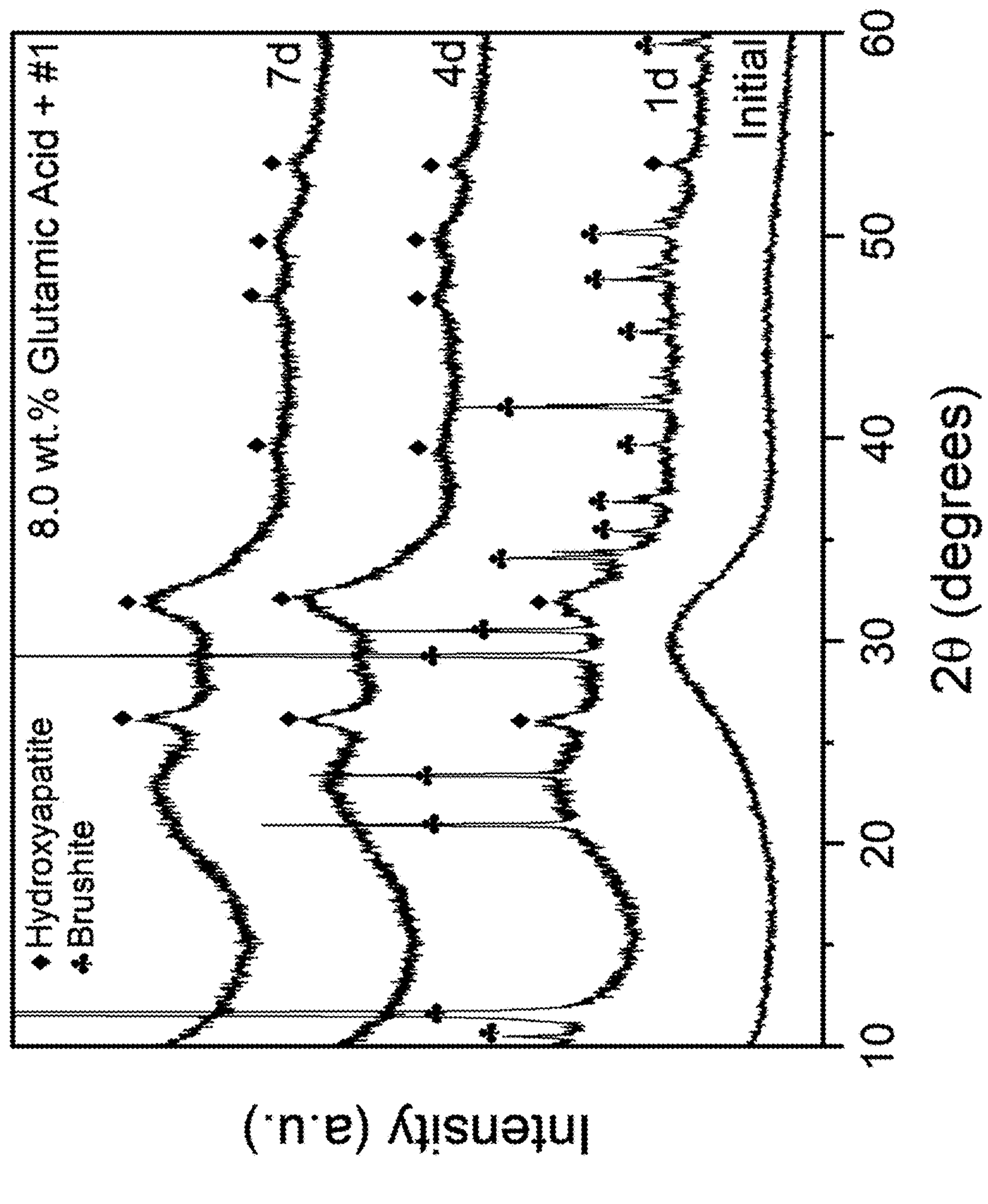
FIG. 2 is a powder XRD spectrum illustrating hydroxyapatite and brushite formation within one day for an example bioactive glass upon immersion in an aqueous composition comprising artificial saliva and an amino acid (glutamic acid), followed by hydroxyapatite being the only phase within 4 and 7 days.
Figure 10A:
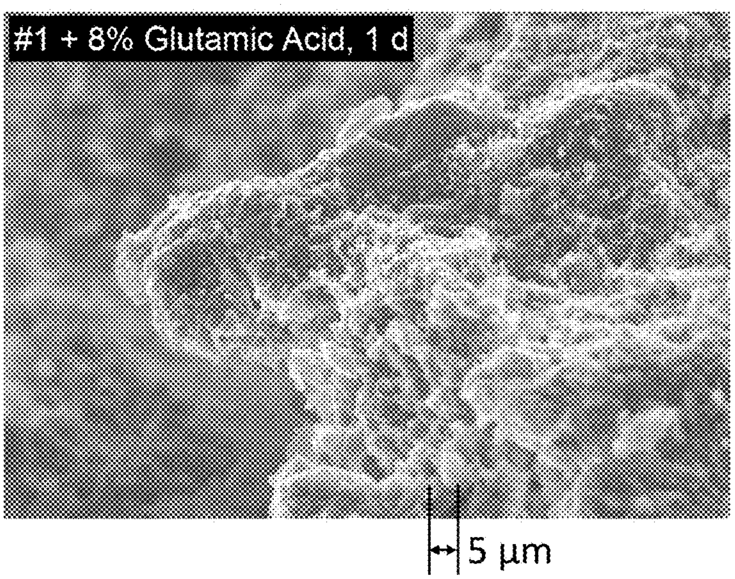
FIGS. 10A, 10B, and 10C are SEM images illustrating crystal growth on the surface of a bioactive glass disclosed herein after immersion in artificial saliva comprising glutamic acid.
Figure 10B:
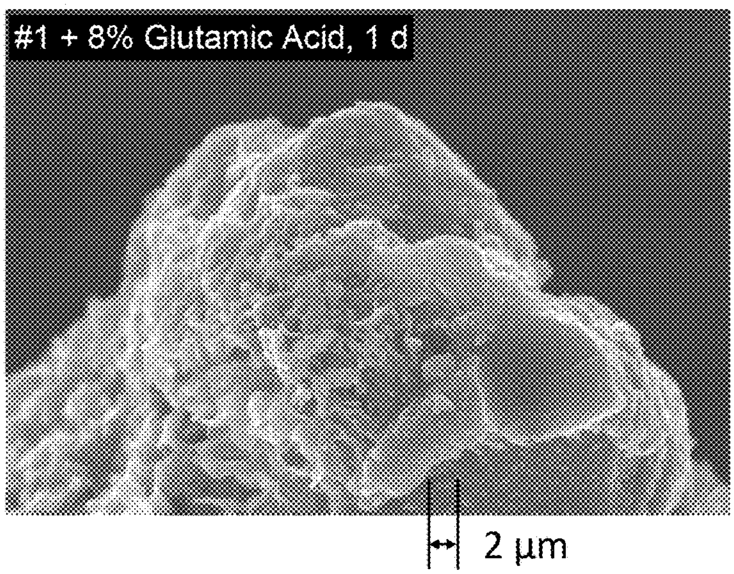
Figure 10C:
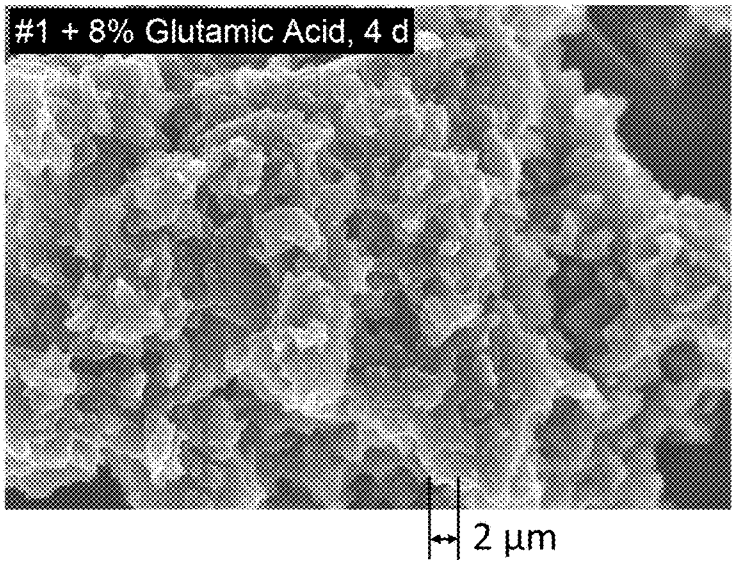

FIG. 2 is a powder XRD spectrum illustrating hydroxyapatite and brushite formation within one day for bioactive glass 1 of Table A upon immersion in an aqueous composition comprising the artificial saliva of Table C and an amino acid (8 wt. % glutamic acid). The XRD peaks for hydroxyapatite grow as the submersion time increases from 1 day, to 4 days, to 7 days. Brushite forms with bioactive glass 1 within 1 day and then disappears as the submission time increases up to 7 days. Brushite is a potential precursor to hydroxyapatite, and brushite may initially form but then convert substantially or completely to hydroxyapatite over time. FIGS. 10A, 10B, and 10C depict SEM images of bioactive glass 1 of Table A after immersion in artificial saliva comprising 8 wt. % glutamic acid after 1 day (FIGS. 10A and 10B) and after 4 days (panel C). The SEM parameters are as follows: FIG. 10A: 5.0 kV 6.2 mm×10.0 k SE(M), scale marks 5.00 microns; FIG. 10B: 5.0 kV 6.3 mm×25.0 k SE(M), scale marks 2.00 microns; FIG. 10C: 5.0 kV 6.4 mm×25.0 k SE(M), scale marks 2.00 microns. Compared with FIGS. 11A, 11B, and 11C (arginine), significantly more crystal growth is observed on the surface of bioactive glass 1 when employing glutamic acid (FIGS. 10A, 10B, and 10C). However, in some aspects, it may be desirable to employ arginine, alone or in combination with other amino acids, so as to tune the amount and type of crystal growth.

Figure 3:
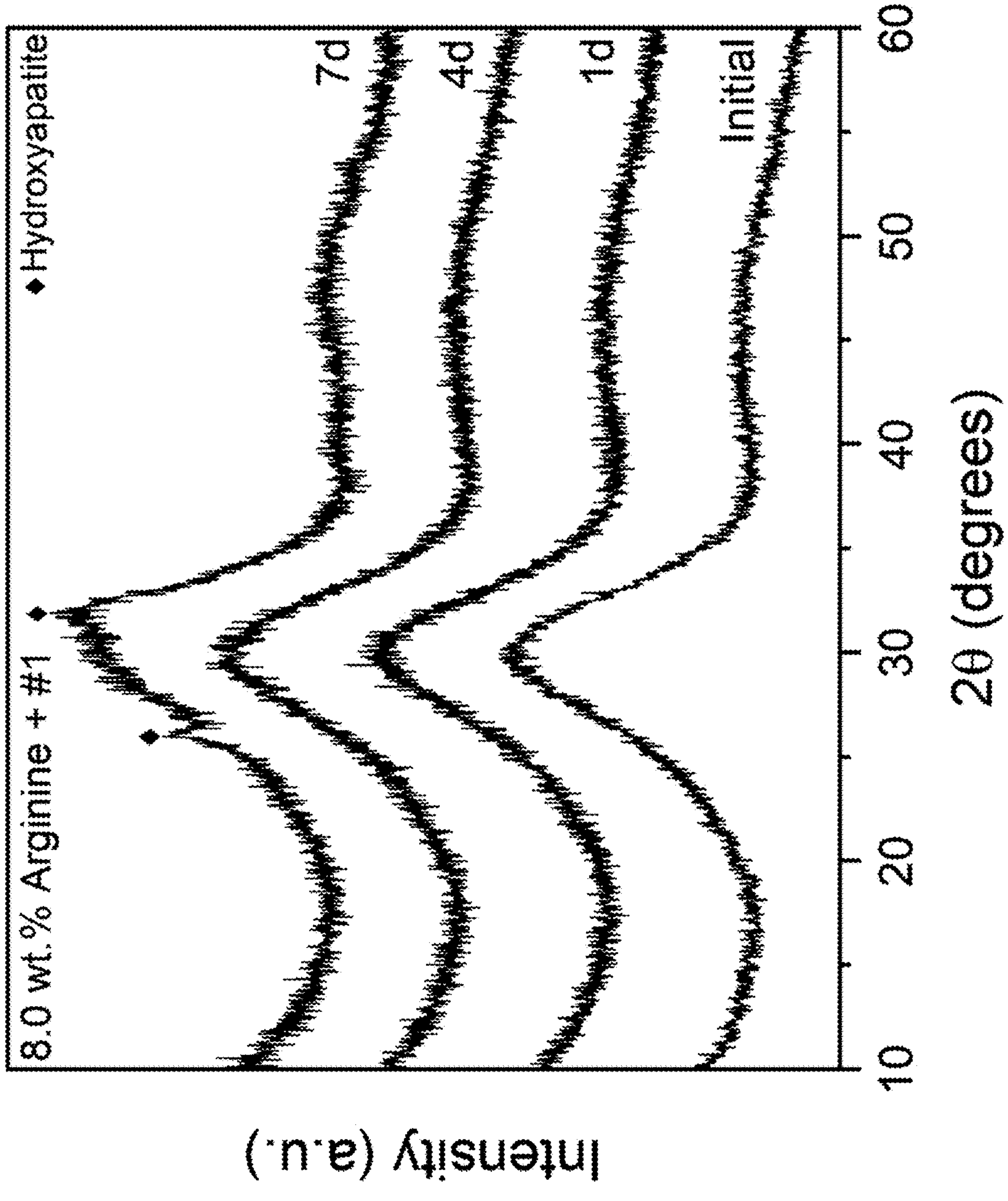
FIG. 3 is a powder XRD spectrum illustrating hydroxyapatite formation at 7 days for an example bioactive glass upon immersion in an aqueous composition comprising artificial saliva and an amino acid (arginine).
Figure 11A:
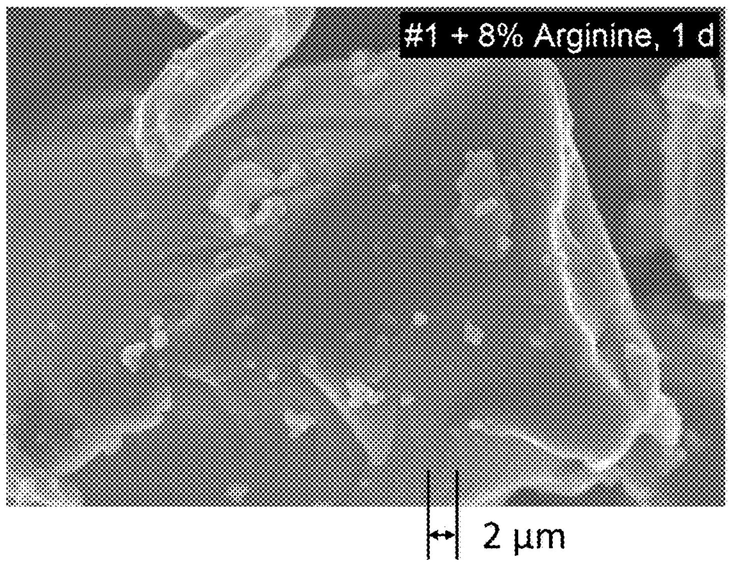
FIGS. 11A, 11B, and 11C are SEM images illustrating crystal growth on the surface of a bioactive glass disclosed herein after immersion in artificial saliva comprising arginine.
Figure 11B:
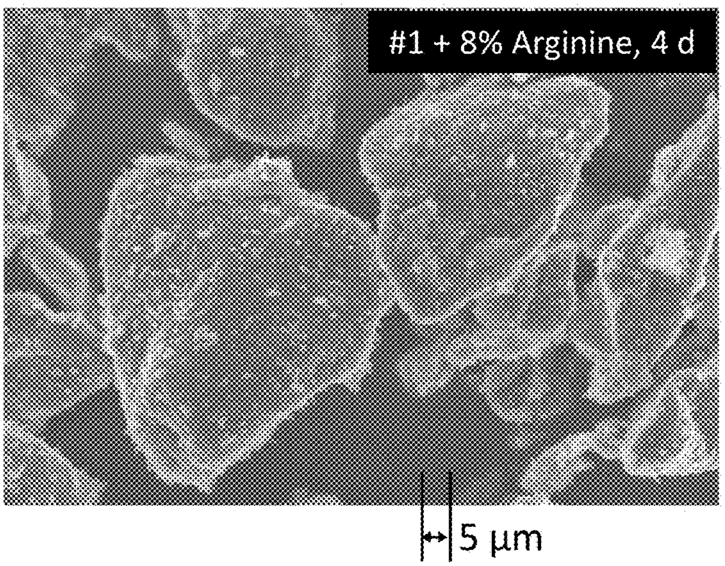
Figure 11C:
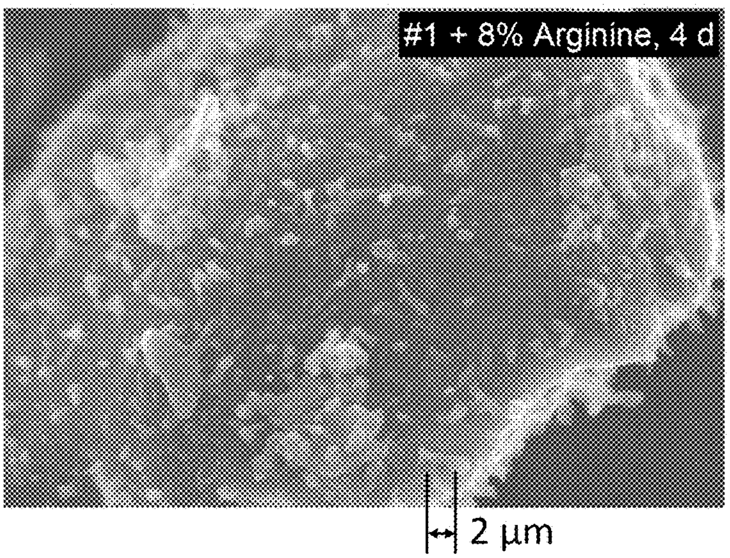

FIG. 3 is a powder XRD spectrum illustrating hydroxyapatite formation at 7 days for bioactive glass 1 of Table A upon immersion in an aqueous composition comprising the artificial saliva of Table C and an amino acid (8 wt. % arginine). FIGS. 11A, 11B, and 11C depict SEM images of bioactive glass 1 of Table A after immersion in artificial saliva comprising 8 wt. % arginine after 1 day (FIG. 11A) and after 4 days (FIGS. 11B and 11C). The SEM parameters are as follows: FIG. FIG. 11A: 5.0 kV 6.4 mm×25.0 k SE(M), scale marks 2.00 microns; 11B: 5.0 kV 6.3 mm×10.0 k SE(M), scale marks 5.00 microns; FIG. 11C: 5.0 kV 6.3 mm×25.0 k SE(M), scale marks 2.00 microns. Compared with FIGS. 9A, 9B, and 9C (glycine) and FIGS. 10A, 10B, and 10C (glutamic acid), significantly less crystal growth is observed on the surface of bioactive glass 1 when employing arginine (FIGS. 11A, 11B, and 11C). However, in some aspects, it may be desirable to employ arginine, alone or in combination with other amino acids, so as to tune the amount and type of crystal growth.

Figure 4:
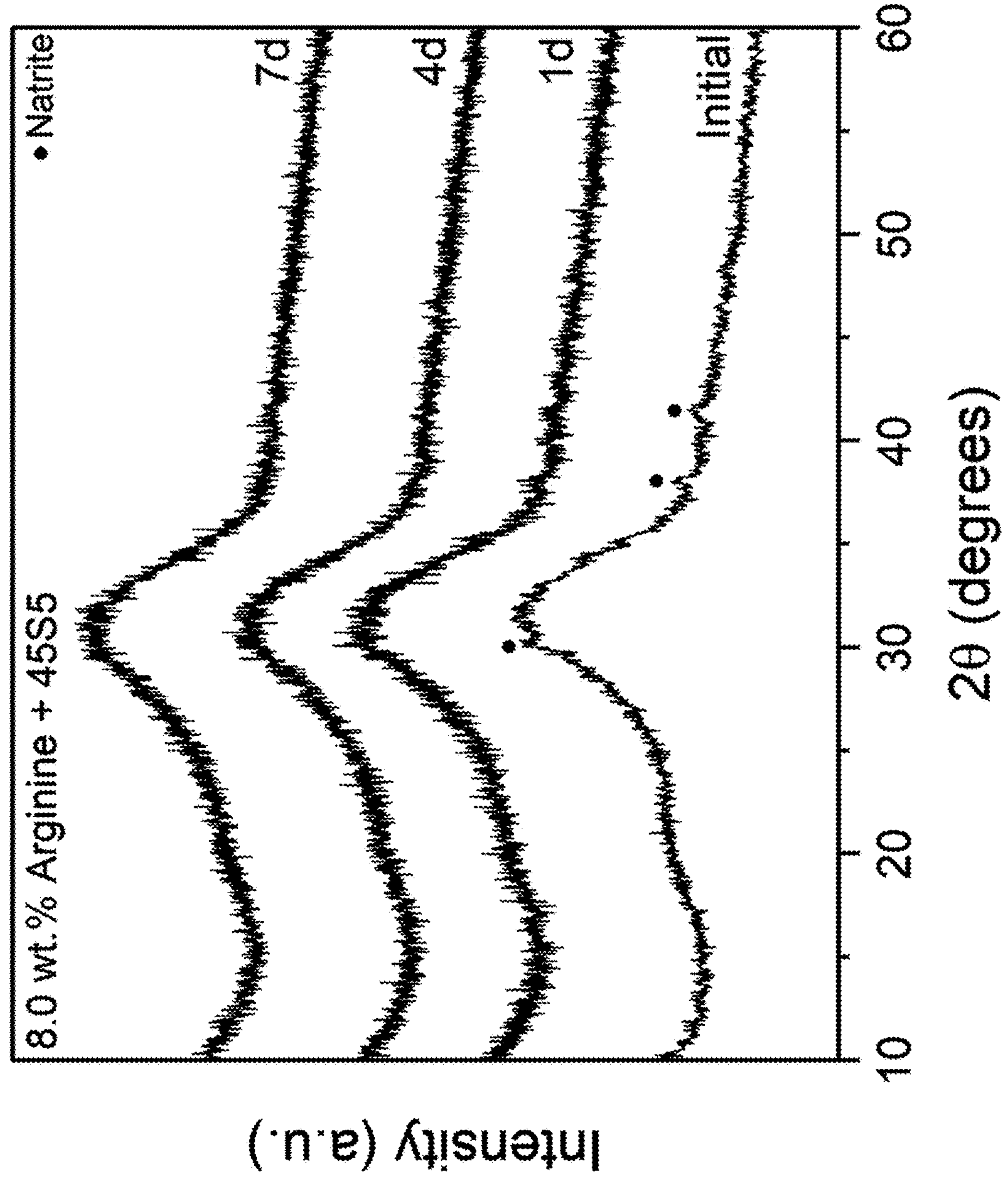
FIG. 4 is a powder XRD spectrum illustrating no hydroxyapatite formation within 7 days for a comparative glass composition (45S5 Bioglass®) upon immersion in an aqueous composition comprising artificial saliva and an amino acid (arginine).

FIG. 4 is a powder XRD spectrum illustrating no mineral phase formation, including no hydroxyapatite formation, within 7 days for the 45S5 Bioglass® comparative glass composition upon immersion in an aqueous composition comprising the artificial saliva of Table C and 8 wt. % arginine. As specified by ASTM F1538-03, bioactive materials only refer to those that can form apatite in vitro or in vivo. It is believed that the formation of natrite would not produce a direct bond with bony tissues due to its chemical difference from bone; thus, natrite is not regarded as bioactive. The inclusion of relatively high concentrations of CaO and $P_2O_5$ oxides, as well as the believed nucleating and crystal growth promoting ability of amino acids, for the compositions disclosed herein facilitates the formation of an apatite phase in artificial saliva while the 45S5 comparative glass composition (which has appreciably lower concentrations of CaO and $P_2O_5$) only forms a natrite phase in an aqueous composition comprising arginine. Due to its chemical similarity with bone, apatite can form a direct bond with bony tissue while natrite cannot.

Figure 8:
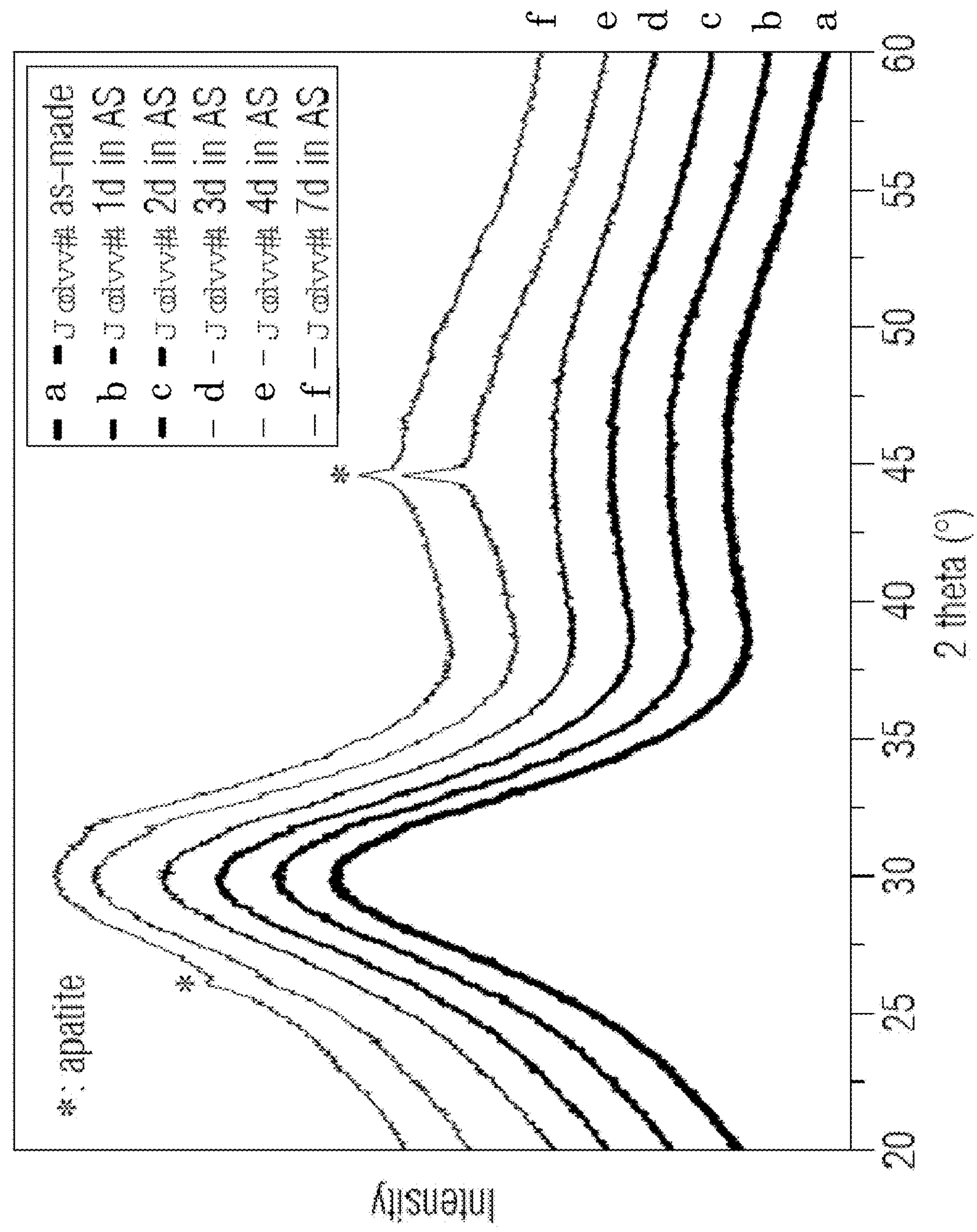
FIG. 8 is a powder XRD spectrum illustrating apatite formation occurred within 4 days of soaking bioactive glass in artificial saliva without amino acid present, and significant additional formation of apatite did not occur between days 4 and 7.

For comparison purposes, bioactive glass 1 was immersed in an artificial saliva manufactured by Modus Laboratories in the absence of any added amino acid. The results are shown in FIG. 8. Specifically, six XRD plots were collected, including bioactive glass 1 in its as-made form, and then after immersion for 1 day, after 2 days, after 3 days, after 4 days, and after 7 days in the artificial saliva. The XRD plots in FIG. 8 show that apatite formation occurred on the bioactive glass within 4 days of soaking in artificial saliva without amino acid present, and significant additional formation of apatite did not occur between days 4 and 7. This shows that inclusion of amino acid in the artificial saliva results in much more rapid apatite formation (within 1 day) than when amino acid is omitted (within 4 days).

Example 2—pH as a Function of Immersion Time

The two bioactive glasses of Table A were immersed in the artificial saliva of Table C, along with 8 wt. % of specific amino acids (glycine, glutamic acid, or arginine), and the pH monitored over 7 days. The pH of the artificial saliva of Table C was 6.8.

Figure 5:
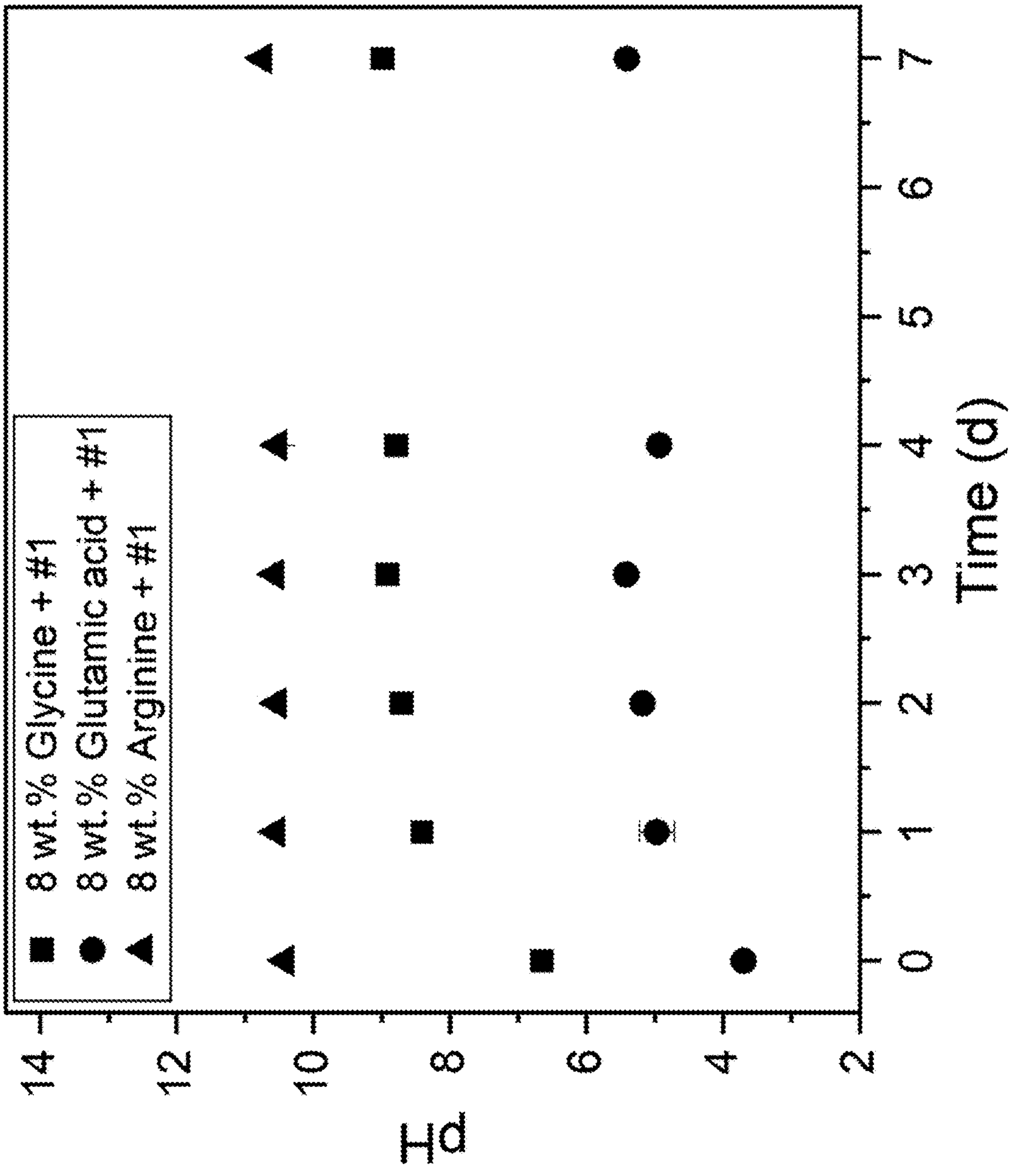
FIG. 5 is a graph illustrating pH change over time upon separately immersing an example bioactive glass in an aqueous composition comprising artificial saliva and three different amino acids (glycine, glutamic acid, and arginine).

FIG. 5 is a graph illustrating pH change over time upon separately immersing bioactive glass 1 of Table A in an aqueous composition comprising the artificial saliva of Table C and three different amino acids (glycine, glutamic acid, and arginine). As illustrated in FIG. 5, the pH increases over time, which, without wishing to be bound by theory, is believed to result from dissolution of the glass over time.

Figure 6:
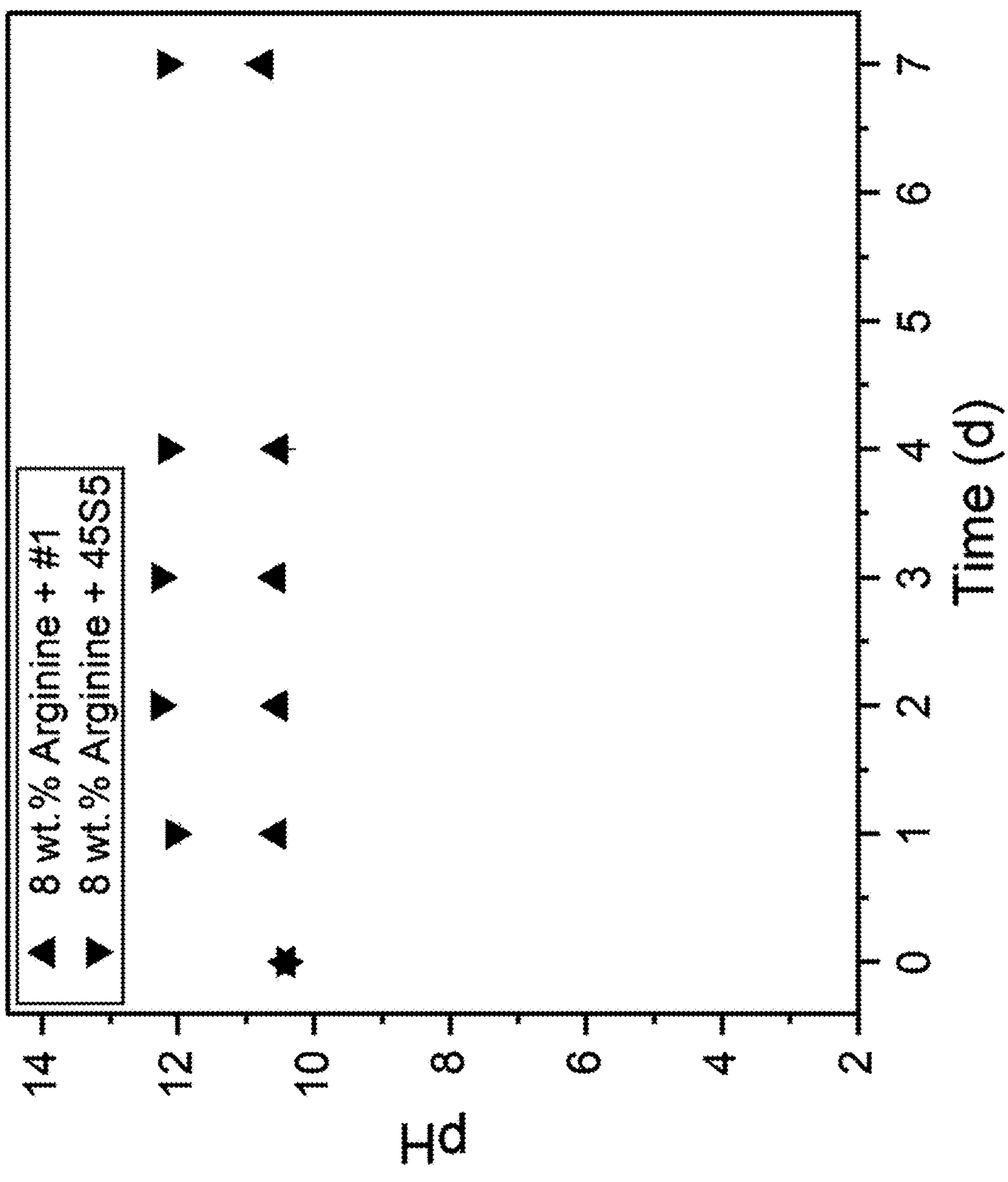
FIG. 6 is a graph illustrating pH change over time upon separately immersing an example bioactive glass and a comparative glass composition (45S5 Bioglass®) in an aqueous composition comprising artificial saliva and an amino acid (arginine).

In contrast, FIG. 6 compares the pH over time for bioactive glass 1 of Table A with the pH over time for 45S5 Bioglass®, where both glasses are immersed in an aqueous composition comprising the artificial saliva of Table C in combination with 8 wt. % arginine. As shown in FIG. 6, the 45S5 glass reached higher pH values, possibly due to relatively greater dissolution of the 45S5 glass compared to bioactive glass 1.

Example 3-45S5 without Amino Acid

This example demonstrates that 45S5 Bioglass® fails to form a crystalline phase when immersing in artificial saliva for 7 days without any amino acid present.

Figure 7:
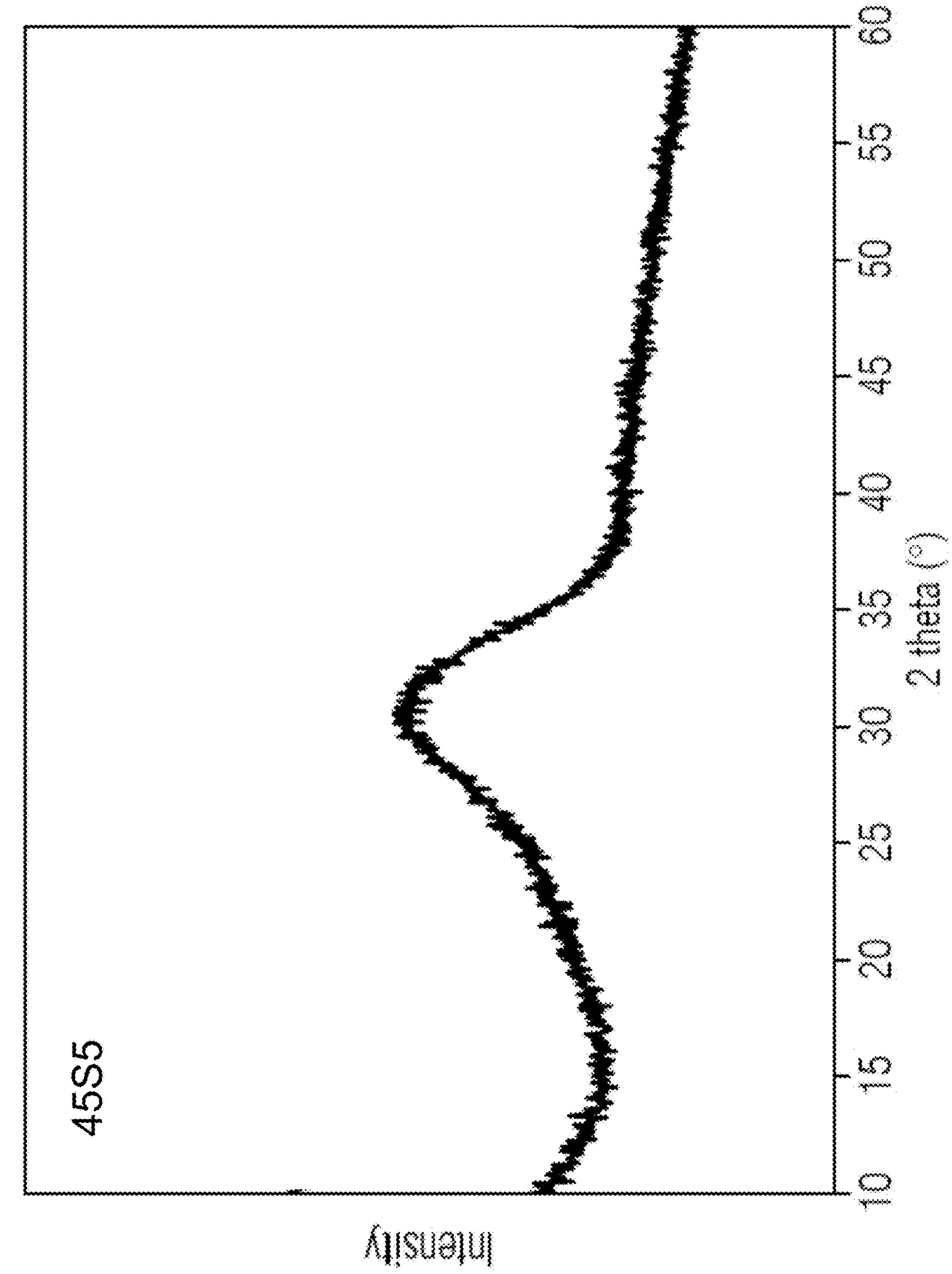
FIG. 7 is a powder XRD spectrum illustrating no crystal phase formation within 7 days for a comparative glass composition (45S5 Bioglass®) upon immersion in artificial saliva.

45S5 Bioglass® particles were soaked in artificial saliva manufactured by Modus Laboratories, without any amino acid present. XRD analysis was then performed on the particles. The XRD result in FIG. 7 show no detectable crystalline phase was observed in 45S5 Bioglass® after 7 days. Again, as discussed above, as specified by ASTM F1538-03, bioactive materials only refer to those that can form apatite in vitro or in vivo. In this context for 45S5

Bioglass®, without the formation of apatite, a direct bond with bony tissues would not result.

45S5 Bioglass®, described in U.S. Pat. No. 4,234,972, is a glass known to convert to apatite; however, as shown in Examples 1 and 3, no detectable crystalline phases were observed for 45S5 Bioglass® after immersion for 7 days in a composition comprising artificial saliva both with (Example 1) and without (Example 3) amino acid. It is desirable to form an apatite phase from bioactive glass within a reasonable amount of time.

Forming apatite in artificial saliva with the bioactive glasses disclosed herein is possible at the 4-day mark (see Example 1) when there is no amino acid present. However, it was found that by including amino acid, crystal phase formation occurs much more rapidly, within 1 day. This step change in the rate of formation of biologically compatible mineral phases represents a significant finding that can have monumental impact in the field of oral care, such as for the rapid treatment of tooth sensitivity or for dental enamel repair.

Example 4

Non-limiting examples of amounts of precursor oxides for forming the embodied glasses are listed in Table D, along with the properties of the resulting glasses. Anneal points were measured using a beam bending viscometry (BBV) method.

TABLE D

| Oxide (wt. %) | Comp. Ex. 1 | Comp. Ex. 2 | 13 | 14 | 15 | 16 | 17 | 18 | 19 | 20 | 21 | 22 | 23 |
|---|---|---|---|---|---|---|---|---|---|---|---|---|---|
| $SiO_2$ | 70.8 | 45 | 42.9 | 42.4 | 42.0 | 41.2 | 31.8 | 21.1 | 54.3 | 46.3 | 38.7 | 38.7 | 38.7 |
| $Al_2O_3$ | 0 | 0 | 0 | 0 | 0 | 0 | 0 | 0 | 0 | 0 | 2.5 | 0 | 0 |
| $Na_2O$ | 24.3 | 24.5 | 0 | 0 | 0 | 0 | 0 | 0 | 0 | 0 | 0 | 0 | 0 |
| $K_2O$ | 6 | 0 | 0 | 0 | 0 | 0 | 0 | 0 | 0 | 0 | 0 | 0 | 0 |
| MgO | 0 | 0 | 14.5 | 14.3 | 14.2 | 13.9 | 10.6 | 7.0 | 8.0 | 18.5 | 14.5 | 14.5 | 14.5 |
| CaO | 4.9 | 24.5 | 32.4 | 32.1 | 31.8 | 31.2 | 36.1 | 41.7 | 29.9 | 27.8 | 30.0 | 27.5 | 30.0 |
| SrO | 0 | 0 | 0 | 0 | 0 | 0 | 0 | 0 | 0 | 0 | 0 | 5.0 | 0 |
| ZnO | 0 | 0 | 0 | 0 | 0 | 0 | 0 | 0 | 0 | 0 | 0 | 0 | 2.5 |
| $F^-$ | 0 | 0 | 0.8 | 0.8 | 0.8 | 0.8 | 1.4 | 2.2 | 0 | 0 | 0.8 | 0.8 | 0.8 |
| $P_2O_5$ | 8 | 6 | 9.5 | 9.4 | 9.3 | 9.1 | 16.2 | 24.2 | 5.9 | 5.6 | 9.5 | 9.5 | 9.5 |
| $ZrO_2$ | 0 | 0 | 0 | 1.0 | 2.0 | 3.8 | 3.8 | 3.8 | 2.0 | 1.9 | 4.0 | 4.0 | 4.0 |
| Anneal Pt (° C.) | 600 | 500 | 400 | 400 | 400 | 400 | 375 | 350 | 450 | 450 | 425 | 425 | 425 |

The bioactive glass compositions disclosed herein exhibit high chemical durability and excellent bioactivity and can be in any form that is useful for the medical and dental processes disclosed. The compositions can be in the form of, for example, particles, powder, microspheres, fibers, sheets, beads, scaffolds, woven fibers. The compositions of Table D may be melted at temperatures below 1300° C., or at temperatures below 1250° C., or at temperatures below 1200° C., thereby making it possible to melt in relatively small commercial glass tanks.

In some embodiments, the compositions of Table D demonstrate improved chemical stability over Comparative Example 1 (an alkali-containing bioactive glass) or Comparative Example 2 (45S5 glass).

Figure 12:
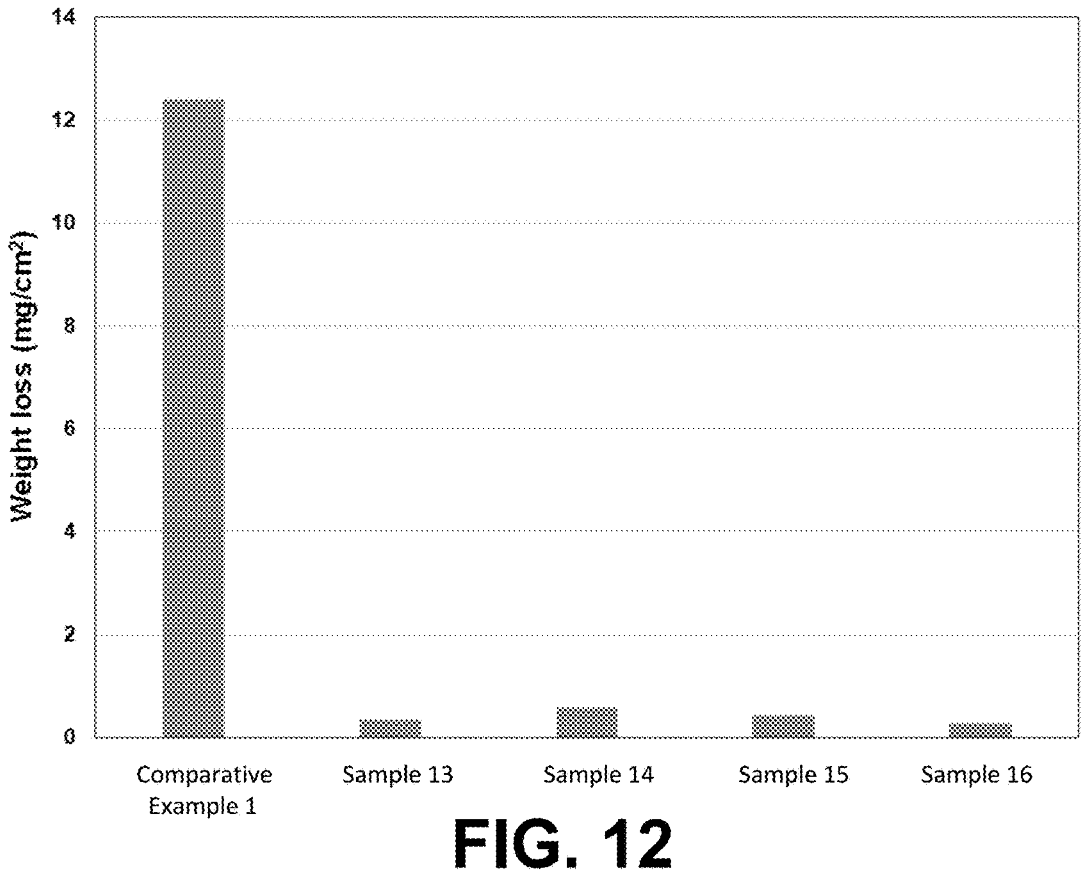
FIG. 12 illustrates weight loss characterization of Samples 13-16 and Comparative Example 1 when immersed in artificial saliva at 37° C. for 7 days, according to some embodiments.

FIG. 12 illustrates weight loss characterization of Samples 13-16 and Comparative Example 1 when immersed in artificial saliva at 37° C. for 7 days. Weight loss of glass in FIG. 12 was calculated by measuring the weight of a glass disc (12.7 mm in diameter×2 mm in thickness) before and after soaking in artificial saliva. From FIG. 12, Samples 13 and 14 fall within HGB 2 category, while Comparative Examples 1 and 2 fall within HGB 5+, based on ISO 719 testing in aqueous water. HGB stands for hydrolytic resistance of glass grains under a boiling water test. A smaller number HGB indicates a higher resistance (greater durability), according to ISO 719. This indicates a significant improvement in water durability for at least Samples 13 and 14. In other words, when tested in artificial saliva, the weight loss for Samples 13-16 is less than one twentieth of Comparative Example 1.

Figure 13:
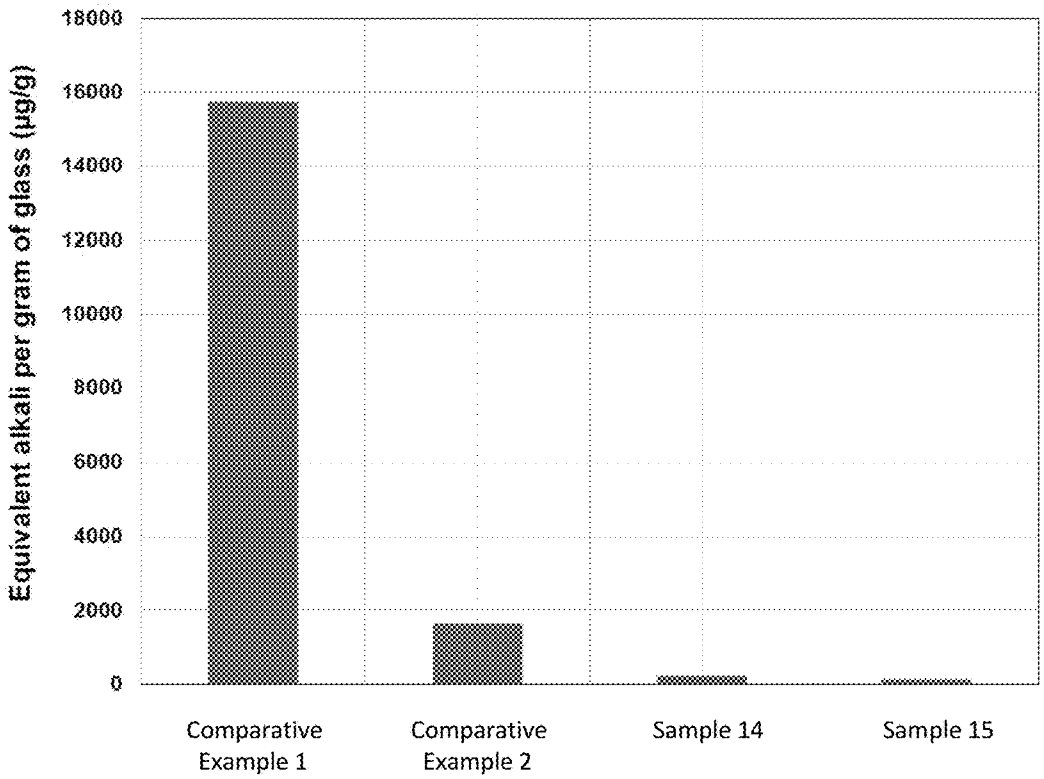
FIG. 13 illustrates equivalent alkali per gram of Samples 13 and 14 and Comparative Examples 1 and 2 when tested in water at 98° C. for 1 hr according to ISO 719 standard procedure, according to some embodiments.

FIG. 13 illustrates equivalent alkali per gram of Samples 13 and 14 and Comparative Examples 1 and 2 when tested in water at 98° C. for 2 hrs according to ISO 719 standard procedure. In other words, equivalent alkali release in FIG. 13 was measured using a titration method of 50 mL of DI water containing glass grains for 2 hrs at 98° C., as specified by ISO 719. The solution is titrated with 0.01 M HCl using methyl red as an indicator and reported as g neutralized alkali per gram of grains, as described in ISO 719. A higher alkali release indicates a lower water durability of the glass composition. Thus, because the equivalent alkali release from Sample 13 and Sample 14 is about one tenth of that from Comparative Example 2 (45S5), Comparative Example 2 has a lower water durability than either Sample 13 or Sample 14. What the data in FIGS. 12 and 14 indicate is that glass compositions with higher durability ensures a longer shelf time when being used in an aqueous solution. With respect to Comparative Example 2, dental applications using this compositions are currently formulated with a non-aqueous solution. The current Samples of Table D, which have improved water durability, allow flexibility in formulating with both aqueous and non-aqueous solutions, making them better candidates in dental or oral care or beauty product applications.

Figure 14:
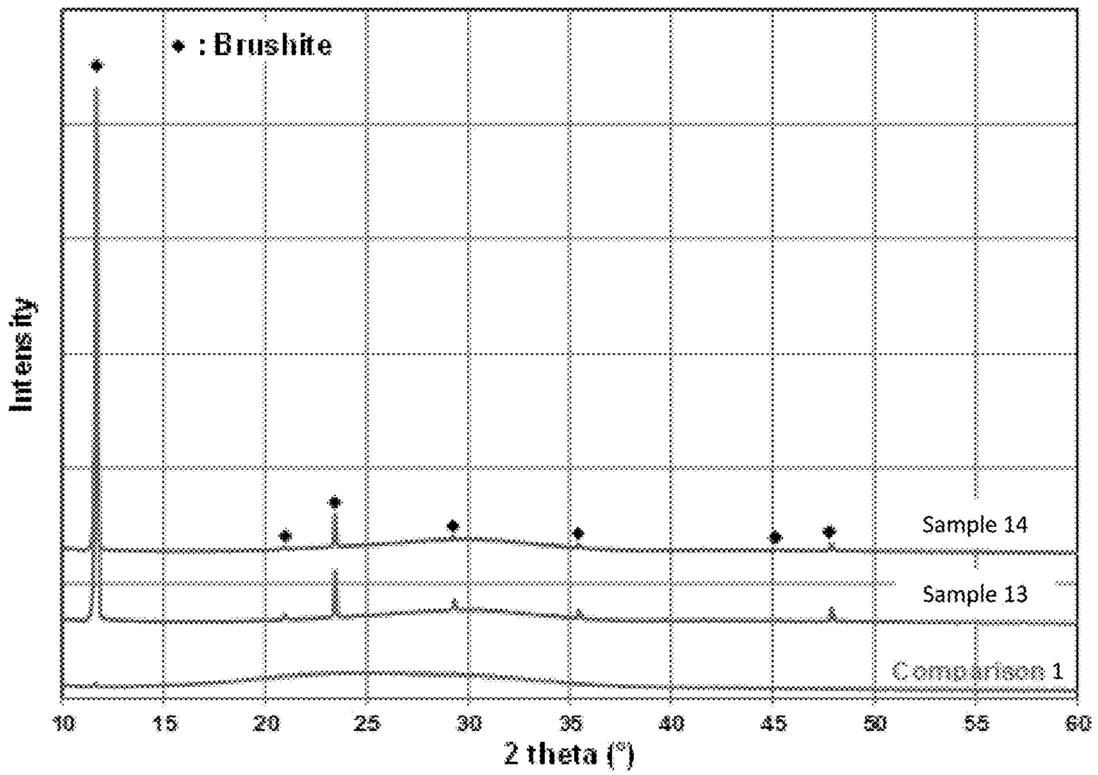
FIG. 14 illustrates powder x-ray diffraction (XRD) analysis on Samples 13 and 14 and Comparative Example 1 after soaking in $KH_2PO_4$ at 25° C. for 14 days, according to some embodiments.

FIG. 14 illustrates powder x-ray diffraction (XRD) analysis on Samples 13 and 14 and Comparative Example 1 after soaking in potassium phosphate ($KH_2PO_4$) at 25° C. for 14 days. Both Samples 13 and 14 form brushite ($CaHPO_4 \cdot 2H_2O$), a known bioactive ceramic, which suggests a higher crystallinity and better bioactivity than Comparative Example 1, within which very little amount of brushite is observed due to very low rates of formation. Because calcium is a key component in brushite, a higher CaO concentration favors faster brushite formation. Both Samples 13 and 14 have much higher concentrations of CaO than Comparative Example 1.

Example 5

Non-limiting examples of amounts of precursor oxides for forming the embodied glasses are listed in Table E, along with the properties of the resulting glasses. The annealing point (° C.) may be measured using a beam bending viscometer (ASTM C598-93).

TABLE E

| Oxide (wt. %) | Comparative Example 2 | 24 | 25 | 26 | 27 | 28 | 29 | 30 |
|---|---|---|---|---|---|---|---|---|
| $SiO_2$ | 45 | 42.9 | 41.2 | 43.5 | 37.7 | 37.7 | 37.7 | 37.7 |
| $Al_2O_3$ | 0 | 0 | 0 | 0 | 0 | 0 | 0 | 0 |
| $Li_2O$ | 0 | 0 | 0 | 0 | 5 | 0 | 0 | 0 |
| $Na_2O$ | 24.5 | 0 | 0 | 0 | 0 | 5 | 0 | 0 |
| $K_2O$ | 0 | 0 | 0 | 0 | 0 | 0 | 5 | 0 |
| MgO | 0 | 14.5 | 13.9 | 14.5 | 14.5 | 14.5 | 14.5 | 14.5 |
| CaO | 24.5 | 32.4 | 31.2 | 32.5 | 32.5 | 32.5 | 32.5 | 32.5 |
| SrO | 0 | 0 | 0 | 0 | 0 | 0 | 0 | 0 |
| ZnO | 0 | 0 | 0 | 0 | 0 | 0 | 0 | 0 |
| $F^-$ | 0 | 0.8 | 0.8 | 0 | 0.8 | 0.8 | 0.8 | 0.8 |
| $P_2O_5$ | 6 | 9.5 | 9.1 | 9.5 | 9.5 | 9.5 | 9.5 | 9.5 |
| $ZrO_2$ | 0 | 0 | 3.8 | 0 | 0 | 0 | 0 | 2 |
| Anneal Pt (° C.) | 500 | 400 | 400 | 375 | 400 | 400 | 400 | 400 |

The bioactive glass compositions disclosed herein exhibit high chemical durability and excellent bioactivity and can be in any form that is useful for the medical and dental processes disclosed. The compositions can be in the form of, for example, particles, powder, microspheres, fibers, sheets, beads, scaffolds, woven fibers, or other form depending on the application. The compositions of Table E may be melted at temperatures below 1300° C., or at temperatures below 1250° C., or at temperatures below 1200° C., thereby making it possible to melt in relatively small commercial glass tanks.

In some embodiments, the compositions of Table E demonstrate significantly higher chemical durability and bioactivity over Comparative Example 2 (45S5 glass).

Figure 15:
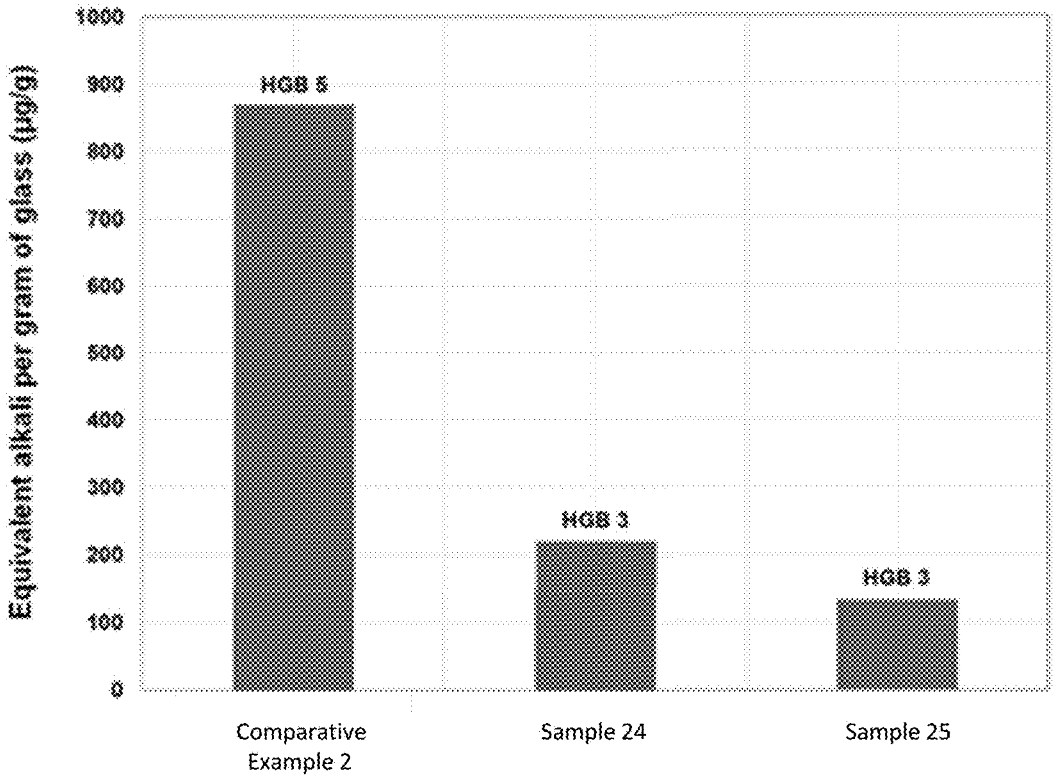
FIG. 15 illustrates equivalent alkali per gram of Samples 24 and 25 and Comparative Example 2, when tested in water at 98° C. for 2 hrs, according to ISO 719 standard procedure, according to some embodiments.
Figure 16A:
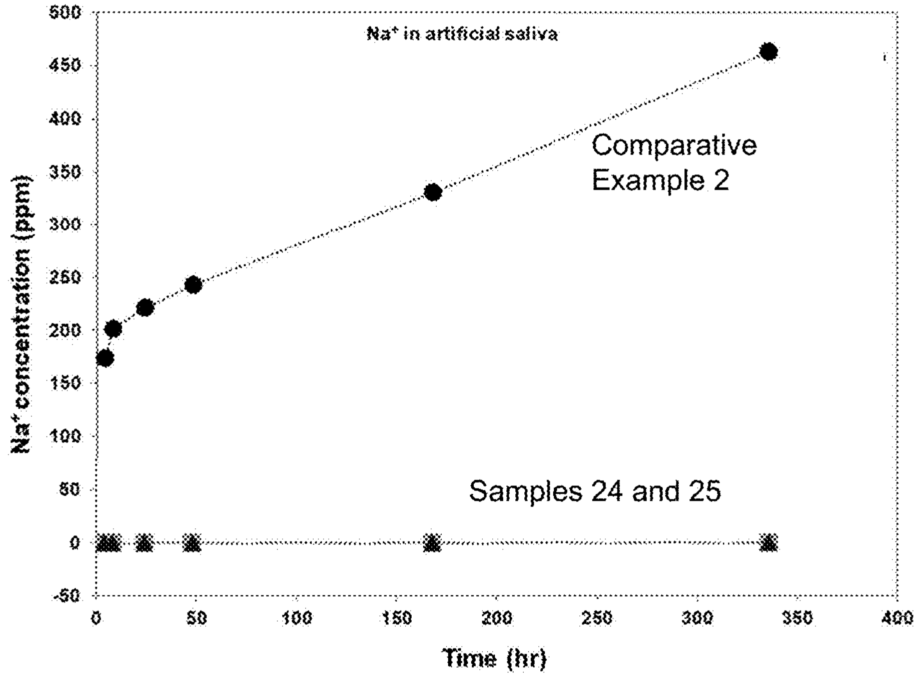
FIGS. 16A-16D illustrate inductively coupled plasma (ICP) analysis of released $Na^+$ (FIG. 16A), $Ca^{2+}$ (FIG. 16B), $Si^{4+}$ (FIG. 16C), and $Ps^+$ (FIG. 16D) ion concentrations in artificial saliva solutions after soaking glass powder samples of Samples 24 and 25 and Comparative Example 2 therein, according to some embodiments.
Figure 16B:
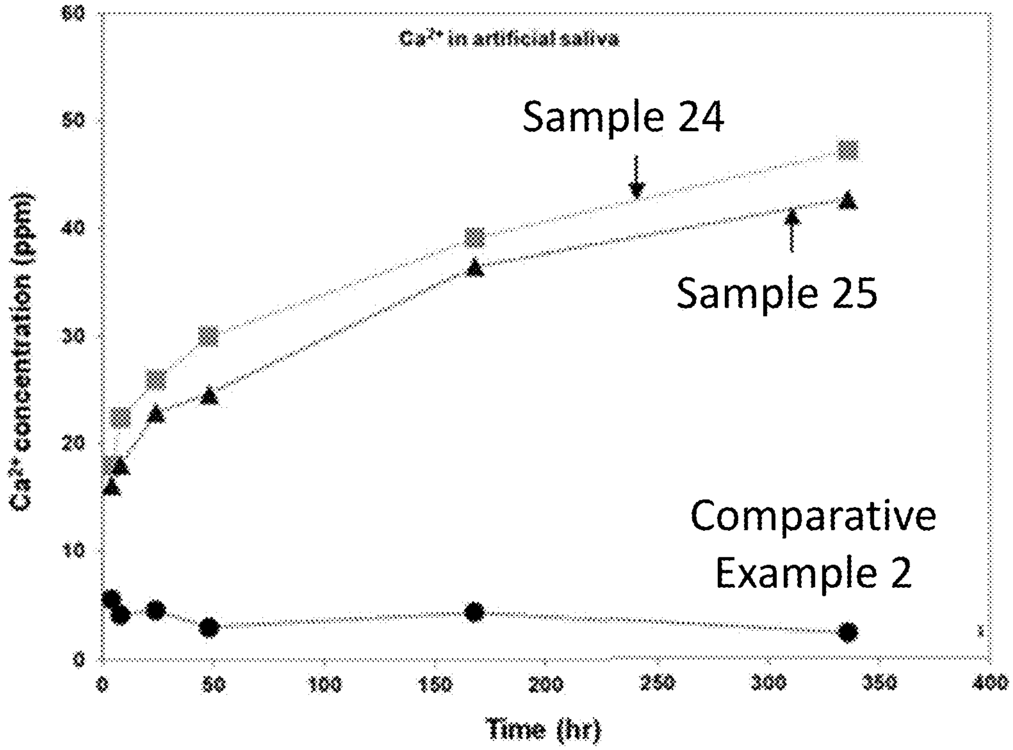
Figure 16C:
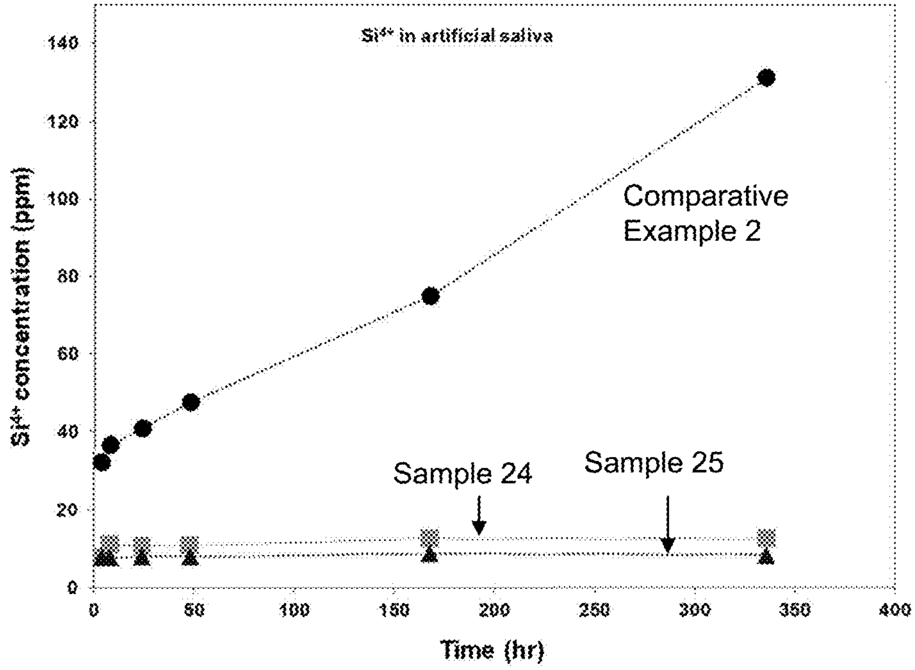
Figure 16D:
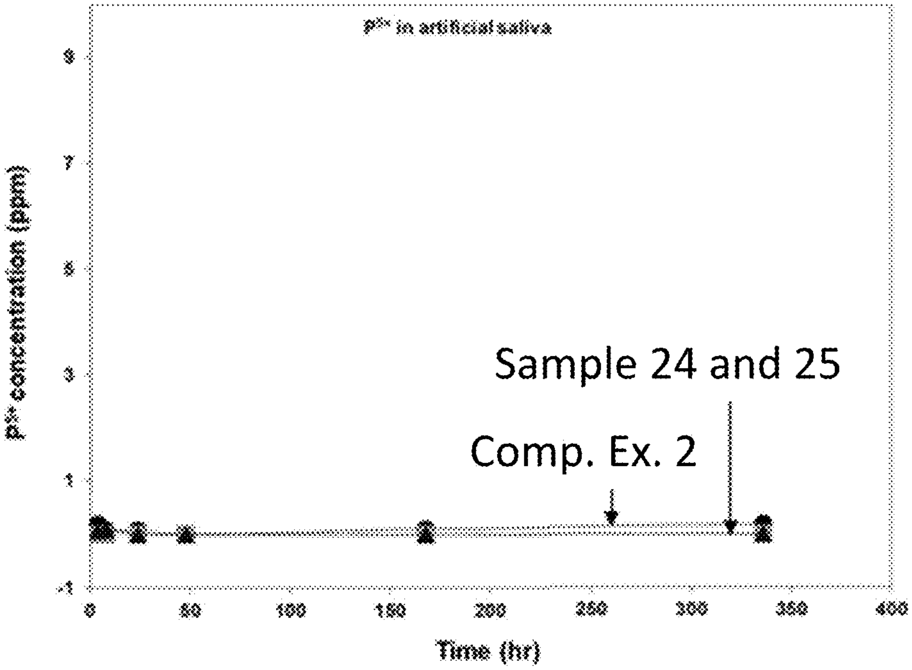

FIG. 15 illustrates equivalent alkali per gram of Samples 24 and 25 and Comparative Example 2, when tested in water at 98° C. for 2 hrs, according to ISO 719 standard procedure, according to some embodiments. In other words, equivalent alkali release in FIG. 15 was measured using a titration method of 50 mL of DI water containing glass grains for 2 hrs at 98° C., as specified by ISO 719. The solution is titrated with 0.01 M HCl using methyl red as an indicator and reported as g neutralized alkali per gram of grains, as described in ISO 719. A higher alkali release indicates a lower water durability of the glass composition. Thus, because the equivalent alkali release from Sample 24 and Sample 25 is about one fifth to one tenth of that from Comparative Example 2 (45S5), Comparative Example 2 has a lower water durability than either Sample 24 or Sample 25. The improved hydrolytic resistance of Samples 24 and 25 (and by extension, Samples 26-30) may be attributed to their lower alkali (i.e., $Na_2O$, $K_2O$, $Li_2O$) content as compared with Comparative Example 2.

Moreover, from FIG. 15, Samples 24 and 25 fall within HGB 3 category, while Comparative Example 2 falls within HGB 5 based on ISO 719 testing in water. HGB stands for hydrolytic resistance of glass grains under a boiling water test. A smaller number HGB indicates a higher resistance (greater durability), according to ISO 719. This suggests a significant improvement in water durability in the sample compositions.

What FIG. 15 indicates is that glass compositions with higher durability ensures a longer shelf time when being used in an aqueous solution. With respect to Comparative Example 2, dental applications using this compositions are currently formulated with a non-aqueous solution. The current Samples of Table E, which have improved water durability, allow flexibility in formulating with both aqueous and non-aqueous solutions, making them better candidates in dental or oral care or beauty product applications.

FIGS. 16A-16D illustrate inductively coupled plasma (ICP) analysis of released $Na^+$ (FIG. 16A), $Ca^{2+}$ (FIG. 16B), $Si^{4+}$ (FIG. 16C), and $P^{5+}$ (FIG. 16D) ion concentrations in artificial saliva solutions after soaking glass powder samples of Samples 24 and 25 and Comparative Example 2 therein. ICP analysis was conducted with an Agilent 5800 ICP-OES device to analyze the ion concentration in the artificial saliva. From FIG. 16A, ICP data confirms that a much lower $Na^+$ ion concentration was detected for Samples 24 and 25 than for Comparative Example 2. Similarly, from FIG. 16C, a much lower $Si^{4+}$ ion concentration was detected for Samples 24 and 25 than for Comparative Example 2, suggesting that the novel compositions exhibit higher resistance to water corrosion than 45S5 glass, given that silicon dioxide serves as the primary glass-forming oxide component of the tested glasses. Higher $Ca^{2+}$ ion concentrations were measured in Samples 24 and 25 than in Comparative Example 2, which is consistent with higher CaO content in those Samples than in 45S5. In other words, higher calcium content in glass compositions may result in a higher released Ca amount. For Samples 24 and 25 and Comparative Example 2, not all calcium may be bonded with phosphorus to form apatite. There is excess calcium released in the saliva, as detected by ICP in higher CaO compositions. From FIG. 16D, there is no measurable $P^{5+}$ in the saliva, suggesting a reaction of phosphorus with calcium to form apatite. These results provide additional support of the improved durability of the exemplified compositions over 45S4 glass. Higher apatite was formed in the sample compositions, as confirmed by XRD in FIGS. 17A-17C (high peak intensity and sharper peaks indicate a higher amount of apatite).

Figure 17A:
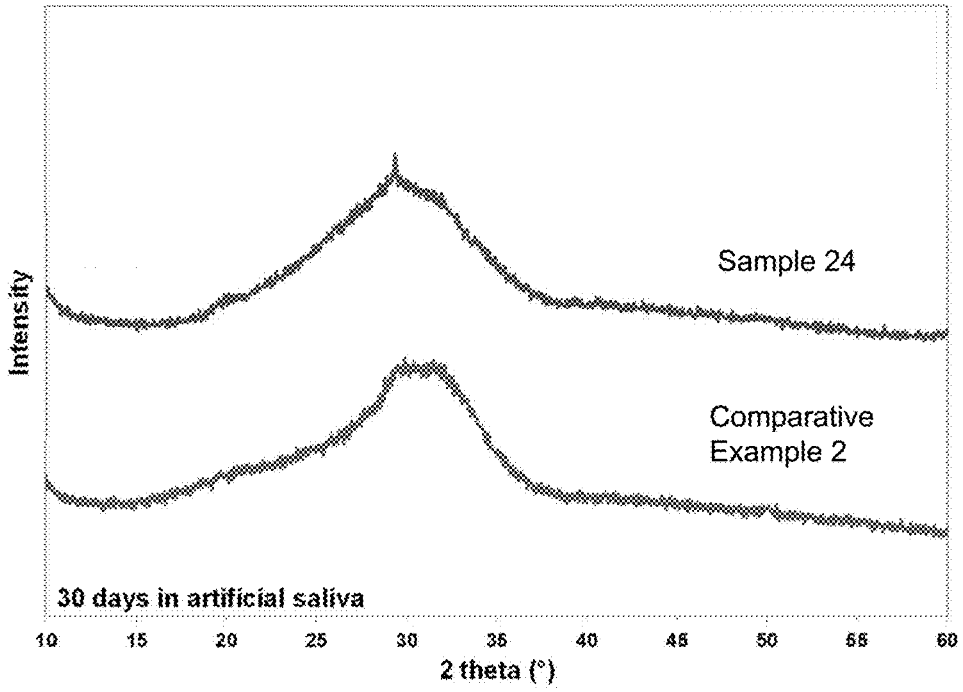
FIGS. 17A-17C illustrate powder x-ray diffraction (XRD) analysis on Sample 24 and Comparative Example 2 after immersion in artificial saliva (maintained at 37° C.) for 30 days (FIG. 17A), 47 days (FIG. 17B), and 61 days (FIG. 17C), according to some embodiments. Samples were dried and ground before XRD analysis.
Figure 17B:
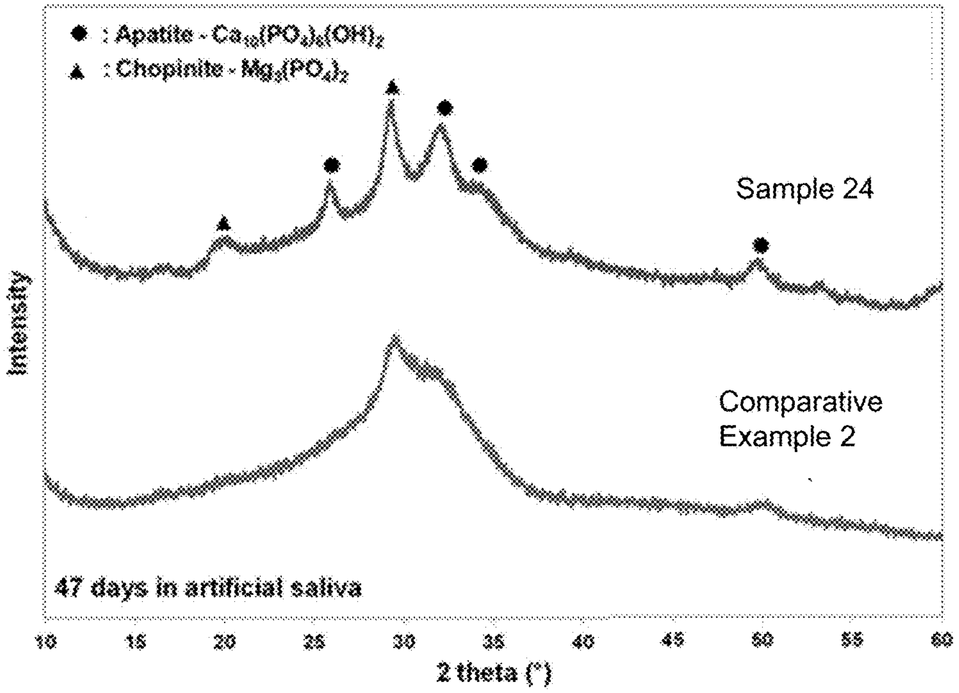
Figure 17C:
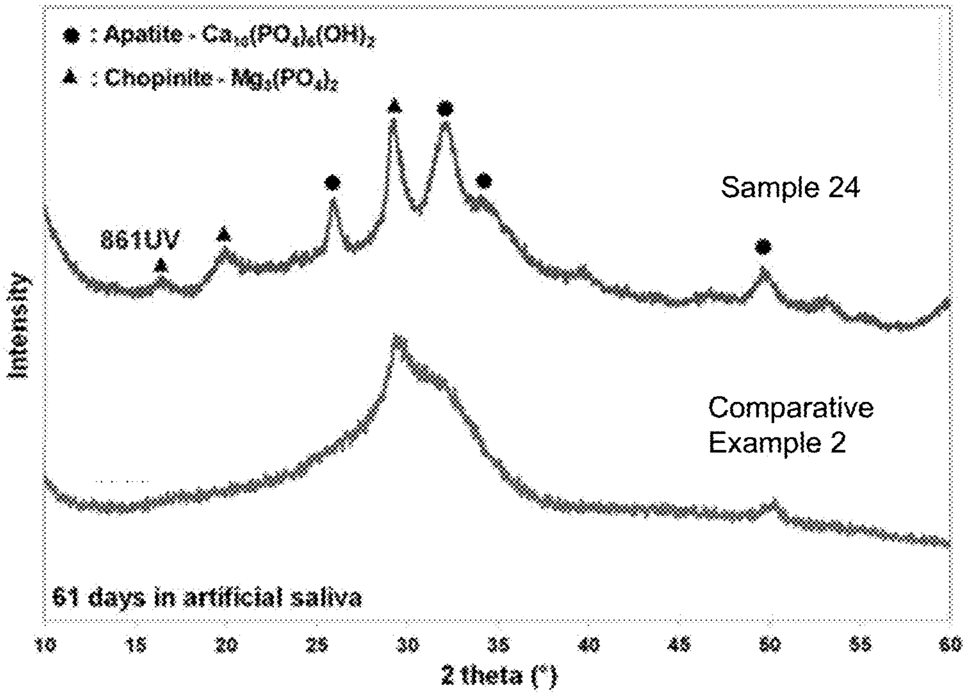

FIGS. 17A-17C illustrate powder x-ray diffraction (XRD) analysis on Sample 24 and Comparative Example 2 after immersion in artificial saliva (maintained at 37° C.) for 30 days (FIG. 17A), 47 days (FIG. 17B), and 61 days (FIG. 17C). Samples were dried and ground before XRD analysis. Samples were prepared for XRD analysis by grinding to a fine powder using a Rocklabs ring mill. The powder was then analyzed using a Bruker D4 Endeavor device equipped with a LynxEye™ silicon strip detector. X-ray scanning was conducted from 5° to 80° (2θ) for data collection. As explained above, apatite is an inorganic mineral in bone and teeth, and the formation thereof in a simulated body fluid is one criteria for a material to be bioactive. The XRD data in FIGS. 17A-17C shows that although no crystalline phases were detected in Sample 24 or Comparative Example 2 (45S5 glass) after 30 days (FIG. 17A) in artificial saliva, apatite was identified in Sample 24 after 47 days (FIG. 17B), with the peaks growing more pronounced by 61 days (FIG. 17C). In contrast, no well-developed apatite phase was detected in Comparative Example 2 even after soaking in artificial saliva after 61 days. This suggests that Sample 24 has a higher crystallinity and better bioactivity than Comparative Example 2. Because calcium is a key component in apatite, a higher CaO concentration favors faster apatite formation. Sample 24 has higher concentrations of CaO than Comparative Example 2.

Figure 18A:
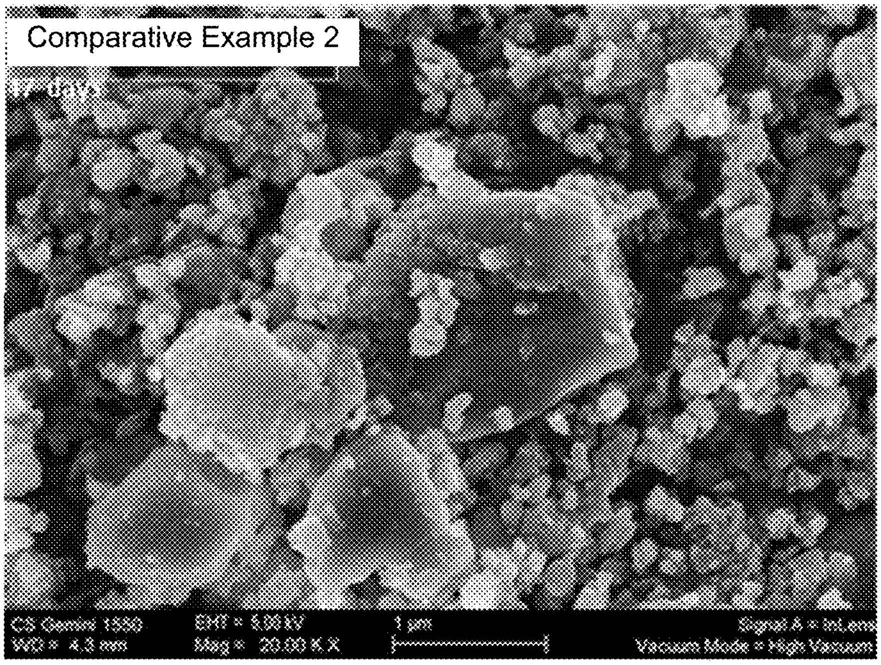
FIGS. 18A and 18B illustrate scanning electron microscopy (SEM) images of Comparative Example 2 (FIG. 18A) and Sample 24 (FIG. 18B) after immersion in artificial saliva (maintained at 37° C.) for 47 days, according to some embodiments. Samples were dried before SEM analysis.
Figure 18B:
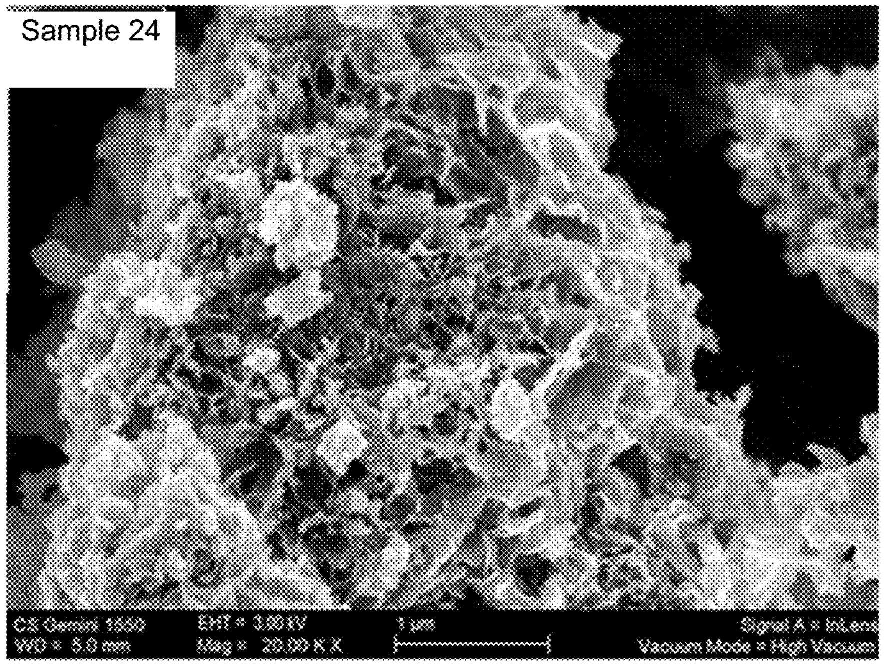

FIGS. 18A and 18B illustrate scanning electron microscopy (SEM) images of Comparative Example 2 (FIG. 18A) and Sample 24 (FIG. 18B) after immersion in artificial saliva (maintained at 37° C.) for 47 days. Samples were dried before SEM analysis. A conductive carbon coating was applied to the glass powder to reduce surface charging and then observed in a Zeiss Gemini 500 SEM. The SEM images provide further evidence of the needle-like apatite phase on the surface of Sample 24 versus spherical nuclei in Comparative Example 2. Results from XRD and SEM provide additional support of a higher bioactivity in the exemplified compositions than in 45S5 glass.

Example 6—Compositions

Non-limiting examples of amounts of precursor oxides for forming the embodied glasses are listed in Table F, along with the properties of the resulting glasses. The annealing point (° C.) may be measured using a beam bending viscometer (ASTM C598-93).

1400° C., or at temperatures below 1200° C., thereby making it possible to melt in relatively small commercial glass tanks.

Example 7—Improved Bioactivity

Figure 19A:
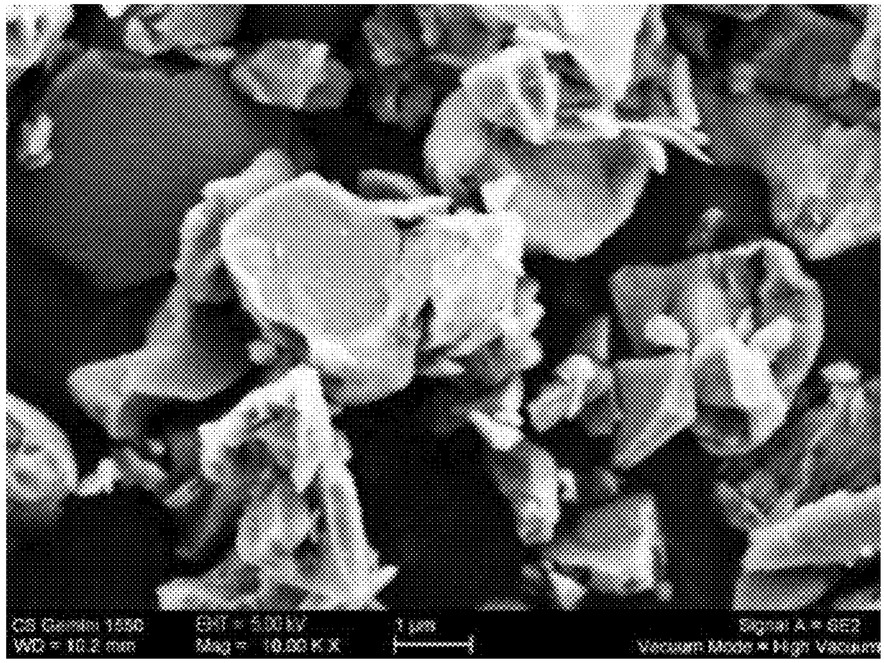
FIGS. 19A-19I illustrate scanning electron microscopy (SEM) images of Sample 39 after one day (FIGS. 19A-19C), four days (FIGS. 19D-19F), and seven days (FIGS. 19G-19I) in artificial saliva, according to embodiments. Samples were dried and sputter coated with a conductive carbon before SEM analysis.
Figure 19B:
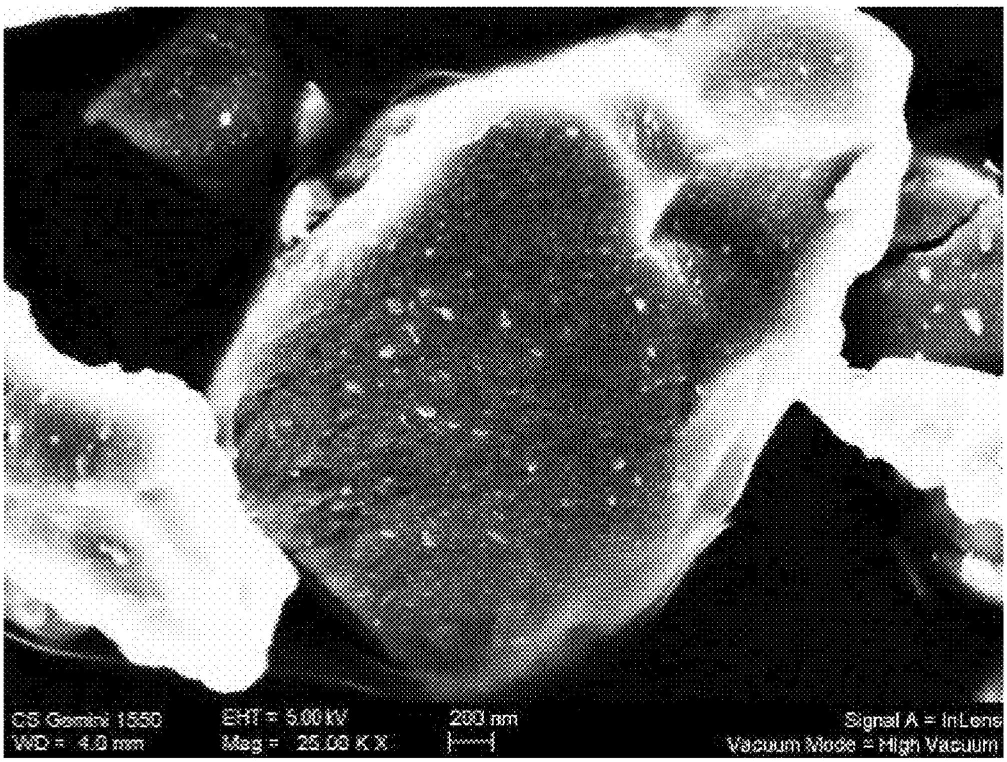
Figure 19C:
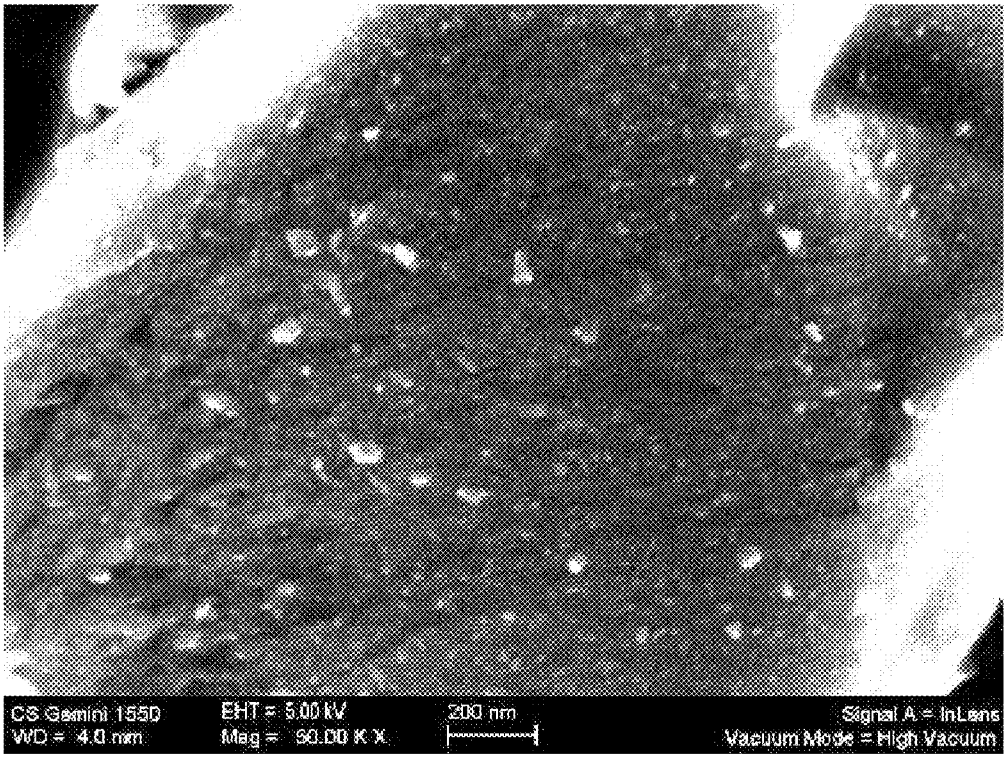
Figure 19D:
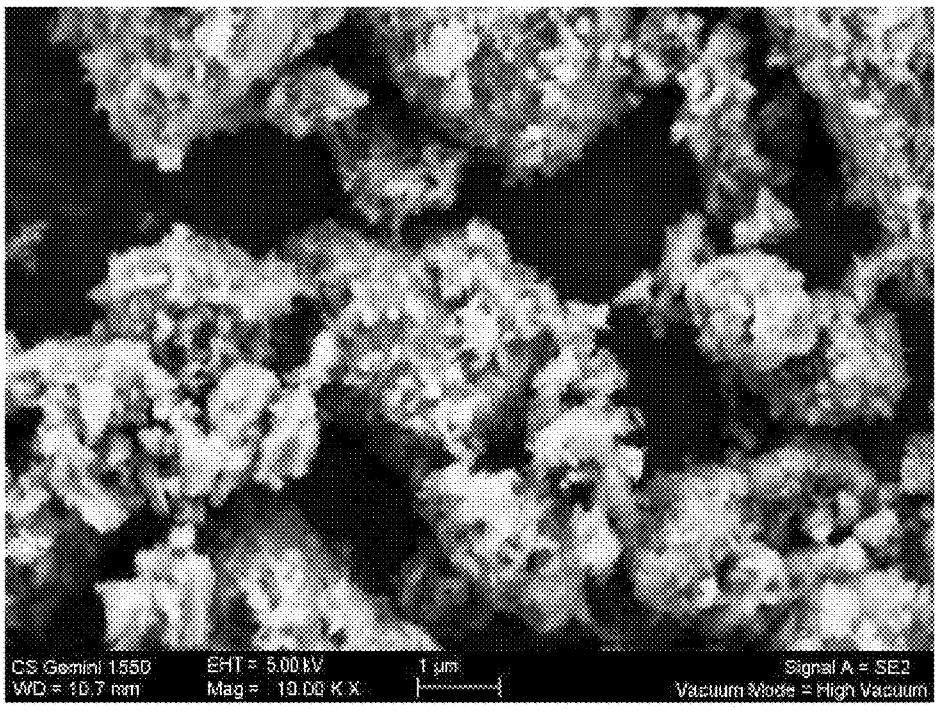
Figure 19E:
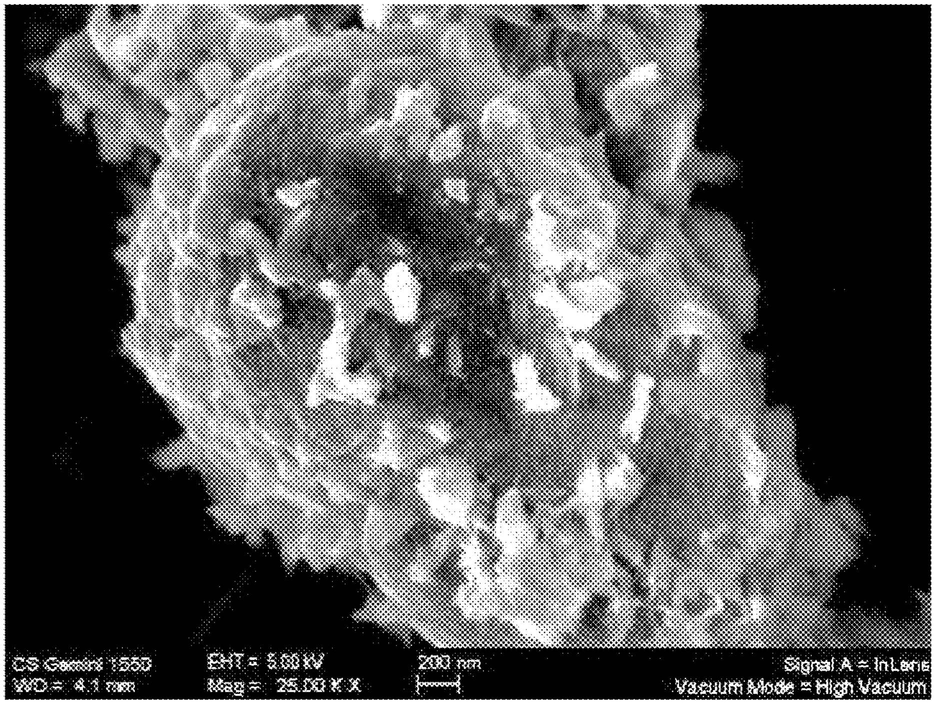
Figure 19F:
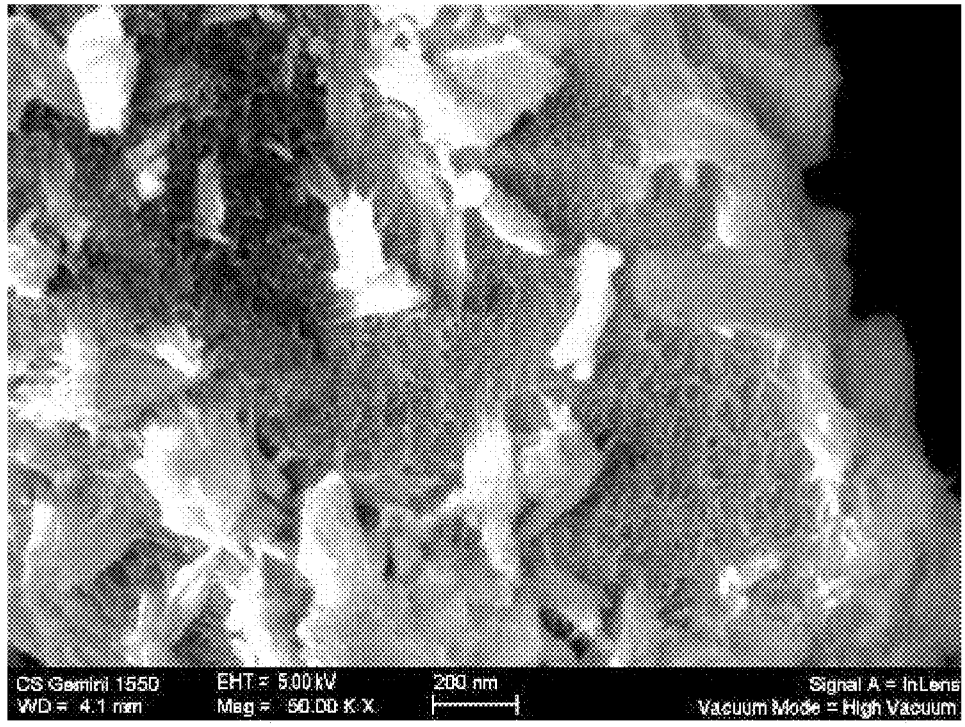
Figure 19G:
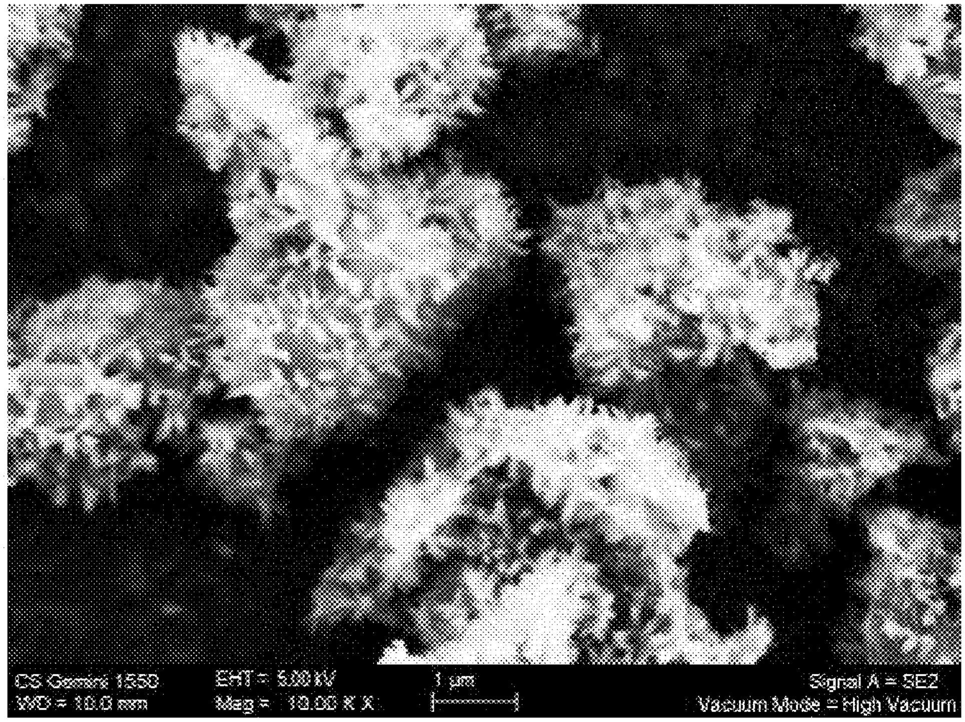
Figure 19H:
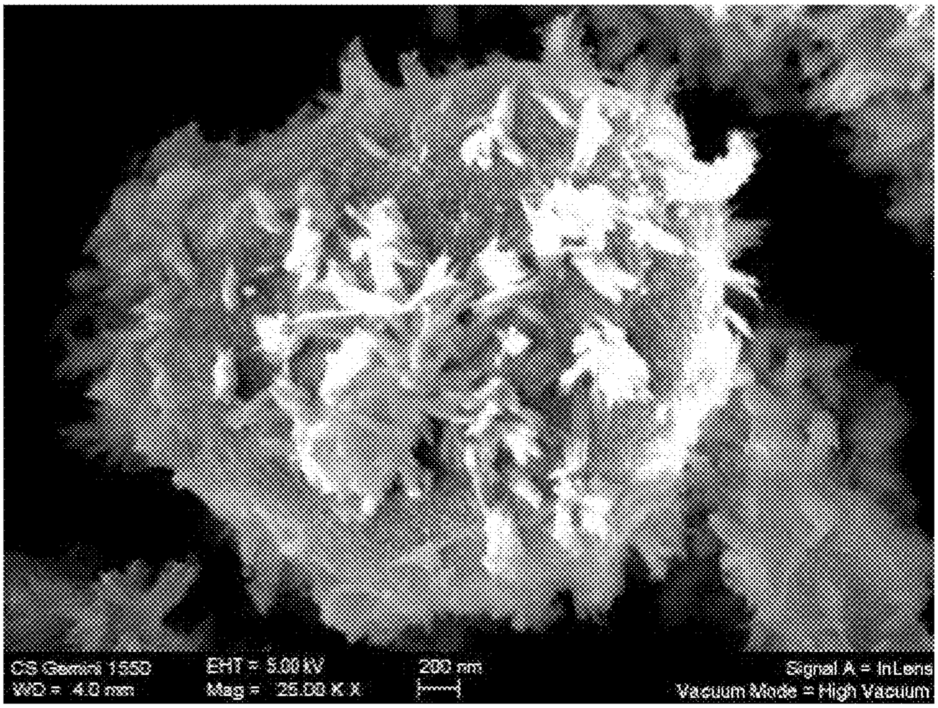
Figure 19I:
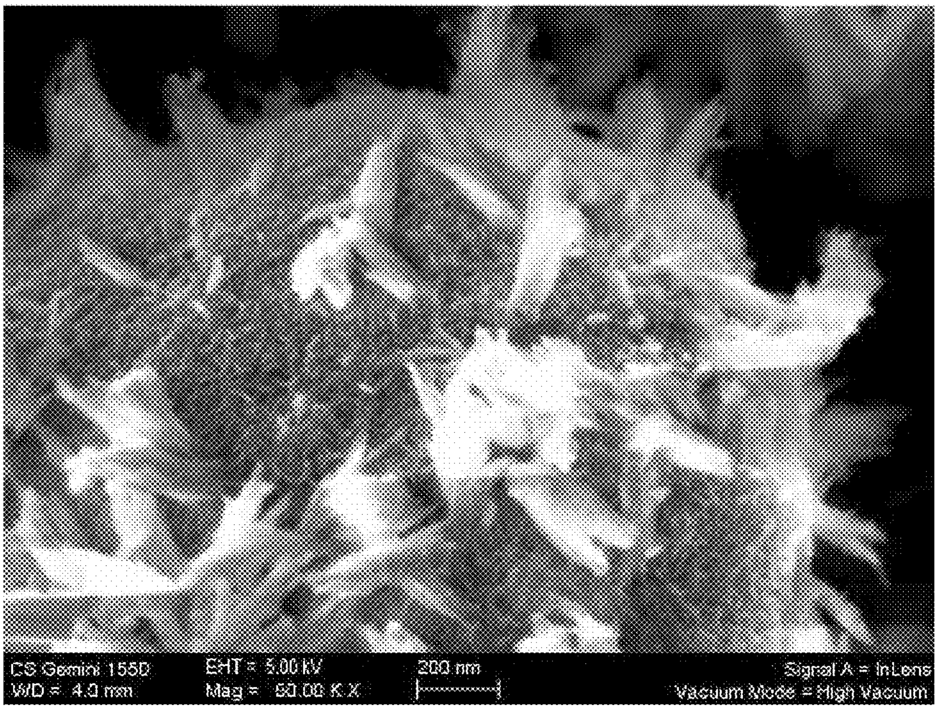

FIGS. 19A-19I illustrate scanning electron microscopy (SEM) images of Sample 39 after one day (FIGS. 19A-19C), four days (FIGS. 19D-19F), and seven days (FIGS. 19G-19I) in artificial saliva. In embodiments, the compositions of Table F exhibit remarkably high bioactivity, at least ten times higher than Comparative Example 2. For example, within a very short time-one day after soaking in artificial saliva—a surface reaction layer was observed in Sample 39 (FIGS. 19A-19C). The surface layer may result from a hydrolytic reaction with the glass. No clear crystalline morphology is observed at one day. After four days (FIGS. 19D-19F), Sample 9 was covered with a well-developed crystalline phase. Combined with XRD, the well-developed crystalline phase is determined to be apatite, which is different from the surface reaction layer formed at one day. After seven days (FIGS. 19G-19I), Sample 39 shows higher quantities of crystals of larger size.

Figure 21:
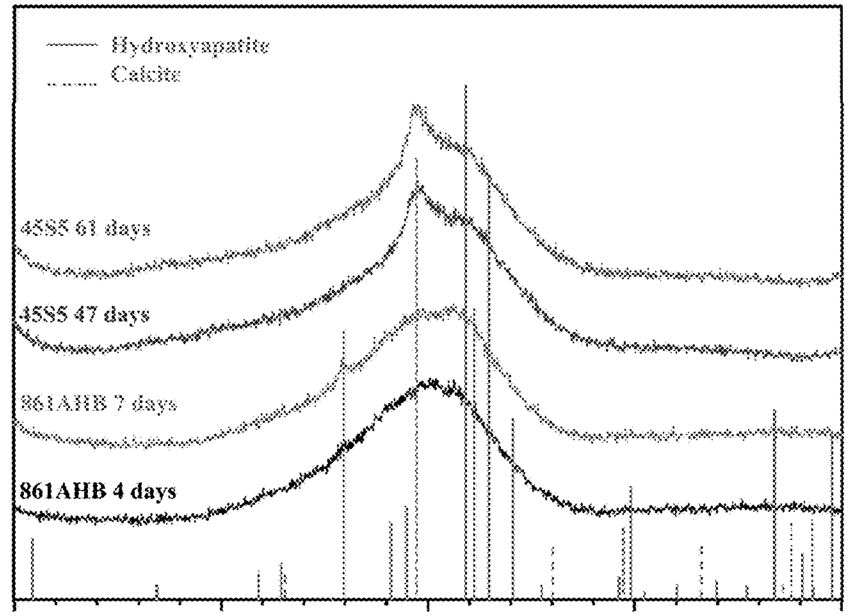
FIG. 21 illustrates powder x-ray diffraction (XRD) analysis of Sample 39 and Comparative Example 2 after soaking in artificial saliva for various times, according to embodiments. Samples were dried and ground before XRD analysis.

FIG. 21 illustrates powder x-ray diffraction (XRD) analysis of Sample 39 and Comparative Example 2 after soaking in artificial saliva for various times. Combining the SEM studies of FIGS. 19A-19I with the XRD results of FIG. 21, the crystal growth shown after 4 and 7 days was determined to be hydroxyapatite. Depending on the ions in the reaction media and in the glass composition, fluorapatite, chlorapatite or hydrocarbon apatite can be formed. As explained above, apatite is an inorganic mineral in bone and teeth, and the formation thereof in a simulated body fluid is one criteria for a material to be bioactive (ASTM F1538-03, 2017). The presence of apatite ensures the formation of a direct bond with physiological features, such as bone or teeth, and is an indication of the bioactivity of an implanted material.

TABLE F

| Oxide (wt. %) | Comp. Ex. 2 | 31 | 32 | 33 | 34 | 35 | 36 | 37 | 38 | 39 | 40 | 41 | 42 |
|---|---|---|---|---|---|---|---|---|---|---|---|---|---|
| $SiO_2$ | 45.0 | 39.5 | 39.5 | 39.5 | 39.5 | 39.5 | 39.5 | 37.5 | 34.5 | 29.5 | 24.5 | 24.5 | 20.5 |
| $Na_2O$ | 24.5 | 0 | 0 | 0 | 0 | 0 | 0 | 0 | 0 | 0 | 0 | 0 | 0 |
| MgO | 0 | 0 | 4.5 | 9.5 | 14.5 | 0 | 0 | 4.5 | 4.5 | 4.5 | 4.5 | 4.5 | 4.5 |
| CaO | 24.5 | 47 | 42.5 | 37.5 | 32.5 | 32.5 | 32.5 | 42.5 | 42.5 | 42.5 | 42.5 | 42.5 | 42.5 |
| SrO | 0 | 0 | 0 | 0 | 0 | 14.5 | 0 | 0 | 0 | 0 | 0 | 0 | 0 |
| ZnO | 0 | 0 | 0 | 0 | 0 | 0 | 14.5 | 0 | 0 | 0 | 0 | 0 | 0 |
| $P_2O_5$ | 6.0 | 9.5 | 9.5 | 9.5 | 9.5 | 9.5 | 9.5 | 11.5 | 14.5 | 19.5 | 24.5 | 22.5 | 22.5 |
| $ZrO_2$ | 0 | 4 | 4 | 4 | 4 | 4 | 4 | 4 | 4 | 4 | 4 | 6 | 10 |
| Density | 2.71 | 3.03 | 2.96 | 2.95 | 2.99 | 3.18 | 3.15 | 2.98 | 2.99 | 3.03 | 3.12 | 3.16 | 3.26 |
| Anneal Pt (° C.) | 514.8 | 759.1 | 743.2 | 738.3 | 757.3 | 729.2 | 687.0 | 738.0 | 730.2 | 717.6 | 702.2 | 805.9 | 704.3 |
| Refractive index, $n_d$ | 1.562 | 1.639 | 1.638 | 1.630 | 1.620 | 1.632 | 1.635 | 1.647 | 1.634 | 1.628 | 1.623 | 1.634 | 1.653 |

The bioactive glass compositions disclosed herein (e.g., Table F) exhibit significantly higher chemical durability and excellent bioactivity, as compared to currently available glasses, and can be in any form that is useful for the medical and dental processes disclosed. In embodiments, the compositions of Table F demonstrate significantly higher chemical durability and bioactivity over Comparative Example 2 (45S5 glass).

Figure 20A:
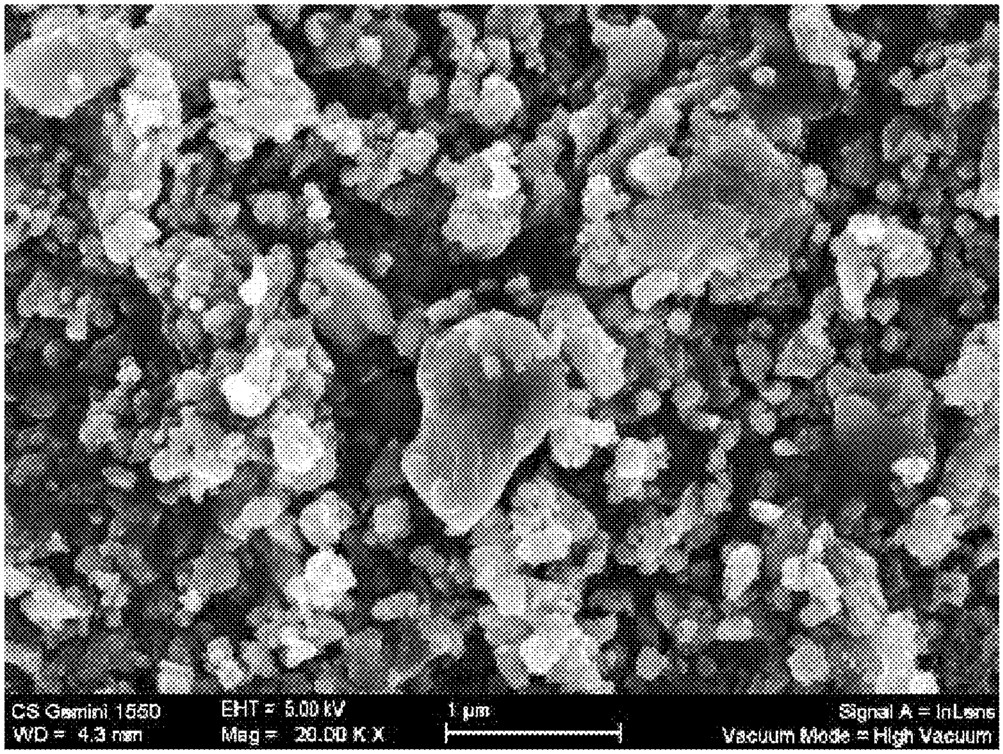
FIGS. 20A and 20B illustrate SEM images of Comparative Example 2 after soaking in artificial saliva for 47 days, according to embodiments. Samples were dried and sputter coated with a conductive carbon before SEM analysis.
Figure 20B:
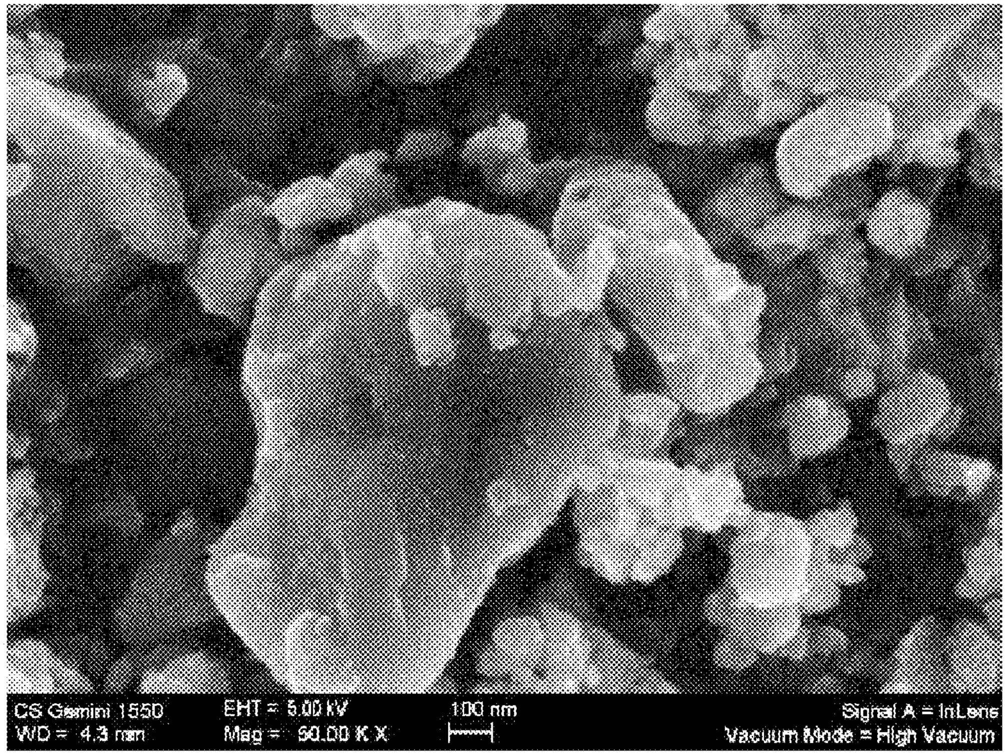

The compositions can be in the form of, for example, particles, powder, microspheres, fibers, sheets, beads, scaffolds, woven fibers, or other form depending on the application. The compositions of Table F may be melted at temperatures below 1600° C., or at temperatures below FIGS. 20A and 20B illustrate SEM images of Comparative Example 2 after soaking in artificial saliva for 47 days (much longer than the seven day study for Sample 39 from FIGS. 19A-19I). Though a calcite ($CaCO_3$) phase started to form after 47 days soaking in artificial saliva, Comparative Example 2 showed no hydroxyapatite formation even after 61 days in artificial saliva. As specified by ASTM F1538-03, bioactive materials only refer to those that can form apatite in vitro or in vivo. The formation of calcite does not produce a direct bond with bony tissues due to its chemical difference from bone; thus, calcite is not regarded as bioactive. FIGS. 20A and 20B provide morphological evidence of a typical calcite phase in Comparative Example 2 after 47 days. The inclusion of high concentrations of CaO and $P_2O_5$ oxides in the example compositions ensures the formation of an apatite phase in artificial saliva while the comparative composition (which has appreciably lower concentrations of CaO and $P_2O_5$) only forms a calcite phase. The slow (i.e., negligible) conversion to hydroxyapatite and the formation of calcite in Comparative Example 2 after over one month in artificial saliva suggests its relatively lower bioactivity as compared to Sample 39. Due to its chemical similarity with bone, apatite can form a direct bond with bony tissue while calcite cannot.

The compositions of Table F demonstrate a step change in bioactivity, which can be a significant advantage for cavity and hypersensitivity treatment. High CaO and $P_2O_5$ contents, along with lower $SiO_2$ quantities may account for their improved bioactivity over current reported bioactive glasses by having a ten times faster rate of apatite (e.g., hydroxyapatite) formation. Because calcium is a key component in apatite, higher CaO concentrations favor faster apatite formation. Sample 39 has higher concentrations of CaO than Comparative Example 2 (42.5 wt. % versus 24.5 wt. %).

Example 8—Improved Chemical Stability

The compositions from Table F also demonstrate improved chemical stability over Comparative Example 2. Many Example compositions fall within HGB 3 category while Comparative Example 2 is in HGB 5, based on the ISO 719 testing procedure. According to ISO 719, testing was conducted by measuring the amount of leached alkali ions after soaking glass grains (300-425 μm) of the Sample compositions and Comparative Example 2 in water at 98° C. for 1 hr. HGB stands for hydrolytic resistance of glass grains under the prescribed boiling water test. A higher alkali release (higher HGB number) indicates a lower water durability (lower resistance) of the glass composition. Conversely, a lower alkali release (lower HGB number) indicates a higher water durability of the glass composition. Table G illustrates the ISO 719 testing results of the Sample compositions and Comparative Example 2.

TABLE G

| Example | Conversion of mols leached to μg neutralized alkali (as $Na_2O$) per gram glass grain tested (μg/g) | Glass Classification per ISO 719 |
|---|---|---|
| Comp. Ex. | 871.1 | HGB 5 |
| 31 | 233.9 | HGB 3 |
| 32 | 132.2 | HGB 3 |
| 33 | 101.3 | HGB 3 |
| 34 | 88.9 | HGB 3 |
| 35 | 180.6 | HGB 3 |
| 37 | 173.1 | HGB 3 |
| 38 | 129.6 | HGB 3 |
| 39 | 113.1 | HGB 3 |

The results from Table G indicate a significant improvement in water durability in the Sample compositions over Comparative Example 2. The equivalent alkali release from the Sample compositions is about one-tenth to one-fifth of that from Comparative Example 2. In other words, because the equivalent alkali release from Sample Nos. 1-5, 7-9 is lower than that of Comparative Example 2, the Examples disclosed herein have a higher water durability. The improved hydrolytic resistance of the Sample compositions (Sample Nos. 1-5, 7-9) may be attributed to their lower alkali contents, higher quantities of CaO, and the addition of $ZrO_2$, as compared to Comparative Example 2.

What the results in Table G indicate is that the higher water durability ensures a longer shelf time when being used in an aqueous solution. Dental applications utilizing Comparative Example 2 are currently restricted to non-aqueous solution formulations. The current Sample of Table F, which have improved water durability, allow flexibility in formulating with both aqueous and non-aqueous solutions, making them better candidates in dental or oral care or beauty product applications.

Example 9—Measurement

Microstructures of the glass powder after soaking in artificial saliva was observed using a Zeiss Gemini 450 SEM. After applying a conductive carbon coating to the glass powder to reduce surface charging, backscattered images were obtained at 5 kV accelerating potentials on the carbon-coated, polished cross-section samples.

Crystalline phases formed in the glass powder after soaking in artificial saliva were detected using X-ray diffraction (XRD). Powder x-ray diffraction (XRD) analysis was conducted by preparing the samples by first drying and then grinding to a fine powder using a Rocklabs ring mill. The powder was then analyzed using a Bruker D4 Endeavor device equipped with a LynxEye™ silicon strip detector. X-ray scanning was conducted from 5° to 80° (2θ) for data collection.

Example 10

Twelve bioactive glass samples according to embodiments disclosed and described herein were prepared by conventional glass melting and forming techniques. The density, annealing point, and refractive index of the twelve samples were then compared to the conventional glass composition 45S5 Bioglass® (Comparative Example 2). The compositions of 45S5 Bioglass® and the twelve samples are provided in Table H below. The annealing point and refractive index of the twelve samples and 45S5 Bioglass® are also shown in Table H.

TABLE H

| Oxides (wt %) | Comp. Ex. 2 | 43 | 44 | 45 | 46 | 47 | 48 |
|---|---|---|---|---|---|---|---|
| $SiO_2$ | 45.0 | 39.5 | 39.5 | 39.5 | 39.5 | 39.5 | 39.5 |
| $Na_2O$ | 24.5 | 0.0 | 0.0 | 0.0 | 0.0 | 0.0 | 0.0 |
| MgO | 0.0 | 0 | 4.5 | 9.5 | 14.5 | 0 | 0 |
| CaO | 24.5 | 47 | 42.5 | 37.5 | 32.5 | 32.5 | 32.5 |
| SrO | 0.0 | 0 | 0 | 0 | 0 | 14.5 | 0 |

TABLE H-continued

| | | | | | | | |
|---|---|---|---|---|---|---|---|
| ZnO | 0.0 | 0 | 0 | 0 | 0 | 0 | 14.5 |
| $P_2O_5$ | 6.0 | 9.5 | 9.5 | 9.5 | 9.5 | 9.5 | 9.5 |
| $ZrO_2$ | 0.0 | 4 | 4 | 4 | 4 | 4 | 4 |
| Density (g/cm$^3$) | 2.71 | 3.03 | 2.96 | 2.95 | 2.99 | 3.18 | 3.15 |
| Annealing point (° C.) | 514.80 | 759.1 | 743.2 | 738.3 | 757.3 | 729.2 | 687 |
| Refractive index, $n_d$ | 1.562 | 1.639 | 1.638 | 1.630 | 1.620 | 1.632 | 1.635 |

| Oxides (wt %) | 49 | 50 | 51 | 52 | 53 | 54 |
|---|---|---|---|---|---|---|
| $SiO_2$ | 37.5 | 34.5 | 29.5 | 24.5 | 24.5 | 20.5 |
| MgO | 4.5 | 4.5 | 4.5 | 4.5 | 4.5 | 4.5 |
| CaO | 42.5 | 42.5 | 42.5 | 42.5 | 42.5 | 42.5 |
| $P_2O_5$ | 11.5 | 14.5 | 19.5 | 24.5 | 22.5 | 22.5 |
| $ZrO_2$ | 4.0 | 4.0 | 4.0 | 4.0 | 6 | 10 |
| Density (g/cm$^3$) | 2.98 | 2.99 | 3.03 | 3.12 | 3.16 | 3.26 |
| Annealing point (° C.) | 738.00 | 730.20 | 717.60 | 702.20 | 805.90 | 704.30 |
| Refractive index, $n_d$ | 1.647 | 1.634 | 1.628 | 1.623 | 1.634 | 1.653 |

Example 11

The bioactive glass composition of Sample 51 from Example 10 was ground into bioactive glass particles having a particle size distribution D99 that was less than 10 μm. The weight of the bioactive glass particles was measured to obtain an initial weight. The bioactive glass particles were then soaked in deionized water for 7 days. The weight of the bioactive glass particles was measured after 1 day of soaking in water, after 4 days of soaking in water, and after 7 days of soaking in water. The weight of the glass particles after soaking in water for 1 day, soaking in water for 4 days, and soaking in water for 7 days was compared to the initial weight to determine the weight loss percentage on day 1, on day 4, and on day 7.

Figure 22:
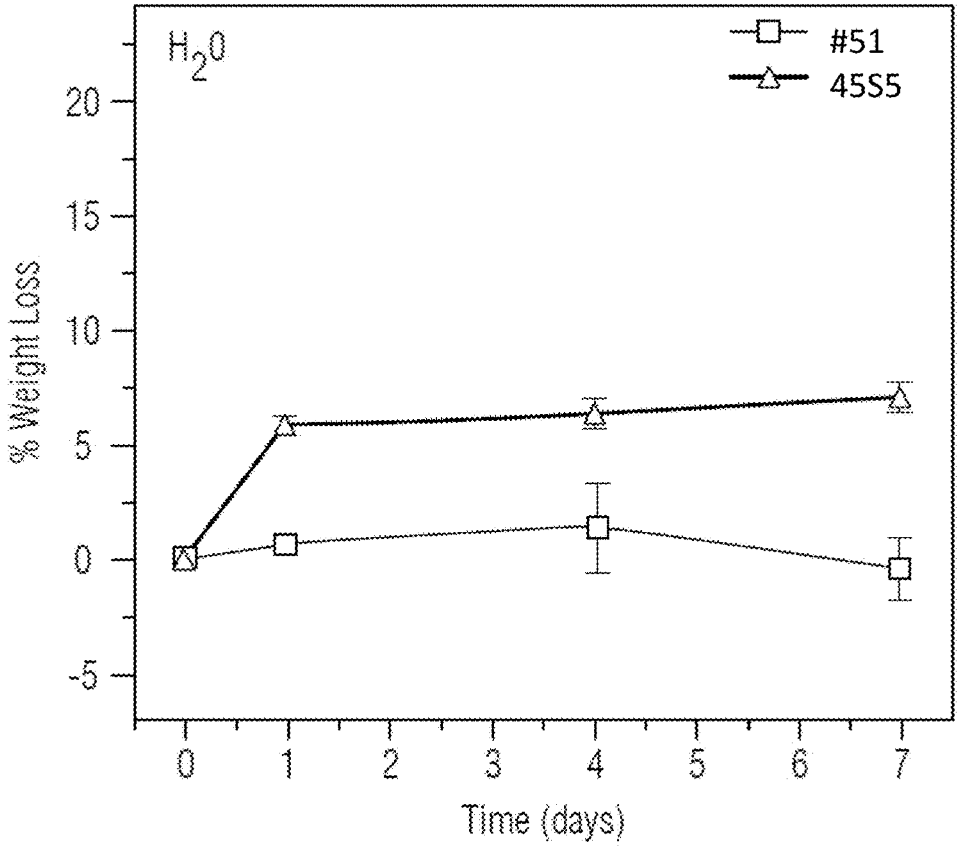
FIG. 22 graphically depicts weight loss versus time of bioactive glass compositions according to embodiments disclosed and described herein and conventional glass compositions in water.

The above weight loss measurements were also performed on conventional 45S5 Bioglass®. The results of this weight loss test are provided in FIG. 22. As shown in FIG. 22, the weight loss of the bioactive glass of Sample 51 is below 2.5% and near 0% even after 7 days of soaking in water, whereas 45S5 Bioglass® has a weight loss of nearly 6% after only 1 day of soaking in water. This shows that the bioactive glass of Sample 51 has much better durability in water than 45S5 Bioglass® and, therefore, is suitable for use in aqueous dentifrice formulations.

Example 12

The bioactive glass composition of Sample 51 from Example 10 was ground into bioactive glass particles having a particle size distribution D99 that was less than 10 μm. The weight of the bioactive glass particles was measured to obtain an initial weight. The bioactive glass particles were then soaked in artificial saliva manufactured by Modus Laboratories water for 7 days. The weight of the bioactive glass particles was measured after 1 day of soaking in artificial saliva, after 4 days of soaking in artificial saliva, and after 7 days of soaking in artificial saliva. The weight of the glass particles after soaking in artificial saliva for 1 day, soaking in artificial saliva for 4 days, and soaking in artificial saliva for 7 days was compared to the initial weight to determine the weight loss percentage on day 1, on day 4, and on day 7.

Figure 23:
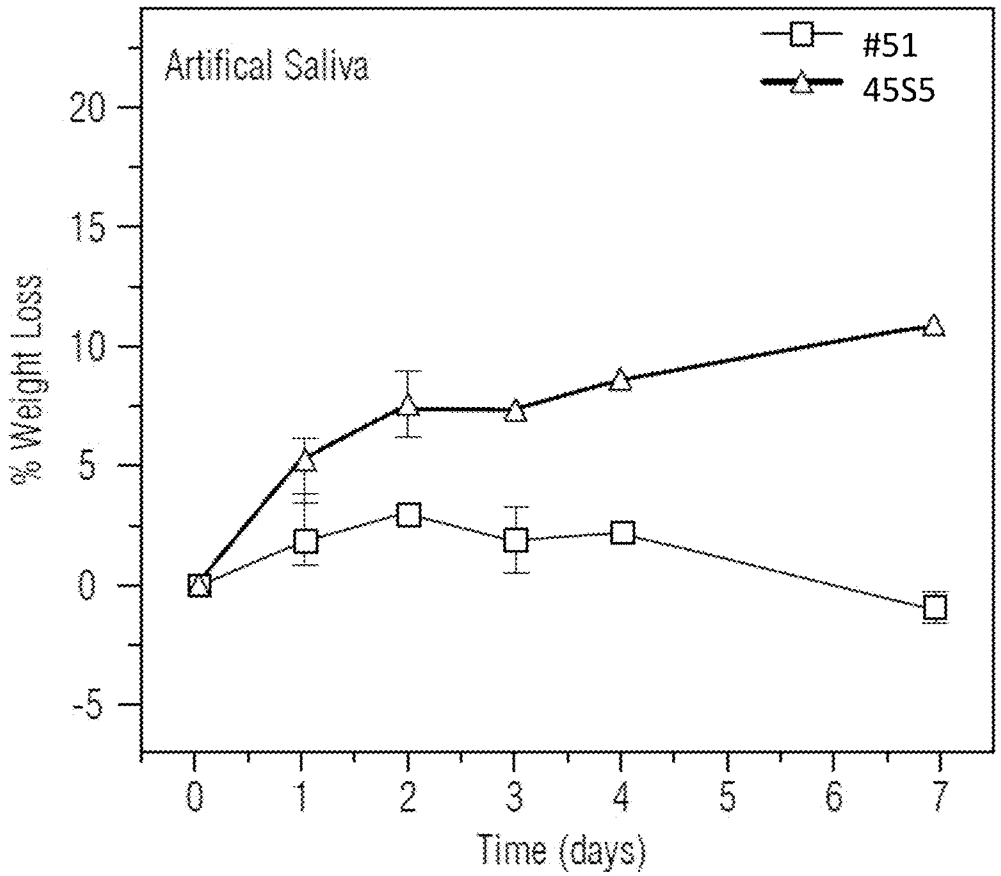
FIG. 23 graphically depicts weight loss versus time of bioactive glass compositions according to embodiments disclosed and described herein and conventional glass compositions in artificial saliva.

The above weight loss measurements were also performed on conventional 45S5 Bioglass®. The results of this weight loss test are provided in FIG. 23. As shown in FIG. 23, the weight loss of the bioactive glass of Sample 51 is below 2.5% and near 0% even after 7 days of soaking in artificial saliva, whereas 45S5 Bioglass® has a weight loss of nearly 6% after only 1 day of soaking in artificial saliva. This shows that the bioactive glass of Sample 51 has much better durability in artificial saliva than 45S5 Bioglass® and, therefore, is better suited to non-aqueous dentifrice formulations than 45S5 Bioglass.

Example 13

Figure 24:
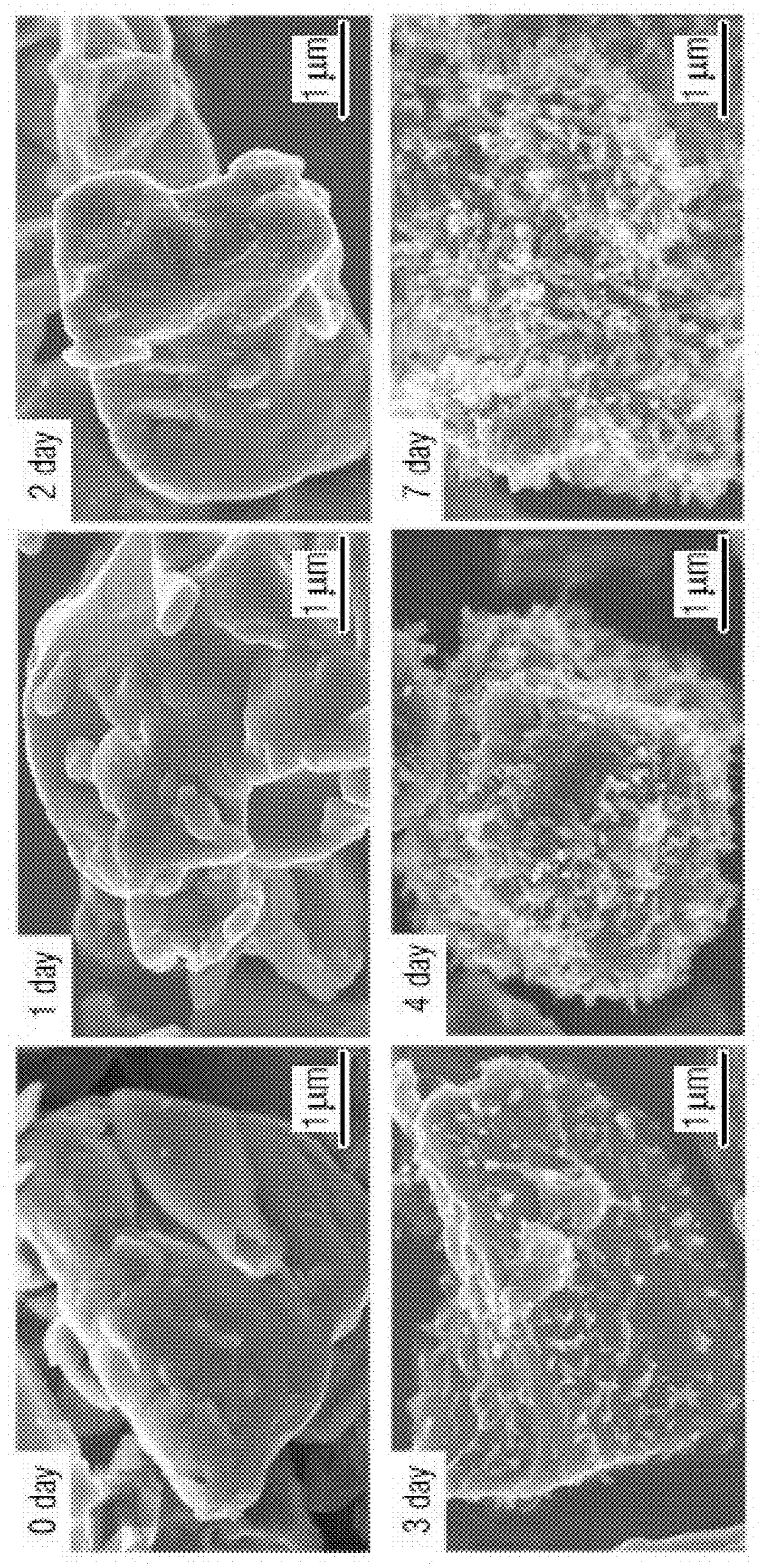
FIG. 24 is scanning electron microscope (SEM) images of bioactive glass compositions according to embodiments disclosed and described herein before and after exposure to artificial saliva.

The bioactive glass composition of Sample 51 from Example 10 was ground into bioactive glass particles having a particle size distribution that was less than 10 μm. The bioactive glass particles were then soaked in artificial saliva manufacture by Modus Laboratories. Scanning electron microscope (SEM) images were taken before soaking began, after 1 day of soaking in artificial saliva, after 2 days of soaking in artificial saliva, after 3 days of soaking in artificial saliva, after 4 days of soaking in artificial saliva, and after 7 days of soaking in artificial saliva. The SEM images are provided in FIG. 24. As shown in FIG. 24, within 2 days after soaking in artificial saliva, formation of scattered crystals was observed. The number and size of crystals increased with time. After 4 days, the whole surface of the bioactive glass particles was covered with a well-developed crystalline phase.

Figure 25:
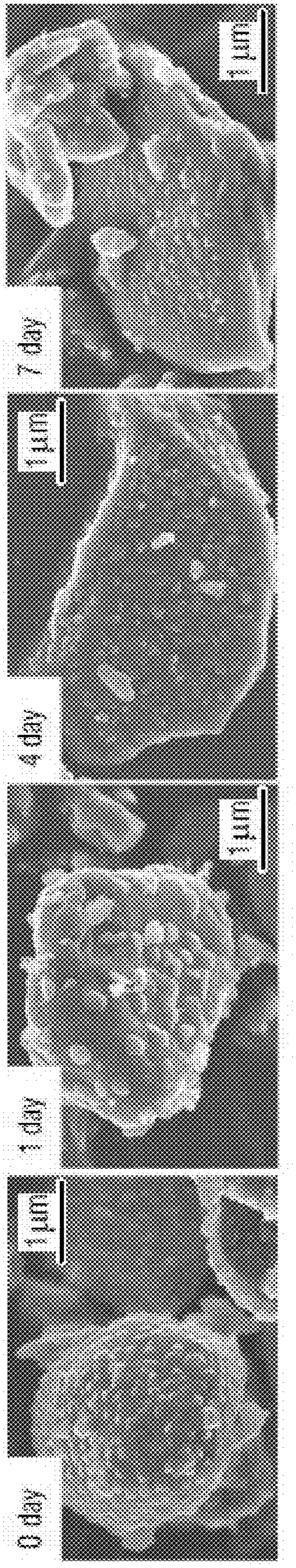
FIG. 25 is SEM images of conventional glass compositions before and after exposure to artificial saliva.

For a comparison, 45S5 Bioglass® particles were soaked in artificial saliva manufacture by Modus Laboratories. SEM images were taken before soaking began, after 1 day of soaking in artificial saliva, after 4 days of soaking in artificial saliva, and after 7 days of soaking in artificial saliva. The SEM images are provided in FIG. 25. As shown in FIG. 25, the surface morphology of 45S5 Bioglass® did not change after soaking for up to 7 days.

Figure 26:
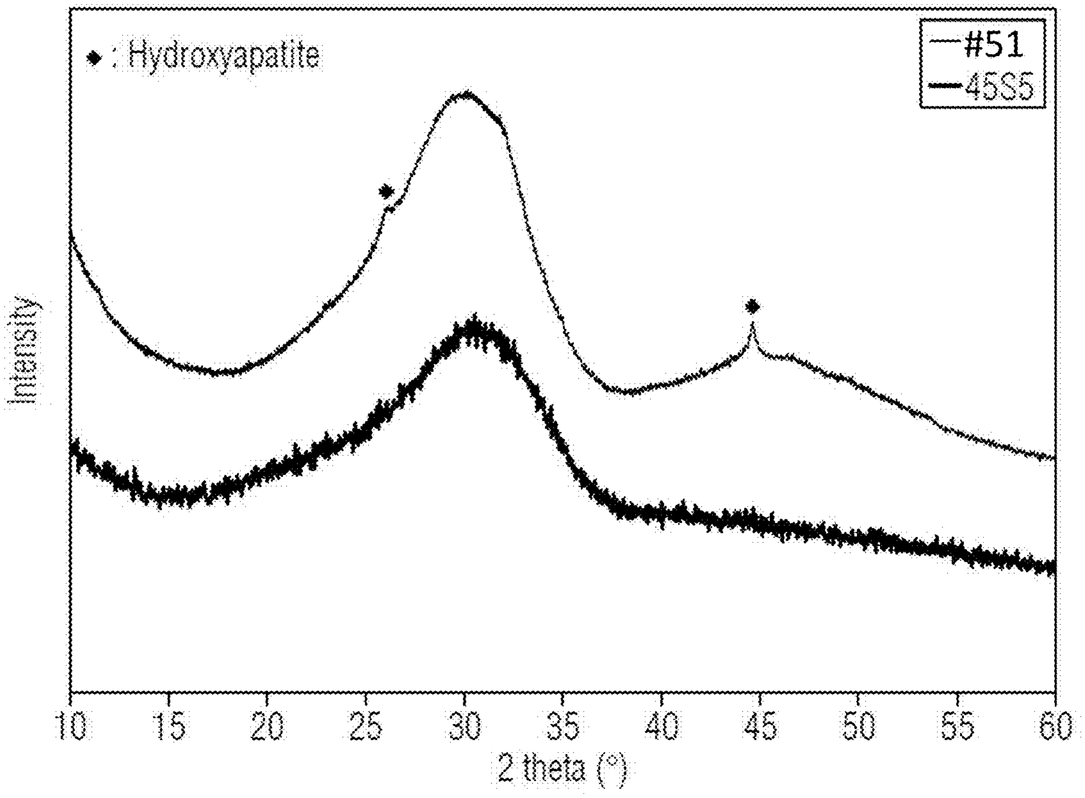
FIG. 26 is a graph showing x-ray diffraction (XRD) data of bioactive glass compositions according to embodiments disclosed and described herein and conventional glass compositions after exposure to artificial saliva.

To determine the phase of the crystalline structure formed on the surface of the bioactive glass of Sample 51 from Example 10, x-ray diffraction (XRD) was conducted on the bioactive glass of Sample 51 from Example 10 after soaking in artificial saliva for 7 days. Similarly, XRD was conducted on the 45S5 Bioglass® sample after soaking in saliva for 7 days. The XRD data for both bioactive glass of Sample 51 from Example 10 and 45S5 Bioglass® are shown in FIG. 26. The XRD result in FIG. 26 show crystals formed in the bioactive glass of Sample 51 from Example 10 were hydroxyapatite while no detectable crystalline phase was observed in 45S5 Bioglass®. The bioactive glass of Sample 51 from Example 10 demonstrate a step change in bioactivity, which can be of significant advantage for cavity and hypersensitivity treatment.

Figure 27:
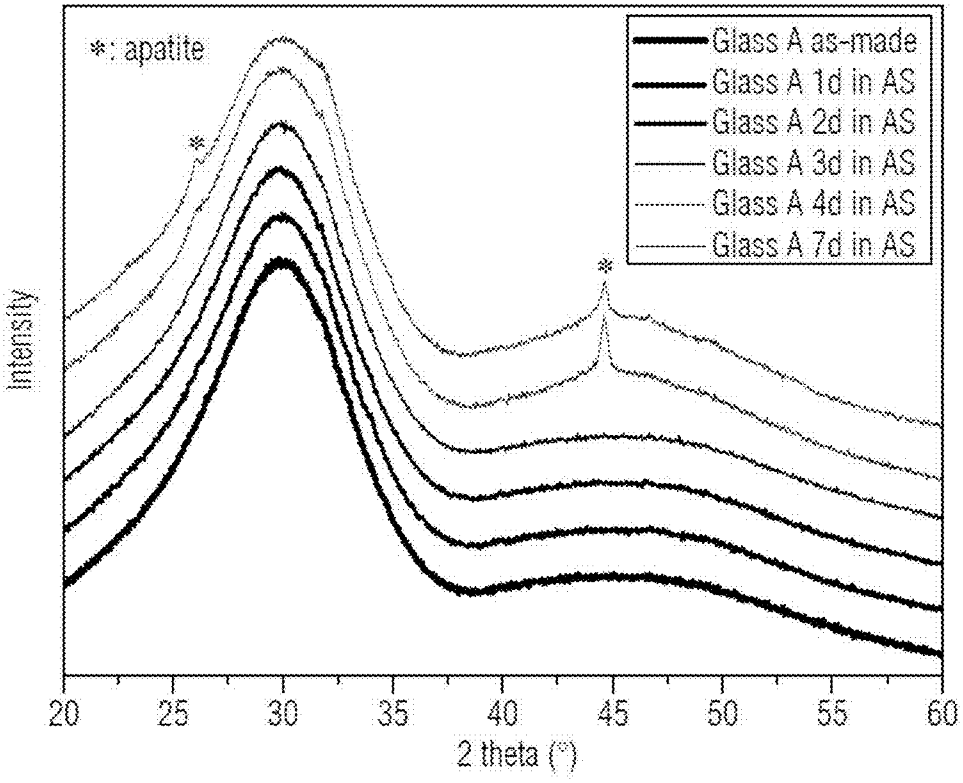
FIG. 27 is a graph showing XRD data of bioactive glass compositions according to embodiments disclosed and described herein before and after exposure to artificial saliva.

In addition to the XRD data shown in FIG. 26, additional XRD data was collected on the bioactive glass of Sample 51 from Example 10 and is shown in FIG. 27. As shown in FIG. 27, six XRD plots were collected. Namely, XRD was measured on the bioactive glass of Sample 51 from Example 10 in its as-made form, after 1 day in artificial saliva, after 2 days in artificial saliva, after 3 days in artificial saliva, after 4 days in artificial saliva, and after 7 days in artificial saliva. The XRD plots in FIG. 27 show that apatite formation occurred on the bioactive glass of Sample 51 from Example 10 with 4 days of soaking in artificial saliva, and significant additional formation of apatite did not occur between days 4 and 7 of soaking in artificial saliva. This shows the increased bioactivity of the bioactive glass of Sample 51 from Example 10.

Example 14

Additional testing was conducted to determine corrosion of the bioactive glass of Sample 51 from Example 10 compared to 45S5 Bioglass®. Initial tests were conducted by soaking the bioactive glass of Sample 51 from Example 10 and 45S5 Bioglass® in artificial saliva comprising 28 ppm $Na^+$, 80 ppm $K^+$, and 6 ppm $Mg^{2+}$ for seven days. This artificial saliva had a pH of 7.1. XRD data was collected on the as-made samples, after 1 day soaking in the artificial saliva, after 4 days soaking in the artificial saliva, after 7 days soaking in the artificial saliva, after 14 days soaking in the artificial saliva, after 21 days soaking in the artificial saliva, and after 30 days soaking in the artificial saliva.

Figure 28:
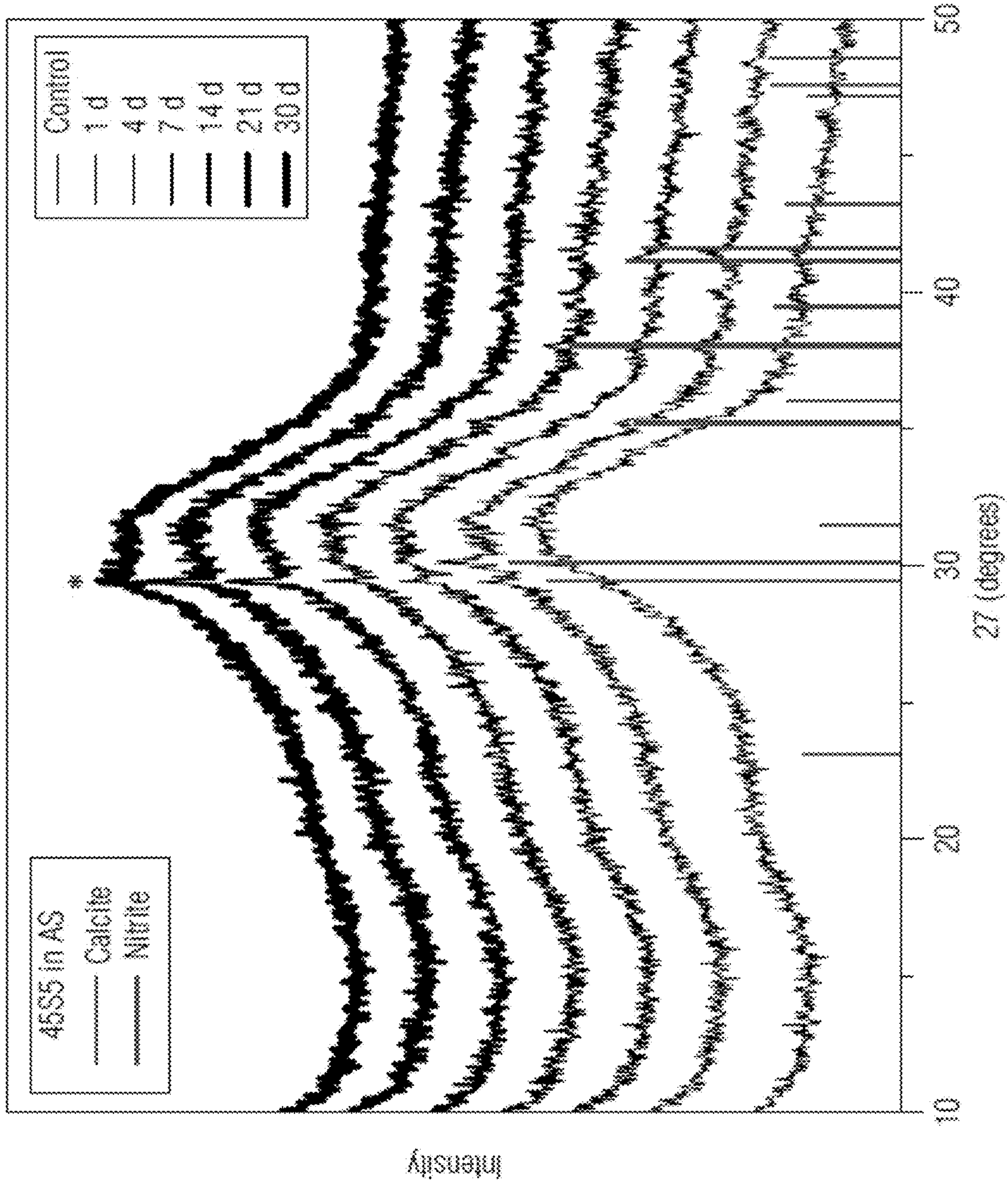
FIG. 28 is a graph showing XRD data of conventional glass compositions before and after exposure to artificial saliva.

XRD data for 45S5 Bioglass® is shown in FIG. 28 and shows that natrite ($Na_2CO_3$) was present on the surface of the 45S5 Bioglass® even before soaking in the artificial saliva, and only non-bioactive calcite ($CaCO_3$) forms on the 45S5 Bioglass® after 30 days of soaking in the artificial saliva. Accordingly, 45S5 Bioglass® is not particularly bioactive.

Figure 29:
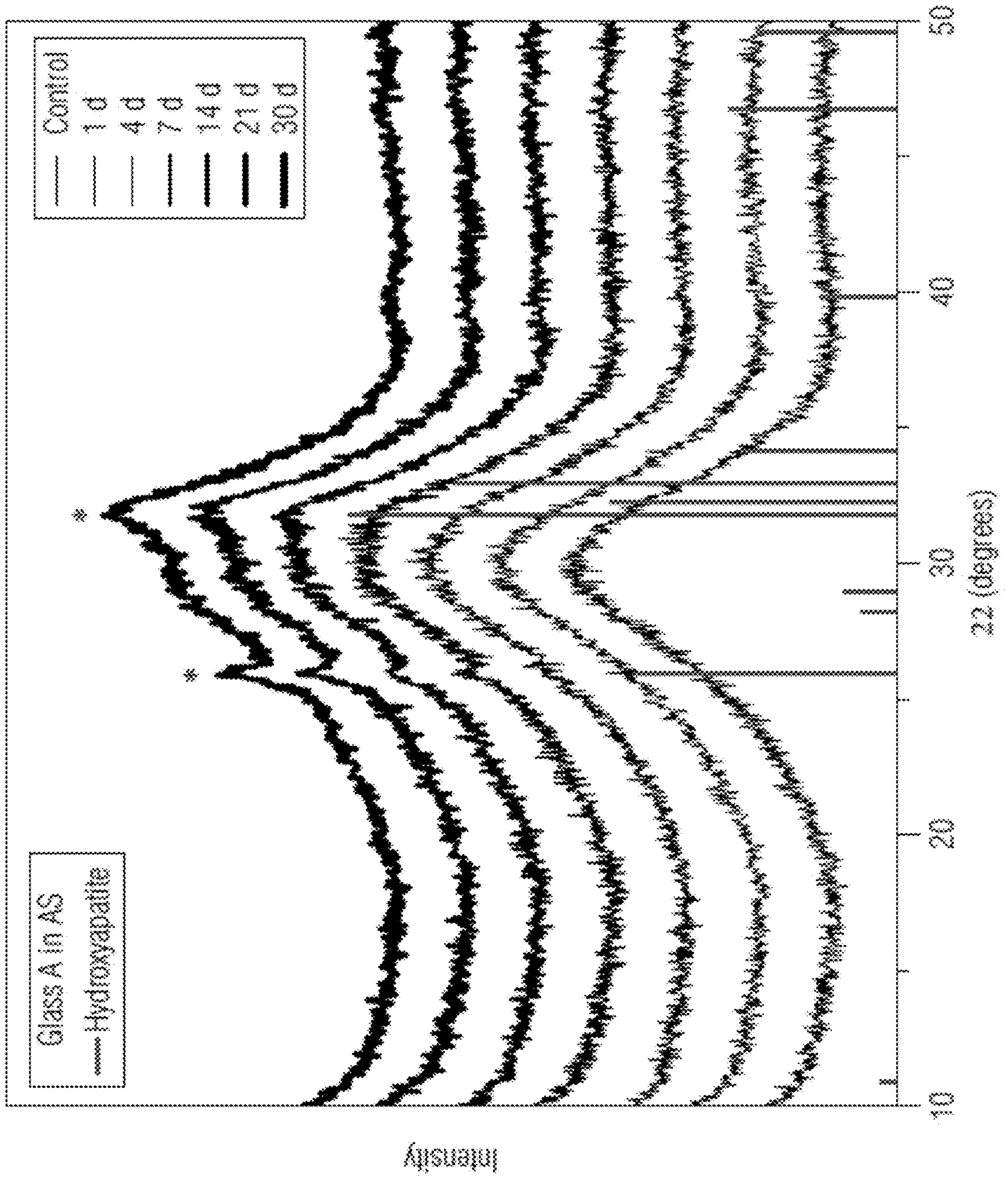
FIG. 29 is a graph showing XRD data of bioactive glass compositions according to embodiments disclosed and described herein before and after exposure to artificial saliva.

XRD data for the bioactive glass of Sample 51 from Example 10 is shown in FIG. 29 and confirms what was shown in the above examples that hydroxyapatite forms on the bioactive glass of Sample 51 from Example 10 in seven days or less.

Example 15

Corrosion was also tested using artificial saliva manufactured by Modus Laboratories. XRD data was collected for the as-made bioactive glass of Sample 51 from Example 10 and the as-made 45S5 Bioglass®. The bioactive glass of Sample 51 from Example 10 and 45S5 Bioglass® were then soaked in the artificial saliva manufactured by Modus Laboratories for seven days and XRD data was collected on each sample after soaking.

Figure 30:
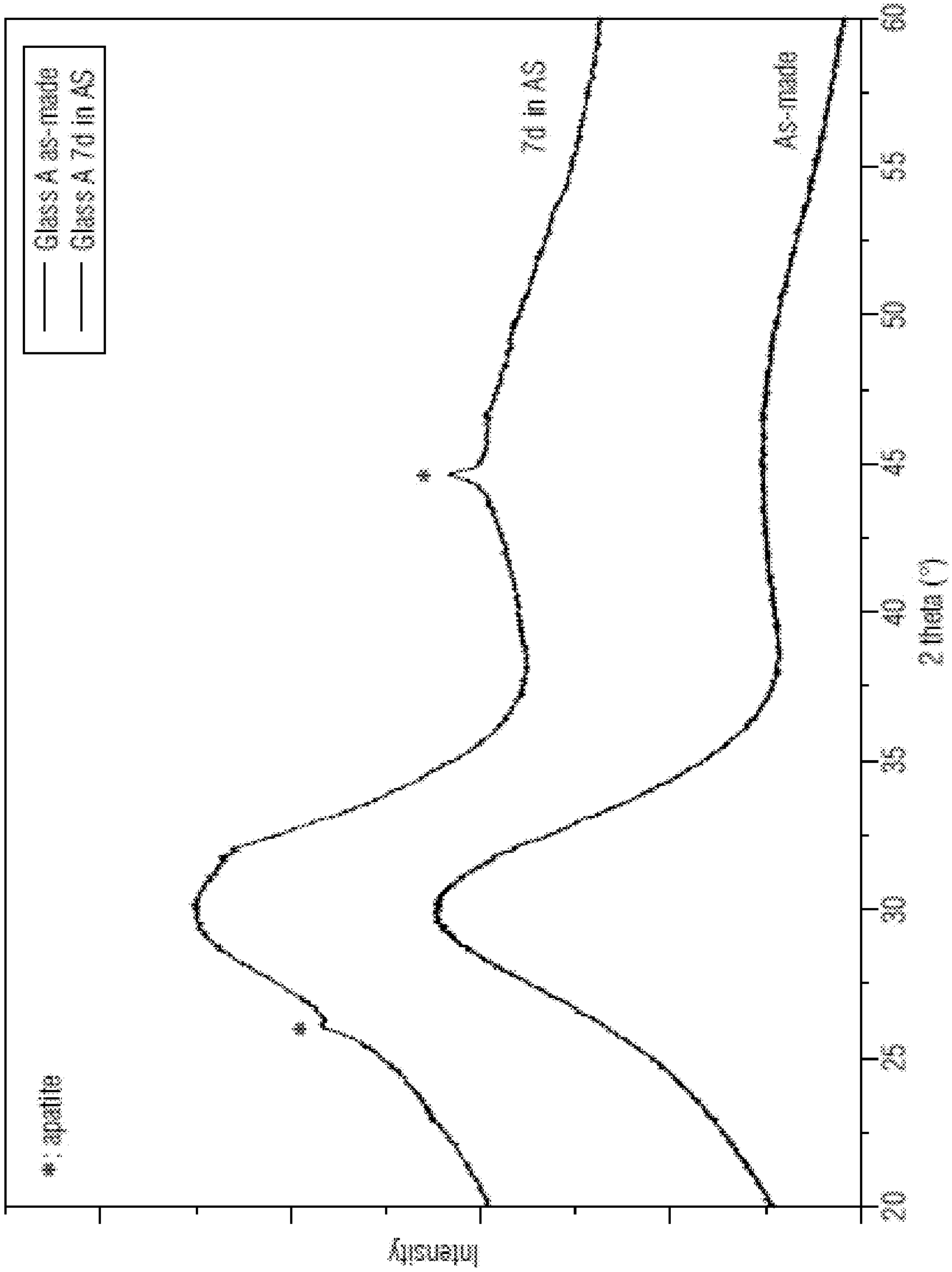
FIG. 30 is a graph showing XRD data of bioactive glass compositions according to embodiments disclosed and described herein before and after exposure to artificial saliva.

FIG. 30 shows the XRD data for the bioactive glass of Sample 51 from Example 10. This XRD data confirms what was shown in previous examples that apatite was formed within 7 days of soaking, and no nitrite to calcite was formed. Moreover, the bioactive glass of Sample 51 from Example 10 was free of surface corrosion after a year of storage.

Figure 31:
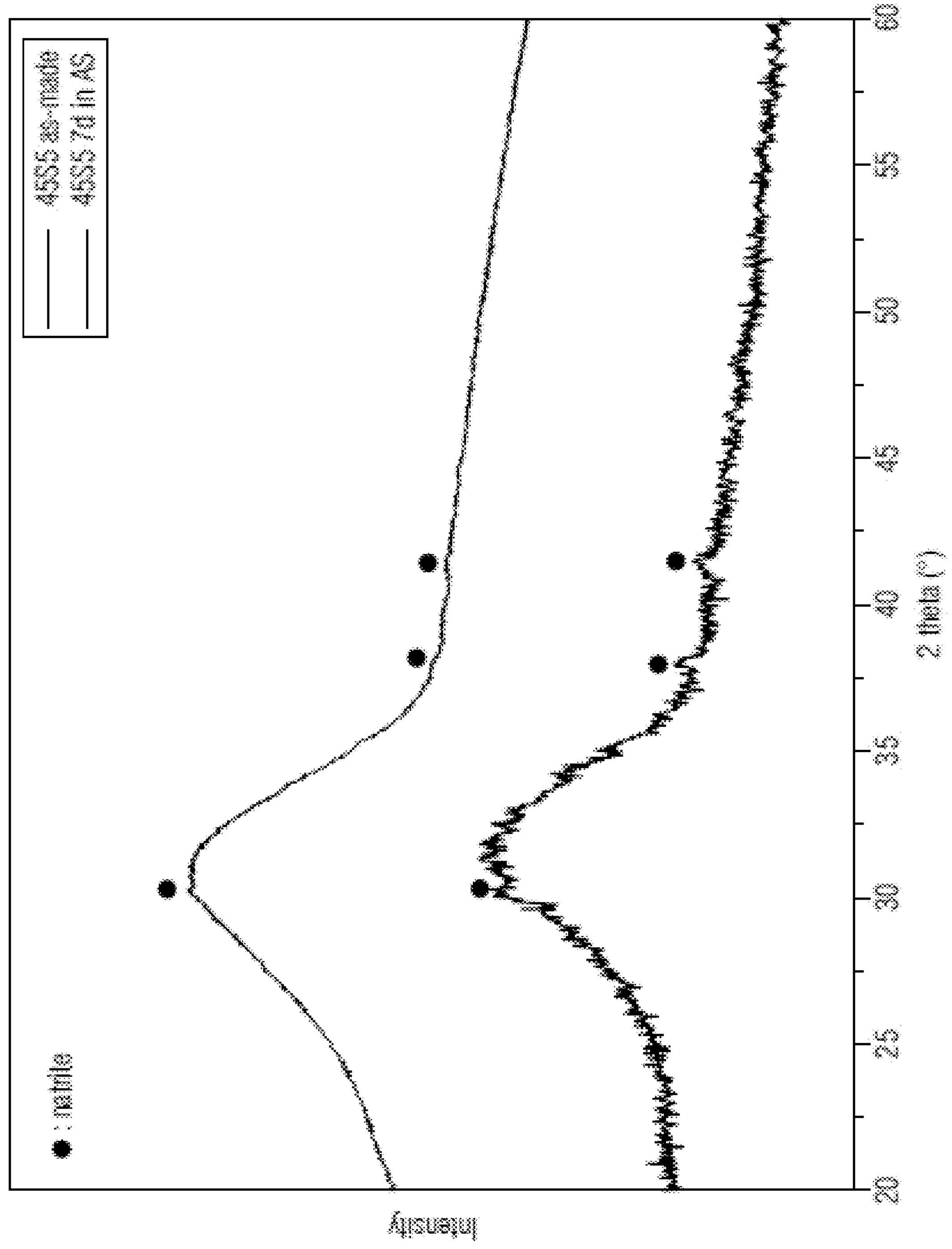
FIG. 31 is a graph showing XRD data of conventional glass compositions before and after exposure to artificial saliva.

FIG. 31 is XRD data for 45S5 Bioglass® and shows that natrite was detected in the as-made 45S5 Bioglass® in only days after powder was prepared, which indicates surface corrosion. Moreover, no apatite was formed in the 45S5 Bioglass®.

Example 16

The effect of the bioactive glass of Sample 51 from Example 10 and 45S5 Bioglass® on the pH of artificial saliva was also studied.

Figure 32:
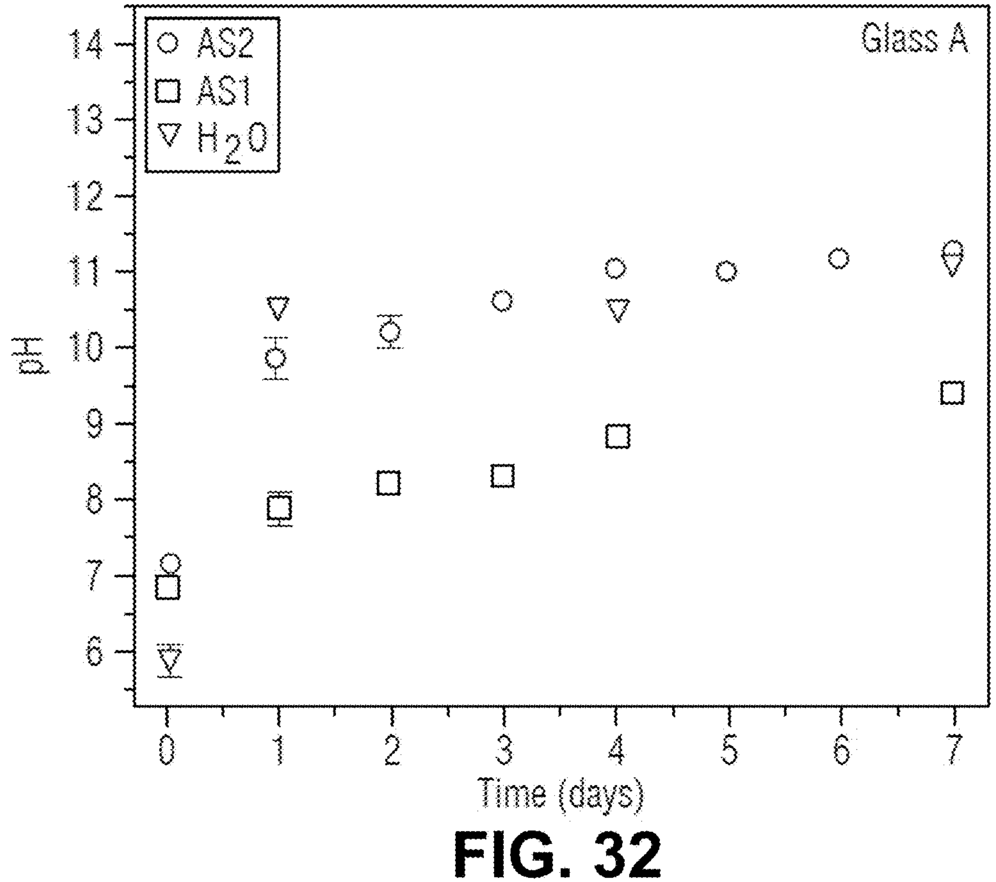
FIG. 32 is a graph showing pH versus time of bioactive glass compositions according to embodiments disclosed and described herein in artificial saliva and water.

The bioactive glass of Sample 51 from Example 10 was soaked in deionized water (referred to as "$H_2O$") for seven days, soaked in artificial saliva manufactured by Modus Laboratories (referred to as "AS 1") for seven days, and soaked in artificial saliva comprising 28 ppm $Na^+$, 80 ppm $K^+$, and 6 ppm $Mg^{2+}$ and having a pH of 7.1 (referred to as "AS 2") for seven days. The pH of the $H_2O$, AS 1, and AS 2 were measured before the bioactive glass of Sample 51 from Example 10 (referred to as day 0 in the figures) and every day thereafter for seven days. The results of this test is shown in FIG. 32.

Figure 33:
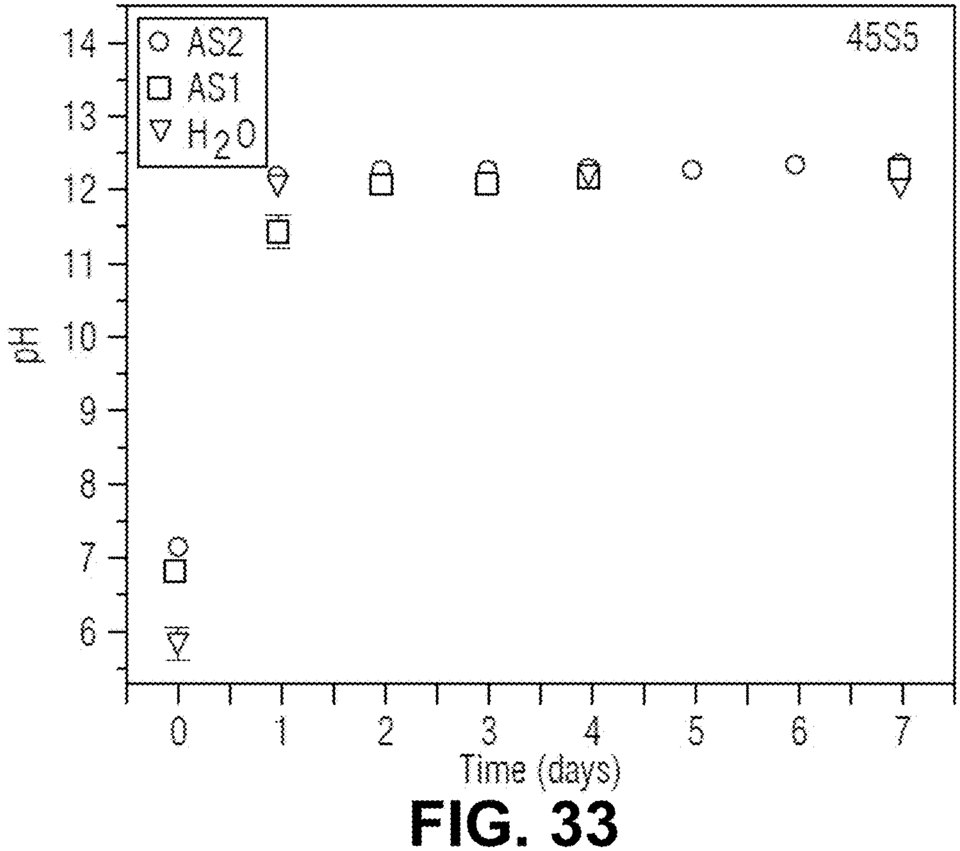
FIG. 33 is a graph showing pH versus time of conventional glass compositions in artificial saliva and water.

The 45S5 Bioglass® was soaked in $H_2O$ for seven days, soaked in AS 1 for seven days, and soaked in AS 2 for seven days. The pH of the $H_2O$, AS 1, and AS 2 were measured before the 45S5 Bioglass® (referred to as day 0 in the figures) and every day thereafter for seven days. The results of this test is shown in FIG. 33.

For both the bioactive glass of Sample 51 from Example 10 and 45S5 Bioglass®, the pH of each solution ($H_2O$, AS 1, and AS 2) increased quickly after adding the glass. After about one day of soaking, the pH of each solution leveled off and stayed relatively consistent for the next six days. The bioactive glass of Sample 51 from Example 10 showed less of pH increase than the 45S5 Bioglass®, and particularly, the bioactive glass of Sample 51 from Example 10 showed the least pH increase in AS 1, while 45S5 Bioglass® showed a greater pH increase that bioactive glass of Sample 51 from Example 10 in each of $H_2O$, AS 1, and AS 2 and particularly in AS 2.

Example 17

The normalized loss of various components in the bioactive glass of Sample 51 from Example 10 and 45S5 Bioglass® in AS 1 was also studied.

The bioactive glass of Sample 51 from Example 10 (referred to as "Glass A" in the figures) and 45S5 Bioglass® were soaked in AS 1 for seven days. The normalized loss ($mg/m^2$) of sodium and silicon was measured for 45S5 Bioglass®, and the normalized loss of calcium and silicon was measured for bioactive glass of Sample 51 from Example 10 (the bioactive glass of Sample 51 from Example 10 does not comprise sodium).

Figure 34:
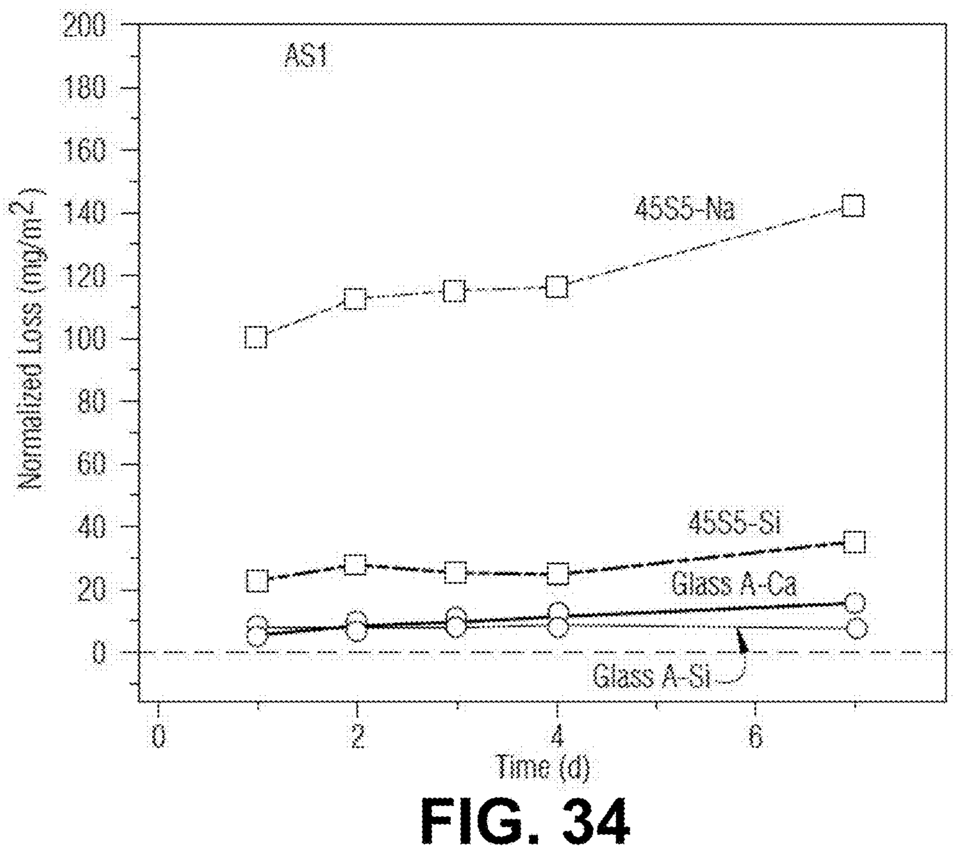
FIG. 34 is a graph showing normalized loss versus time of bioactive glass compositions according to embodiments disclosed and described herein and conventional glass compositions in artificial saliva and water.

FIG. 34 shows the results of this test. As shown in FIG. 34, the bioactive glass of Sample 51 from Example 10 shows minimal normalized loss of calcium and silicon, while 45S5 Bioglass® shows much greater normalized loss of silica and extremely high normalized loss of sodium. The significant normalized loss of sodium in 45S5 Bioglass® shows that this glass dissolves much quicker than bioactive glass of Sample 51 from Example 10, and the higher normalized loss of silicon in the 45S5 Bioglass® shows that even the glass matrix is reacting in the artificial saliva. In contrast, the bioactive glass of Sample 51 from Example 10 is much less reactive.

The normalized loss was calculated by equation 1 below:

$$\text{Normalized Loss} = \frac{(c_{i,t} - c_0) * V}{SSA * m * f_i},$$

Where $C_{i,t}$ is the concentration of element i at time t, $C_0$ is the blank solution concentration, V is the solution volume, SSA is the specific surface area (measure by BET), m is the starting sample mass, and $f_i$ is the mass fraction of element i.

Example 18

The normalized loss of various components in the bioactive glass of Sample 51 from Example 10 and 45S5 Bioglass® in AS 2 was also studied.

The bioactive glass of Sample 51 from Example 10 (referred to as “Glass A” in the figures) and 45S5 Bioglass® were soaked in AS 2 for thirty days. The normalized loss (mg/m$^2$) of sodium, silicon, and calcium was measured for 45S5 Bioglass®, and the normalized loss of calcium and silicon was measured for bioactive glass of Sample 51 from Example 10 (the bioactive glass of Sample 51 from Example 10 does not comprise sodium).

Figure 35:
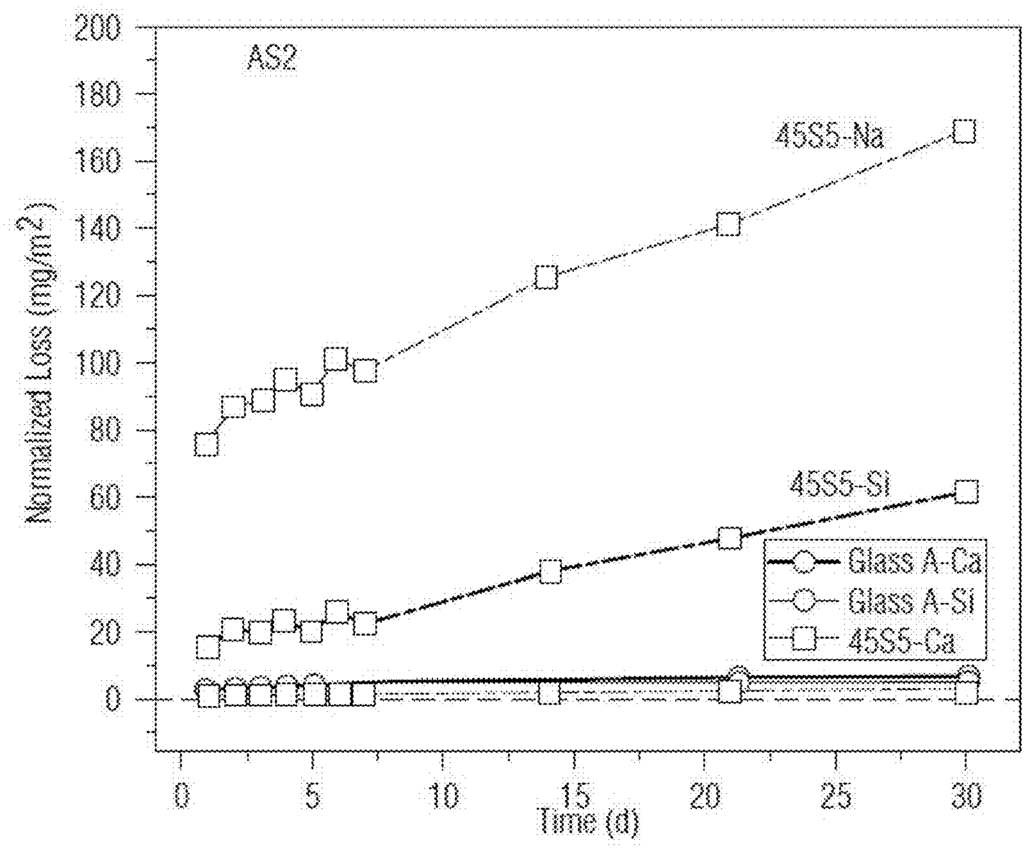
FIG. 35 is a graph showing normalized loss versus time of bioactive glass compositions according to embodiments disclosed and described herein and conventional glass compositions in artificial saliva and water.

FIG. 35 shows the results of this test. As shown in FIG. 35, the bioactive glass of Sample 51 from Example 10 shows minimal normalized loss of calcium and silicon, while 45S5 Bioglass® shows much greater normalized loss of silica and extremely high normalized loss of sodium. The significant normalized loss of sodium in 45S5 Bioglass® shows that this glass dissolves much quicker than bioactive glass of Sample 51 from Example 10, and the higher normalized loss of silicon in the 45S5 Bioglass® shows that even the glass matrix is reacting in the artificial saliva. In contrast, the bioactive glass of Sample 51 from Example 10 is much less reactive.

The normalized loss of each component was calculated using Equation 1 from Example 17.

Example 19

The normalized loss of silicon in the bioactive glass of Sample 51 from Example 10 and 45S5 Bioglass® in $H_2O$, AS 1, and AS 2 was further studied.

The bioactive glass of Sample 51 from Example 10 (referred to as “Glass A” in the figures) and 45S5 Bioglass® were soaked in $H_2O$, AS 1, and AS 2 for seven days. The normalized loss (mg/m$^2$) of silicon was measured for the bioactive glass of Sample 51 from Example 10 and for 45S5 Bioglass®.

Figure 36:
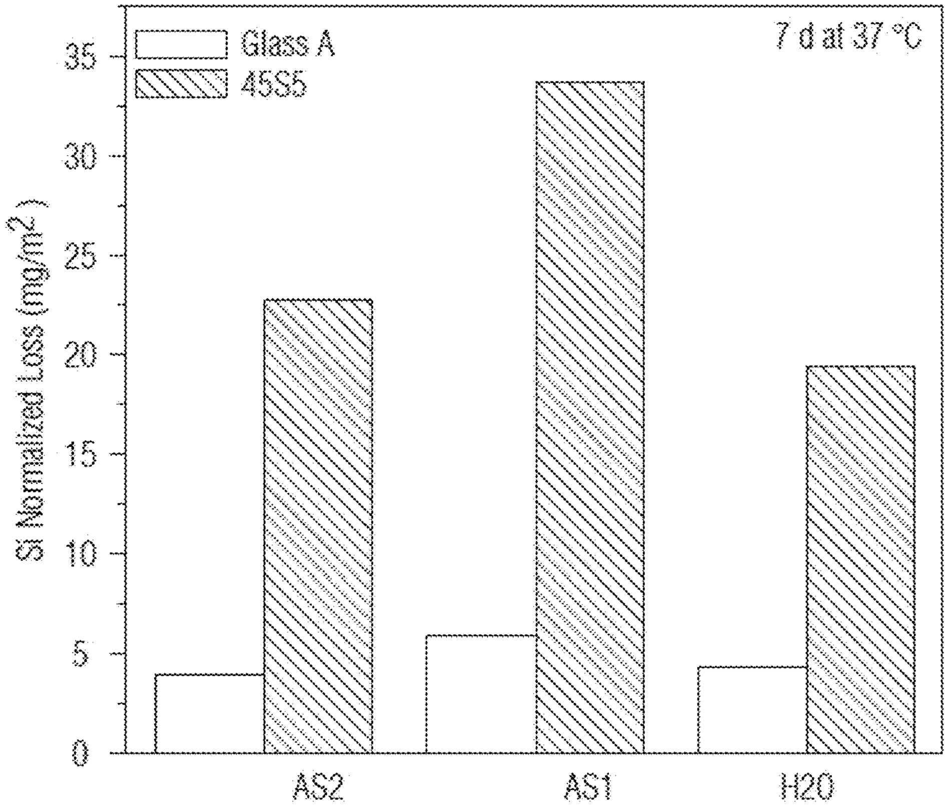
FIG. 36 is a bar graph of silicon normalized loss of bioactive glass compositions according to embodiments disclosed and described herein and conventional glass compositions after exposure to artificial saliva and water.

FIG. 36 shows the results of this test. As shown in FIG. 36, the bioactive glass of Sample 51 from Example 10 shows minimal normalized loss of silicon in each of $H_2O$, AS 1, and AS 2. In contrast, 45S5 Bioglass® shows significant normalized loss of silicon in each of $H_2O$, AS 1, and AS 2. The large normalized loss of silicon in 45S5 Bioglass® shows the increased reactivity of the glass and that even the glass matrix is reacting. Without being bound to any particular theory, it is believed that the high concentration of calcium in the bioactive glass of Sample 51 from Example 10 provides low reactivity.

The normalized loss of each component was calculated using Equation 1 from Example 17.

Example 20

The water durability of the bioactive glass of Sample 51 from Example 10 and 45S5 Bioglass® was further studied.

Figure 37:
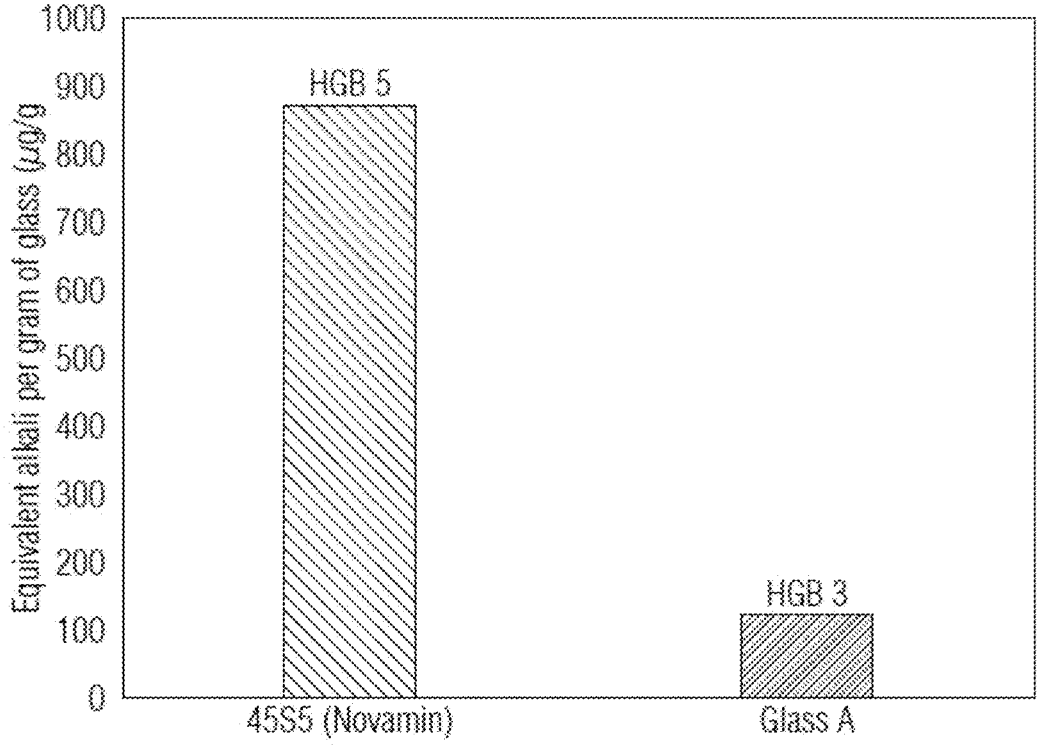
FIG. 37 is a bar graph showing the results of ISO 719 testing on bioactive glass compositions according to embodiments disclosed and described herein and conventional glass compositions.

The bioactive glass of Sample 51 from Example 10 (referred to as “Glass A” in the figures) and 45S5 Bioglass® were subjected to the ISO 719 test to determine the hydrolytic resistance of glass grains (300 μm to 425 μm) at 98° C. for 1 hour in water. FIG. 37 shows the results of this test.

As shown in FIG. 37, the bioactive glass of Sample 51 from Example 10 was rated as HGB 3 and 45S5 Bioglass® was rated as HGB 5, showing vastly increased water durability of the bioactive glass of Sample 51 from Example 10 compared to 45S5 Bioglass®.

Example 21

Twelve aqueous dentifrice formulations were composed using the bioactive glass sample 51 from Example 10 above. The remaining components of the aqueous dentifrice formulation is provided in Table I below. It should be noted that glycerin is used as a humectant in the formulations in Table I.

TABLE I

| | 1 | 2 | 3 | 4 | 5 | 6 | 7 |
|---|---|---|---|---|---|---|---|
| Bioactive glass | 2 | 5 | 10 | 15 | 2 | 5 | 10 |
| Water | 43.6 | 40.6 | 35.6 | 30.6 | 44.38 | 41.38 | 36.38 |
| Sorbitol | 26 | 26 | 26 | 26 | 26 | 26 | 26 |
| Glycerin | 20 | 20 | 20 | 20 | 20 | 20 | 20 |
| Sodium monofluorophosphate | 1.1 | 1.1 | 1.1 | 1.1 | 0 | 0 | 0 |
| sodium fluoride | 0 | 0 | 0 | 0 | 0.32 | 0.32 | 0.32 |
| Stannous fluoride | 0 | 0 | 0 | 0 | 0 | 0 | 0 |
| Flavor | 1 | 1 | 1 | 1 | 1 | 1 | 1 |
| sodium lauryl sulfate | 1 | 1 | 1 | 1 | 1 | 1 | 1 |
| Sweetener | 0.2 | 0.2 | 0.2 | 0.2 | 0.2 | 0.2 | 0.2 |
| Titanium dioxide | 0.1 | 0.1 | 0.1 | 0.1 | 0.1 | 0.1 | 0.1 |
| Silica | 5 | 5 | 5 | 5 | 5 | 5 | 5 |
| Total | 100 | 100 | 100 | 100 | 100 | 100 | 100 |

| | 8 | 9 | 10 | 11 | 12 |
|---|---|---|---|---|---|
| Bioactive glass | 15 | 2 | 5 | 10 | 15 |
| Water | 31.38 | 44.24 | 41.24 | 36.24 | 31.24 |
| Sorbitol | 26 | 26 | 26 | 26 | 26 |

TABLE I-continued

| | | | | | |
|---|---|---|---|---|---|
| Glycerin | 20 | 20 | 20 | 20 | 20 |
| Sodium monofluorophosphate | 0 | 0 | 0 | 0 | 0 |
| sodium fluoride | 0.32 | 0 | 0 | 0 | 0 |
| Stannous fluoride | 0 | 0.46 | 0.46 | 0.46 | 0.46 |
| Flavor | 1 | 1 | 1 | 1 | 1 |
| sodium lauryl sulfate | 1 | 1 | 1 | 1 | 1 |
| Sweetener | 0.2 | 0.2 | 0.2 | 0.2 | 0.2 |
| Titanium dioxide | 0.1 | 0.1 | 0.1 | 0.1 | 0.1 |
| Silica | 5 | 5 | 5 | 5 | 5 |
| Total | 100 | 100 | 100 | 100 | 100 |

Each of these dentifrice formulations had good mouth feel and stability over time. The formulations include, in part, a bioactive glass that is useful in treating or preventing various disorders of the oral cavity through enamel remineralization and caries remineralization.

Example 22

Twelve non-aqueous dentifrice formulations were composed using the bioactive glass Sample 51 from Example 10 above. The remaining components of the aqueous dentifrice formulation is provided in Table J below. It should be noted that glycerin is used as a solvent in the non-aqueous dentifrice formulations.

TABLE J

| Ingredient | 1 | 2 | 3 | 4 | 5 | 6 | 7 |
|---|---|---|---|---|---|---|---|
| Bioactive glass | 2 | 5 | 10 | 15 | 2 | 5 | 10 |
| Glycerin | 69.6 | 66.6 | 61.6 | 56.6 | 70.38 | 67.38 | 62.38 |
| Polyethylene glycol | 20 | 20 | 20 | 20 | 20 | 20 | 20 |
| Sodium monofluorophosphate | 1.1 | 1.1 | 1.1 | 1.1 | 0 | 0 | 0 |
| sodium fluoride | 0 | 0 | 0 | 0 | 0.32 | 0.32 | 0.32 |
| Stannous fluoride | 0 | 0 | 0 | 0 | 0 | 0 | 0 |
| Flavor | 1 | 1 | 1 | 1 | 1 | 1 | 1 |
| sodium lauryl sulfate | 1 | 1 | 1 | 1 | 1 | 1 | 1 |
| Sweetener | 0.2 | 0.2 | 0.2 | 0.2 | 0.2 | 0.2 | 0.2 |
| Titanium dioxide | 0.1 | 0.1 | 0.1 | 0.1 | 0.1 | 0.1 | 0.1 |
| Silica | 5 | 5 | 5 | 5 | 5 | 5 | 5 |
| Total | 100 | 100 | 100 | 100 | 100 | 100 | 100 |

| Ingredient | 8 | 9 | 10 | 11 | 12 |
|---|---|---|---|---|---|
| Bioactive glass | 15 | 2 | 5 | 10 | 15 |
| Glycerin | 57.38 | 70.24 | 67.24 | 62.24 | 57.24 |
| Polyethylene glycol | 20 | 20 | 20 | 20 | 20 |
| Sodium monofluorophosphate | 0 | 0 | 0 | 0 | 0 |
| sodium fluoride | 0.32 | 0 | 0 | 0 | 0 |
| Stannous fluoride | 0 | 0.46 | 0.46 | 0.46 | 0.46 |
| Flavor | 1 | 1 | 1 | 1 | 1 |
| sodium lauryl sulfate | 1 | 1 | 1 | 1 | 1 |
| Sweetener | 0.2 | 0.2 | 0.2 | 0.2 | 0.2 |
| Titanium dioxide | 0.1 | 0.1 | 0.1 | 0.1 | 0.1 |
| Silica | 5 | 5 | 5 | 5 | 5 |
| Total | 100 | 100 | 100 | 100 | 100 |

Each of these dentifrice formulations had good mouth feel and stability over time. The formulations include, in part, a bioactive glass that is useful in treating or preventing various disorders of the oral cavity through enamel remineralization and caries remineralization.

Example 23

Non-limiting examples of amounts of precursor oxides for forming the glass compositions are listed in Table K.

TABLE K

| Oxide (wt. %) | 55 | 56 | 57 | 58 | 59 | 60 | 61 | 62 | 63 | 64 |
|---|---|---|---|---|---|---|---|---|---|---|
| $SiO_2$ | 33.5 | 33.5 | 33.5 | 33.5 | 41 | 31.5 | 41.5 | 28.5 | 30 | 38.5 |
| MgO | 4.5 | 4.5 | 4.5 | 4.5 | 4.5 | 1 | 4.5 | 4.5 | 4.5 | 4.5 |
| CaO | 42.5 | 42.5 | 42.5 | 42.5 | 30 | 42.5 | 42.5 | 42.5 | 42.5 | 42.5 |
| $P_2O_5$ | 15 | 14.5 | 13.5 | 11.5 | 20 | 15 | 10 | 20 | 15 | 10 |
| $ZrO_2$ | 4 | 4 | 4 | 4 | 4 | 6 | 1 | 4 | 4 | 4 |
| $F^-$ | 0.5 | 1 | 2 | 4 | 0.5 | 4 | 0.5 | 0.5 | 4 | 0.5 |

Figure 38:
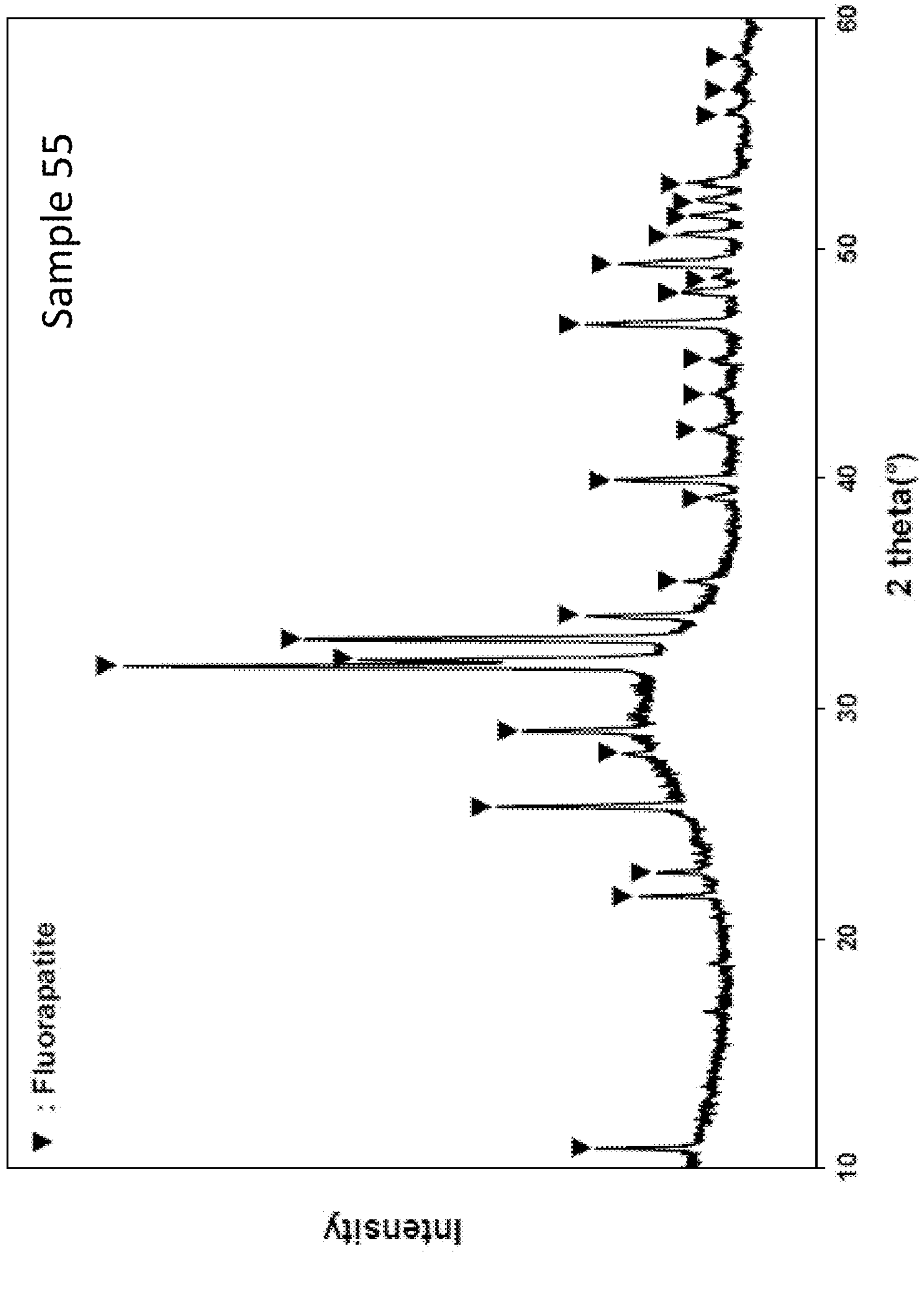
FIG. 38 is a powder X-ray diffraction (XRD) spectrum illustrating formation of a fluorapatite glass-ceramic upon cooling a melted glass mixture without a subsequent heat treatment step.

The glass compositions of Table K were prepared by combining each component of the glass composition to form a mixture, heating the mixture to a temperature of 1500° C. or less, and then cooling the melted mixture, which spontaneously resulted in at least partial crystallization into a fluorapatite crystal phase (see, e.g., FIG. 38). In this regard, typical glass compositions generally do not spontaneously crystallize upon cooling, but instead generally require an additional heat treatment step of the cooled mixture in order to form a crystalline phase. However, with the glass compositions disclosed herein, the additional heat treatment step of the cooled mixture is not necessary, since upon cooling of the original melted mixture, a crystalline phase of fluorapatite forms spontaneously.

In this regard, FIG. 38 illustrates powder x-ray diffraction (XRD) analysis of Sample 55 in Table K prepared in accordance with the disclosures herein. The location of XRD peaks corresponding to fluorapatite formation are shown in FIG. 38. Powder XRD analysis was conducted by preparing the samples by first drying and then grinding to a fine powder using a Rocklabs ring mill. The powder was then analyzed using a Bruker D4 Endeavor device equipped with a LynxEye™ silicon strip detector. X-ray scanning was conducted from 5° to 80° (2θ) for data collection.

Example 24

Non-limiting examples of amounts of precursor oxides for forming the glass compositions are listed in Table L.

TABLE L

| Oxide (wt. %) | Comp. Ex. 2 | 65 | 66 | 67 | 68 | 69 | 70 |
|---|---|---|---|---|---|---|---|
| $SiO_2$ | 45.0 | 33.45 | 33.3 | 31.4 | 33.4 | 30.4 | 31.4 |
| $Na_2O$ | 24.5 | 0 | 0 | 0 | 0 | 0 | 0 |
| MgO | 0 | 4.5 | 4.5 | 4.5 | 4.5 | 4.5 | 4.5 |
| CaO | 24.5 | 42.5 | 42.5 | 42.5 | 42.5 | 42.5 | 42.5 |
| $P_2O_5$ | 6.0 | 15.5 | 15.5 | 17.5 | 15.5 | 18.5 | 17.5 |
| $ZrO_2$ | 0 | 4 | 4 | 4 | 4 | 4 | 4 |
| $F^-$ | 0 | 0.05 | 0.2 | 0.1 | 0.1 | 0.1 | 0.1 |

| Oxide (wt. %) | 71 | 72 | 73 | 74 | 75 | 76 |
|---|---|---|---|---|---|---|
| $SiO_2$ | 33.4 | 35.4 | 42 | 41 | 40 | 38 |
| $Na_2O$ | 0 | 0 | 0 | 0 | 0 | 0 |
| MgO | 4.5 | 4.5 | 4.5 | 4.5 | 4.5 | 4.5 |
| CaO | 42.5 | 42.5 | 42.5 | 42.5 | 42.5 | 42.5 |
| $P_2O_5$ | 15.5 | 13.5 | 6 | 6 | 8 | 10 |
| $ZrO_2$ | 4 | 4 | 4 | 4 | 4 | 4 |
| $F^-$ | 0.1 | 0.1 | 1 | 2 | 1 | 1 |

The glass compositions of Table L may be melted at temperatures below 1500° C., or at temperatures below 1400° C., or at temperatures below 1200° C., thereby making it possible to melt in relatively small commercial glass tanks. The glass compositions disclosed herein (e.g., Table L) exhibit significantly higher chemical durability and excellent bioactivity, as compared to currently available glasses, and can be in any form that is useful for the medical and dental processes disclosed. In some aspects, the compositions of Table L demonstrate significantly higher chemical durability and bioactivity over the Comparative Example 2 (45S5 glass).

Figure 39:
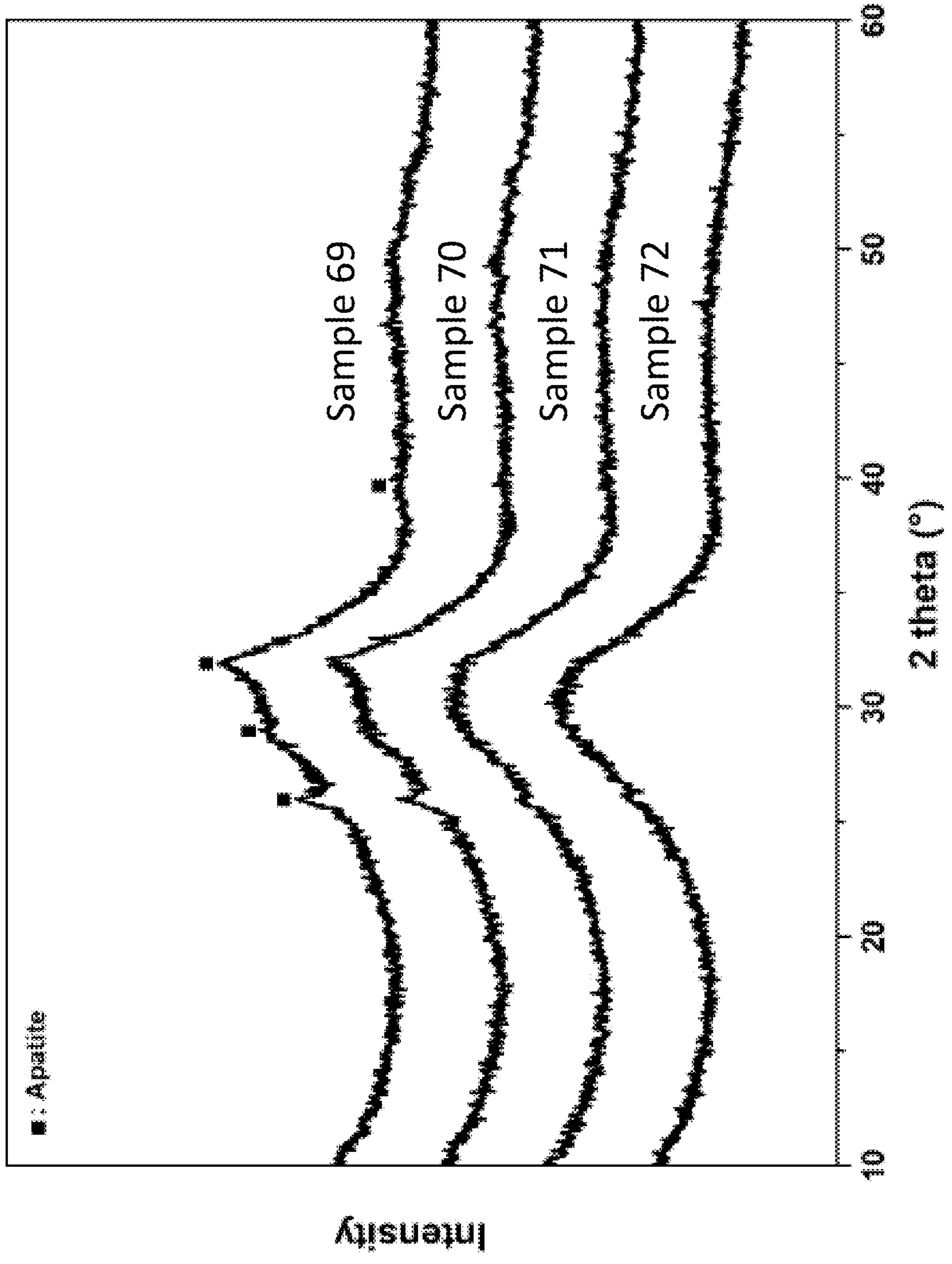
FIG. 39 is a powder X-ray diffraction (XRD) spectrum illustrating apatite formation after immersion in artificial saliva for 14 days of glass compositions prepared in accordance with the disclosures herein.

FIG. 39 illustrates powder x-ray diffraction (XRD) analysis of four sample compositions prepared in accordance with the disclosures herein that have been soaked in artificial saliva for 14 days. The location of XRD peaks corresponding to apatite formation are shown in FIG. 39, indicating the formation of apatite in sample compositions. Powder XRD analysis was conducted by preparing the samples by first drying and then grinding to a fine powder using a Rocklabs ring mill. The powder was then analyzed using a Bruker D4 Endeavor device equipped with a LynxEye™ silicon strip detector. X-ray scanning was conducted from 5° to 80° (2θ) for data collection.

Figure 40:
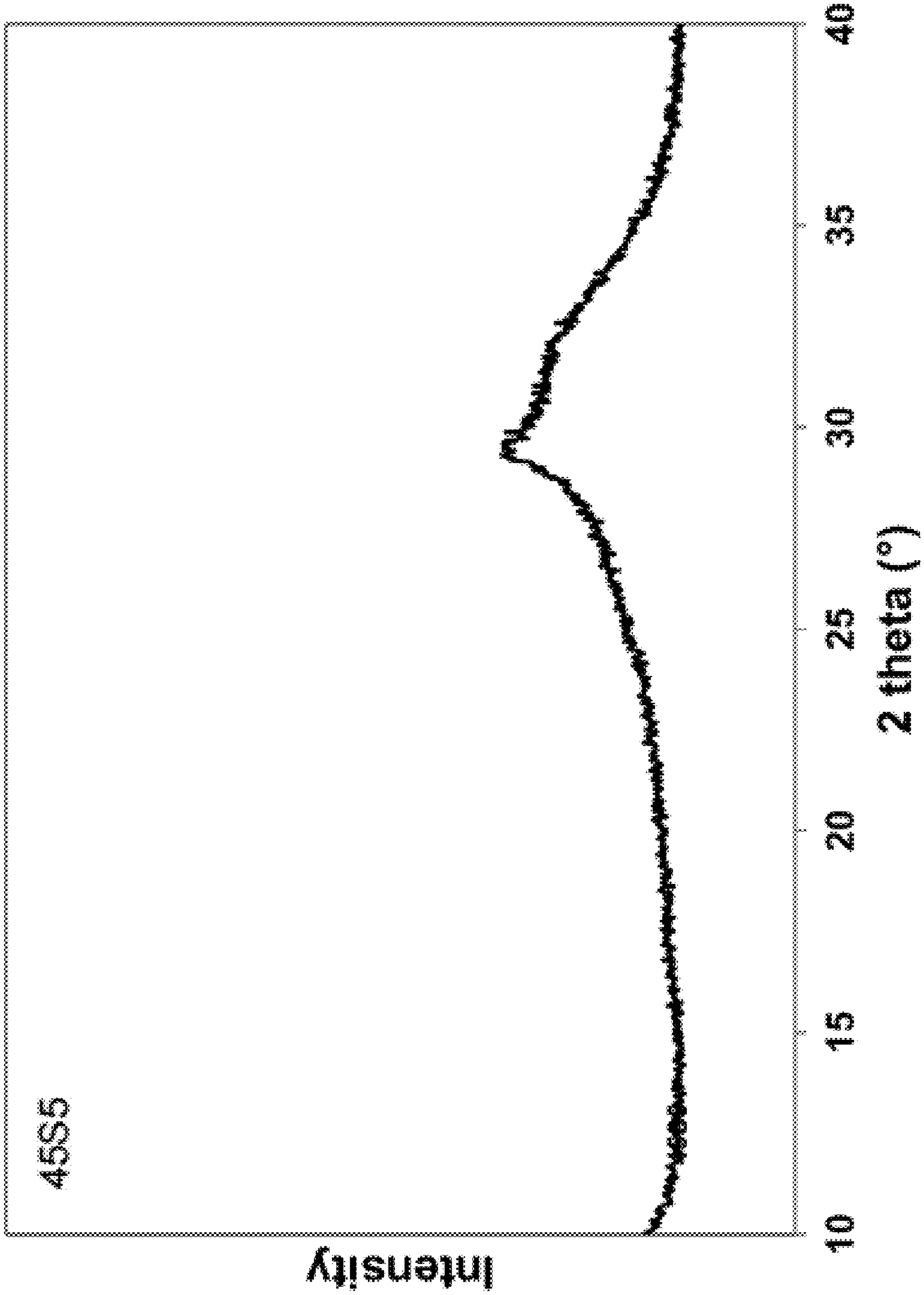
FIG. 40 is a powder XRD spectrum illustrating no apatite formation of a comparative glass composition after immersion in artificial saliva for 61 days.

In contrast, FIG. 40 illustrates powder XRD analysis of Comparative Example 2 (45S5 Bioglass®) after soaking in artificial saliva for 61 days. Though a calcite ($CaCO_3$) phase started to form after 47 days soaking in artificial saliva (data not shown), Comparative Example 2 showed no hydroxyapatite formation even after 61 days in artificial saliva.

As specified by ASTM F1538-03, bioactive materials only refer to those that can form apatite in vitro or in vivo. The formation of calcite does not produce a direct bond with bony tissues due to its chemical difference from bone; thus, calcite is not regarded as bioactive. The inclusion of relatively high concentrations of CaO and $P_2O_5$ oxides, as well as $F^-$, in the sample compositions facilitates the formation of an apatite phase in artificial saliva while Comparative Example 2 composition (which has appreciably lower concentrations of CaO and $P_2O_5$ and no $F^-$) only forms a calcite phase. Due to its chemical similarity with bone, apatite can form a direct bond with bony tissue while calcite cannot.

Because the apatite phase forms in the sample compositions without the inclusion of a fluoride ion source (i.e., beyond the $F^-$ contained within the glass composition itself), there is no need to supply any external fluoride ion in addition to the glass composition (e.g., by way of typical fluoride ion sources present in oral care products, such as calcium fluoride, magnesium fluoride, sodium fluoride, potassium fluoride, stannous fluoride, sodium monofluorophosphate, sodium difluorophosphate, or any combination thereof). However, in some aspects, it still may be desirable to include such an external fluoride ion source in addition to the glass composition (i.e., which generally already contains $F^-$).

Example 25—Stability in Deionized Water

This example demonstrates the stability of an inventive bioactive glass (Sample 77) disclosed herein as compared to Comparative Example 2 (45S5).

Glasses having the compositions shown in Table M below were prepared according to the general procedures described elsewhere herein.

TABLE M

| Oxides (wt. %) | Comp. Ex. 2 | 77 |
|---|---|---|
| $SiO_2$ | 45.0 | 29.5 |
| CaO | 24.5 | 42.5 |
| $P_2O_5$ | 6.0 | 19.5 |
| $ZrO_2$ | 0.0 | 4.0 |
| $Na_2O$ | 24.5 | 0.0 |
| MgO | 0.0 | 4.5 |
| $K_2O$ | 0.0 | 0.0 |
| Density* | 2.71 | 2.99 |

*density (g/cm$^3$)

After preparing the glasses, cullets were ground into a powder using an air jet mill to a size of less than 10 microns (an example particle size distribution is disclosed elsewhere herein).

A 5 g sample of the glass powder was then soaked in 100 mL of deionized water at 37° C. for 7 days, with weight measurements made at 0 days (before soaking in water), 1 day, 4 days, and 7 days. Prior to weight measurement, the glass powder was dried at 100° C. for 1 hour to remove residual water.

Figure 41:
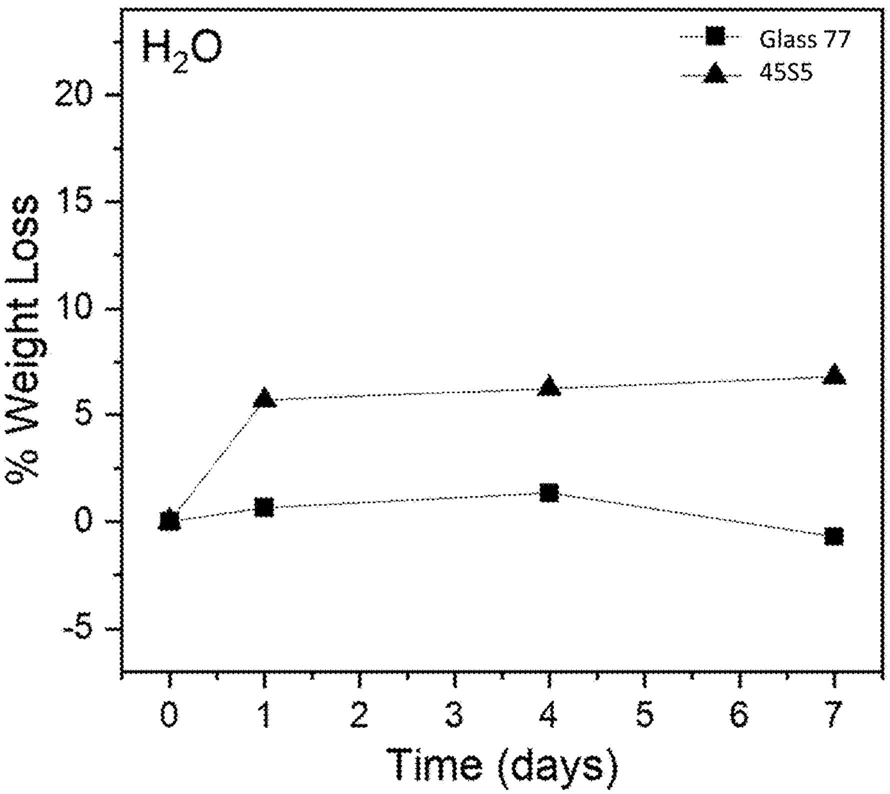
FIG. 41 is a line graph illustrating weight loss characterization of Sample 77 and Comparative Example 2 when immersed in deionized water at 37° C. for 0-7 days.

The results for the weight loss measurements are shown in FIG. 41, demonstrating that Sample 77 had less weight loss after 1-7 days than the comparative 45S5 glass. In particular, Sample 77 had very little weight loss, typically less than 2.5 wt. % or even less (e.g., <2 wt. % or <1 wt. %), whereas the comparative glass 45S5 had weight loss of over 6 wt. %.

Figure 42:
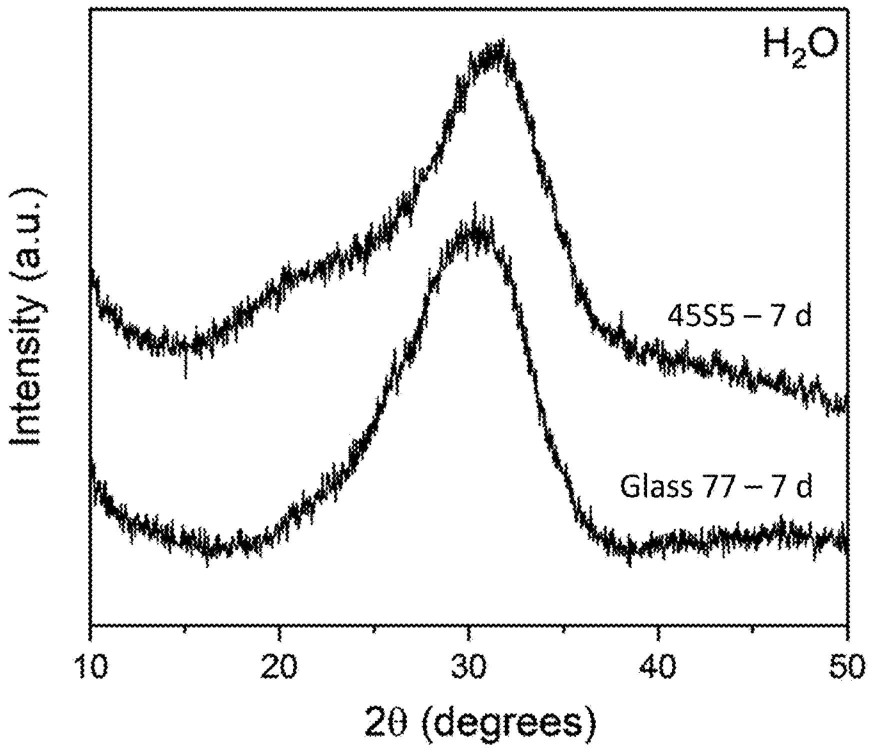
FIG. 42 is a powder X-ray diffraction (XRD) spectrum illustrating no crystalline phase formation for either Sample 77 or Comparative Example 2 (45S5) after soaking in deionized water at 37° C. for 7 days.

The glass samples that had been soaking in deionized water for 7 days at 37° C. were also measured by XRD for crystal formation. As shown in FIG. 42, Sample 77 did not exhibit a crystalline phase after 7 days of soaking in deionized water at 37° C. The XRD of the comparative 45S5 glass also showed no detectable crystalline phase.

The ion release from the inventive and comparative glass compositions was also measured using ICP-OES. Specifically, the liquid phase in which a 5 g sample of glass powder had been soaking for 7 days at 37° C. was analyzed for ion content using ICP-OEP. The results are shown below in Table N, indicating that the inventive bioactive glass released significantly less ions, particularly Na and Si ions, as compared to the 45S5 glass.

TABLE N

| Glass | Ca (ppm) | Na (ppm) | P (ppm) | Si (ppm) |
|---|---|---|---|---|
| Sample 77 | 15.6 | 690 | 0.15 | 168 |
| Comp. Ex. 2 | 27.4 | 0.8 | 0.47 | 27.2 |

The weight loss, XRD results, and/or ion release measurements reported in this and other examples indicate that the inventive bioactive glasses are stable and should have longer shelf life duration when included in aqueous formulations, such as aqueous dentifrice formulations like toothpaste, as compared to the comparative 45S5 glass.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

References herein to the positions of elements (e.g., "top," "bottom," "above," "below," "first," "second," etc.) are merely used to describe the orientation of various elements in the FIGURES. It should be noted that the orientation of various elements may differ according to other exemplary embodiments, and that such variations are intended to be encompassed by the present disclosure. Moreover, these relational terms are used solely to distinguish one entity or action from another entity or action, without necessarily requiring or implying any actual such relationship or order between such entities or actions.

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims, as interpreted according to the principles of patent law, including the doctrine of equivalents.

It will be understood by one having ordinary skill in the art that construction of the described disclosure, and other components, is not limited to any specific material. Other exemplary embodiments of the disclosure disclosed herein may be formed from a wide variety of materials, unless described otherwise herein.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. As used herein, the indefinite articles "a," "an," and the corresponding definite article "the" mean "at least one" or "one or more," unless otherwise specified. It also is understood that the various features disclosed in the specification and the drawings can be used in any and all combinations.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

Unless otherwise specified, all compositions are expressed in terms of as-batched weight percent (wt. %). As will be understood by those having ordinary skill in the art, various melt constituents (e.g., silicon, alkali- or alkaline-based, boron, etc.) may be subject to different levels of volatilization (e.g., as a function of vapor pressure, melt time and/or melt temperature) during melting of the constituents. As such, the as-batched weight percent values used in relation to such constituents are intended to encompass values within ±0.5 wt. % of these constituents in final, as-melted articles. With the forgoing in mind, substantial compositional equivalence between final articles and as-batched compositions is expected.

It will be apparent to those skilled in the art that various modifications and variations can be made without departing from the spirit or scope of the claimed subject matter. Accordingly, the claimed subject matter is not to be restricted except in light of the attached claims and their equivalents.

What is claimed is:

1. An aqueous dentifrice formulation, comprising:
- a carrier; and
- a bioactive glass comprising:
  - 15-65 wt. % $SiO_2$;
  - 15-60 wt. % CaO;
  - 1-30 wt. % $P_2O_5$; and
  - either >0-20 wt. % $ZrO_2$, >0-25 wt. % MgO, or both;
- wherein the bioactive glass exhibits at least one of:
  - a hydrolytic resistance of glass grains (HGB) of at most 4, when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum in which total crystallinity of the bioactive glass is less than 5 wt. % crystalline phase after soaking 5 g of the bioactive glass in powder form in 100 mL of deionized water for 7 days at 37° C.; or
  - any combination thereof; and
- wherein, when the bioactive glass is contacted with artificial saliva, the bioactive glass forms a bioactive crystalline phase.

2. The aqueous dentifrice formulation of claim 1, wherein the bioactive glass releases less than 600 ppm of sodium ions and less than 150 ppm of silicon ions upon soaking 5 g of the bioactive glass in powder form in 100 mL of deionized water for 7 days at 37° C., when measured using inductively coupled plasma—optical emission spectrometer (ICP-OES).

3. The aqueous dentifrice formulation of claim 1, wherein the bioactive crystalline phase forms within 1 day when contacted with the artificial saliva.

4. The aqueous dentifrice formulation of claim 1, wherein the bioactive crystalline phase comprises apatite, brushite, whitlockite, or a combination thereof.

5. The aqueous dentifrice formulation of claim 4, wherein the bioactive crystalline phase comprises apatite, and the apatite comprises hydroxyapatite, fluorapatite, carbonated apatite, or any combination thereof.

6. The aqueous dentifrice formulation of claim 1, wherein the bioactive glass comprises:
- 25-40 wt. % $SiO_2$;
- 30-50 wt. % CaO; and
- 9.5-25 wt. % $P_2O_5$.

7. The aqueous dentifrice formulation of claim 6, wherein the bioactive glass further comprises:
- 3.5-10 wt. % $ZrO_2$; and
- >0-14.5 wt. % MgO.

8. The aqueous dentifrice formulation of claim 6, wherein the bioactive glass comprises at least one of:
- >0-5.0 wt. % MgO;
- >0-14.5 SrO;
- >0-14.5 ZnO;
- >0-10 wt. % $F^-$;
- 32.5 -70 wt. % MO, wherein MO is the sum of MgO, CaO, SrO, BeO, and BaO;
- 0-30 wt. % $R_2O$, wherein $R_2O$ is the sum of $Na_2O$, $K_2O$, $Li_2O$, $Rb_2O$, and $Cs_2O$;
- any combination thereof.

9. The aqueous dentifrice formulation of claim 1, wherein the bioactive glass comprises a crystalline phase optionally selected from apatite, brushite, calcium silicate, calcium phosphate, calcium fluoride, whitlockite, or any combination thereof.

10. The aqueous dentifrice formulation of claim 1, wherein the bioactive glass is free of a crystalline phase.

11. The aqueous dentifrice formulation of claim 1, further comprising >0 -40 wt. % of an amino acid.

12. The aqueous dentifrice formulation of claim 11, wherein the amino acid is glycine, glutamic acid, arginine, or any combination thereof.

13. The aqueous dentifrice formulation of claim 1, wherein the aqueous dentifrice formulation is free of a fluoride ion source other than that derived from the bioactive glass, if any.

14. The aqueous dentifrice formulation of claim 1, wherein the aqueous dentifrice formulation is in a form of a toothpaste, mouthwash, gel, varnish, rinse, spray, ointment, salve, cream, or oral formulation.

15. A bioactive glass, comprising:
- 15-65 wt. % $SiO_2$:
- 15-60 wt. % CaO;
- 1-30 wt. % $P_2O_5$; and
- either >0-20 wt. % $ZrO_2$, >0-25 wt. % MgO, or both
- wherein the bioactive glass exhibits at least one of:
  - a hydrolytic resistance of glass grains (HGB) of at most 4, when measured by International Organization for Standardization section 719 (ISO 719);
  - a weight loss of 5 wt. % or less after soaking 5 g of the bioactive glass in powder form in 100 mL of deionized water for 7 days at 37° C.;
  - an XRD spectrum in which total crystallinity of the bioactive glass is less than 5 wt. % crystalline phase after soaking 5 g of the bioactive glass in powder form in 100 mL of deionized water for 7 days at 37° C.; or
  - any combination thereof;
- wherein, when the bioactive glass is contacted with artificial saliva, the bioactive glass forms a bioactive crystalline phase.

16. The bioactive glass of claim 15, wherein the bioactive crystalline phase forms within 1 day or within 7 days when contacted with the artificial saliva.

17. The bioactive glass of claim 15, wherein the bioactive crystalline phase comprises apatite, brushite, whitlockite, or a combination thereof.

18. The bioactive glass of claim 15, wherein the bioactive crystalline phase comprises apatite, and the apatite comprises hydroxyapatite, fluorapatite, carbonated apatite, or any combination thereof.

19. The bioactive glass of claim 15, comprising:

25-40 wt. % $SiO_2$;

30-50 wt. % CaO;

9.5-25 wt. % $P_2O_5$;

3.5-10 wt. % $ZrO_2$; and

>0-14.5 wt. % MgO.

20. The bioactive glass of claim 19, comprising at least one of:

>0-5.0 wt. % MgO;

>0-14.5 wt. % SrO;

>0-14.5 wt. % ZnO; or any combination thereof.

* * * * *